US010428320B2

(12) United States Patent
Mihelič et al.

(10) Patent No.: US 10,428,320 B2
(45) Date of Patent: Oct. 1, 2019

(54) **CRYSTAL STRUCTURE OF *STAPHYLOCOCCUS AUREUS* AUTOLYSIN E, METHOD OF PRODUCING THE CRYSTAL AND ITS USE IN SCREENING METHODS**

(71) Applicant: J. Stefan Institute, Ljubljana (SI)

(72) Inventors: Marko Mihelič, Kamnik (SI); Miha Renko, Radece (SI); Dusan Turk, Ljubljana (SI)

(73) Assignee: J. Stefan Institute, Ljubljana (SI)

( * ) Notice: Subject to any disclaimer, the term of this patent is extended or adjusted under 35 U.S.C. 154(b) by 58 days.

(21) Appl. No.: 15/568,923

(22) PCT Filed: Apr. 27, 2015

(86) PCT No.: PCT/EP2015/000865
§ 371 (c)(1),
(2) Date: Oct. 24, 2017

(87) PCT Pub. No.: WO2016/173603
PCT Pub. Date: Nov. 3, 2016

(65) Prior Publication Data
US 2018/0119124 A1    May 3, 2018

(51) Int. Cl.
*C12N 9/24* (2006.01)
*G16B 15/00* (2019.01)
*G01N 33/573* (2006.01)
*C12N 9/36* (2006.01)

(52) U.S. Cl.
CPC ......... *C12N 9/2402* (2013.01); *C12N 9/2462* (2013.01); *C12Y 302/0105* (2013.01); *G01N 33/573* (2013.01); *G16B 15/00* (2019.02); *C07K 2299/00* (2013.01); *G01N 2333/31* (2013.01); *G01N 2333/924* (2013.01)

(58) Field of Classification Search
None
See application file for complete search history.

(56) References Cited

PUBLICATIONS

Andrejasic et al., "PURY: A database of geometric restraints of hetero compounds for refinement of complexes with macromolecular structures," Acta Crystallogr Biol Crystallogr. 64:1093-1109 (2008).
Archer et al., "*Staphylococcus aureus* biofilms: properties, regulation, and roles in human disease," Virulence (5):445-59 (2011).
Bai et al., "Structure of pneumococcal peptidoglycan hydrolase LytB reveals insights into the bacterial cell wall remodeling and pathogenesis," J Biol Chem. 289(34):23403-16 (2014).
Biswas et al., "Activity of the major staphylococcal autolysin Atl," FEMS Microbiol Lett. 259(2): 260-8 (2006).
Boneca et al., "Characterization of *Staphylococcus aureus* cell wall glycan strands, evidence for a new beta-N-acetylglucosaminidase activity," J Biol Chem. 275(14):9910-8 (2000).
Bublitz et al., "Structural basis for autoinhibition and activation of Auto, a virulence-associated peptidoglycan hydrolase of Listeria monocytogenes," Mol. Microbiol. 71(6):1509-1522 (2009).
Büttner et al., "Structure-function analysis of *Staphylococcus aureus* amidase reveals the determinants of peptidoglycan recognition and cleavage," J Biol Chem. 289(16):11083-94 (2014).
Cantarel et al., "The Carbohydrate-Active EnZymes database (CAZy): an expert resource for glycogenomics," Nucleic Acids Res. 37(Database issue):D233-D238 (2009).
Dantes et al., "National burden of invasive methicillin-resistant *Staphylococcus aureus* infections, United States, 2011," JAMA Intern Med. 173(21):1970-8 (2013).
Davies et al., "Nomenclature for sugar-binding subsites in glycosyl hydrolases," Biochem J. 321(Pt 2):557-9 (1997).
Ericsson et al., "Thermofluorbased high-throughput stability optimization of proteins for structural studies," Anal Biochem. 357(2):289-298 (2006).
Eschenfeldt et al., "A Family of LIC Vectors for High-Throughput Cloning and Purification of Proteins," Availabl in PMC Jan. 1, 2010, publisehd in final edited form as: Methods Mol Biol. 498:105-115 (2009) (11 pages).
Gardete et al., "Mechanisms of vancomycin resistance in *Staphylococcus aureus*," J Clin Invest. 124(7):2836-40 (2014).
Gille et al., "STRAP: editor for STRuctural Alignments of Proteins," Bioinformatics 17(4):377-8 (2001).
Guerrero et al., "Production of selenomethionine-labelled proteins using simplified culture conditions and generally applicable host/vector systems," Appl Microbiol Biotechnol. 56(5-6):718- 23 (2001).
Hanberger et al., "Increased mortality associated with methicillin-resistant *Staphylococcus aureus* (MRSA) infection in the intensive care unit: results from the EPIC II study," Int J Antimicrob Agents. 38(4):331-5 (2011).
Hashimoto et al., "Crystal structure of the glycosidase family 73 peptidoglycan hydrolase FlgJ," Biochem. Biophys. Res. Commun. 381(1):16-21 (2009).
Haynes, W. M., ed., CRC Handbook of Chemistry and Physics, CRC Press (2014).
Heilmann et al., "Evidence for autolysin-mediated primary attachment of *Staphylococcus epidermidis* to a polystyrene surface," Mol Microbiol. 24(5):1013-1024 (1997).
Helland et al., "Crystal structures of g-type lysozyme from Atlantic cod shed new light on substrate binding and the catalytic mechanism," Cell. Mol. Life Sci. 66(15):2585-98 (2009).
Hiramatsu et al., "Methicillin resistant *Staphylococcus aureus* clinical strain with reduced vancomycin susceptibility," J Antimicrob. Chemother. 40(1):135-136 (1997).
Ho et al., "Site-directed mutagenesis by overlap extension using the polymerase chain reaction," Gene. 77(1):51-9 (1989).

(Continued)

*Primary Examiner* — Suzanne M Noakes
(74) *Attorney, Agent, or Firm* — Clark & Elbing LLP

(57) ABSTRACT

The invention concerns the determination and evaluation of the crystal structure of autolysin E (AtlE) of *Staphylococcus aureus* (*S. aureus*), or a crystallizable fragment of AtlE, a method for producing a crystal of AtlE and the respective crystallization kit, and its use in a method for screening an inhibitor of the N-acetylglucosaminidase activity of AtlE, for obtaining atomic spatial relationship data, and for identifying a binding compound of AtlE, e.g. by in silico screening.

16 Claims, 15 Drawing Sheets
Specification includes a Sequence Listing.

(56) References Cited

PUBLICATIONS

Joti et al., "Nonlinear temperature dependence of the crystal structure of lysozyme: correlation between coordinate shifts and thermal factors," Acta Crystallogr D Biol Crystallogr. 58(Pt 9):1421-32 (2002).
Kantoci et al., "A convenient synthetic route to the disaccharide repeating-unit of peptidoglycan," Carbohydr. Res. 162(2):227-235 (1987).
Keglevic et al., "Synthesis and conformational analysis of muramic acid delta-lactam structures and their 4-O-(2-acetamido-2-deoxy-beta-D-glucopyranosyl) derivatives, characteristic of bacterial spore peptidoglycan," Carbohydr. Res. 241:131-152 (1993).
Keglevic et al., "Aminolysis of N-Acetylmuramic Acid Lactones by Amino Acid and Peptide Esters—A Synthetic Route to N-Acetylmuramoylamide Derivatives," Croat. Chem. Acta 58, 569-581 (1985).
Kelly et al., "X-ray crystallography of the binding of the bacterial cell wall trisaccharide NAM-NAG-NAM to lysozyme," Nature 282(5741):875-8 (1979).
Lowy, "*Staphylococcus aureus* infections," New England Journal of Medicine 339(8):520-532 (1998).
Meesters et al., "Structural characterization of the alphahemolysin monomer from *Staphylococcus aureus*," Proteins 75(1):118-26 (2009).
Merritt et al., "Raster3D: photorealistic molecular graphics," Methods Enzymol. 277:505-24 (1997).
Merritt et al., "Growing and analyzing static biofilms," Available in PMC Sep. 14, 2015, published in final edited form as: Curr Protoc Microbiol. Chapter 1:Unit 1 B.1 (2005) (29 pages).
Minor et al., "HKL-3000, the integration of data reduction and structure solution. From diffraction images to an initial model in minutes," Acta Crystallogr D Biol Crystallogr. 62(Pt 8):859-866 (2006).
Murshudov et al., "Refinement of Macromolecular Structures by the Maximum-Likelihood method," Acta Crystallogr D Biol Crystallogr. 53(Pt 3):240-255 (1997).
Nashed et al., "Oligosaccharides from "standardized intermediates." Synthesis of a branched tetrasaccharide glycoside related to the blood group B determinant," J. Am. Chem. Soc 104(25):7282-7286 (1982).
Nunes et al., Heterogeneous resistance to vancomycin and teicoplanin among *Staphylococcus* spp. isolated from bacteremia. Braz J Infect Dis. 11(3):345-350 (2007).
Odintsov et al., "Latent LytM at 1.3A resolution," J Mol Biol. 335(3):775-85 (2004).
Oshida et al., "A *Staphylococcus aureus* autolysin that has an N-acetylmuramoyl-L-alanine amidase domain and an endo-beta-N-acetylglucosaminidase domain: cloning, sequence analysis, and characterization," PNAS 92(1):285-289 (1995).
Otwinowski et al., "Processing of X-ray Diffraction Data Collected in Oscillation Mode, Methods in Enzymology," vol. 276: Macromolecular Crystallography, part A, p. 307-326, 1997,C.W. Carter, Jr. & R. M. Sweet, Eds., Academic Press (New York) (1997).
Smith, et al., "Autolysins of Bacillus subtilis: multiple enzymes with multiple functions," Microbiology 146(Pt 2):249-262 (2000).
Sugai et al., "Identification of endo-beta-N-acetylglucosaminidase and Nacetylmuramyl-L-alanine amidase as cluster-dispersing enzymes in *Staphylococcus aureus*," J Bacteriol. 177(6):1491-6 (1995).
Turk, "MAIN software for density averaging, model building, structure refinement and validation," Acta Crystallogr D Biol Crystallogr(6). 69:1342-1357 (2013).
Varrone et al., "Anti-Glucosaminidase Monoclonal Antibodies as a Passive Immunization for Methicillin-Resistant *Staphylococcus aureus* (MRSA) Otrhopaedic Infections," Available in PMC Apr. 1, 2012, published in final eidted form as: Bonekey Osteovision. 8:187-194 (2011) (9 pages).
Vincent et al., "International study of the prevalence and outcomes of infection in intensive care units," JAMA. 302(21):2323-9 (2009).
Vollmer et al., "Bacterial peptidoglycan (murein) hydrolases," FEMS Microbiol Rev. 32(2): 259-286 (2008).
Weaver et al., "The refined structures of goose lysozyme and its complex with a bound trisaccharide show that the "goose-type" lysozymes lack a catalytic aspartate residue," J Mol Biol. 245(1):54-68 (1995).
Weaver et al., "Structure of bacteriophage T4 lysozyme refined at 1.7 A resolution," J Mol Biol. 193(1):189-99 (1987).
Ye et al., "Flexible structure alignment by chaining aligned fragment pairs allowing twists," Bioinformatics 19:246-255 (2003).
Zetola et al., "Community-acquired methicillin-resistant *Staphylococcus aureus*: an emerging threat," Lancet Infect Dis. 5(5):275-86 (2005).
Zoll et al., "Structural basis of cell wall cleavage by a Staphylococcal autolysin," PLoS Pathog. 6(3):e1000807 (2010).
Zoll, "Crystal structures of the major Staphylococcal", Universität Tübingen, Jan. 1, 2011 (https://publikationen.uni-tuebingen.de).
Zoll et al., "Ligand-Binding Properties and Conformational Dynamics of Autolysin Repeat Domains in Staphylococcal Cell Wall Recognition", J Bacteriol. 194(15):3789-802 (2012).
International Search Report for International Patent Application No. PCT/EP2015/000865, dated Jul. 29, 2015 (4 pages).
Written Opinion of the International Searching Authority for International Patent Application No. PCT/EP2015/000865, dated Jul. 29, 2015 (7 pages).
International Preliminary Report on Patentability for International Patent Application No. PCT/EP2015/000865, dated Oct. 31, 2017 (8 pages).

1   MKKNFKLRISTLLLIVILVVFAVLLIVNETKLFNDVNYSFDEAVSMQQGKGIVQTKEED 60
61  GKFVEANNNEIAKAMTISHKDNDMKYMDITEKVPMSESEVNQLLKGKGILENRGKVFLEA 120
121 QEKYEVNVIYLVSHALVETGNGKSELAKGIKDGKKRYYNFFGIGAFDSSAVRSGKSYAEK 180
181 EQWTSPDKAIIGGAKFIRNEYFENNQLNLYQMRWNPENPAQHQYASDIRWADKIAKLMDK 240
241 SYKQFGIKKDDIRQTYYK   258

Figure 5

```
                                                                              *      *
    AtlE   82 NDMKYMDITE KVPMSESEVN QLLK----GK GILENRGKVF LEAQEKY-EV NVIYLVSHAL VETGNGKSEL AKG-------
 LytB_SP  130 .PFLfK.1.. ATNY.AE.ld KvFSLLNINN Sl...k.AT. K..e.H.-Hi .al..1A.Sa l.sNW.r.Ki ..D-------
     Lmo   78                        QQ TFinSISTQA MdlCK..-nl YPSVMiAQ.a l.sNW.r.-- EL.-------
    FlgJ  153                        aQ aFvdATWPQA aK.AqSL-G. PaHf..AQ.a l...W...-- QIR-------
    ACOD   42                        A.r --M.KYKSFI NnvAK.H-V. dPaViaAIiS R.sRA.NV-- iFN-------
    HLYZ    1                        KVF ERC.LARTlK RLgMdG.RGi SlaNWMCL.K W.s.YNTR-- .TNYNAGDRS

AtlE  150 IKDGKKRY-- -----YNFFG IGA------- ---------- ---FDS---- ---------- -SAVRSGKSY AEKEQWT--S
 LytB_SP  202 K--------- -----N.... .T-------- ---------- ---------- ---------- ---------- -------.FDD
     Lmo  120 K----APN-- ------..L.. .KgS------ -----YN--- GKSVTMKTWE YSDSKGWYQI NANF------ .K---YP--.
    FlgJ  195 N...-GTPS- ------..L.N .K.GSN---- -----WT--- GKVVeARTV- -------KVR VERF------ RA---YD--.
    ACOD   83 TTP---PGWG DNYNGfGLMQ vD-------- ---------- ---------- ---------- -------KR YHEPRGA--W
    HLYZ   52 T------D-- -----.GI.Q .NSRYWCNDG KTPGAVNACH LS-------- ---------- ---------- -C---SA--L

*                                                                          * *
    AtlE  186 ----PD-KAI IGGAKFIRNE -----YFENN ---------Q L--------- NLY----QMR -------WNP ENPAQHQYAS
 LytB_SP  214 ----V.-.g. l.aT.W.ken ------IdRG ---------R T--------- F.GNKASG.N -------V-- ------e...
     Lmo  164 ----HK-ESl EDN..Kl..G PSWDSSyYKG ---------A WRENAKTYKD ATA----WLQ -------G-- -----R-..t
    FlgJ  236 ----Ye-Q.F QDY.DLvG.S -----PRYAK ---------V aG--KTDGHA FaR----ALQ -------E-- -----GG..t
    ACOD  112 ----NSEEH. DQaTGIlV.F -----IQLIq KKFPSWSTE. Q--------- LKG----AIA AYNTGDGRVE SYESVDSRTt
    HLYZ   85 LQDNIA-D.v aCaKrVv-Rd -----PQG-- ---------- ---------- ---------- ---------- -----IRAWV

*  *  *
    AtlE  227 --DIRWADKI AKLMDKSYKQ -FGIKKDDIR QTYYK
 LytB_SP  251 --.PY.ge.. .Sv.M.INEK LG.KD
     Lmo  211 --.NTY.S.l NT.ISSYNLT QyD
    FlgJ  277 --.PSY...1 .rvInGNALR QRLMASAASA RGLE
    ACOD  170 --GKDYSnDv vARAqWYK.n -GF
    HLYZ  111 AWRN.CQnrD vrQYVQGCGV
```

Figure 9

```
                             00000000 0000000000 00
SAV2307_AtlE    35 NDVNYSFDEA VSMQQGKG-I VQTKE-EDGK FVEANNNEIA KAMTIS----
SAV0909       1012    SP.t.Kq. lDK.Mar.-N PKKSn-AW.- Wan.TRAqTS S..NvKRIWE
SAV1775        413 eKl.VtLnd. aKK.INNYTS Q.VSnKKnDA WRd.SAT..K S..DSGTFID
SAV2644         46 PASdDKAnqK S.SKdNQSMS DSALdSILDQ yS.DAKKTQK DYAsQ.KKDK
SAV1052_AtlA   206 .qTGMtLnqv aQI.A.LQYK P.VQR-VP.. WTd..F.dvK H..DTKRLAQ SAV2307_AtlE    79 HKDNDMKYMD ITEKVPMSE- ---------- -----SEVNQ LLKGKGILEN
SAV0909       1057 SNTqCYQMLn lGKYQGV.V- ---------- ------Al.K i.....T.n.
SAV1775        463 NEKqKYQfL. lsKYQGIDK- ---------- -----NRiKC M.VDrPT.LK
SAV2644         96 NEKSnT.NPq lPTQDELKHK SKPAQSFNND VNQKDtRaTS .FETDPSiS.
SAV1052_AtlA   255 DPALKYQfLR lDqPQNI.I- ---------- -----DKi.. F.....v...

1111111
SAV2307_AtlE   113 R--------- ---------- --GKVFLEAQ EKYEVNVIYL VSHALVETGN
SAV0909       1091 Q--------- ---------- --..a.a..C K.Hni.E... iA..Fl.s.Y
SAV1775        497 H--------- ---------- --TDD..K.A KDKH..Ev.. i....1...A
SAV2644        146 NDDSGQFNVV DSKDTRQFVK SIa.DAHRiG qDNdiYaSVM iAQ.il.sDS
SAV1052_AtlA   289 Q--------- ---------- --.Aa.NK.A qM.Gi.Ev.. i....1....

22222 22
SAV2307_AtlE   142 GKSELAKGI- -------KDG KKRYYNFFGI GAFDSSAVRS GKSYAEKEQW
SAV0909       1120 .T.nF.N--- ----------. .DGV..y... ..y.NNPN-Y aMtf.RNKG.
SAV1775        526 V.....N.-- ------VEID G.k....y.v ..L.KDPikt .AE..K.HG.
SAV2644        196 .r.A...SPN HN---LFGIK GAFEG.SVPF NTLeADGNkL YSIN.GFRKY
SAV1052_AtlA   318 .T.q....aD VVNNKVVTnS NTk.H.V... a.y.NDPl.E .IK..KQAG.

333333        4 4   444444 4444444444
SAV2307_AtlE   184 TSPDKAIIGG AKFIRNEYFE -NNQLNLYQM RWNPENPAQH QYASDIRWAD
SAV0909       1157 ...A...M.. .S.v.Kd.In -KG.NT..RI ....K...T. ...tA.E.Cq
SAV1775        568 Dt.e...S.. .D..HKHfLS STd.NT..S. ....K..Ge. ...t..k..e
SAV2644        243 P.TKESlKDY SDL.k.GIDG ---nRTi.KP T.KS.ADS-- -.KDATSHlS
SAV1052_AtlA   368 DtVS...v.. ....G.S.VK -AG.NT..K. ....AH.GT. ...t.vD..n

SAV2307_AtlE   233 KIAKLMDKSY KQFGIKKDDI RQTYYK
SAV0909       1206 HQ.NTIA.L. ..I.l.GIYF TRDK..
SAV1775        618 SN.TiIADF. .nMKTEGKYF kYFV..SKHL NK
SAV2644        287 .TYATDPNYA .KLNSIIKHY QL.QfDDERM PDLHDK
SAV1052_AtlA   417 IN..iIKGY. DKI.EVGKYF DIPQ..
```

Figure 11
a
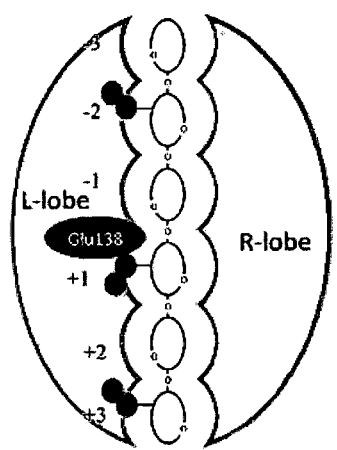
b
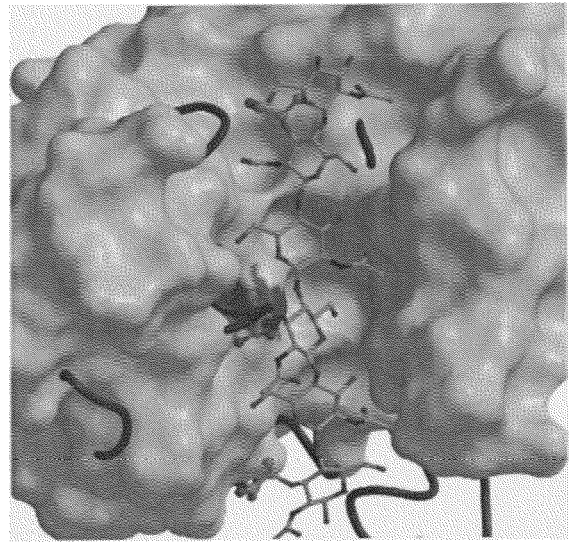
Figure 12
a
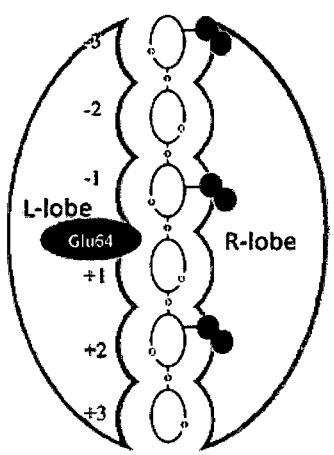
b
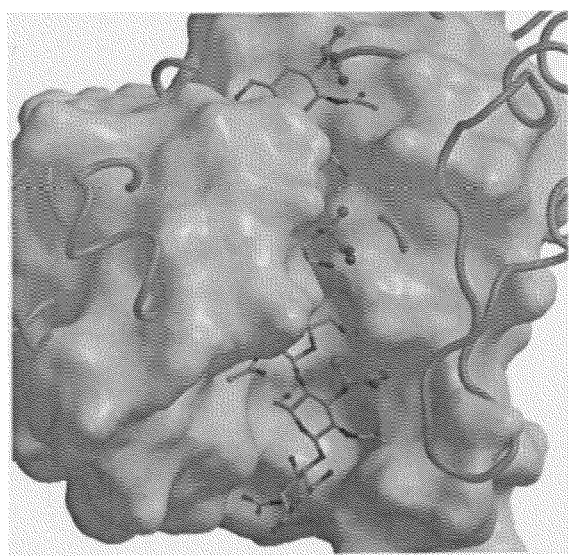

Digestion products expected

MG$^{red}$ + MG$^{red}$
[M+H]$^+$= 499.21

NAG-NAM

SEQUENCE LISTING

<160> NUMBER OF SEQ ID NOS: 11

<210> SEQ ID NO 1
<211> LENGTH: 258
<212> TYPE: PRT
<213> ORGANISM: Staphylococcus aureus

<400> SEQUENCE: 1

```
Met Lys Lys Asn Phe Lys Leu Arg Ile Ser Thr Leu Leu Leu Ile Val
1               5                   10                  15

Ile Leu Val Val Phe Ala Val Leu Leu Ile Val Asn Glu Thr Lys Leu
            20                  25                  30

Phe Lys Asn Asp Val Asn Tyr Ser Phe Asp Glu Ala Val Ser Met Gln
        35                  40                  45

Gln Gly Lys Gly Ile Val Gln Thr Lys Glu Glu Asp Gly Lys Phe Val
    50                  55                  60

Glu Ala Asn Asn Asn Glu Ile Ala Lys Ala Met Thr Ile Ser His Lys
65                  70                  75                  80

Asp Asn Asp Met Lys Tyr Met Asp Ile Thr Glu Lys Val Pro Met Ser
                85                  90                  95

Glu Ser Glu Val Asn Gln Leu Leu Lys Gly Lys Gly Ile Leu Glu Asn
            100                 105                 110

Arg Gly Lys Val Phe Leu Glu Ala Gln Glu Lys Tyr Glu Val Asn Val
```

```
                    115                 120                 125
        Ile Tyr Leu Val Ser His Ala Leu Val Glu Thr Gly Asn Gly Lys Ser
            130                 135                 140

Glu Leu Ala Lys Gly Ile Lys Asp Gly Lys Lys Arg Tyr Tyr Asn Phe
        145                 150                 155                 160

Phe Gly Ile Gly Ala Phe Asp Ser Ser Ala Val Arg Ser Gly Lys Ser
                        165                 170                 175

Tyr Ala Glu Lys Glu Gln Trp Thr Ser Pro Asp Lys Ala Ile Ile Gly
                    180                 185                 190

Gly Ala Lys Phe Ile Arg Asn Glu Tyr Phe Glu Asn Asn Gln Leu Asn
                195                 200                 205

Leu Tyr Gln Met Arg Trp Asn Pro Glu Asn Pro Ala Gln His Gln Tyr
            210                 215                 220

Ala Ser Asp Ile Arg Trp Ala Asp Lys Ile Ala Lys Leu Met Asp Lys
        225                 230                 235                 240

Ser Tyr Lys Gln Phe Gly Ile Lys Lys Asp Asp Ile Arg Gln Thr Tyr
                        245                 250                 255

Tyr Lys

<210> SEQ ID NO 2
<211> LENGTH: 224
<212> TYPE: PRT
<213> ORGANISM: Staphylococcus aureus

<400> SEQUENCE: 2

Asn Asp Val Asn Tyr Ser Phe Asp Glu Ala Val Ser Met Gln Gln Gly
        1               5                   10                  15

Lys Gly Ile Val Gln Thr Lys Glu Glu Asp Gly Lys Phe Val Glu Ala
                        20                  25                  30

Asn Asn Asn Glu Ile Ala Lys Ala Met Thr Ile Ser His Lys Asp Asn
                    35                  40                  45

Asp Met Lys Tyr Met Asp Ile Thr Glu Lys Val Pro Met Ser Glu Ser
                50                  55                  60

Glu Val Asn Gln Leu Leu Lys Gly Lys Gly Ile Leu Glu Asn Arg Gly
        65                  70                  75                  80

Lys Val Phe Leu Glu Ala Gln Glu Lys Tyr Glu Val Asn Val Ile Tyr
                        85                  90                  95

Leu Val Ser His Ala Leu Val Glu Thr Gly Asn Gly Lys Ser Glu Leu
                    100                 105                 110

Ala Lys Gly Ile Lys Asp Gly Lys Lys Arg Tyr Tyr Asn Phe Phe Gly
                115                 120                 125

Ile Gly Ala Phe Asp Ser Ser Ala Val Arg Ser Gly Lys Ser Tyr Ala
        130                 135                 140

Glu Lys Glu Gln Trp Thr Ser Pro Asp Lys Ala Ile Ile Gly Gly Ala
                        145                 150                 155                 160

Lys Phe Ile Arg Asn Glu Tyr Phe Glu Asn Asn Gln Leu Asn Leu Tyr
                    165                 170                 175

Gln Met Arg Trp Asn Pro Glu Asn Pro Ala Gln His Gln Tyr Ala Ser
                180                 185                 190

Asp Ile Arg Trp Ala Asp Lys Ile Ala Lys Leu Met Asp Lys Ser Tyr
            195                 200                 205

Lys Gln Phe Gly Ile Lys Lys Asp Asp Ile Arg Gln Thr Tyr Tyr Lys
        210                 215                 220
```

```
<210> SEQ ID NO 3
<211> LENGTH: 220
<212> TYPE: PRT
<213> ORGANISM: Staphylococcus aureus

<400> SEQUENCE: 3

Ser Pro Tyr Thr Phe Lys Gln Ala Leu Asp Lys Gln Met Ala Arg Gly
1               5                   10                  15

Asn Pro Lys Lys Ser Asn Ala Trp Gly Trp Ala Asn Ala Thr Arg Ala
            20                  25                  30

Gln Thr Ser Ser Ala Met Asn Val Lys Arg Ile Trp Glu Ser Asn Thr
        35                  40                  45

Gln Cys Tyr Gln Met Leu Asn Leu Gly Lys Tyr Gln Gly Val Ser Val
    50                  55                  60

Ser Ala Leu Asn Lys Ile Leu Lys Gly Lys Gly Thr Leu Asn Asn Gln
65                  70                  75                  80

Gly Lys Ala Phe Ala Glu Ala Cys Lys Lys His Asn Ile Asn Glu Ile
                85                  90                  95

Tyr Leu Ile Ala His Ala Phe Leu Glu Ser Gly Tyr Gly Thr Ser Asn
            100                 105                 110

Phe Ala Asn Gly Lys Asp Gly Val Tyr Asn Tyr Phe Gly Ile Gly Ala
        115                 120                 125

Tyr Asp Asn Asn Pro Asn Tyr Ala Met Thr Phe Ala Arg Asn Lys Gly
    130                 135                 140

Trp Thr Ser Pro Ala Lys Ala Ile Met Gly Gly Ala Ser Phe Val Arg
145                 150                 155                 160

Lys Asp Tyr Ile Asn Lys Gly Gln Asn Thr Leu Tyr Arg Ile Arg Trp
                165                 170                 175

Asn Pro Lys Asn Pro Ala Thr His Gln Tyr Ala Thr Ala Ile Glu Trp
            180                 185                 190

Cys Gln His Gln Lys Asn Thr Ile Ala Ser Leu Lys Gln Phe Ile Ile
        195                 200                 205

Leu Lys Gly Ile Tyr Phe Thr Arg Asp Lys Tyr Lys
    210                 215                 220

<210> SEQ ID NO 4
<211> LENGTH: 237
<212> TYPE: PRT
<213> ORGANISM: Staphylococcus aureus

<400> SEQUENCE: 4

Glu Lys Leu Pro Val Thr Leu Asn Asp Ala Lys Lys Gln Ile Asn
1               5                   10                  15

Asn Tyr Thr Ser Gln Lys Val Ser Asn Lys Asn Asp Ala Trp Arg
            20                  25                  30

Asp Ala Ser Ala Thr Gln Thr Lys Ser Ala Met Asp Ser Gly Thr Phe
        35                  40                  45

Ile Asp Asn Glu Lys Gln Lys Tyr Gln Phe Leu Asn Leu Ser Lys Tyr
    50                  55                  60

Gln Gly Ile Asp Lys Asn Arg Ile Lys Cys Met Leu Val Asp Arg Pro
65                  70                  75                  80

Thr Leu Leu Lys His Thr Asp Asp Phe Ala Lys Ala Lys Asp Lys
                85                  90                  95

His Val Asn Glu Val Tyr Leu Ile Ala His Ala Phe Leu Glu Ser Gly
            100                 105                 110

Ala Val Thr Ser Asn Phe Ala Asn Gly Val Glu Ile Asp Gly Asp Lys
```

|     |     | 115 |     |     |     | 120 |     |     |     | 125 |     |
| --- | --- | --- | --- | --- | --- | --- | --- | --- | --- | --- | --- |

Val Tyr Asn Tyr Tyr Gly Val Gly Ala Leu Asp Lys Asp Pro Ile Lys
130                     135                     140

Thr Ala Ala Glu Phe Ala Lys Asn His Gly Trp Asp Thr Pro Glu Lys
145                     150                     155                     160

Ala Ile Ser Gly Gly Ala Asp Phe Val His Lys His Phe Leu Ser Ser
                165                     170                     175

Thr Asp Gln Asn Thr Leu Tyr Ser Met Arg Trp Asn Pro Lys Asn Pro
                180                     185                     190

Gly Glu His Gln Tyr Ala Thr Ala Ile Lys Trp Cys Glu Ser Asn Gln
                195                     200                     205

Thr Ile Ile Ala Asp Phe Leu Lys Asn Met Lys Thr Glu Gly Lys Tyr
210                     215                     220

Phe Lys Tyr Phe Val Lys Lys Ser Lys His Leu Asn Lys
225                     230                     235

<210> SEQ ID NO 5
<211> LENGTH: 277
<212> TYPE: PRT
<213> ORGANISM: Staphylococcus aureus

<400> SEQUENCE: 5

Pro Ala Ser Asp Asp Lys Ala Asn Gln Lys Ser Lys Ser Lys Asp Asn
1               5                       10                      15

Gln Ser Met Ser Asp Ser Ala Leu Asp Ser Ile Leu Asp Gln Tyr Ser
                20                      25                      30

Asp Asp Ala Lys Lys Thr Gln Lys Asp Tyr Ala Ser Gln Gly Lys Lys
                35                      40                      45

Asp Lys Asn Glu Lys Ser Asn Thr Gln Asn Pro Gln Leu Pro Thr Gln
50                      55                      60

Asp Glu Leu Lys His Lys Ser Lys Pro Ala Gln Ser Phe Asn Asn Asp
65                      70                      75                      80

Val Asn Gln Lys Asp Thr Arg Ala Thr Ser Met Phe Glu Thr Asp Pro
                85                      90                      95

Ser Ile Ser Lys Asn Asp Asp Ser Gly Gln Phe Asn Val Val Asp Ser
                100                     105                     110

Lys Asp Thr Arg Gln Phe Val Lys Ser Ile Ala Asp Ala His Arg
                115                     120                     125

Ile Gly Gln Asp Asn Asp Ile Tyr Ala Ser Val Met Ile Ala Gln Ala
130                     135                     140

Ile Leu Glu Ser Asp Ser Val Arg Ser Ala Phe Ala Asn Ser Pro Asn
145                     150                     155                     160

His Asn Leu Phe Gly Ile Lys Gly Ala Phe Glu Gly Asn Ser Val Pro
                165                     170                     175

Phe Asn Thr Leu Glu Ala Asp Gly Asn Lys Leu Tyr Ser Ile Asn Ala
                180                     185                     190

Gly Phe Arg Lys Tyr Pro Thr Thr Lys Glu Ser Leu Lys Asp Tyr Ser
                195                     200                     205

Asp Leu Val Lys Lys Gly Ile Asp Gly Asn Arg Thr Ile Tyr Lys Pro
                210                     215                     220

Thr Trp Lys Ser Lys Ala Asp Ser Tyr Lys Asp Ala Thr Ser His Leu
225                     230                     235                     240

Ser Ser Thr Tyr Ala Thr Asp Pro Asn Tyr Ala Lys Lys Leu Asn Ser
                245                     250                     255

```
Ile Ile Lys His Tyr Gln Leu Phe Gln Phe Asp Asp Glu Arg Met Pro
            260                 265                 270

Asp Leu His Asp Lys
        275

<210> SEQ ID NO 6
<211> LENGTH: 237
<212> TYPE: PRT
<213> ORGANISM: Staphylococcus aureus

<400> SEQUENCE: 6

Pro Gln Thr Gly Met Thr Leu Asn Gln Val Ala Gln Ile Lys Ala Asn
1               5                   10                  15

Leu Gln Tyr Lys Pro Ser Val Gln Arg Val Pro Asp Gln Trp Thr Asp
            20                  25                  30

Asp Ala Phe Lys Asp Val Lys His Tyr Ala Asp Thr Lys Arg Leu Ala
        35                  40                  45

Gln Asp Pro Ala Leu Lys Tyr Gln Phe Leu Arg Leu Asp Gln Pro Gln
    50                  55                  60

Asn Ile Lys Ile Asp Lys Ile Thr Ser Phe Phe Glu Thr Asp Pro Val
65                  70                  75                  80

Ile Ser Lys Gln Ala Ala Ala Asn Lys Ile Ala Gln Met Asn Gly
                85                  90                  95

Ile Tyr Glu Val Val Met Ile Ala Gln Ala Ile Leu Ser Asp Ser
            100                 105                 110

Val Thr Ser Gln Phe Ala Asn Ser Ala Asp Val Val Asn Asn Lys Val
        115                 120                 125

Val Thr Asn Ser Asn Thr Lys Glu His Asn Val Val Pro Phe Ala Thr
    130                 135                 140

Tyr Glu Asn Asp Pro Leu Lys Glu Tyr Ile Lys Asn Ala Lys Gln Ala
145                 150                 155                 160

Gly Tyr Asp Thr Val Ser Glu Ser Leu Val Asp Tyr Ser Asp Leu Val
                165                 170                 175

Gly Lys Ser Ile Val Lys Ala Gly Asn Asn Thr Ile Tyr Lys Pro Thr
            180                 185                 190

Trp Lys Ser Ala His Asp Gly Thr His Gln Tyr Lys Thr Ala Val Asp
        195                 200                 205

His Leu Asn Ile Asn Tyr Ala Ile Ile Lys Gly Tyr Ala Asp Lys Ile
    210                 215                 220

Asn Glu Val Gly Lys Tyr Phe Asp Ile Pro Gln Phe Asp
225                 230                 235

<210> SEQ ID NO 7
<211> LENGTH: 144
<212> TYPE: PRT
<213> ORGANISM: Streptococcus pneumoniae

<400> SEQUENCE: 7

Asn Pro Phe Leu Phe Lys Asp Leu Thr Glu Ala Thr Asn Tyr Ser Ala
1               5                   10                  15

Glu Glu Leu Asp Lys Val Phe Ser Leu Leu Asn Ile Asn Asn Ser Leu
            20                  25                  30

Leu Glu Asn Lys Gly Ala Thr Phe Lys Glu Ala Glu Glu His Tyr His
        35                  40                  45

Ile Asn Ala Leu Tyr Leu Leu Ala His Ser Ala Leu Glu Ser Asn Trp
    50                  55                  60
```

Gly Arg Ser Lys Ile Ala Lys Asp Lys Asn Asn Phe Phe Gly Ile Thr
65                  70                  75                  80

Thr Phe Asp Asp Val Asp Lys Gly Ile Leu Gly Ala Thr Lys Trp Ile
                85                  90                  95

Lys Glu Asn Tyr Ile Asp Arg Gly Arg Thr Phe Leu Gly Asn Lys Ala
            100                 105                 110

Ser Gly Met Asn Val Glu Tyr Ala Ser Asp Pro Tyr Trp Gly Glu Lys
        115                 120                 125

Ile Ala Ser Val Met Met Lys Ile Asn Glu Lys Leu Gly Gly Lys Asp
    130                 135                 140

<210> SEQ ID NO 8
<211> LENGTH: 154
<212> TYPE: PRT
<213> ORGANISM: Listeria monocytogenes

<400> SEQUENCE: 8

Gln Gln Thr Phe Ile Asn Ser Ile Ser Thr Gln Ala Met Asp Leu Cys
1               5                   10                  15

Lys His Tyr Asn Leu Tyr Pro Ser Val Met Ile Ala Gln Ser Ala Leu
            20                  25                  30

Glu Ser Asn Trp Gly Arg Ser Glu Leu Asp Lys Ala Pro Asn Asn Asn
        35                  40                  45

Leu Phe Gly Ile Lys Gly Ser Tyr Asn Gly Lys Ser Val Thr Met Lys
    50                  55                  60

Thr Trp Glu Tyr Ser Asp Ser Lys Gly Trp Tyr Gln Ile Asn Ala Asn
65                  70                  75                  80

Phe Ala Lys Tyr Pro Asp His Lys Glu Ser Leu Glu Asp Asn Thr Lys
                85                  90                  95

Lys Leu Lys Glu Gly Pro Ser Trp Asp Ser Ser Tyr Tyr Lys Gly Ala
            100                 105                 110

Trp Arg Glu Asn Ala Lys Thr Tyr Lys Asp Ala Thr Ala Trp Leu Gln
        115                 120                 125

Gly Arg Tyr Ala Thr Asp Asn Thr Tyr Gly Ser Lys Leu Asn Thr Val
    130                 135                 140

Ile Ser Ser Tyr Asn Leu Thr Gln Tyr Asp
145                 150

<210> SEQ ID NO 9
<211> LENGTH: 156
<212> TYPE: PRT
<213> ORGANISM: Sphingomonas sp. strain A1

<400> SEQUENCE: 9

Ala Gln Ala Phe Val Asp Ala Thr Trp Pro Gln Ala Ala Lys Leu Ala
1               5                   10                  15

Gln Ser Leu Gly Leu Pro Ala His Phe Met Ile Ala Gln Ser Ala Leu
            20                  25                  30

Glu Ser Asn Trp Gly Arg Ser Gln Ile Arg Asn Lys Asp Gly Thr Pro
        35                  40                  45

Ser Asn Asn Leu Phe Asn Ile Lys Gly Gly Ser Asn Trp Thr Gly Lys
    50                  55                  60

Val Val Glu Ala Arg Thr Val Lys Val Arg Val Glu Arg Phe Arg Ala
65                  70                  75                  80

Tyr Asp Asp Tyr Glu Gln Ser Phe Gln Asp Tyr Thr Asp Leu Val Gly
                85                  90                  95

Glu Ser Pro Arg Tyr Ala Lys Val Ala Gly Lys Thr Asp Gly His Ala
            100                 105                 110

Phe Ala Arg Ala Leu Gln Glu Gly Gly Tyr Ala Thr Asp Pro Ser Tyr
        115                 120                 125

Gly Ser Lys Leu Asn Arg Val Ile Asn Gly Asn Ala Leu Arg Gln Arg
    130                 135                 140

Leu Met Ala Ser Ala Ala Ser Ala Arg Gly Leu Glu
145                 150                 155

<210> SEQ ID NO 10
<211> LENGTH: 148
<212> TYPE: PRT
<213> ORGANISM: Atlantic cod

<400> SEQUENCE: 10

Ala Ala Arg Met Asp Lys Tyr Lys Ser Phe Ile Asn Asn Val Ala Lys
1               5                   10                  15

Ser His Val Leu Asp Pro Ala Val Ile Ala Ala Thr Ile Ser Arg Glu
            20                  25                  30

Ser Arg Ala Gly Asn Val Ile Phe Asn Thr Thr Pro Pro Gly Trp Gly
        35                  40                  45

Asp Asn Tyr Asn Gly Phe Gly Leu Met Gln Val Asp Lys Arg Tyr His
    50                  55                  60

Glu Pro Arg Gly Ala Trp Asn Ser Glu Glu His Phe Asp Gln Ala Thr
65                  70                  75                  80

Gly Ile Leu Val Glu Phe Ile Gln Leu Ile Gln Lys Lys Phe Pro Ser
                85                  90                  95

Trp Ser Thr Glu Val Gln Leu Lys Gly Ala Ile Ala Ala Tyr Asn Thr
            100                 105                 110

Gly Asp Gly Arg Val Glu Ser Tyr Glu Ser Val Asp Ser Arg Thr Thr
        115                 120                 125

Gly Lys Asp Tyr Ser Asn Asp Val Val Ala Arg Ala Gln Trp Tyr Lys
    130                 135                 140

Leu Asn Gly Phe
145

<210> SEQ ID NO 11
<211> LENGTH: 130
<212> TYPE: PRT
<213> ORGANISM: Homo sapiens

<400> SEQUENCE: 11

Lys Val Phe Glu Arg Cys Asp Leu Ala Arg Thr Leu Lys Arg Leu Gly
1               5                   10                  15

Met Asp Gly His Arg Gly Ile Ser Leu Ala Asn Trp Met Cys Leu Ile
            20                  25                  30

Lys Trp Glu Ser Arg Tyr Asn Thr Arg Ile Thr Asn Tyr Asn Ala Gly
        35                  40                  45

Asp Arg Ser Thr Asp Phe Gly Ile Met Gln Val Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp His Val Ala Cys Ala
                85                  90                  95

Lys Arg Val Val Arg Asp Pro Gln Gly Ile Arg Ala Trp Val Ala Trp
            100                 105                 110

```
Arg Asn Asp Cys Gln Asn Arg Asp Val Arg Gln Tyr Val Gln Gly Cys
        115                 120                 125
Gly Val
    130
```

CRYSTAL STRUCTURE OF STAPHYLOCOCCUS AUREUS AUTOLYSIN E, METHOD OF PRODUCING THE CRYSTAL AND ITS USE IN SCREENING METHODS

SUMMARY

The present invention concerns the determination and evaluation of the crystal structure of Autolysin E (AtlE) of Staphylococcus aureus (S. aureus), or a crystallizable fragment of AtlE, a method for producing a crystal of AtlE and the respective crystallization kit, and its use in a method for screening an inhibitor of the N-acetylglucosaminidase activity of AtlE, for obtaining atomic spatial relationship data, and for identifying a binding compound of AtlE and other GH73 family glucosaminidases from S. aureus, e.g. by in silico screening.

BACKGROUND

A characteristic structural component of the cell wall of bacteria is peptidoglycan. The peptidoglycan cell wall surrounds the bacterial cell, provides structural support, and shields the bacterial membrane against osmotic rapture. It is composed of alternating N-acetylglucosamine (NAG) and N-acetylmuramic acid (NAM) residues connected with β(1, 4)-glycosidic bonds [Boneca et al., 2000] and cross-linked with short polypeptide chains. Bacterial growth, division, colonization, and biofilm formation heavily relies on the ability of the cells to remodel their cell wall. Therefore, many antibiotics, such as penicillin, target the biosynthesis of the cell wall. Due to the increasing resistance of bacteria to antibiotics, it is important to find alternative targets for the treatment of bacterial infections, e.g. enzymes involved in the cell wall degradation. Cell wall degradation is performed by peptidoglycan hydrolases, also known as autolysins [Smith et al, 2000]. Among them are glycosidases which hydrolyze glycosidic bonds in NAM-NAG polymers. There exists two major types of glycosidases, N-acetylglucosaminidases and N-acetylmuramidases (lysozyme-like proteins), which cleave the β(1,4)-glycosidic bonds between NAG-NAM, and NAM-NAG residues, respectively [Vollmer et al., 2008]. As glucosaminidases and muramidases act on the same substrate, it is generally useful to gain insight into their biochemical properties and reveal features which enable them to perform the two distinct functions.

Staphylococci represent a large group of bacteria which inhabit humans and can cause severe infections to people with weak or compromised immune system. Among them is Staphylococcus aureus (S. aureus) which is responsible for most of hospital acquired infections [Vincent et al., 2009]. S. aureus is a Gram-positive bacterial pathogen that is responsible for severe medical conditions in humans, including bacteremia, endocarditis, metastatic infections, sepsis and toxic shock syndrome [Lowy, 1998], osteomyelitis [Varonne et al., 2011]. S. aureus possesses the capability to form biofilms during the progress of infection which is of advantage of the bacteria. Biofilms offer protection of the cells against antibiotics and the host immune response which leads to the development of a long and persisting chronic disease [Archer et al. 2011]. Since S. aureus was the first human pathogen treated with antibiotics, strains resistant to the antibiotics already emerged a while ago, e.g. resistance against β-lactame antibiotics as penicillin, methicillin (Methicillin Resistant S. Aureus—MRSA) or vancomycin (Vancomycin Resistant S. Aureus—VRSA) [Hiramatsu et al., 1997], [Zetola et al., 2005], [Dantes et al., 2013], [Gardete and Tomasz, 2014].

The genome of a S. aureus strain, which is resistant to vancomycin (Mu50), encodes five putative GH73 family (Glycoside Hydrolase Family 73) members. Four of them, SAV2307, SAV1052, SAV1775, and SAV2644, are widely distributed through the genomes of S. aureus strains. In addition, the genome of S. aureus Mu50 strain encodes SAV0909, which was inserted into the genome through the integration of Bacteriophage phi mu1.The best studied among them is (SAV1052) Major Bifunctional Autolysin (AtlA) [Oshida et al., 1995]. The AtlA deletion mutants form large cell clusters and are biofilm negative [Heilmann et al. 1997, Biswas et al. 2006, Sugai et al. 1995]. The AtlA gene encodes two activities: amidase and glucosaminidase encoded at the N-terminal and C-terminal regions of the sequence, respectively. The amidase activity of AtlA was confirmed and analyzed by structural studies of a homologous enzyme from Staphylococcus epidermis [Zoll et al., 2010] and later S. aureus [Buttner et al, 2014]. However, the glucosaminidases and their role in biofilm formation remained unexplored.

The crystal structures of two GH73 members from Lysteria monocytogenes [Bublits et al., 2009] and of the C-terminal domain of the flagellar protein FlgJ from Sphingomonas sp. [Hasihimoto et al., 2011] and recently endo-N-acetylglucosaminidase from Streptococcus pneumoniae (LytB SP) [Bai et al., 2014] were determined. While the first two proteins exhibit only remote sequence homology to S. aureus, the last one is in part closely related, yet distinct from GH73 family of glucosaminidases from S. aureus. This indicates that members of the GH73 family are sequentially divergent and constitute distinct subfamilies.

General Description of the Invention

It is a general object of the present invention to provide means and methods to find novel antibiotics with activities against a pathogenic, antibiotic resistant bacteria, in particular S. aureus. As a consequence of the experimental results disclosed herein, it was surprisingly discovered that, due to the specific recognition mechanism of NAG-NAM binding by glucosaminidases disclosed herein, potential inhibitors against glucosaminidases can be easier identified than inhibitors against muramidases.

Therefore, the present invention concerns a crystal of autolysin E (AtlE) of Staphylococcus aureus (S. aureus), or a crystallizable fragment of AtlE, and a method for producing said crystal with the help of a special crystallization buffer or a kit containing the special crystallization buffer.

The present invention also concerns a method for screening a binding compound or inhibitor of the N-acetylglucosaminidase activity of AtlE of S. aureus on the basis of said crystals, e.g. by obtaining atomic spatial relationship data followed by in silico screening.

DETAILED DESCRIPTION OF THE INVENTION

According to the present invention it was discovered that autolysin E (AtlE) encoded by the SAV2307 gene is a glucosaminidase with a surprisingly unique active site. Comparison of binding of NAG-NAM or muropeptide (MurP) (NAM-ALA-D-GLU) to AtlE, and polyNAG and NAM saccharides to lysozymes revealed the differences of N-acetylglucosaminidases and murein hydrolases. A comparison of the effects of AtlE and glu-AtlA on *S. aureus* living cells in a biofilm formation assays indicated that these enzymes are involved in distinct cellular pathways of *S. aureus* pathogenesis, despite their high sequence homology.

A comparison of the structures of AtlE and lyzozyme complexes explains the difference between the glucosaminidase and muramidase activities. Since the peptidoglycan substrate is the same, each kind of enzyme must approach the substrate from a different side in order to achieve the productive binding.

A specific, conserved region among the GH73 family members of *S. aureus* indicates that successful antibacterial drugs can be developed to target specific species.

Consequently, the present invention concerns a crystal of AtlE of *S. aureus*, or a crystallizable fragment of AtlE. In a preferred embodiment said AtlE, or a crystallizable fragment of said AtlE, contains a glutamic acid or an equivalent thereof as the catalytic residue of the enzyme or the fragment thereof. The equivalent of the glutamic acid can be either a functionally active amino acid, e.g. an acidic amino acid, like aspartic acid, or a functionally non-active amino acid, e.g. a hydrophobic amino acid, e.g. alanine, valine, isoleucine, leucine, or phenylalanine. The crystallizable fragment of AtlE can, for example, be a N-terminal truncation of AtlE which particularly still contains the active site of the molecule, where the catalytic residue resides. Consequently, a preferred example of a crystallizable fragment of AtlE lacks the N-terminal transmembrane region, e.g. as shown in FIG. 2 (SEQ ID NO: 2). Alternative fragments of AtlE comprise the amino acid sequence of the glucosaminidase domain of SEQ ID NO: 3, SEQ ID NO: 4, SEQ ID NO: 5, or SEQ ID NO: 6. These domains are highly conserved among the strains of *S. aureus*.

In addition, the above mentioned crystal can also be a co-crystal of AtlE or its crystallizable fragment, as explained above, and a substrate, ligand and/or a candidate compound. Such substrate, ligand or candidate compound can be a natural or synthetic compound, e.g. NAG-NAM, or any other compound mentioned herein, or a chemical substance from a chemical substance library, in particular from a chemical compound library as stored in a computer.

Said crystal or crystallizable fragment thereof is, in particular, characterized by its space group symmetry and/or its unit cell dimensions. In the present case the space group symmetry can be $P2_1P2_1P2_1$. The unit cell dimensions can be as follows: a=46.6 Å±1-2 Å, b=69.9 Å±1-2 Å and c=73.3 Å±1-2 Å, in particular a=46.6 Å±1 Å, b=69.9 Å±1 Å and c=73.3 Å±1 Å, with α=90°, β=90° and γ=90°. Specific examples of unit cell dimensions can also be taken from Table 1. The specific X-ray diffraction data can be taken from Table 2.

The present invention additionally concerns a method for producing said crystal or a crystallizable fragment thereof. In a preferred embodiment, the method comprises the steps of (a) preparing a solution of said AtlE or a crystallizable fragment thereof in a crystallization buffer, and (b) crystallizing said AtlE.

The solution, preferably a concentrated solution of AtlE or a crystallizable fragment thereof can be induced to crystallize by several methods including, without limitation, vapor diffusion, liquid diffusion, batch crystallization, dialysis or a combination thereof, preferably vapor diffusion. Generally, in a vapor diffusion method the concentrated solutions of a protein, here AtlE or a crystallizable fragment thereof, become supersaturated and form crystals of the protein at a constant temperature by diffusion of solvent(s), in which the protein is not generally soluble, into the protein solution. Devices for promoting crystallization can include, without limitation, the generally known hanging-drop, sitting-drop, sandwich-drop, dialysis or microtube batch devices. The hanging-drop, sitting-drop, sandwich-drop and some adaptations of the microbatch methods produce crystals by vapor diffusion. For example, the hanging-drop, sitting-drop or sandwich-drop containing the crystallizable composition is equilibrated in a reservoir containing a higher or lower concentration of the precipitant. As the drop approaches equilibrium with the reservoir, the saturation of the protein in the solution leads to the formation of crystals. In the present case the crystallization drop preferably contains equal amounts of the protein solution and of a crystallization buffer. The crystallization buffer in particular contains NaCl and $(NH_4)_2SO_4$, preferably 2 M NaCl and 2 M $(NH_4)_2SO_4$. As explained above, the crystallization process can be preferably initiated by a vapor diffusion method. In a particularly preferred embodiment, the crystallization drop contains equal amounts of a protein solution containing AtlE or a crystallizable fragment thereof, e.g. a concentrated protein solution in HEPES buffer, as for example 15 mg/ml protein in 20 mM HEPES and 100 mM NaCl (pH 7.5), and a crystallization buffer, e.g. the buffers as mentioned above. After the crystallization of the protein, the crystals can be cryoprotected by soaking in the crystallization buffer containing a cryoprotectant, e.g. glycerol, in particular 30% glycerol. Generally, the crystallization process is preferably carried out at a constant temperature, e.g. in a range of 10° C.±1° C. to 37° C.±1° C., specifically from 18° C.±1° C. to 25° C.±1° C., more specifically at room temperature, e.g. at 22° C.±1° C.

Consequently, the invention is also directed to crystals obtained by the method of the present invention, and to a kit containing a solution of autolysin AtlE, or a crystallizable fragment thereof as explained above, e.g. in said HEPES buffer or an equivalent buffer, and a crystallization buffer, preferably containing NaCl and $(NH_4)_2SO_4$, in particular 2 M NaCl and 2 M $(NH_4)_2SO_4$.

As already explained, said crystal or the characteristic data of said crystal can be used to identify novel, naturally occurring or synthetic, binding compounds, e.g. a novel ligand or a novel inhibitor, of the N-acetylglucosaminidase activity of AtlE and/or the other four enzymes of the GH73 family of *S. aureus* either by means of a classical screening assay or by means of a computer (in silico screening).

Therefore, the present invention additionally concerns a method for screening a binding compound or inhibitor of the N-acetylglucosaminidase activity of AtlE. Preferably said method comprises the steps of:

(a) providing a solution of said AtlE or a crystallizable fragment thereof, (b) contacting at least one candidate compound with the AtlE in said solution, (c) preparing crystals of said AtlE, and (d) identifying a binding compound of said AtlE.

The solution can be the same solution as explained above. Prior to or after contacting at least one candidate compound with the AtlE or a crystallizable fragment thereof, a crystallization buffer can be added. Preferably the candidate compound, e.g. a naturally occurring or synthetic compound as explained above, is soluble in said HEPES puffer with or without a crystallization buffer, preferably the crystallization buffer as mentioned above. In a particularly preferred embodiment, a solution of AtlE or a crystallizable fragment thereof in said HEPES buffer, or an equivalent buffer, is provided which may already contain the candidate compound. Alternatively, the candidate compound is added to the solution of said AtlE or a crystallizable fragment thereof. The preparation of the crystals can be enhanced by a vapor diffusion method. After having obtained the crystals, the crystals are analyzed with respect to the binding of any candidate compound. For example, in step (d) the binding of the candidate compound to the active site is determined. The active site is preferably characterized by the regions of SEQ ID NO: 1 from methionine 47 (M) to glutamic acid 65 (E), from leucine 136 (L) to glycine 140 (G), from asparagine 159 (N) to glutamic acid 181 (E), from phenylalanine 196 (F) to asparagine 204 (N) and/or from proline 219 (P) to lysine 233 (K), and in particular characterized by the catalytic glutamic acid (E) at position 138, and optionally further by an aspartic acid (D) at position 167, an phenyl alanine (F) at position 224, an aspartic acid (D) at position 227 and/or a tyrosine (Y) at position 201

An inhibitor of AtlE can, for example, be identified by analyzing the binding of a candidate compound to the said active site. Candidate compounds which bind to said active site can, therefore, be identified as novel, naturally occurring or synthetic, ligands or inhibitors of AtlE and the GH73 family members from *S. aureus*. Examples of such candidate compounds or binding compounds can be antibodies or small molecules with molecules below 600 Da. binding fragments thereof, or fragments of bacterial cell wall components and their derivatives or biopolymers like, but not limited to single chain antibodies or Fv-fragments or ankyrines or DNA fragments.

Consequently, the present invention also provides data to computational methods for using the crystal structure of the AtlE protein and/or of an AtlE-binding compound complex as explained above, e.g. the atomic spatial relationship data, to screen for, identify, design, or optimize a compound binding to AtlE and the GH73 family members from *S. aureus*. Various computational methods for structure determination and modeling of the protein structure or a protein-complex structure can be used, in particular to evaluate the binding of a binding compound to the active site, as explained above. Such analyses can be carried out in well known crystallographic software applications, such as HKL-3000 software [Minor et al., 2006], the MAIN software [Turk, 2013], the REFMAC software [Murshudov, 1997] and/or the molecular modeling from sequence through lead optimization (e.g. SYBYL® from Certara, L. P., Princeton, N.J., USA). The computational method usually contains the following four steps:

(a) loading the structure coordinates of the structures to be compared, here e.g. the structure coordinates of AtlE, or a crystallizable fragment thereof, as disclosed herein, and the structure coordinates of a candidate compound e.g. obtained from a data bank;
(b) defining the atom equivalences in these structures;
(c) performing a fitting operation on the structures, e.g. including the crystal structure determination, in particular including steps such as molecular replacement, model building and rebuilding, and/or refinement;
(d) and analyzing the results, e.g. on the basis of the structure coordinates of a complex of AtlE, or a crystallizable fragment thereof, and a candidate compound, as e.g. obtained by the method disclosed herein;

or alternatively:

(a) loading the structure coordinates of the structures to be compared, here e.g. the structure coordinates of AtlE, or a crystallizable fragment thereof, as disclosed herein, and the structure coordinates of a candidate compound e.g. obtained from a data bank;

(b) specifying selected residues of interest, e.g. the residue(s) of the active site, as disclosed herein;
(c) defining the atom equivalences in the selected residues of interest;
(c) performing a fitting operation on the selected residues of interest;
(d) and analyzing the results, e.g. on the basis of the structure coordinates of a complex of AtlE, or a crystallizable fragment thereof, and a candidate compound, as e.g. obtained by the method disclosed herein.

Therefore, the crystal(s) as described herein can also be used for in silico screening of the ability of a candidate compound to bind to said AtlE and/or the other four enzymes of the GH73 family of *S. aureus*, in particular to bind to the active site of said related autolysins, as explained herein.

Structure coordinates for candidate compounds, other substrates and/or complexes with AtlE or a crystallizable fragment thereof can either be obtained from a data bank, e.g. the RCSB Protein Data Bank (RCSB PDB), Marseille Protein Crystallization Database (MPCD), and any other data bank containing crystal data, e.g. the CRC Handbook of Chemistry and Physics, or from X-ray crystallography as e.g. described herein.

The present invention also encompasses a machine-readable data storage medium comprising a data storage material encoded with machine-readable data, wherein said data comprises the atomic spatial relationship data as detailed above, i.e. at least the space group symmetry and the unit cell dimensions of AtlE or a crystallizable fragment thereof. A machine-readable data storage medium can also comprise structure coordinates of a candidate compound. The computational processing can be performed on a computer as explained above. The computer of the present invention, therefore, comprise a working memory for storing instructions for processing the machine-readable data, a central-processing unit coupled to the working memory and to the machine-readable data storage medium for processing the machine-readable data into the three-dimensional structure. Usually, the computer further comprises a display for displaying the three-dimensional structure as a graphical representation e.g. produced by a software program to display the graphical representation. Such software programs are commercially or freely available.

Consequently, a computer of the present invention comprises executable code for:

(a) using structure coordinates as disclosed herein;
(b) analyzing a binding site of the 3-dimensional model, in particular the active site as explained herein; and
(c) screening in silico a library of candidate compounds; and optionally
(d) controlling a unit for assaying a potential binding compound identified in step (c) in a protein binding assay or an enzymatic competition assay using e.g. a synthetic substrate as disclosed herein.

With the respect to the enzymatic competition assay, the substrate competes with the potential binding compound at the active site of AtlE or a fragment thereof containing the active site, e.g. an AtlE lacking the N-terminal transmembrane region as disclosed herein. In case the substrate is not bound or not cleaved or degraded by AtlE or said fragment, the potential binding compound is identified as an active binding compound, e.g. as a ligand or inhibitor of the N-acetylglucosaminidase activity of AtlE.

Therefore, the hardware components of a computer comprises a machine-readable data storage medium comprising a data storage material encoded with machine-readable data of the present invention, a working memory for storing instructions for processing the machine-readable data of the present invention, a central processing unit (CPU) coupled to the working memory and to the machine-readable data storage medium for processing the machine readable data of the present invention as well as instruction(s) for generating 3-dimensional structure information in particular of the active site as described according to the present invention, and output hardware coupled to the CPU for outputting 3-dimensional structure information and optionally for assaying a potential binding compound identified in a protein binding assay or an enzymatic competition assay as described above. The output hardware usually includes monitor(s), touchscreen(s), printer(s), modem(s), CD-ROM(s) and/or robot(s), i.e. a high-throughput robotic system.

Finally, the structure information or atomic spatial relationship data as disclosed herein can be used e.g. in conjunction with a computer or at least a machine-readable data storage medium for e.g. identifying, designing or even optimizing a binding compound, as described herein, by e.g. performing a fitting operation between a binding compound and the 3-dimensional structure information of AtlE or a fragment thereof containing the active site as described herein. Therefore, the present invention also concerns a method for evaluating the potential of a candidate compound to associate with AtlE and the GH73 family members from *S. aureus* or said fragment, as described herein, e.g. comprising the steps of (a) performing a fitting operation between the candidate compound and AtlE or a fragment thereof;
(b) analyzing the results of said fitting operation to quantify the association between the candidate compound and AtlE or a fragment thereof; and
(c) illustrating said quantified association preferably in the form of a 3-dimensional structure or graphical representation thereof, e.g. on a output hardware such as a monitor or printer.

BRIEF DESCRIPTION OF THE DRAWINGS

FIG. 5 concerns the structure based sequence alignment of AtlE (SEQ ID NO: 2), LytB SP (SEQ ID NO: 7), ACOD (SEQ ID NO: 10), LMO (SEQ ID NO: 8), FLGJ (SEQ ID NO: 9), HLYZ (SEQ ID NO: 11) of the proteins from FIG. 4. Alignment was performed with Strap [Gille and Frommel, 2001]. The regions at N-termini, which do not exhibit any similarity among the structures, were excluded from this alignment. Hyphens correspond to deletions, whereas dots, small and capital characters correspond to the identical residues, similar and different residues to the sequence on the top, respectively. The catalytic E and the residues, which are important in substrate binding, are marked with an asterisk. 3D images of folds were prepared with Chimera and MAIN [Turk, 2013] and rendered with Raster3D [Merrit, 1997].

FIG. 9 concerns a comparison of parts of the amino acid sequences corresponding to glucosaminidase domains of *S. aureus* GH73 family members. Multiple sequence alignments of sequences with AtlE are shown on the top: SAV2307 AtlE (SEQ ID NO: 2), SAV0909 (SEQ ID NO: 3), SAV1775 (SEQ ID NO: 4), SAV2644 (SEQ ID NO: 5), SAV1052 AltA (SEQ ID NO: 6). Hyphens correspond to deletions, whereas dots, small and capital characters correspond to the identical residues, similar and different residues to the sequence on the top, respectively. The regions defining the active site are marked with numbers 0, 1, 2, 3, 4. The alignment was made with Clustalw.

FIGS. 11 and 12 show the structural differences between glucosaminidases and muramidases (lysozymes) in binding of glycan cell wall components. Images of 3D models were prepared with MAIN [Turk, 2013] and rendered with Raster3D [Merrit, 1997].

FIGS. 11a) and 12a) represent a schematic presentation of approach of glucosaminidases and muramidases to the poly NAG-NAM saccharide, where the lactyl moieties are oriented towards L- and R-lobe, which correspond to glucosaminidase and muramidase binding, respectively.

FIGS. 11b) and 12b) show models of hexasaccharide (NAG-NAM).sub.3 bound into the AtlE and ACOD active sites. They are shown in ball and stick presentation against the surface of the targeted enzyme. Nitrogen and oxygen atoms are in bold face as in the hexasaccharide model shown in FIG. 13.

FIG. 15 is a mass spectrometer analysis of the digestion products of AtlE, and FIG. 16 of the digestion products of gluAtlA. The expected molecular peaks are annotated. The same amount substrate/digestion products were analyzed in both cases.

ABBREVIATIONS

Figure 1:
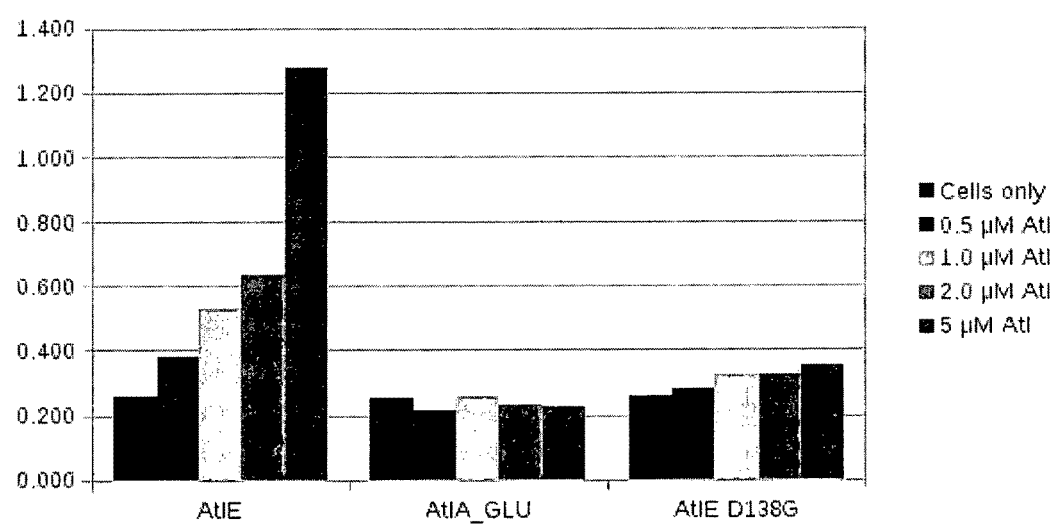
FIG. 1 concerns the effect of AtlE, glu-AtlA, and the catalytic mutant of AtlE on biofilm formation of *S. aureus*-cells. The figure shows the extent of biofilms formed. The results are shown on the same scale. Each group of results was performed in the same manner by addition various concentrations of the proteins added in the solution as indicated at the left.

AtlE: autolysin E; DCM: dichloromethane; ESI-MS: electrospray ionization mass spectrometry; EtOAc: ethyl acetate; EtOH: ethanol; GH73 domain: C-terminal domain of LytB SP (Streptococcus pneumoniae); HOAc: acetic acid; iPrOH: isopropanol; MeOH: methanol; MurP: muropeptide (NAM-ALA-D-GLU); NAG: N-acetylglucosamine; NAM: N-acetylmuramic acid; Phth: phthaloyl; SeMet: seleno-methionine; rt: room temperature; VdW: Van der Waals;

EXAMPLES

A) Materials and Methods
1. Expression of Recombinant Proteins
   AtlE is 259 amino acid long protein encoded by the SAV2307 gene loci in the genome of S. aureus strain Mu50. The truncated sequences of glucosaminidase domains of AtlE, lacking the first 34 residues and glu AtlA from S1012 onwards, include additional four amino acids (SAAA, i.e. Ser-Ala-Ala-Ala) that belong to the recognition site of TEV protease. The nucleotide sequences were amplified from the genomic DNA of S. aureus Mu50 using KOD Hot Start Polymerase and cloned into pMCSG 7 plasmid in the frame with N-terminal His-Tag as described [Eschenfeldt et al., 2009]. The mutants were prepared by the overlap extension method [Ho et al., 1989]. The proteins were expressed in BL21(DE3) E. coli expression strain grown in YZM5052 auto induction medium. To facilitate the expression of proteins in soluble form, the cells were initially grown at 37° C. When optical density (OD) measured at 600 nm reached the value of 1, the cells were transferred to 25° C. After 16 hours the cells were pelleted by centrifugation (15 minutes at 7000× g), re-suspended in the buffer A (0.03 mM Tris, 0.4 M NaCl, pH 7.5) supplemented with 1 mg/ml of lysozyme, and frozen and disrupted by the freezing thawing cycles and sonication. The proteins were purified from the cell lysate on AKTAxpress FPLC system (GE Healthcare) using two-step purification protocol. The first purification step was Ni$^{2+}$-affinity chromatography on HiTrap IMAC FF column (GE Healthcare) equilibrated in buffer A with 10 mM imidazole. The bound proteins were eluted with the buffer A containing 300 mM imidazole and applied to the HiPrep 26/60 Sephacryl S-200 size exclusion column (GE Healthcare) equilibrated in the buffer A. The fractions containing the pure protein were collected, concentrated, desalted against 20 mM HEPES, 100 mM NaCl, pH 7.5, and stored at −20° C.

2. Biochemical Analysis of AtlE and AtlA Activities
   AtlE and glu AtlA were tested against S. aureus cell wall and against two synthetic substrates (NAM-NAG)$_{2red}$ tetrasaccharide (Figure S1) and (NAG)$_{6red}$. The degradation products were analyzed by mass spectroscopy. A single cleavage between the central NAG-NAM residues should indicate the classic N-acetyl-glucosaminidase activity by generating the NAM-NAG and NAM-NAG$_{red}$ disaccharides, whereas NAM$_{red}$ and NAG-NAM-NAG$_{red}$ would indicate the muraminidase activity. In accordance with expectations only NAM-NAG$_{red}$ with Mw of 499.21 Da was found. Besides, the glucosaminidase activity of the putative glucosaminidase domain from AtlA (glu AtlA) was tested and exhibited the same specificity profile (FIG. 1c). Surprisingly, the (NAG)6 was not degraded at all.

3. Isolation of S. aureus Peptidoglycan
   S. aureus cells were grown overnight in Brain Hearth Infusion Broth (BHI) (37° C., 250 rpm) pelleted by centrifugation (15 minutes at 6000× g), washed three times with the 30 mM Tris, 0.4 M NaCl buffer and then re-suspended in the same buffer. After heat inactivation, the insoluble pellet was re-suspended in 4% SDS and incubated 30 minutes at 80° C. After 30 minutes of centrifugation at 40,000× g, the pellet was re-suspended and washed six times in water. Proteins that remained associated with the peptidoglycan were digested overnight by incubation with trypsin (1 mg/ml) in 30 mM Tris, 0.4 M NaCl, 10 mM MgCl2, pH 7.5 buffer. After pelleting (30 minutes at 40000× g) peptidoglycan was treated overnight with 5 ml 40% aqueous hydrogen fluoride to remove teichoic acid, pelleted again (30 minutes at 40000× g) and washed extensively with water. Saturated suspension of the pure peptidoglycan solution in water was stored at −20° C.

4. Biochemical Peptidoglycan Degradation and Labeling with Remazol Brilliant Blue
   For the colorimetric assays, peptidoglycan was labeled with Remazol Brilliant Blue as described [Odintsov et al., 2004]. In short, 50 ul of water suspension of Remazol Brilliant Blue labeled peptidoglycan was mixed with 10 ul of 1 M buffer solutions at pH of 4.5, 5. and 5.5, 25 ml of 4 M NaCl, different amounts of enzymes and filled with water to the final volume 100 ml. The final concentration of buffer and NaCl in the reaction mixture was therefore 100 mM. During the reaction the sample was shaken at 30° C. and in time intervals 10 ml aliquots were taken from reaction mixture, centrifuged for 3 minutes at 15000× g and the absorbance at 595 nm was measured on NanoVue spectrophotometer (GE Healthcare).

Depending on the desired pH the following stock buffer solutions were used: 1 M NaOAc pH 4.5, 5 and 5.5, 1 M potassium phosphate pH 6 and 6.5 and 1 M Tris, pH 7.0, 7.5, 8 and 8.5.

5. Biofilm Formation Assay

The effect of recombinant autolysins on the *S. aureus* biofilm formation was performed as described [Merritt et al. 2011]. In brief, saturated culture of *S. aureus* grown overnight in BHI medium was diluted 1:100 in buffered BHI medium (supplemented with 0.1 M phosphate buffer pH 6.0 containing 0, 0.5, 1, 2 and 5 µM concentration of individual enzyme. 100 µl of each diluted culture was pipetted in 96-well plate (TPP). The plates were covered and incubated in a humidified incubator at 30° C. After 48 hours, the media was removed and the plates were three times washed with water. After the last washing step all remaining liquid was removed and 125 µl of 0.1% crystal violet was added to each well to dye the attached cells. After 10 minutes of incubation at the room temperature, the solution of crystal violet was removed and plates were washed several times with water until all unbound dye was removed. After the plates were completely dried at room temperature, the dyed biofilms were dissolved in 200 µl of 30% acetic acid. After 20 minutes of incubation at room temperature, the plates were briefly mixed and 100 µl of the crystal violet/acetic acid solution was transferred to a fresh 96 well micro-titer plate and the optical density of the samples was measured ad 595 nm. All experiments were performed in triplicates with AtlE, AtlA A138E mutant, and glu-AtlA domain assayed at pH 6.

6. Seleno-Methionine Derivative Expression

The structure of AtlE was phased with the help of seleno-methionine residues because at the time of structure determination no close homologues of AtlE were found in the protein data bank of RCSB (PDB database). SeMet minimal medium (SeMetMM) [Guerrero et al (2001)] was prepared by dissolving $NH_4Cl$ (1 g), $KH_2PO_4$ (3 g) and $Na_2HPO_4.7H_2O$ (6 g) in 1 l of deionised water and autoclaved. To this, 100 ml of a filter-sterilized solution containing 20% (w/v) glucose, 0.3% (w/v) ($MgSO_4$), 10 mg $Fe_2(SO_4)_3$ and 10 mg thiamine were added and the pH adjusted to 7.4. Finally, L-SeMet was added to the medium to a final concentration of 50 µg/ml.

A subculture of the *E. coli* BL21(DE3) pMCSG7-AtlE transformants was grown overnight in 20 ml of LB medium supplemented with ampicillin (100 µg/ml) at 37° C. with shaking at 250 rpm. The next day, this cell suspension was used as the inoculum for 1 l of the same medium and OD600 was measured until it reached the value of 1. Cell culture was then centrifuged for 15 min at 4000 rpm and the pellet was re-suspended in 1 l of SeMet minimal medium followed by adding IPTG to a final concentration of 1 mM and incubation at 18° C. and 250 rpm for additional 20 hours.

7. NAG-NAM Disaccharide Synthesis

The NAG-NAM disaccharide 2-acetamido-4-O-(2-acetamido-2-deoxy-β-d-glucopyranosyl)-3-O-[(R)-1-carboxyethyl]-2-deoxy-α-d-glucopyranose (NAG-NAM) was prepared, with some revisions, according the protocol introduced by Kantoci and Keglević (1987) and papers cited therein (Figure S2). Selective opening of the 4,6-benzylidene ring of benzyl 2-acetamido-4,6-O-benzylidene-3-O-[(R)-1-(methoxy-carbonyl)ethyl]-2-deoxy-α-d-glucopyranoside (1) to give benzyl 2-acetamido-6-O-benzyl-3-O-[(R)-1-(methoxycarbonyl)ethyl]-2-deoxy-α-d-glucopyranoside (2) was performed with iodine and triethylsilane instead of sodium cyanoborohydride as was previously described (Keglević et al. 1985). Glycosidic bond formation between activated glucosamine 3,4,6-tri-O-acetyl-2-deoxy-2-phthalimido-β-d-glucopyranosyl chloride (3) and selectively protected muramic acid 2 in presence of silver triflate in extremely dry conditions gave 2-acetamido-4-O-(3,4,6-tri-O-acetyl-2-deoxy-2-phthalimido-β-d-glucopyranosyl)-6-O-benzyl-2-deoxy-3-O-[(R)-1-methoxycarbonyl)-ethyl]-α-d-glucopyranoside (4). Removal of the phthalimido group from compound 4 with hydrazine followed by acetylation gave benzyl 2-acetamido-4-O-(2-acetamido-3,4,6-tri-O-acetyl-2-deoxy-β-d-glucopyranosyl)-6-O-benzyl-2-deoxy-3-O-[(R)-1-(methoxycarbonyl)ethyl]-α-d-glucopyranoside (5). Saponification of acetyl and methyl groups, and removal of benzyl groups with catalytic hydrogenation gave NAG-NAM (Kantoci and Keglević, 1987; Keglević et al., 1985).

Synthesis of Benzyl 2-acetamido-6-O-benzyl-3-O-[(R)-1-(methoxycarbonyl)ethyl]-2-deoxy-α-d-glucopyranoside (2)

Compound 1 (630 mg; 1.3 mmol) was dissolved in dry DCM (10 mL), iodine (370 mg) and $Et_3SiH$ (3.7 mL) were added. Reaction was stirred in ice-bath and after 30 min and 1 h additional portions of iodine (37 mg) and $Et_3SiH$ (370 µL) were added. Reaction was finished after 2 h, diluted with DCM (40 mL) and washed with (a) $NaHCO_3$ (20 mL) and (b) water (20 mL). Organic layers were dried with $Na_2SO_4$ evaporated and chromatographed on silica gel column in solvent systems DCM:acetone 3:2 and DCM:MeOH 9:1. Crystallization from acetone:diisopropyl ether gave compound 2 (330 mg; 52%). ESI-MS: C26H33NO8 488.4 $[M+H]^+$ calc. 488.5; Rf=0.65 (DCM:MeOH 9:1).

Synthesis of Benzyl 2-acetamido-4-O-(3,4,6-tri-O-acetyl-2-deoxy-2-phthalimido-β-d-glucopyranosyl)-6-O-benzyl-2-deoxy 3-O-[(R)-1-(methoxycarbonyl) ethyl]-α-d-gluco-pyranoside (4)

The glucosyl chloride 3 (280 mg; 0.62 mmol) and protected muramic acid 2 (100 mg; 0.21 mmol) with silver triflate (AgTf; 210 mg; 0.82 mmol) as catalyst were subjected to the Anderson's apparatus for glycosidic coupling (Nashed and Anderson, 1982), molecular sieves and dry DCM (2 mL) were added and reaction was stirred under nitrogen at room temperature overnight. Thereafter, chloroform was added to the formed suspension and centrifuged. The residue was washed two times with chloroform. Collected chloroform's supernatants were washed with saturated aqueous solution of $NaHCO_3$, water, and dried over $Na_2SO_4$. Solvent was evaporated and product purified by flash silica gel column chromatography in solvent systems diethyl ether:petroleum ether:iPrOH 8:4:1 and DCM:MeOH 9:1. After the second column compound 4 (62 mg; 33%) was obtained.

ESI-MS: C46H53N2O17 905.4 [M+H]$^+$ calc. 905.3; C46H52N2NaO17 927.4 [M+Na]$^+$ calc. 927.3; Rf=0.54 (diethyl ether:petroleum ether:isopropanol 8:4:1).

Benzyl 2-acetamido-4-O-(2-acetamido-3,4,6-tri-O-acetyl-2-deoxy-β-d-glucopirano-syl)-6-O-benzyl-2-deoxy-3-O-[(R)-1-(methoxycarbonyl)ethyl]-α-d-glucopyranoside(5)

Disaccharide 4 (45 mg; 0.0498 mmol) was dissolved in dry MeOH (1.376 mL) with addition of 0.1 M NaOMe/MeOH (145 µL). Reaction was stirred at room temperature for 1 h after which additional portion of 0.1 M NaOMe/MeOH (145 µL) was added and stirring was continued for 15 min. The reaction solution was neutralized with Amberlite IR-120 (H$^+$), filtrated and evaporated. The residue was dissolved in 96% EtOH (2.25 mL) and hydrazine hydrate (16.88 µL). The reaction was stirred for 2 h under reflux (80° C.). Reaction mixture was evaporated with toluene addition. Residue was dissolved in pyridine:acetic anhydride 1:1 (1.2 mL) and stirred overnight. After that solvent was evaporated with toluene addition and the residue was purified by flash silica gel column chromatography in EtOAc:iPrOH:petroleum ether 2:3:1 to give compound 5 (27 mg; 67%).

ESI-MS: C40H52N2NaO16 839.3 [M+Na]$^+$ calc. 839.3; Rf=0.50 (EtOAc: iPrOH: petroleum ether 2:3:1).

2-Acetamido-4-O-(2-acetamido-2-deoxy-β-d-glucopyranosyl)-3-O-[(R)-1-carboxy-ethyl]-2-deoxy-α-d-glucopyranose (NAG-NAM)

Compound 5 (35 mg; 0.043 mmol) was dissolved in dioxane (1.75 mL) and 0.5 M KOH (0.875 mL) was added to adjust pH 12. Reaction was stirred at room temperature 48 h, and then neutralized with addition of Amberlite IR-120 (H$^+$), filtered and evaporated. Residue was dissolved in EtOH:HOAc:water 6:1.5:1.5 (5.25 mL) and Pd/C (10%; 46 mg) was added. The reaction was hydrogenated at room temperature overnight. After that the reaction was filtered over small column of Celite to remove catalyst, and filtrate was evaporated. The residue was crystallized from MeOH:ether 1:10 to give NAG-NAM (15 mg; 70%).

ESI-MS: C19H32N2NaO13 519.2 [M+Na]$^+$ calc. 519.2; Rf=0.55 (n-butanol:HOAc:EtOAc:water 1:1:1:1).

8. Protein Crystallization and Structure Determination

The crystals of AtlE E (concentrated to 15 mg/ml in 20 mM HEPES, 100 mM NaCl, pH 7.5) were grown in 2 M NaCl, 2 M (NH4)$_2$SO$_4$ using vapor diffusion method. The crystallization drop consisted of 1 µl of the protein solution and 1 µl of crystallization buffer. The crystals were cryoprotected by soaking in the crystallization buffer containing 30% Glycerol. The native and seleno-methionine (SeMet) derivative crystal diffraction data were collected at Elettra synchrotron at XRD beamline.

The native structure was solved with the help of SeMet derivative with data collected at the remote wavelength exploiting the anomalous signal from seven SeMet residues using HKL-3000 software [Minor et al., 2006]. The native structure was rebuild, refined, and solvent inserted using MAIN [Turk, 2013] and REFMAC [Murshudov, 1997] and deposited to PDB (4PIA).

NAG-NAM disaccharide was synthesized as described above, whereas NAM-ALA-D-GLU (MurP) was purchased. NAG-NAM and MurP complexes were obtained with soaking of native crystals with 10 mM solution of the ligands. Data from crystals of MurP in complex with the native protein and NAG-NAM in complex with E138A mutant were collected at Bessy synchrotrone (Beam line 14.1), whereas the diffraction data for the NAG-NAM in complex with the native enzyme were collected at home X-ray source (Bruker proteum). The diffraction data were integrated with HKL-2000 [Otwinowski and Minor, 1997]. Structures were build with MAIN using topology library and geometric restraints provided by PURY [Andrejasic et al., 2008] and finally refined with REFMAC for deposition. The geometry of binding of disaccharide was in the two crystal structures equivalent, therefore only the complex with the native sequence is shown in the figures, however, all four crystal structures were deposited in PDB. Data and refinement statistics are provided in Table 1.

9. Identification of Catalytic Residues

The structural similarity of the GH 73 enzymes presented (FIG. 3b) exposed the E138 (glutamic acid at position 138 of SEQ ID NO: 1) as the catalytic residue in the AtlE structure. Its mutation to alanine indeed abolished its activity in the assay with S. aureus purified peptidoglycan.

Figure 3:
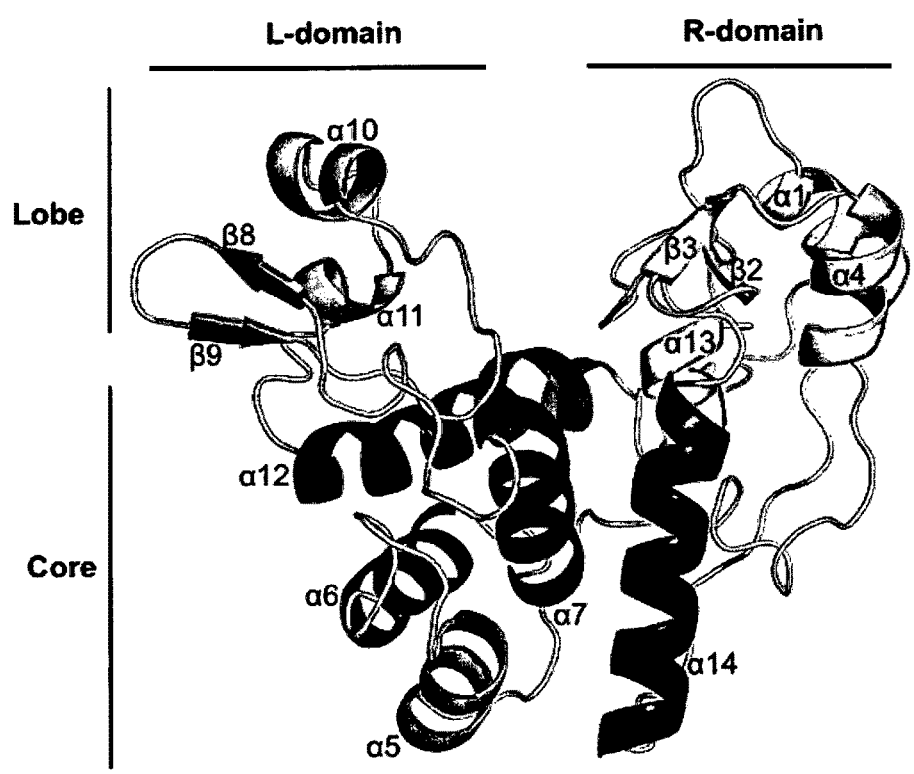
FIG. 3 concerns the fold of AtlE with the secondary structure elements. Also the conserved four helices in the core region are shown and the secondary structure elements belonging to the L- and R-lobes.

Inspection of superimposed structures from FIG. 3 suggested additional candidates for the second carboxylic group involved in the hydrolysis of glycosidic bonds: E145, D167, and D227 due to their position in respect to the similarly positioned acidic residues in Lmo, ACOD, and LytB SP structures. On the R-side E145 is positioned closely to the E129 of the superimposed Lmo structure, D167 is positioned similarly as the D90 and D101 of ACOD, and D227 is equivalent to D262 of LytB SP. The first two residues lie above the catalytic E138 on top of two different features of the L-lobe. The closest distances between the oxygen atoms of carboxylic groups of the catalytic E138 and the two candidates for the secondary catalytic residue D167 and E145 are 11 and 14 Å, respectively. The carboxylic group oxygen of the R-lobe candidate D227 is positioned is 8.4 Å away from the closest oxygen E138. The large distance unlikely makes them the second catalytic residue. Nevertheless, mutants were produced and tested for their activity against the cell wall substrate as described above. The activity of the AtlE D167A and D227A mutants were halved in comparison with the native enzyme, whereas the E145A mutant exhibited activity equivalent to the native enzyme. Hence, D167 and D227 are important residues for hydrolysis of the cell wall, however, the activity of the enzyme was not reduced to the level which would allow us to conclude that either of them is the second catalytic residue. More likely, they are contributing to substrate binding, as for example the Y201, which mutation to alanine abolished the enzymatic activity. From this analysis we concluded that the lack of the second catalytic residue in AtlE suggests a reaction mechanism which is different from the reaction mechanism of lysozyme. Instead of the second carboxylic group, AtlE likely uses of an external nucleophile, likely a water molecule.

10. Molecular Modeling of NAG-NAM Substrates

The hexa N-acetylglucosamine (NAG) was built first. The $(NAG)_6$ model was build by filling the gap between the $(NAG)_2$ and $(NAG)_3$ parts of the ACOD structure [Hellman et al, 2009] (3GXR) with the missing NAG residue. The resulting hexasaccharide was energetically minimized by constraining the matching NAG residues to the experimental structure using software MAIN [Turk, 2013]. In order to build a model corresponding to muramidase activity of lysozymes, residues -3, -1, and 2 were mutated to N-acetylmuramic acid (NAM). Thereby the lactyl group was added to the NAG residue. The resulting hexasaccharide was energetically minimized again.

In order to build the substrate model corresponding to the N-acetylglucosaminidase activity, the structures of AtlE and ACOD were superimposed by software Fat-Cat [Ye et al., 2003]. By use of the superimposition parameters, the $(NAG)_6$ model was transferred from the ACOD environment to the AtlE structure. Then, the −2, +1, and +3 residues were mutated to NAM, the model was shifted slightly to the right to match the NAG-NAM position in the complex with AtlE, and then energetically minimized by constraining the positions of atoms in −3, −2 residues to the position observed in the crystal structure.

B) Results

1. Characterization of AtlE Activity

Figure 14:
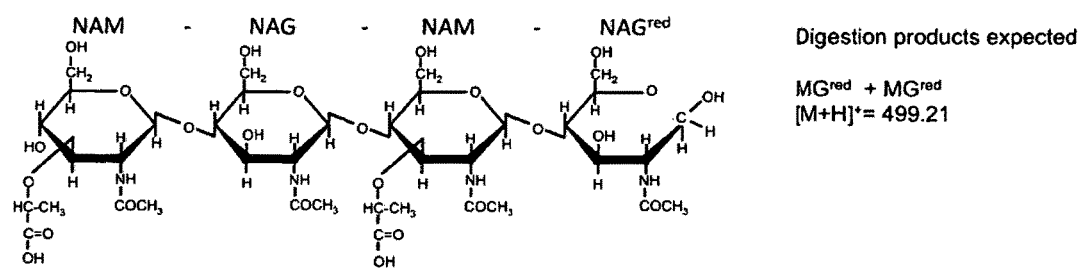
FIG. 14 is a schematic representation of the tetrasaccharide substrate with the expected digestion products.
Figure 15:
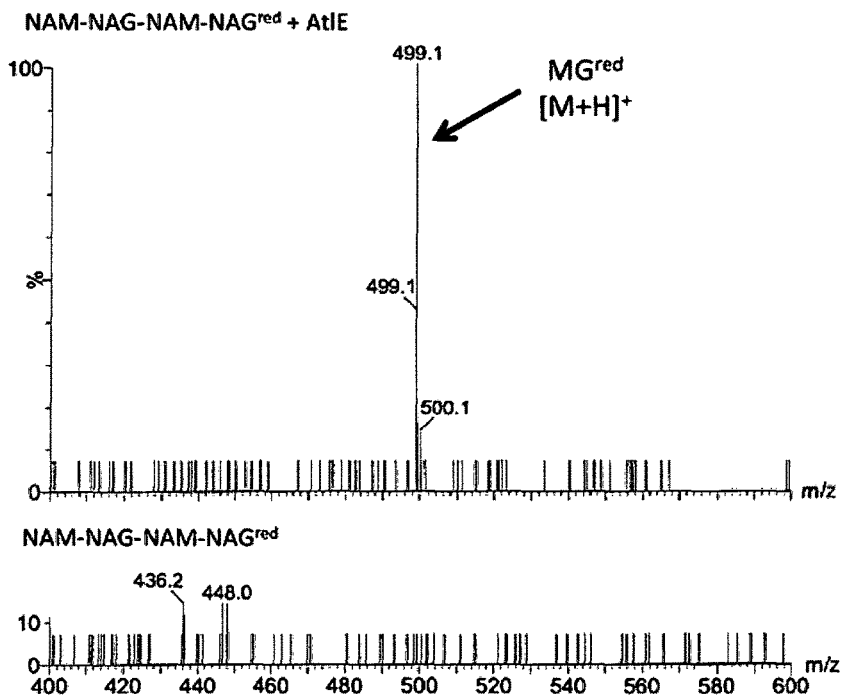
FIGS. 15 and 16 show the analysis of AtlE and gluAtlA digestion products of (NAM-NAG) 2red substrate.
Figure 16:
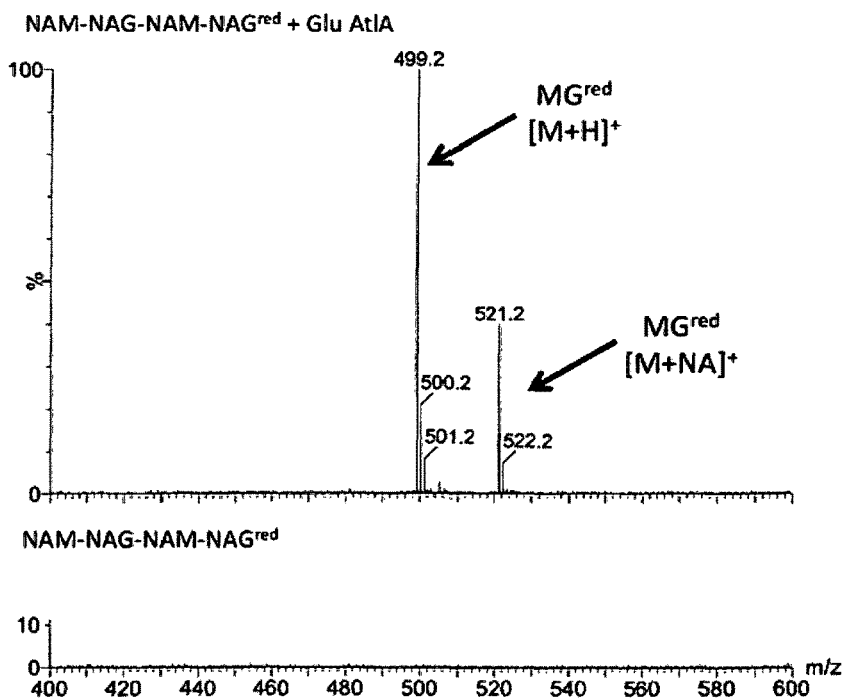
Figure 17:
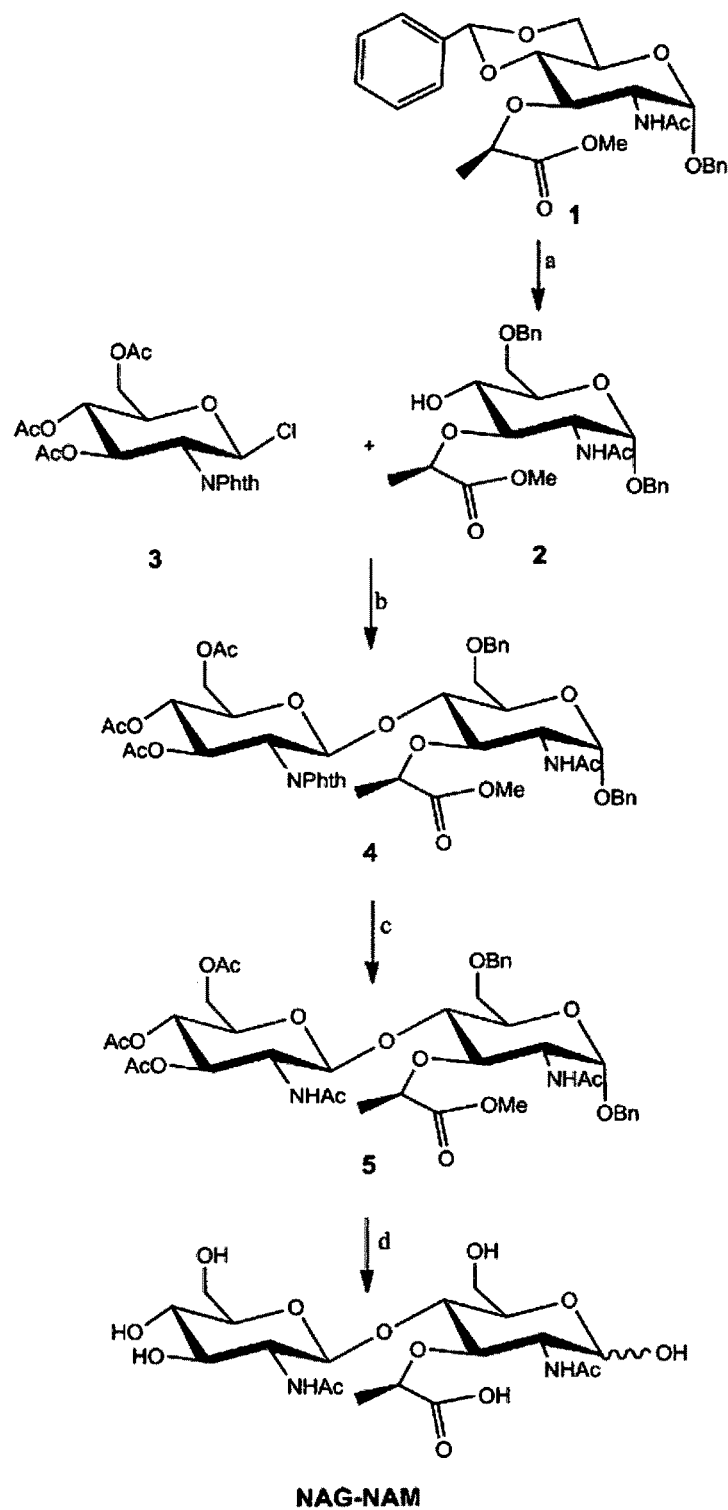
FIG. 17 shows the synthesis of the disaccharide NAG-NAM with the following reagents and conditions: a) Et$_3$SiH, I$_2$, 0° C., 2 h; b) AgTf, rt, 18 h; c) NaOMe, MeOH, rt, 1 h; hydrazine hydrate, EtOH, 80° C., 2 h; pyridine, acetic anhydride, rt, 18 h; d) 0.5 M KOH, dioxane, rt, 48 h; H$_2$, Pd/C, EtOH:HOAc:water; rt, 18 h.
Figure 18:
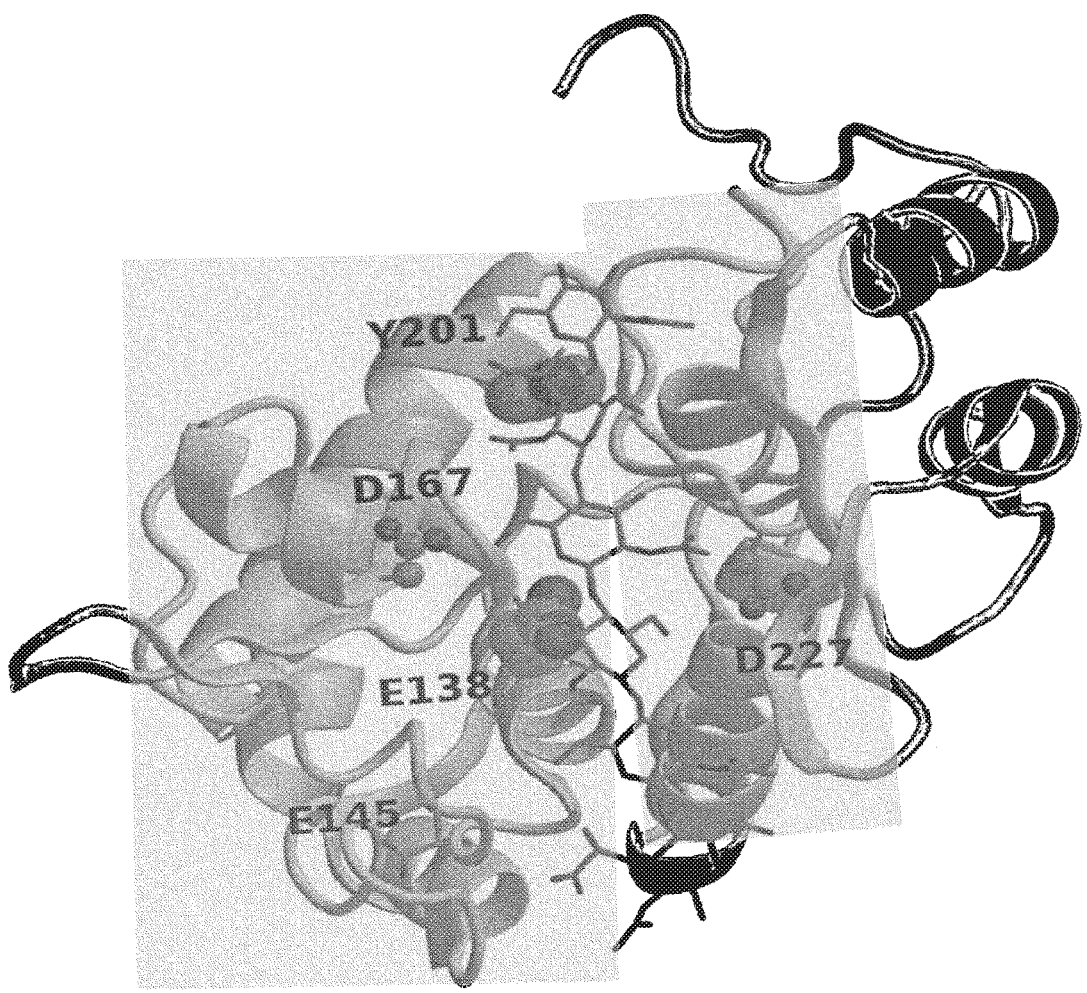
FIG. 18 shows the effect of mutations of residues involved biochemical analysis of cell wall degradation. Fold of AtlE structure is shown in light. The side chains of mutated residues are shown in ball and stick presentation. Oxygen and carbon atoms are shown in dark. The residues are marked. The radii of atom balls of the mutated residues correspond to the level of reduced activity of the mutants. So, the 100% drop of activity corresponds to the 100% of VdW radii of side chain atoms, whereas the mutated resides which did not effect activity are shown as sticks only. E138 and Y201 mutants resulted in zero activity, the D167A and D227A resulted in halved activity, whereas E145A mutant exhibited the activity of native enzyme.

Lysozymes (muraminidases) are among the most studied enzymes. They exhibit a broad specificity profile. They cleave poly NAG and (NAG-NAM) substrates, much less it is however known about glucosaminidases. To provide insight into the biochemical activity of AtlE and AtlA the corresponding parts of the sequence were expressed and tested against the *S. aureus* cell wall and two synthetic substrates $(NAM-NAG)_{2red}$ tetrasaccharide (FIG. 14) and $(NAG)_{2red}$. Both proteins were active against the cell wall substrate and both cleaved only the NAG-β(1,4)-NAM glycosidic bond, and are N-acetylglucosaminidases only, whereas $(NAG)_6$ was not cleaved at all.

Having confirmed the enzymatic activity of the two proteins, indications about their involvement in the biofilm formation were obtained. AtlE and gluAtlA were added to the solution of *S. aureus* culture in a biofilm formation assay. Addition of AtlE to the solution increased the formation of biofilms in a concentration dependent manner (FIG. 1). In contrast, addition of gluAtlA exhibited no effect on biofilm formation regardless of the enzyme concentration. To find out whether the induced biofilm formation is a consequence of the catalytic activity of the enzyme, the test with the catalytic mutant E138A of AtlE was also performed. It was demonstrated that the catalytic activity of AtlE in the media is indeed responsible for facilitating the biofilm formation under the applied conditions. Hence, this experiment revealed that different glucosaminidases behave differently and indicated that the presence of AtlE may be important for *S. aureus* biofilm formation process.

2. Structural Analysis

Figure 2:
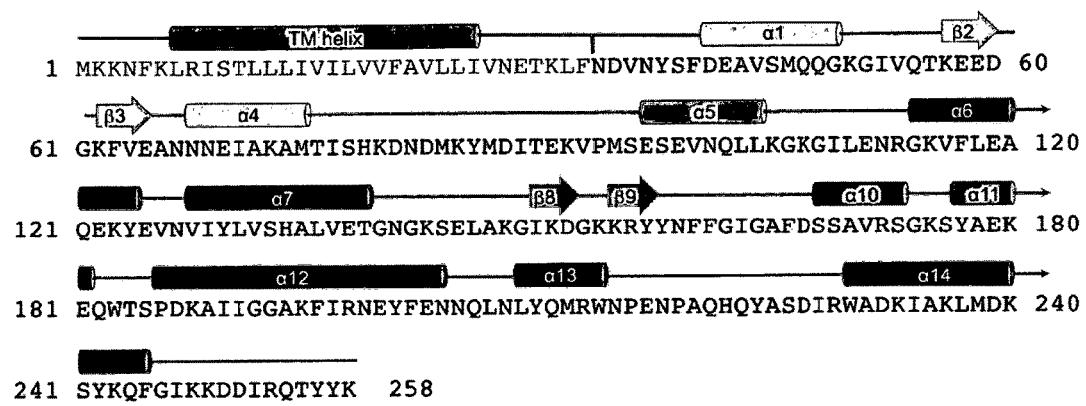
FIG. 2 concerns the amino acid sequence of AtlE comprising SEQ ID NO: 1 with the putative transmembrane region. The gray print indicates the part excluded from expression.

To gain insight into the 3-dimensional structure of AtlE, the crystal structure of AtlE was determined. The sequence analysis of the full length protein suggested that it consists of a short N-terminal cytoplasmic tail followed by a transmembrane helix (Ile9 to Val27) and the outer domain (FIG. 2; SEQ ID NO: 1). The truncated sequence lacking the first 34 residues was expressed and the protein crystallized. The refined model of the naked AtlE structure consists of 228 amino acid, 352 molecules of water and 10 chloride ions.

3. Overall Structure Description

Figure 4:
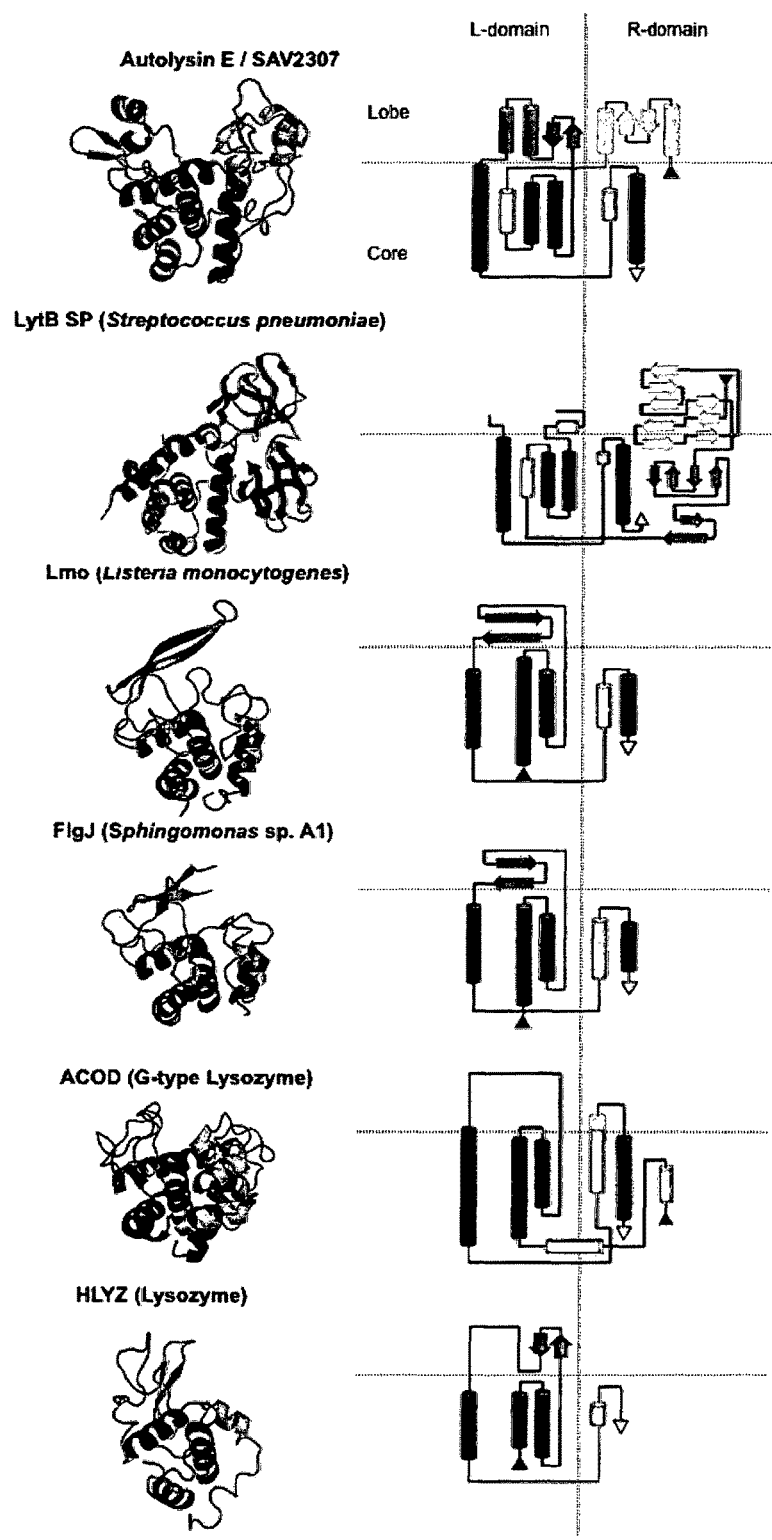
FIG. 4 concerns the structural similarity of AtlE. AtlE and the related structures of LytB SP (4Q2W), Lmo (3Fl7), FlgJ (3K3T), ACOD (3GXK), and HLYZ (1 1WT) are presented in the order from the top to the bottom. The left column shows the chain trace with the secondary structure elements in the same orientation, whereas in the column on the right, the architecture of the folds is presented schematically. The helices are show as cylinders and .beta. strands as arrows.

AtlE adopts a heart like globular fold composed of left (L-) and right (R-) domains (FIG. 3). To address structural parts easier, the structure, the core and lobe regions were divided. The compact α-helical structural core is the lower part of both domains, whereas the R- and L-lobes containing short α-helical and β-strand regions reside on the top of L- and R-domain, correspondingly. Between the lobes, there is a long groove that runs across the entire central part of the molecule (FIG. 4). The secondary structure elements in the figures are numbered in the order they follow in the amino acid sequence. The polypeptide chain first builds the R-lobe, then enters the L-domain, in which the L-lobe is inserted between the helices α7 and α12, and then returns into R-domain and builds the R-core region. The core of the structure consists of 6 helices of different length: α5, α6, α7 and α12 from the L-domain and α13 and α14 from to the R-domain, whereas each lobe contains two short α-helices and two β-hairpins. In the L-lobe, the β-hairpin precedes the two α-helices, whereas in the R-lobe the β-hairpin is positioned between them (α1 and α4). Both domains are connected through two regions: an extended loop connecting the α4 and α5 helices and a short linker region connecting the α12 and α13 helices.

4. Similarity to Other Structures

Using the determined structure of AtlE DALI server identified several similar structures. The closest structural homologues were *Pneumococcal* peptidoglycan hydrolase LytB (LytB SP) (4Q2W, Z-score=16.9) [Bai et al., 2014], autolysin Lmo1076 (Lmo) (3FI7, Z-score=8.0) [Bublits et al., 2009] and FlgJ (2ZYC, Z-score=7.3) [Hashimoto et al., 2009]. They all belong to the GH73 family of glycosyl hydrolases. The list continued with the G-type lysozyme from Atlantic cod (ACOD) (3GXR) [Hellman et al., 2009] which belongs to GH23 family (Z-score=6.7). Due to the similarity in architecture, even though not spotted by the DALI server, also the human lysozyme structure (HLYZ; 1IWT) was included as a representative of the goose-type lysozymes [Joti et al., 2002]. The structural and sequence alignment of the six enzymes shown in FIG. 4 reflects their structural similarity, but also points out their diversity.

Superimposition of the structures revealed that all six helices comprising the core of the AtlE fold are similar to the C-terminal domain of LytB SP, named "GH73 domain", whereas only the four helices α6, α7, α12, and α14 shown in dark (FIGS. 3 and 4), which form the central core of AtlE structure, have counterparts in Lmo, FlgJ, HLYZ, and ACOD. (FIG. 4). Conservation of these four helices is typical for the proteins that adopt the lysozyme-like fold. A slight exception is the HLYZ structure in which the C-terminal helix is broken in two parts (α6) and extended. Another exception is also the α3 helix from the ACOD structure which is curved, extended, and wrapped along the inter domain interface from where the chain folds back and around the C-terminal helix and contacts the L-domain from below.

The L- and R-cores are in all compared structures build from a-helical elements (FIG. 4). The L-cores are built similarly, whereas the R-cores differ in the size and structure. The three helices from the L-core of AtlE are present in all compared structures, whereas the AtlE α5 helix is present in the AtlE and LytB SP structures only. In the R-core, the C-terminal helix is present in all structures except HLYZ. In AtlE, and ACOD/GLYZ structures the R-core is built from the N- and C-terminal parts of the chain, whereas in the HLYZ, Lmo, and FlgJ structures the R-core is folded entirely from the C-terminal part of the chain. In the LytB SP structure, the R-core is absent from the GH73 domain apart from the conserved helix, which is positioned similarly as in the Lmo and FlgJ structures.

The R-lobe is unique to AtlE structure and absent in all others. It is build from the N-terminal terminal parts of the sequence. Also in the LytB SP structure, the GH73 domain does not have an R-lobe. Its space is, however, occupied by the N-terminal domain WW.

The L-lobes are present in all listed structures. They are built from the elements of β-structures, yet they differ in the folding pattern and their positioning. Only the HLYZ structure contains a three-strand β-sheet, whereas in the Lmo and FlgJ structures there are long β-hairpins which extend into the upper part of the structure above the inter domain interface. Additional β-hairpins are found in the AtlE and FlgJ structures. They, however, extend towards the left and in the direction away from the inter domain interface. In contrast, the LytB SP has there a small number of residues which structure is partially disordered.

Structural sequence alignment of the six enzymes shown in FIG. 5 performed with STRAP [Gille and Frommel, 2001] shows that the GH73 domain from LytB SP is a close homologue of AtlE. Being insufficient for degradation of cell wall by itself, this comparison provides explanation for the need of the WV domain and the linking SH3b domain [Bai et al., 2014]. This figure also shows that all these enzymes share only a single residue conserved in all sequences. In the AtlE sequence it is E138, the catalytic residue of the lysozyme-like enzymes as confirmed by the abolished activity of the E138A mutant, whereas an additional catalytic residue was not identified. E138 is positioned at the C-terminus of the central helix, α7 in the AtlE structure. This helix lies in the L-domain with the E138 residue positioned at the bottom of the cleft formed between the two domain interface.

To summarize, the AtlE structure is a lysozyme-like enzyme, yet it differs from the currently known ones suggesting that the S. aureus GH 73 family members have unique properties which can be exploited as potential drug targets.

5. Structures of Disaccharide and Muropeptide in Complex with AtlE

To gain insight into the binding of substrate experimentally, the crystal structures of AtlE in complex with disaccharide NAG-NAM and muropeptide NAM-ALA-D-GLU (MurP) were determined.

Figure 6:
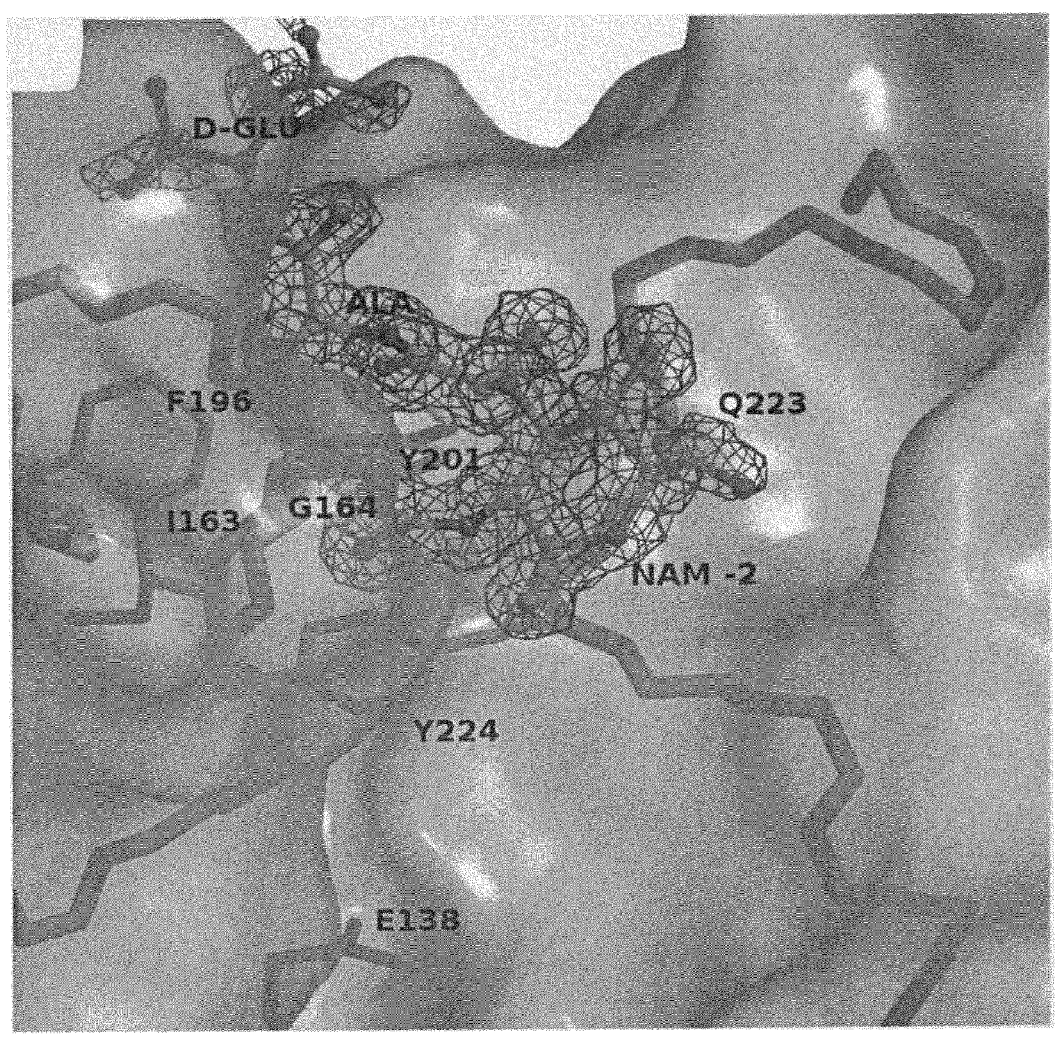
FIGS. 6 and 7 concern complexes of AtlE with NAG-NAM and muropeptide. AtlE structure is presented with transparent surface which makes the regions and residues in contact with the ligands visible. Electron densities around the ligands are shown as wired model in FIG. 6 (muropeptide) and FIG. 7 (disaccharide NAG-NAM) contoured at 0.8 and 1.2.sigma., respectively. The ligands residues and AtlE residues in contact with the ligands are marked and their side chain drawn in stick representation. The main chain is drawn thicker. The binding sites are built from three regions as shown. The figures were prepared with MAIN [Turk, 2013] and rendered with Raster3D [Merrit, 1997].
Figure 7:
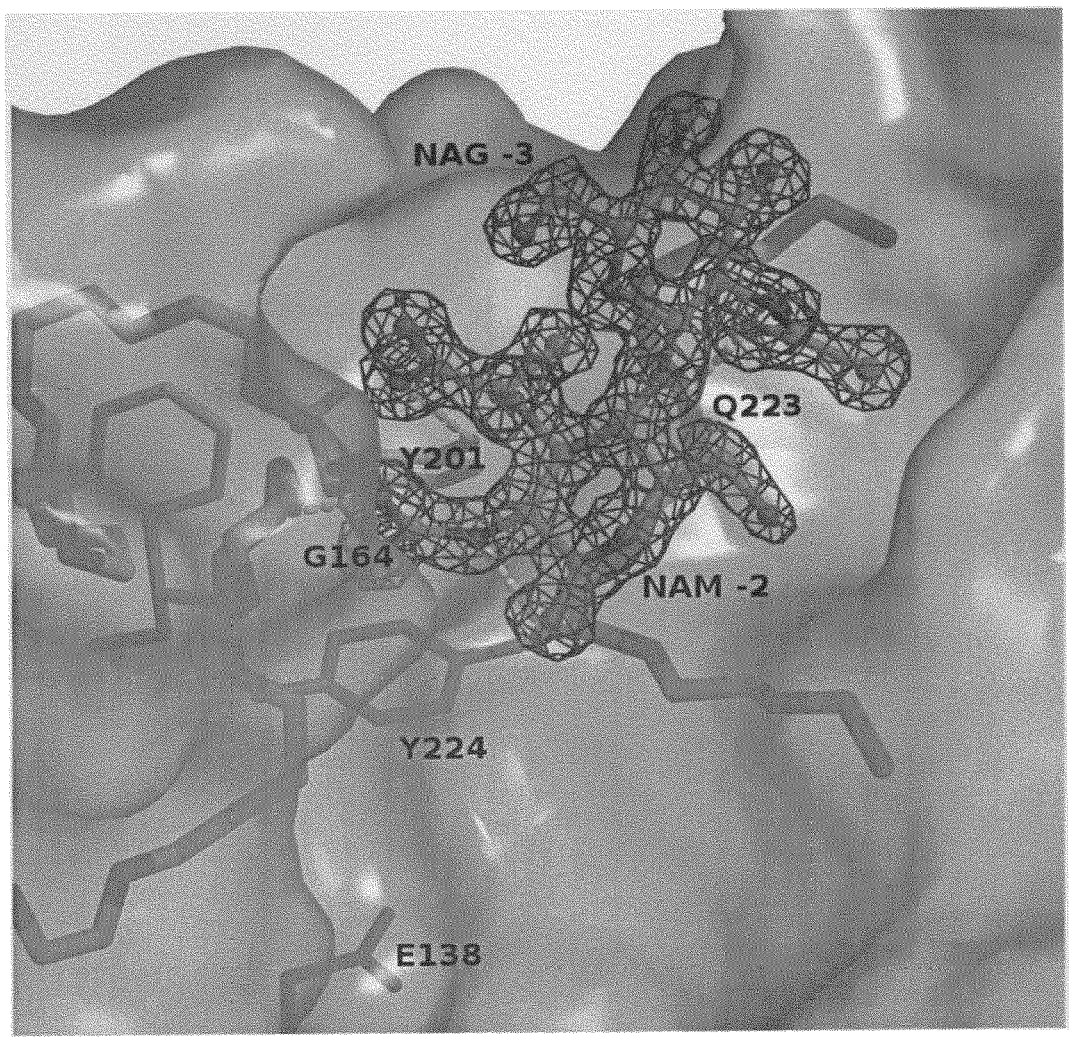

In FIGS. 6 and 7, three regions, which form the interactive surface for disaccharide and muropeptide binding, and the catalytic residue are shown:
the α7 on which C-terminus the catalytic E138 resides;
the left flank region with G164 involved in binding of NAM residue and I163 forming a hydrophobic surface for the muropeptide alanine;
the L-lobe region at the back with the aromatic residues F196 and Y201, the later is involved in binding of NAM residue;
the L-lobe loop region with Q223 and Y224 residues involved in binding of N-acetyl moieties of NAM and NAG residue (Y224 is conserved in all structures, but HLYZ which has W).

Figure 8:
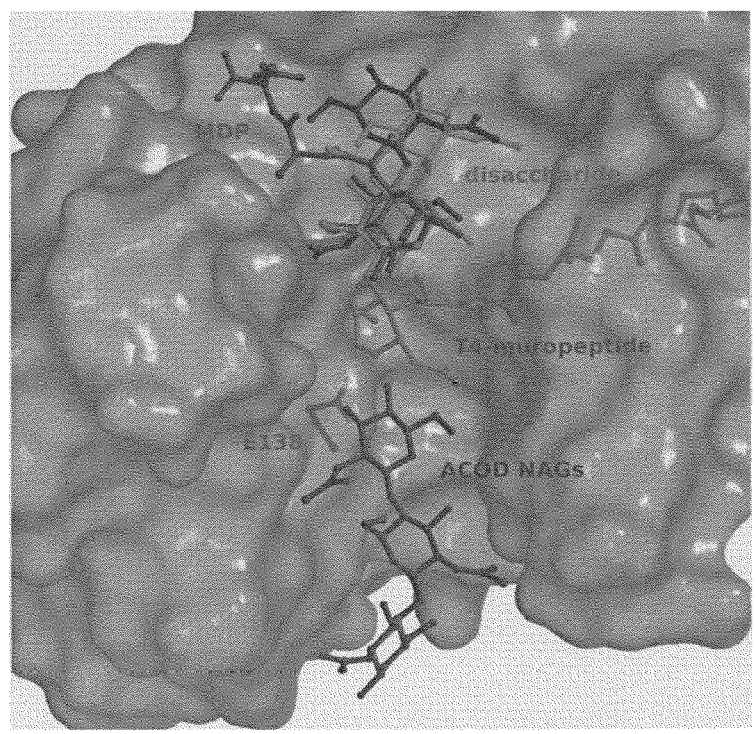
FIG. 8 concerns a comparison of similar ligands superimposed to AtlE structure. AtlE is shown as transparent white surface with the catalytic E138 side chain labeled. The crystal structures of muropeptide and NAG-NAM disaccharide determined in the complex with AtlE are shown as stick models. They are marked as "MurP" and "DISACCHARIDE". The muropeptide ligand bound to T4 lysozyme (148 L) is marked with T4 MurP. The di- and tri-saccharide structures determined in the complex with ACOD (3GXR) are marked with ACOD NAG. The figure was prepared with MAIN [Turk, 2013] and rendered with Raster3D [Merrit, 1997].

Besides the three regions shown in FIG. 8 and indicated in FIG. 9 as regions 2, 3, 4, the substrate binding surface is additionally build from the region on the left with the chain extending from the catalytic E138 which starts the L-lobe and from the region on the right where the K57-V64 loop extends the R-lobe surface. These two regions are indicated as 0 and 1 in the FIG. 9.

In the case of the NAG-NAM complex, only a single molecule of disaccharide was bound to the AtlE active site (FIG. 6). As the closest atom to the catalytic residue E138, the O1 atom from NAM residue is positioned 6.7 Å away from the carboxylic group OE2 atom. The disaccharide is positioned above the Q221-S226 loop shown in green. It is pined to the surface at the bottom of the cleft with four hydrogen bonds, three formed by NAM residue and one by NAG. The N-acetyl group of NAM is pinned to the surface of AtlE by the hydrogen bonds with the main chain atoms G164 NH group and Y224 carbonyl. The oxygen atom of the lactyl moiety of the NAM residue forms hydrogen bond with OH group of Y201 side chain. The N-acetyl group of NAG residue forms hydrogen bond with main chain NH group of Q223. Numerous solvent molecules, two chloride ions and a sulfate ion are positioned in the region around the disaccharide.

In the MupP, the NAM and alanine residues are unambiguously resolved by the electron density map, whereas the positioning of the atoms of D-glutamic acid residue is less defined as indicated by the electron density map (FIG. 7). The NAM moiety of MurP binds to AtlE structure equivalently to that observed in the NAG-NAM AtlE complex (FIG. 6). The alanine hydrophobic side chain is positioned within the hydrophobic environment formed by the side chains of I163, G164, and F196 whereas the D-GLU residue is disordered and points into the solvent.

6. Substrate Binding Site

To analyze the binding of NAG-NAM disaccharide and the muropeptide in the light of other related complexes, both AtlE complexes were superimposed with the crystal structures of the NAG trisaccharides bound to goose-type lysozyme from Atlantic cod (ACOD) [Hellman et al., 2009], (154 L), with the NAG-NAM-peptide in the complex with T4 lysozyme [Weaver and Matthews, 1987], (148 L), with NAG trisaccharide bound to the goose lysozyme structure of the complex [Weaver et al., 1995] (154 L), and NAM-NAG-NAM trisaccharide in complex with chicken lysozyme [Kelly et al., 1979] (9LYZ). The five resolved NAG carbohydrate rings from the ACOD structure fit into the active site of AtlE. A similar position is also occupied by the NAG trisaccharide in the complexes with the goose lysozyme structure (GLYZ) and chicken trisaccharide (9LYZ). Taken together, these structures indicate the positions of sub-site binding from −3 to +3 using the nomenclature proposed by Davies [Davies, 1997] or the B to G nomenclature as applied in the ACOD structural paper [Hellmann et al., 2009]. According to Davis nomenclature, the observed NAM residues in the AtlE complexes (FIG. 8) bind into the −2 sugar binding subsite and NAG into the −3 subsite.

Hence, the substrate binding site runs across the central core of the AtlE molecule and is limited on the left and right side by the structural elements of L- and R-lobe.

7. Similarity of *S. aureus* GH73 Family

Figure 10:
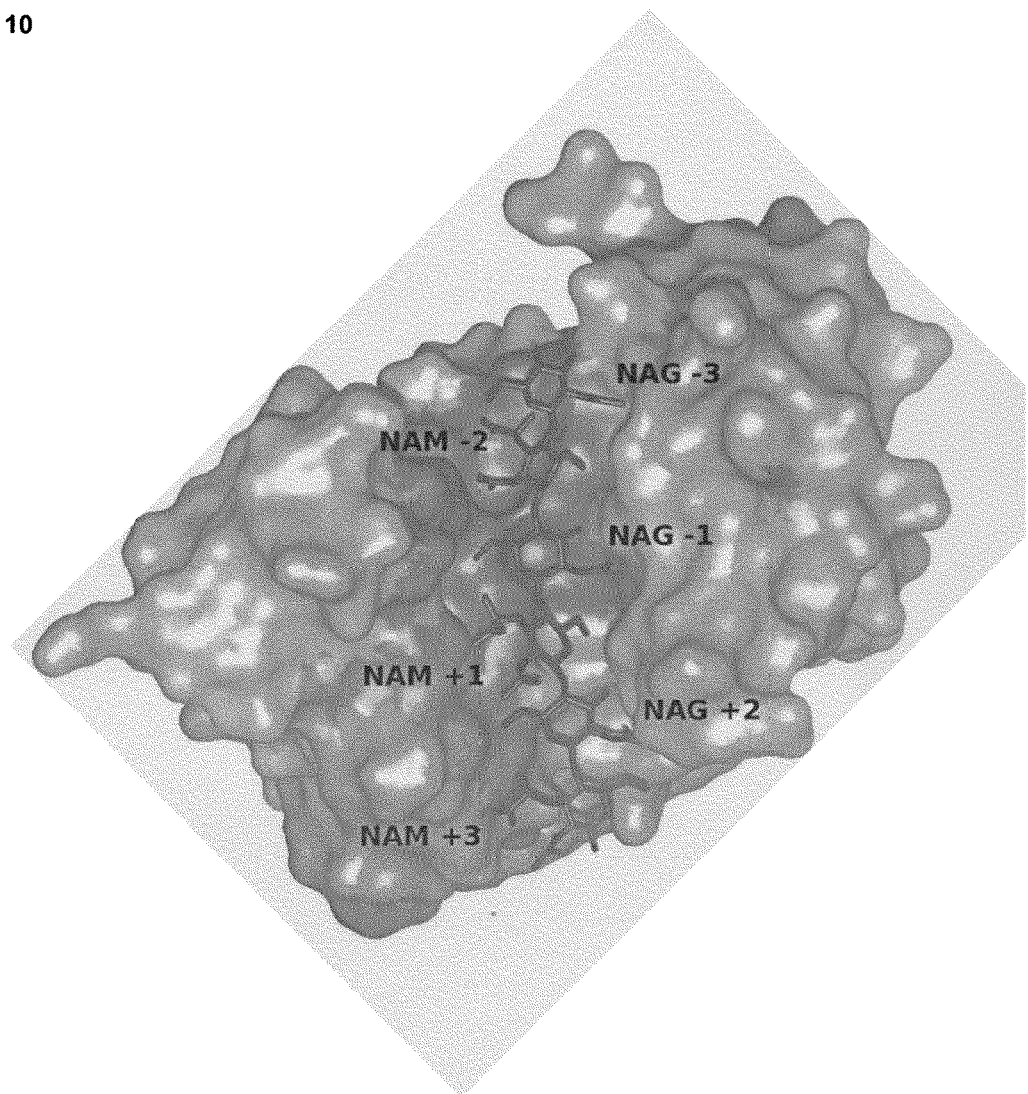
FIG. 10 concerns the surface representation of AtlE structure with mapped identity of residues. Amino acids are shadowed according to their identity corresponding to the counts of dots in the FIG. 9). Dark shadows reflect 100% identity, whereas lighter shadows indicate lower levels of similarity. White indicates no identity. The view into the active site is shown. The figure was prepared with MAIN [Turk, 2013] and rendered with Raster3D [Merrit, 1997].

As the analysis of available crystal structures of glucosaminidases indicated that this group of enzymes differs too much to enable their inhibition with a single compound, the target potential of *S. aureus* GH73 members was explored. To gain insight into the similarity and diversity of the active sites of the *S. aureus* GH 73 family members a sequence alignment of the glucosaminidase domains were made (FIG. 9). To visualize distribution of sequential identity, the sum of identical residues at the surface of AtlE were mapped using (FIG. 10), where the dark areas correspond to the position of the conserved residues in all five sequences, whereas the white areas to none. Since the majority of the surface is white, this mapping indicates that also among the *S. aureus* GH 73 members are substantial differences in their structure. However, the sequentially most conserved region lies in the −3, −2, −1 and +1 substrate binding sub-sites. On the right, G162 is positioned next to catalytic E138. Together with Y224 and A225 residues, they build the surface of −1 and −2 sub-sites. A165 builds the surface above, on the left, S144 is positioned at +2 sub-site below. Interestingly, the Y201 residue involved in the hydrogen bond with the lactyl group of the NAM residue at −2 sub-site cannot be found in SAV1775 and SAV2644 sequences, where there are F and I respectively. Assuming that these two enzymes are glucosaminidases, they likely contain a different anchor for the lactyl moiety. In addition the Y201A mutant of AtlE is completely inactive. These together indicates that potential inhibitors of glucosaminidases from GH73 family of *S. aureus* should target the indicated conserved area, its immediate surroundings or parts of it that spanns the binding sites from −3 to +2 which spatial relationships of the whole group of *S. aureus* enzymes from the GH73 famili were revealed by the AtlE crystal structure described herein C) Analysis of the Results First of all, the structural basis of substrate recognition of glucosaminidases and muramidases were explored. As explained above, the complexes of hexasaccharides with alternating sequence of NAG NAM residues were modeled into the structure of the active site clefts of AtlE and ACOD as the representative enzymes for the N-acetylglucosaminidase and muramidase activities, respectively. FIGS. 11 and 12 show 3-dimensional and schematic comparisons of substrate binding. The structures of NAM-NAG disaccharide in complex with AtlE and the NAGs complexes with ACOD provided the template for modeling of binding geometry of hexasaccharide substrates. The chain trace of the AtlE is shown on the background of the ACOD surface and vice versa, while the substrate models correspond to the structures with the shown surface. The pairs of FIGS. 11*a* and 11*b* as well as 12*a* and 12*b* demonstrate the differences between the shape of active site clefts and the way hexasaccharide substrates bind into them. In the AtlE structure the active site is broad, which makes the whole substrate model visible along the whole length. This is in sharp contrast to the narrow active site of ACOD which surface in part obscures the view of the substrate model. Since NAG and NAM residues appear at alternating positions, the lactic moieties are in the AtlE and ACOD models on the left and right side of the active site, respectively. This positioning indicates that features on the left side of the active site cleft of AtlE are responsible for recognition of lactyl moieties and peptides from the glycopeptide network, whereas the features on the right side of the active site cleft of AtlE could enhance rejection or even prevent binding of lactyl moieties and peptides attached to them. The reverse is expected for the ACOD substrate binding. Indeed the FIGS. 11*a* and 11*b* show that at and above the −2 and +1 positions of lactyl moieties of NAM residues bound to the AtlE surface there is enough space to accommodate the peptidyl extensions. They can surround the D175-K175 helical region which builds the top of the L-lobe. However, in the ACOD structure, there are features protruding outside the AtlE surface that can prevent binding of peptidyl extensions attached at these two positions. In accordance with the FIGS. 12*a* and 12*b* the reverse is true for the ACOD bound substrate model. The AtlE hairpin region from G52 to N68 of AtlE positioned at top of the R-lobe of the AtlE structure builds the wall of the active site on the right and thereby prevents binding of peptidyl extensions attached to lactyl group of NAM residues, whereas the lower ACOD surface provides sufficient space to accommodate peptides bound to the lactyl groups of NAM residues. This analysis demonstrates that the L- and R-lobes indeed contain structural features responsible for acceptance and rejection of the peptidyl moiety of glycopeptide cell wall.

Next, the selectivity against the saccharide (NAG-NAM)$_n$ and (NAG)$_n$ substrates with no peptidyl extensions attached were explored. In the substrate binding corresponding to muramidase activity, the lactyl group is positioned in −3, −1, and +2 subsites, whereas in the substrate binding corresponding to the glucosaminidase activity, the lactyl group of N-acetylmuramic acid is positioned in −2, +1, and +3 subsites. Clearly, there is no difference between the glycosidic bonds between the two carbohydrate rings, yet the muramidases cleave the glycosidic bond between O1 NAM-C4 NAG, whereas the glucosaminidases cleave the glycosidic bond between O1 NAG-C4 NAM. In addition, it is known that lysozyme/muramidases can cleave the glycosidic bond between two NAG consecutive residues too, whereas the AtlE and glu-AtlA cannot. In order to get further insight, the structural features responsible for acceptance and rejection of the lactyl moieties of the NAM residues were explored. In PDB there are several entries containing NAM among them are a few in complex with a hydrolase active site related to peptidoglycan substrate recognition. There are the complexes of NAM-peptide intermediate with T4 phage lysozyme (148 L) and NAM-NAG-NAM in the complex with the chicken lysozyme (9LYZ). In either case the lactyl moiety is not stabilized by any interaction with the underlying enzyme structure, whereas the N atom of the amide link in alanine in phage lysozyme, is oriented against the main chain carbonyl group of Q105. This indicates that lysozymes select the side of NAG-NAM polymers by excluding approach of the lactyl moiety from the wrong side, but do not require it at the other. This also explains why lysozymes can cleave also the NAG polymers. The AtlE NAG-NAM complex structure presented here, however, revealed that the lactate group of NAM -2 residue forms a hydrogen bond with Y201 (FIG. 6) and leaving enough space behind it to accommodate the peptidyl moiety (FIG. 7). The recognition of NAM residue leads to twist of the NAG-NAM chain at the −3 position. The absence of AtlE activity against the NAGs substrate can be attributed to the absence of the hydrogen bond between the lactyl moiety of −2 residue and Y201 and the possibly extended, but not twisted, conformation of the NAGs substrate, which disables productive binding at the −3 and −2 positions.

Figure 13:
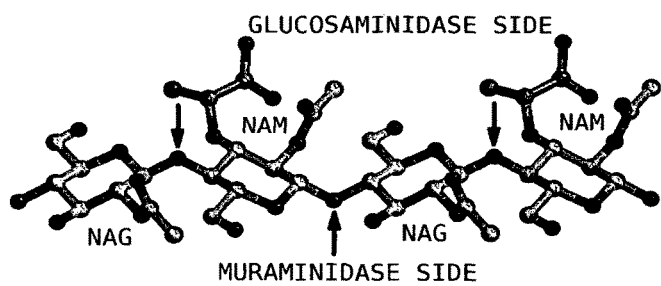
FIG. 13 shows a model of NAG-NAM-NAG-NAM tetrasaccharide with cleavage sites assigned. The ring and glycosidic bonds are shown with thick sticks and atom balls of corresponding radii, whereas the lactyl and amide groups are shown as thin sticks and correspondingly small atomic radii. The cleavage sites by muramidases and glucosaminidases are marked.

Taken together, the structures of AtlE and lyzozyme complexes revealed specific structural features which exclude the binding of the substrate molecules in the incompatible manner and thereby explain the difference between the glucosaminidase and muramidase activity. Since the peptidoglycan substrate is the same, in order to achieve the different binding, each kind of enzyme must approach the substrate molecules from a different side. This binding of the glycan reflects the differences in the chemistry of muramidases and glucosaminidases. The glycans form extended structures with carbohydrate rings are in the chair confirmation. In schematic figures, this important detail may easily escapes attention, however, observation of a 3-dimensional model revealed it according to the present invention. When viewed from a side, a zig-zag structure was found. Namely, the β-glycosidic bonds are separated by five of covalent bonds. The odd number of bonds brings the O4 atom in alternating positions, whether each second points either up or down (FIG. 13). If the glucosaminidases recognized the muramic moieties on the same side as the muramidases, then the catalytic residue from the bottom would not be able to reach the glycosidic bond oxygen atom positioned at the top. Therefore, they must approach from the opposite side, where the O4 atom from the glycosydic bond of the next pair of residues is accessible to the catalytic residue of the enzyme. Consequently, glucosaminidases contain structural features which accept lactate moieties on NAM residues on the R-side of the active site cleft contrary to muramidases. The absence of selective recognition of lactyl group on the L-side, however, enables them to process NAG polymers as well.

Hence, the combined analysis of the AtlE and lyzozyme structures revealed the features that define the glucosaminidase and muramidase activities of the enzymes.

This is achieved at two levels: At the first, their folds enable desired and prevent undesired binding of peptidyl parts of glycopeptidyl substrate. At the second, the detail architecture of the active site takes care for productive binding of the correct glycosidic bond adjusted by the lactyl moieties of NAM residues and approach of the O4 atoms in NAG-NAM polymers to the catalytic carboxylic group.

In the search for potential new targets for antibiotics for treatment of *Staphylococcus aureus* infections, the present invention shows the basic difference in substrate recognition between muramidases, which are one of the most studied enzymes, and glucosaminidases. These two groups of enzymes cleave alternate glycosidic bonds between NAG-NAM residues in a peptidoglycan structures comprising the bacterial cell wall. The difference between the enzymes is a consequence of the structure of NAG-NAM polymers in which only every second glycosidic oxygen atom is positioned at the same side of the polymer. In order to be able to reach alternate oxygen atoms, muramidases and glucosaminidases must dock to the substrate from the opposite sides. They achieve this by differences in the fold enhanced by specific interactions as revealed by the crystal structural analysis of autolysin E and its complexes with NAG-NAM and muropeptide. This gives one the opportunity to develop species specific antibiotics targeting cell wall degradation.

REFERENCES

Andrejasic M., Praznikar J. and Turk D. (2008): PURY: *A database of geometric restrains of hetero compounds for refinement of complexes with macromolecular structures*. Acta Cryst D64, 1093-1109.

Archer NK1, Mazaitis M J, Costerton J W, Leid J G, Powers M E, Shirtliff M E. (2011) *Staphylococcus aureus biofilms: properties, regulation, and roles in human disease*. Virulence, (5):445-59.

Bai X H, Chen H J, Jiang Y L, Wen Z, Huang Y, Cheng W, Li Q, Qi L, Zhang J R, Chen Y, Zhou C Z. (2014) *Structure of pneumococcal peptidoglycan hydrolase LytB reveals insights into the bacterial cell wall remodeling and pathogenesis*. J Biol Chem. 289(34), 23403-16.

Biswas R, Voggu L, Simon U K, Hentschel P, Thumm G, Götz F. (2006) *Activity of the major staphylococcal autolysin Atl*. FEMS Microbiol Lett. 259(2), 260-8.

Boneca I G, Huang Z H, Gage D A, Tomasz A. (2000) *Characterization of Staphylococcus aureus cell wall glycan strands, evidence for a new beta-N-acetylglucosaminidase activity*. J Biol Chem. 275(14), 9910-8.

Bublitz M., Polle L., Holland C., Heinz D. W., Nimtz M., Schubert W. D. (2009) *Structural basis for autoinhibition and activation of Auto, a virulence-associated peptidoglycan hydrolase of Listeria monocytogenes*. Mol. Microbiol. 71:1509-1522.

Cantarel B L, Coutinho P M, Rancurel C, Bernard T, Lombard V, Henrissat B. (2009) *The Carbohydrate-Active EnZymes database (CAZy): an expert resource for glycogenomics*. Nucleic acids research 37. suppl 1: D233-D238.

Davies G J, Wilson K S, and Henrissat B. (1997) *Nomenclature for sugar-binding subsites in glycosyl hydrolases*. Biochem J. 5; 321 (Pt 2):557-9.

Dantes R, Mu Y, Belflower R, Aragon D, Dumyati G, Harrison L H, Lessa F C, Lynfield R, Nadle J, Petit S, Ray S M, Schaffner W, Townes J, Fridkin S (2013) *National burden of invasive methicillin-resistant* (2013) *Staphylococcus aureus infections, United States*, 2011. JAMA InternMed. 173(21), 1970-8.

Ericsson U B, Hallberg B M, Detitta G T, Dekker N, Nordlund P. (2006) *Thermofluor-based high-throughput stability optimization of proteins for structural studies*. Analytical biochemistry 357, 289-298.

Eschenfeldt, W. H. Stols, L., Sanville Millard, C., Joachimiak, A., and Donnelly, M. I. (2009) *A Family of LIC Vectors for High-Throughput Cloning and Purification of Proteins*. Methods Mol Biol. 498, 105-115.

Gille C, Frömmel C. (2001) STRAP: editor for STRuctural Alignments of Proteins. Bioinformatics. 17, 377-8.

Hanberger H, Walther S, Leone M, Barie P S, Rello J, Lipman J, Marshall J C, Anzueto A, Sakr Y, Pickkers P, Felleiter P, Engoren M, Vincent J L; EPIC II Group of Investigators. (2011) *Increased mortality associated with methicillin-resistant Staphylococcus aureus (MRSA) infec-* tion in the intensive care unit: results from the EPIC II study. Int J Antimicrob Agents. 38(4), 331-5.

Hashimoto, W., Ochiai, A., Momma, K., Itoh, T., Mikami, B., Maruyama, Y., Murata, K. Journal: (2009) *Crystal structure of the glycosidase family 73 peptidoglycan hydrolase FlgJ*. Biochem. Biophys. Res. Commun. 381: 16-21

Haynes, W. M., ed., (2014) CRC Handbook of Chemistry and Physics, CRC Press

Helland R, Larsen R L, Finstad S, Kyomuhendo P, Larsen A N (2009) Crystal structures of g-type lysozyme from atlantic cod shed new light on substrate binding and the catalytic mechanism. Cell. Mol. Life Sci. 66, 2585

Heilmann C, Hussain M, Peters G, Götz F.(1997) *Evidence for autolysin-mediated primary attachment of Staphylococcus epidermidis to a polystyrene surface*. Molecular microbiology 24, 1013-1024.

Hiramatsu K, Hanaki H, Ino T, Yabuta K, Oguri T, Tenover F C. (1997) *Methicillin-resistant Staphylococcus aureus clinical strain with reduced vancomycin susceptibility*. J Antimicrob. Chemother. 40, 135-136.

Ho S N, Hunt H D, Horton R M, Pullen J K, Pease L R. (1989) *Site-directed mutagenesis by overlap extension using the polymerase chain reaction*. Gene. 77, 51-9.

Joti Y, Nakasako M, Kidera A, Go N (2002) *Nonlinear temperature dependence of the crystal structure of lysozyme: correlation between coordinate shifts and thermal factors*. Acta Crystallogr.,Sect. D 58, 1421.

Kantoci D., Keglević D. (1987) *A convenient synthetic route to the disaccharide repeating-unit of peptidoglycan*. Carohydr. Res. 162, 227-235.

Keglević D., Kojić-Prodić B., Banić Z., Tomić S., Puntarec V. (1993) *Synthesis and conformational analysis of muramic acid delta-lactam structures and their 4-O-(2-acetamido-2-deoxy-beta-D-glucopyranosyl) derivatives, characteristic of bacterial spore peptidoglycan*. Carbohydr. Res., 241, 131-152.

Keglević D., Pongračić M., Kantoci D. (1985) Croat. Chem. Acta 58, 569-581.

Lowy, F. D. (1998) *Staphylococcus aureus infections*. New England Journal of Medicine 339, 520-532.

Merritt, Judith H., Daniel E. Kadouri, and George A. O'Toole (2005) *Growing and analyzing static biofilms*. Current protocols in microbiology, 1B-1.

Minor W., Cymborowski M., Otwinowski Z., Chruszcz M. (2006) *HKL-3000, the integration of data reduction and structure solution. From diffraction images to an initial model in minutes*. 62, 859-866.

Murshudov, G. N. Vagin, A. A. and Dodson, E. J. (1997) *Refinement of Macromolecular Structures by the Maximum-Likelihood method*. Acta Cryst. D53, 240-255.

Nashed M. A., Anderson L., J. Am. Chem. Soc. (1982) *Oligosaccharides from "standardized intermediates." Synthesis of a branched tetrasaccharide glycoside related to the blood group B determinant* 104, 7282-7286.

Nunes AP1, Schuenck R P, Bastos C C, Magnanini M M, Long J B, Iorio N L, Santos K R. (2007) *Heterogeneous resistance to vancomycin and teicoplanin among Staphylococcus spp. isolated from bacteremia*. Brazilian Journal of Infectious Diseases 11, 345-350.

Odintsov S G, Sabala I, Marcyjaniak M, Bochtler M. (2004) *Latent LytM at 1.3A resolution*. J Mol Biol. 335(3), 775-85.

Oshida T, Sugai M, Komatsuzawa H, Hong Y M, Suginaka H, Tomasz A. (1995) *A Staphylococcus aureus autolysin that has an N-acetylmuramoyl-L-alanine amidase domain and an endo-beta-N-acetylglucosaminidase domain: cloning, sequence analysis, and characterization*. PNAS 92, 285-289.

Otwinowski, Z. and Minor, W (1997) *Processing of X-ray Diffraction Data Collected in Oscillation Mode, Methods in Enzymology*, Volume 276: Macromolecular Crystallography, part A, p.307-326, 1997,C. W. Carter, Jr. & R. M. Sweet, Eds., Academic Press (New York).

Sugai M, Komatsuzawa H, Akiyama T, Hong Y M, Oshida T, Miyake Y, Yamaguchi T, Suginaka H. (1995) *Identification of endo-beta-N-acetylglucosaminidase and N-acetylmuramyl-L-alanine amidase as cluster-dispersing enzymes in Staphylococcus aureus*. J Bacteriol. 177, 1491-6.

Smith, Thomas J., Steve A. Blackman, and Simon J. Foster. *Autolysins of Bacillus subtilis: multiple enzymes with multiple functions*. Microbiology 146.2 (2000): 249-262.

Turk, D. (2013) *MAIN software for density averaging, model building, structure refinement and validation*, Acta Cryst D, 69, 1342-1357.

Varrone J J, Li D, Daiss J L, Schwarz E M. (2011) *Anti-Glucosaminidase Monoclonal Antibodies as a Passive Immunization for Methicillin-Resistant Staphylococcus aureus (MRSA) Orthopaedic Infections*. Bonekey Osteovision. 8, 187-194.

Vincent J L, Rello J, Marshall J, Silva E, Anzueto A, Martin C D, Moreno R, Lipman J, Gomersall C, Sakr Y, Reinhart K. (2009) *International study of the prevalence and outcomes of infection in intensive care units*. JAMA. 302 (21), 2323-9.

Vollmer W, Joris B, Charlier P and Foster S (2008) *Bacterial peptidoglycan (murein) hydrolases*. FEMS microbiology reviews 32, 259-286.

Ye, Y. & Godzik, A. (2003). *Flexible structure alignment by chaining aligned fragment pairs allowing twists*. Bioinformatics 19, 246-255.

Zetola N, Francis J S, Nuermberger E L, Bishai W R. (2005) *Community-acquired methicillin-resistant Staphylococcus aureus: an emerging threat*. Lancet Infect Dis. 5(5): 275-86.

Zoll S1, Pätzold B, Schlag M, Götz F, Kalbacher H, Stehle T. (2010) *Structural basis of cell wall cleavage by a staphylococcal autolysin*. PLoS pathogens 6.3, e1000807.

TABLE 1

Structure and Refinement Statistics

| PDB ID | AtlE<br>4PIA | NAG-NAM<br>AtlE complex<br>4PI7 | NAM-NAG E138A<br>ATIE complex<br>4PI8 | Muropeptide<br>AtlE complex<br>4PI9 |
|---|---|---|---|---|
| Data Collection Statistics | | | | |
| Resolution Range (Å) | 23.0-1.47<br>(1.52-1.47) | 50.0-1.6<br>(1.69-1.60) | 38.4-1.39<br>(1.439-1.39) | 38.75-1.48<br>(1.53-1.48) |

TABLE 1-continued

Structure and Refinement Statistics

| PDB ID | AtlE 4PIA | NAG-NAM AtlE complex 4PI7 | NAM-NAG E138A ATlE complex 4PI8 | Muropeptide AtlE complex 4PI9 |
|---|---|---|---|---|
| Space Group | P 2₁ 2₁ 2₁ | P 2₁ 2₁ 2₁ | P 2₁ 2₁ 2₁ | P 2₁ 2₁ 2₁ |
| Unit Cell (Å) | 46.60, 69.93, 73.27 90°, 90°, 90° | 46.31, 69.78, 73.58 90°, 90°, 90° | 46.011 69.72 73.54 90°, 90°, 90° | 45.63, 69.31, 73.42 90°, 90°, 90° |
| Total Reflections | 229540 | 222199 | 312334 | 251936 |
| Unique Reflections | 41472 (3953) | 31914 (2985) | 48332 (4753) | 39606 (3756) |
| Multiplicity | 5.5 (3.7) | 3.7 (1.9) | 6.5 (6.5) | 6.4 (6.5) |
| Completeness (%) | 99.30 (95.97) | 99.45 (94.82) | 99.92 (99.69) | 99.55 (96.26) |
| Mean I/Sigma(I) | 39.2 (1.4) | 24.24 (3.34) | 26.91 (3.00) | 20.16 (2.07) |
| Wilson B-Factor | 11.72 | 16.14 | 15.96 | 19.66 |
| R-Merge | 0.043 (0.259) | 12.1 (23.4) | 0.03446 (0.5927) | 0.04472 (0.7462) |
| Refinement Statistic | | | | |
| R-Work | 0.1492 | 0.1563 | 0.152 | 0.1772 |
| R-Free | 0.1715 | 0.1868 | 0.1755 | 0.208 |
| Number of Non-Hydrogen Atoms | 2111 | 2116 | 2146 | 2111 |
| Macromolecules | 1844 | 1826 | 1837 | 1832 |
| Ligands | 9 | 50 | 53 | 42 |
| Water | 258 | 240 | 256 | 237 |
| Protein Residues | 225 | 223 | 222 | 223 |
| RMS Bonds (Å) | 0.017 | 0.015 | 0.018 | 0.015 |
| RMS Angles (°) | 1.81 | 1.64 | 1.9 | 1.7 |

TABLE 2

X-RAY DIFFRACTION DATA OF *S. AUREUS* AUTOLYSIN E (AtlE 4PIA) RESIDUES 35-258

Remarks

| REMARK | 2 | RESOLUTION: 1.47 ANGSTROMS. |
| REMARK | 3 | PROGRAM: REFMAC |
| REMARK | 3 | RESOLUTION RANGE HIGH (ANGSTROMS): 1.47 |
| REMARK | 3 | RESOLUTION RANGE LOW (ANGSTROMS): 23.00 |
| REMARK | 3 | DATA CUTOFF (SIGMA(F)): 0.000 |
| REMARK | 3 | COMPLETENESS FOR RANGE (%): 99.3 |
| REMARK | 3 | NUMBER OF REFLECTIONS: 41472 |
| REMARK | 3 | FIT TO DATA USED IN REFINEMENT. |
| REMARK | 3 | CROSS-VALIDATION METHOD: THROUGHOUT |
| REMARK | 3 | FREE R VALUE TEST SET SELECTION: RANDOM |
| REMARK | 3 | R VALUE (WORKING + TEST SET): 0.150 |
| REMARK | 3 | R VALUE (WORKING SET): 0.149 |
| REMARK | 3 | FREE R VALUE: 0.172 |
| REMARK | 3 | FREE R VALUE TEST SET SIZE (%): 5.000 |
| REMARK | 3 | FREE R VALUE TEST SET COUNT: 2090 |
| REMARK | 3 | NUMBER OF NON-HYDROGEN ATOMS USED IN REFINEMENT. |
| REMARK | 3 | PROTEIN ATOMS: 1809 |
| REMARK | 3 | NUCLEIC ACID ATOMS: 0 |
| REMARK | 3 | HETEROGEN ATOMS: 9 |
| REMARK | 3 | SOLVENT ATOMS: 258 |
| REMARK | 3 | B VALUES. |
| REMARK | 3 | FROM WILSON PLOT (A**2): NULL |
| REMARK | 3 | MEAN B VALUE (OVERALL, A**2): 15.92 |
| REMARK | 3 | OVERALL ANISOTROPIC B VALUE. |
| REMARK | 3 | B11 (A**2): 0.04000 |
| REMARK | 3 | B22 (A**2): −0.02000 |
| REMARK | 3 | B33 (A**2): −0.02000 |
| REMARK | 3 | B12 (A**2): 0.00000 |
| REMARK | 3 | B13 (A**2): 0.00000 |
| REMARK | 3 | B23 (A**2): 0.00000 |
| REMARK | 3 | ESTIMATED OVERALL COORDINATE ERROR. |
| REMARK | 3 | ESU BASED ON R VALUE (A): 0.058 |
| REMARK | 3 | ESU BASED ON FREE R VALUE (A): 0.059 |
| REMARK | 3 | ESU BASED ON MAXIMUM LIKELIHOOD (A): 0.034 |
| REMARK | 3 | ESU FOR B VALUES BASED ON MAXIMUM LIKELIHOOD (A**2): 0.862 |
| REMARK | 3 | RMS DEVIATIONS FROM IDEAL VALUES. |
| REMARK | 3 | DISTANCE RESTRAINTS. RMS SIGMA |
| REMARK | 3 | BOND LENGTH (A): NULL; NULL |
| REMARK | 3 | ANGLE DISTANCE (A): NULL; NULL |
| REMARK | 3 | INTRAPLANAR 1-4 DISTANCE (A): NULL; NULL |
| REMARK | 3 | H-BOND OR METAL COORDINATION (A): NULL; NULL |

TABLE 2-continued

X-RAY DIFFRACTION DATA OF S. AUREUS AUTOLYSIN E (AtlE 4PIA) RESIDUES 35-258

| | | |
|---|---|---|
| REMARK | 3 | PLANE RESTRAINT (A): NULL; NULL |
| REMARK | 3 | CHIRAL-CENTER RESTRAINT (A**3): NULL; NULL |
| REMARK | 3 | NON-BONDED CONTACT RESTRAINTS. |
| REMARK | 3 | SINGLE TORSION (A): NULL; NULL |
| REMARK | 3 | MULTIPLE TORSION (A): NULL; NULL |
| REMARK | 3 | H-BOND (X . . . Y) (A): NULL; NULL |
| REMARK | 3 | H-BOND (X-H . . . Y) (A): NULL; NULL |
| REMARK | 3 | CONFORMATIONAL TORSION ANGLE RESTRAINTS. |
| REMARK | 3 | SPECIFIED (DEGREES): NULL; NULL |
| REMARK | 3 | PLANAR (DEGREES): NULL; NULL |
| REMARK | 3 | STAGGERED (DEGREES): NULL; NULL |
| REMARK | 3 | TRANSVERSE (DEGREES): NULL; NULL |
| REMARK | 3 | ISOTROPIC THERMAL FACTOR RESTRAINTS. RMS SIGMA |
| REMARK | 3 | MAIN-CHAIN BOND (A**2): NULL; NULL |
| REMARK | 3 | MAIN-CHAIN ANGLE (A**2): NULL; NULL |
| REMARK | 3 | SIDE-CHAIN BOND (A**2): NULL; NULL |
| REMARK | 3 | SIDE-CHAIN ANGLE (A**2): NULL; NULL |
| REMARK | 3 | OTHER REFINEMENT REMARKS: HYDROGENS HAVE BEEN ADDED IN THE RIDING |
| REMARK | 3 | POSITIONS U VALUES: REFINED INDIVIDUALLY |
| REMARK | 4 | 4PIA COMPLIES WITH FORMAT V. 3.30, 13-JUL-11 |
| REMARK | 200 | EXPERIMENTAL DETAILS |
| REMARK | 200 | EXPERIMENT TYPE: X-RAY DIFFRACTION |
| REMARK | 200 | TEMPERATURE (KELVIN): 100 |
| REMARK | 200 | PH: NULL |
| REMARK | 200 | NUMBER OF CRYSTALS USED: 1 |
| REMARK | 200 | SYNCHROTRON (Y/N): Y |
| REMARK | 200 | RADIATION SOURCE: ELETTRA |
| REMARK | 200 | BEAMLINE: 5.2R |
| REMARK | 200 | X-RAY GENERATOR MODEL: NULL |
| REMARK | 200 | MONOCHROMATIC OR LAUE (M/L): M |
| REMARK | 200 | WAVELENGTH OR RANGE (A): 1.00 |
| REMARK | 200 | MONOCHROMATOR: NULL |
| REMARK | 200 | OPTICS: NULL |
| REMARK | 200 | DETECTOR TYPE: PIXEL |
| REMARK | 200 | DETECTOR MANUFACTURER: DECTRIS PILATUS 6M |
| REMARK | 200 | INTENSITY-INTEGRATION SOFTWARE: HKL |
| REMARK | 200 | DATA SCALING SOFTWARE: HKL |
| REMARK | 200 | NUMBER OF UNIQUE REFLECTIONS: 41563 |
| REMARK | 200 | RESOLUTION RANGE HIGH (A): 1.460 |
| REMARK | 200 | RESOLUTION RANGE LOW (A): 23.000 |
| REMARK | 200 | REJECTION CRITERIA (SIGMA(I)): NULL |
| REMARK | 200 | OVERALL. |
| REMARK | 200 | COMPLETENESS FOR RANGE (%): 99.3 |
| REMARK | 200 | DATA REDUNDANCY: 5.500 |
| REMARK | 200 | R MERGE (I): 0.04300 |
| REMARK | 200 | R SYM (I): NULL |
| REMARK | 200 | <I/SIGMA(I)> FOR THE DATA SET: 39.2000 |
| REMARK | 200 | IN THE HIGHEST RESOLUTION SHELL. |
| REMARK | 200 | HIGHEST RESOLUTION SHELL, RANGE HIGH (A): 1.46 |
| REMARK | 200 | HIGHEST RESOLUTION SHELL, RANGE LOW (A): 1.49 |
| REMARK | 200 | COMPLETENESS FOR SHELL (%): 96.0 |
| REMARK | 200 | DATA REDUNDANCY IN SHELL: 4.00 |
| REMARK | 200 | R MERGE FOR SHELL (I): 0.29100 |
| REMARK | 200 | R SYM FOR SHELL (I): NULL |
| REMARK | 200 | <I/SIGMA(I)> FOR SHELL: NULL |
| REMARK | 200 | DIFFRACTION PROTOCOL: SINGLE WAVELENGTH |
| REMARK | 200 | METHOD USED TO DETERMINE THE STRUCTURE: NULL |
| REMARK | 200 | SOFTWARE USED: NULL |
| REMARK | 200 | STARTING MODEL: NULL |
| REMARK | 200 | REMARK: NULL |
| REMARK | 280 | CRYSTAL |
| REMARK | 280 | SOLVENT CONTENT, VS (%): 46.28 |
| REMARK | 280 | MATTHEWS COEFFICIENT, VM (ANGSTROMS**3/DA): 2.29 |
| REMARK | 280 | CRYSTALLIZATION CONDITIONS: 2 M (NH4)2SO4, 2 M NACL |
| REMARK | 290 | CRYSTALLOGRAPHIC SYMMETRY |
| REMARK | 290 | SYMMETRY OPERATORS FOR SPACE GROUP: P 21 21 21 |
| REMARK | 290 | SYMOP          SYMMETRY |
| REMARK | 290 | NNNMMM          OPERATOR |
| REMARK | 290 | 1555          X, Y, Z |
| REMARK | 290 | 2555          −X+1/2, −Y, Z+1/2 |
| REMARK | 290 | 3555          −X, Y+1/2, −Z+1/2 |
| REMARK | 290 | 4555          X+1/2, −Y+1/2, −Z |
| REMARK | 290 | WHERE NNN -> OPERATOR NMBER |
| REMARK | 290 | MMM -> TRANSLATION VECTOR |
| REMARK | 290 | CRYSTALLOGRAPHIC SYMMETRY TRANSFORMATIONS |
| REMARK | 290 | THE FOLLOWING TRANSFORMATIONS OPERATE ON THE ATOM/HETATM |
| REMARK | 290 | RECORDS IN THIS ENTRY TO PRODUCE CRYSTALLOGRAPHICALLY |
| REMARK | 290 | RELATED MOLECULES. |

TABLE 2-continued

X-RAY DIFFRACTION DATA OF *S. AUREUS* AUTOLYSIN E (AtlE 4PIA) RESIDUES 35-258

| REMARK | 290 | SMTRY1 | 1 | 1.000000 | 0.000000 | 0.000000 | 0.00000 |
|---|---|---|---|---|---|---|---|
| REMARK | 290 | SMTRY2 | 1 | 0.000000 | 1.000000 | 0.000000 | 0.00000 |
| REMARK | 290 | SMTRY3 | 1 | 0.000000 | 0.000000 | 1.000000 | 0.00000 |
| REMARK | 290 | SMTRY1 | 2 | −1.000000 | 0.000000 | 0.000000 | 23.29950 |
| REMARK | 290 | SMTRY2 | 2 | 0.000000 | −1.000000 | 0.000000 | 0.00000 |
| REMARK | 290 | SMTRY3 | 2 | 0.000000 | 0.000000 | 1.000000 | 36.63400 |
| REMARK | 290 | SMTRY1 | 3 | −1.000000 | 0.000000 | 0.000000 | 0.00000 |
| REMARK | 290 | SMTRY2 | 3 | 0.000000 | 1.000000 | 0.000000 | 34.96350 |
| REMARK | 290 | SMTRY3 | 3 | 0.000000 | 0.000000 | −1.000000 | 36.63400 |
| REMARK | 290 | SMTRY1 | 4 | 1.000000 | 0.000000 | 0.000000 | 23.29950 |
| REMARK | 290 | SMTRY2 | 4 | 0.000000 | −1.000000 | 0.000000 | 34.96350 |
| REMARK | 290 | SMTRY3 | 4 | 0.000000 | 0.000000 | −1.000000 | 0.00000 |
| REMARK | 350 | BIOLOGICAL UNIT: MONOMERIC | | | | | |
| REMARK | 350 | SOFTWARE DETERMINED QUATERNARY STRUCTURE: MONOMERIC | | | | | |
| REMARK | 350 | SOFTWARE USED: PISA | | | | | |
| REMARK | 350 | TOTAL BURIED SURFACE AREA: 980 ANGSTROM**2 | | | | | |
| REMARK | 350 | SURFACE AREA OF THE COMPLEX: 11270 ANGSTROM**2 | | | | | |
| REMARK | 350 | CHANGE IN SOLVENT FREE ENERGY: −71.0 KCAL/MOL | | | | | |
| REMARK | 350 | APPLY THE FOLLOWING TO CHAINS: A | | | | | |
| REMARK | 350 | BIOMT1 | 1 | 1.000000 | 0.000000 | 0.000000 | 0.00000 |
| REMARK | 350 | BIOMT2 | 1 | 0.000000 | 1.000000 | 0.000000 | 0.00000 |
| REMARK | 350 | BIOMT3 | 1 | 0.000000 | 0.000000 | 1.000000 | 0.00000 |
| REMARK | 465 | MISSING RESIDUES | | | | | |
| REMARK | 465 | THE FOLLOWING RESIDUES WERE NOT LOCATED IN THE | | | | | |
| REMARK | 465 | EXPERIMENT. (M = MODEL NUMBER; RES = RESIDUE NAME; C = CHAIN | | | | | |
| REMARK | 465 | IDENTIFIER; SSSEQ = SEQUENCE NUMBER; I = INSERTION CODE.) | | | | | |
| REMARK | 465 | M | RES | C | SSSEQ | | I |
| REMARK | 465 | | SER | A | 31 | | |
| REMARK | 465 | | HIS | A | 79 | | |
| REMARK | 465 | | LYS | A | 80 | | |
| REMARK | 500 | GEOMETRY AND STEREOCHEMISTRY | | | | | |
| REMARK | 500 | SUBTOPIC: CLOSE CONTACTS IN SAME ASYMMETRIC UNIT | | | | | |
| REMARK | 500 | THE FOLLOWING ATOMS ARE IN CLOSE CONTACT. | | | | | |
| REMARK | 500 | ATM1 | RES | C | SSSEQ | I | ATM2 RES C SSEQ I DISTANCE |
| REMARK | 500 | O | HOH | A | 586 | | O HOH A 656 2.04 |
| REMARK | 500 | O | HOH | A | 651 | | O HOH A 657 2.08 |
| REMARK | 500 | REMARK: NULL | | | | | |
| REMARK | 500 | GEOMETRY AND STEREOCHEMISTRY | | | | | |
| REMARK | 500 | SUBTOPIC: CLOSE CONTACTS | | | | | |
| REMARK | 500 | THE FOLLOWING ATOMS THAT ARE RELATED BY CRYSTALLOGRAPHIC | | | | | |
| REMARK | 500 | SYMMETRY ARE IN CLOSE CONTACT. AN ATOM LOCATED WITHIN 0.15 | | | | | |
| REMARK | 500 | ANGSTROMS OF A SYMMETRY RELATED ATOM IS ASSUMED TO BE ON A | | | | | |
| REMARK | 500 | SPECIAL POSITION. ATOMS WITH NON-BLANK ALTERNATE | | | | | |
| REMARK | 500 | LOCATION INDICATORS ARE NOT INCLUDED IN THE CALCULATIONS. | | | | | |
| REMARK | 500 | DISTANCE CUTOFF: | | | | | |
| REMARK | 500 | 2.2 ANGSTROMS FOR CONTACTS NOT INVOLVING HYDROGEN ATOMS | | | | | |
| REMARK | 500 | 1.6 ANGSTROMS FOR CONTACTS INVOLVING HYDROGEN ATOMS | | | | | |
| REMARK | 500 | ATM1 | RES | C | SSSEQ | I | ATM2 RES C SSEQI I SSYMOP DISTANCE |
| REMARK | 500 | O | HOH | A | 472 | | O HOH A 501 4445 1.98 |
| REMARK | 500 | REMARK: NULL | | | | | |
| REMARK | 500 | GEOMETRY AND STEREOCHEMISTRY | | | | | |
| REMARK | 500 | SUBTOPIC: COVALENT BOND ANGLES | | | | | |
| REMARK | 500 | THE STEREOCHEMICAL PARAMETERS OF THE FOLLOWING RESIDUES | | | | | |
| REMARK | 500 | HAVE VALUES WHICH DEVIATE FROM EXPECTED VALUES BY MORE | | | | | |
| REMARK | 500 | THAN 6*RMSD (M = MODEL NUMBER; RES = RESIDUE NAME; C = CHAIN | | | | | |
| REMARK | 500 | IDENTIFIER; SSEQ = SEQUENCE NUMBER; I = INSERTION CODE). | | | | | |
| REMARK | 500 | STANDARD TABLE: | | | | | |
| REMARK | 500 | FORMAT: (10X, I3, 1X, A3, 1X, A1, I4, A1, 3(1X, A4, 2X), 12X, F5.1) | | | | | |
| REMARK | 500 | EXPECTED VALUES PROTEIN: ENGH AND HUBER, 1999 | | | | | |
| REMARK | 500 | EXPECTED VALUES NUCLEIC ACID: CLOWNEY ET AL 1996 | | | | | |
| REMARK | 500 | M | RES | C | SSEQ | I | ATM1 ATM2 ATM3 |
| REMARK | 500 | | MET | A | 84 | | CA — CB — CG ANGL. DEV. = 10.6 DEGREES |
| REMARK | 500 | | MET | A | 84 | | CG — SD — CE ANGL. DEV. = −13.6 DEGREES |
| REMARK | 500 | | ASP | A | 88 | | CB — CG — OD1 ANGL. DEV. = 6.5 DEGREES |
| REMARK | 500 | | ASP | A | 227 | | CB — CG — OD1 ANGL. DEV. = 6.5 DEGREES |
| REMARK | 500 | | ASP | A | 227 | | CB — CG — OD2 ANGL. DEV. = −7.0 DEGREES |
| REMARK | 500 | REMARK: NULL | | | | | |
| REMARK | 500 | GEOMETRY AND STEREOCHEMISTRY | | | | | |
| REMARK | 500 | SUBTOPIC: TORSION ANGLES | | | | | |
| REMARK | 500 | TORSION ANGLES OUTSIDE THE EXPECTED RAMACHANDRAN REGIONS: | | | | | |
| REMARK | 500 | (M = MODEL NUMBER; RES = RESIDUE NAME; C = CHAIN IDENTIFIER; | | | | | |
| REMARK | 500 | SSEQ = SEQUENCE NUMBER; I = INSERTION CODE). | | | | | |
| REMARK | 500 | STANDARD TABLE: | | | | | |
| REMARK | 500 | FORMAT: (10X, I3, 1X, A3, 1X, A1, I4, A1, 4X, F7.2, 3X, F7.2) | | | | | |
| REMARK | 500 | EXPECTED VALUES: GJ KLEYWEGT AND TA JONES (1996). PHI/ | | | | | |
| REMARK | 500 | PSICHOLOGY: RAMACHANDRAN REVISITED. STRUCTURE 4, 1395-1400 | | | | | |
| REMARK | 500 | M | RES | C | SSEQ | I | PSI PHI |
| REMARK | 500 | | ASN | A | 159 | | 113.44 −160.04 |

TABLE 2-continued

X-RAY DIFFRACTION DATA OF S. AUREUS AUTOLYSIN E (AtlE 4PIA) RESIDUES 35-258

| | | | | | | | |
|---|---|---|---|---|---|---|---|
| REMARK | 500 | | LYS | A | 175 | 44.96 | -97.51 |
| REMARK | 500 | | ASN | A | 215 | 66.23 | 26.87 |
| REMARK | 500 | | ALA | A | 220 | -4.25 | 79.83 |
| REMARK | 500 | REMARK: NULL | | | | | |
| REMARK | 800 | SITE | | | | | |
| REMARK | 800 | SITE_IDENTIFIER: AC1 | | | | | |
| REMARK | 800 | EVIDENCE_CODE: SOFTWARE | | | | | |
| REMARK | 800 | SITE_DESCRIPTION: binding site for residue CL A 301 | | | | | |
| REMARK | 800 | SITE_IDENTIFIER: AC2 | | | | | |
| REMARK | 800 | EVIDENCE_CODE: SOFTWARE | | | | | |
| REMARK | 800 | SITE_DESCRIPTION: binding site for residue CL A 302 | | | | | |
| REMARK | 800 | SITE_IDENTIFIER: AC3 | | | | | |
| REMARK | 800 | EVIDENCE_CODE: SOFTWARE | | | | | |
| REMARK | 800 | SITE_DESCRIPTION: binding site for residue CL A 303 | | | | | |
| REMARK | 800 | SITE_IDENTIFIER: AC4 | | | | | |
| REMARK | 800 | EVIDENCE_CODE: SOFTWARE | | | | | |
| REMARK | 800 | SITE_DESCRIPTION: binding site for residue CL A 304 | | | | | |
| REMARK | 800 | SITE_IDENTIFIER: AC5 | | | | | |
| REMARK | 800 | EVIDENCE_CODE: SOFTWARE | | | | | |
| REMARK | 800 | SITE_DESCRIPTION: binding site for residue CL A 305 | | | | | |
| REMARK | 800 | SITE_IDENTIFIER: AC6 | | | | | |
| REMARK | 800 | EVIDENCE_CODE: SOFTWARE | | | | | |
| REMARK | 800 | SITE_DESCRIPTION: binding site for residue CL A 306 | | | | | |
| REMARK | 800 | SITE_IDENTIFIER: AC7 | | | | | |
| REMARK | 800 | EVIDENCE_CODE: SOFTWARE | | | | | |
| REMARK | 800 | SITE_DESCRIPTION: binding site for residue CL A 307 | | | | | |
| REMARK | 800 | SITE_IDENTIFIER: AC8 | | | | | |
| REMARK | 800 | EVIDENCE_CODE: SOFTWARE | | | | | |
| REMARK | 800 | SITE_DESCRIPTION: binding site for residue CL A 308 | | | | | |
| REMARK | 800 | SITE_IDENTIFIER: AC9 | | | | | |
| REMARK | 800 | EVIDENCE_CODE: SOFTWARE | | | | | |
| REMARK | 800 | SITE_DESCRIPTION: binding site for residue CL A 309 | | | | | |
| REMARK | 900 | RELATED ENTRIES | | | | | |
| REMARK | 900 | RELATED ID: 4PI8 | RELATED DB: PDB | | | | |
| REMARK | 900 | RELATED ID: 4PI7 | RELATED DB: PDB | | | | |
| REMARK | 900 | RELATED ID: 4PI9 | RELATED DB: PDB | | | | |

| | | | | | | | | | | | | | | |
|---|---|---|---|---|---|---|---|---|---|---|---|---|---|---|
| DBREF | 4PIA | A | 35 | 258 | UNP | | Q99RW6 | Q99RW6_STAAM | | 35 | | 258 | | |
| SEQADV | 4PIA | SER | A | 31 | UNP | | Q99RW6 | EXPRESSION | | | TAG | | | |
| SEQADV | 4PIA | ALA | A | 32 | UNP | | Q99RW6 | EXPRESSION | | | TAG | | | |
| SEQADV | 4PIA | ALA | A | 33 | UNP | | Q99RW6 | EXPRESSION | | | TAG | | | |
| SEQADV | 4PIA | ALA | A | 34 | UNP | | Q99RW6 | EXPRESSION | | | TAG | | | |
| SEQRES | 1 | A | 228 | SER | ALA | ALA | ALA | ASN | ASP | VAL | ASN | TYR | SER | PHE | ASP | GLU |
| SEQRES | 2 | A | 228 | ALA | VAL | SER | MET | GLN | GLN | GLY | LYS | GLY | ILE | VAL | GLN | THR |
| SEQRES | 3 | A | 228 | LYS | GLU | GLU | ASP | GLY | LYS | PHE | VAL | GLU | ALA | ASN | ASN | ASN |
| SEQRES | 4 | A | 228 | GLU | ILE | ALA | LYS | ALA | MET | THR | ILE | SER | HIS | LYS | ASP | ASN |
| SEQRES | 5 | A | 228 | ASP | MET | LYS | TYR | MET | ASP | ILE | THR | GLU | LYS | VAL | PRO | MET |
| SEQRES | 6 | A | 228 | SER | GLU | SER | GLU | VAL | ASN | GLN | LEU | LEU | LYS | GLY | LYS | GLY |
| SEQRES | 7 | A | 228 | ILE | GLU | LEU | ASN | ARG | GLY | LYS | VAL | PHE | LEU | GLU | ALA | GLN |
| SEQRES | 8 | A | 228 | GLU | LYS | TYR | GLU | VAL | ASN | VAL | ILE | TYR | LEU | VAL | SER | HIS |
| SEQRES | 9 | A | 228 | ALA | LEU | VAL | GLU | THR | GLY | ASN | GLY | LYS | SER | GLU | LEU | ALA |
| SEQRES | 10 | A | 228 | LYS | GLY | ILE | LYS | ASP | GLY | LYS | LYS | ARG | TYR | TYR | ASN | PHE |
| SEQRES | 11 | A | 228 | PHE | GLY | ILE | GLY | ALA | PHE | ASP | SER | SER | ALA | VAL | ARG | SER |
| SEQRES | 12 | A | 228 | GLY | LYS | SER | TYR | ALA | GLU | LYS | GLU | GLN | TRP | THR | SER | PRO |
| SEQRES | 13 | A | 228 | ASP | LYS | ALA | ILE | ILE | GLY | GLY | ALA | LYS | PHE | ILE | ARG | ASN |
| SEQRES | 14 | A | 228 | GLU | TYR | PHE | GLU | ASN | ASN | GLN | LEU | ASN | LEU | TYR | GLN | MET |
| SEQRES | 15 | A | 228 | ARG | TRP | ASN | PRO | GLU | ASN | PRO | ALA | GLN | HIS | GLN | TYR | ALA |
| SEQRES | 16 | A | 228 | SER | ASP | ILE | ARG | TRP | ALA | ASP | LYS | ILE | ALA | LYS | LEU | MET |
| SEQRES | 17 | A | 228 | ASP | LYS | SER | TYR | LYS | GLN | PHE | GLY | ILE | LYS | LYS | ASP | ASP |
| SEQRES | 18 | A | 228 | ILE | ARG | GLN | THR | TYR | TYR | LYS | | | | | | |

| | | | | | |
|---|---|---|---|---|---|
| HET | CL | A | 301 | 1 | |
| HET | CL | A | 302 | 1 | |
| HET | CL | A | 303 | 1 | |
| HET | CL | A | 304 | 1 | |
| HET | CL | A | 305 | 1 | |
| HET | CL | A | 306 | 1 | |
| HET | CL | A | 307 | 1 | |
| HET | CL | A | 308 | 1 | |
| HET | CL | A | 309 | 1 | |
| HETNAM | CL | CHLORIDE ION | | | |
| FORMUL | 2 | CL | 9 (CL 1-) | | |
| FORMUL | 11 | HOH | *258(H2 O) | | |

| | | | | | | | | | |
|---|---|---|---|---|---|---|---|---|---|
| HELIX | 1 | AA1 | SER | A | 40 | GLN | A | 49 | 1 | 10 |
| HELIX | 2 | AA2 | ASN | A | 67 | THR | A | 76 | 1 | 10 |
| HELIX | 3 | AA3 | ASP | A | 83 | MET | A | 87 | 5 | 5 |
| HELIX | 4 | AA4 | SER | A | 96 | LYS | A | 105 | 1 | 10 |
| HELIX | 5 | AA5 | LYS | A | 107 | GLU | A | 111 | 5 | 5 |
| HELIX | 6 | AA6 | ARG | A | 113 | GLU | A | 125 | 1 | 13 |
| HELIX | 7 | AA7 | ASN | A | 127 | THR | A | 139 | 1 | 13 |

TABLE 2-continued

X-RAY DIFFRACTION DATA OF *S. AUREUS* AUTOLYSIN E (AtlE 4PIA) RESIDUES 35-258

| | | | | | | | | | | | | | | | | | |
|---|---|---|---|---|---|---|---|---|---|---|---|---|---|---|---|---|---|
| HELIX | 8 | AA8 | GLU | | A | 145 | GLY | A | 149 | 5 | | | | | | | 5 |
| HELIX | 9 | AA9 | ASP | | A | 167 | GLY | A | 174 | 1 | | | | | | | 8 |
| HELIX | 10 | AB1 | SER | | A | 176 | GLU | A | 181 | 1 | | | | | | | 6 |
| HELIX | 11 | AB2 | SER | | A | 185 | TYR | A | 201 | 1 | | | | | | | 17 |
| HELIX | 12 | AB3 | PHE | | A | 202 | ASN | A | 205 | 5 | | | | | | | 4 |
| HELIX | 13 | AB4 | ASN | | A | 208 | ASN | A | 215 | 1 | | | | | | | 8 |
| HELIX | 14 | AB5 | ARG | | A | 229 | GLY | A | 246 | 1 | | | | | | | 18 |
| SHEET | 1 | AA1 | 2 | THE | A | 56 | GLU | A | 59 | 0 | | | | | | | |
| SHEET | 2 | AA1 | 2 | LYS | A | 62 | GLU | A | 65 | -1 | O | LYS | A | 62 | N | GLU | A | 59 |
| SHEET | 1 | AA2 | 2 | ILE | A | 150 | ASP | A | 152 | 0 | | | | | | | |
| SHEET | 2 | AA2 | 2 | LYS | A | 155 | TYR | A | 157 | -1 | O | TYR | A | 157 | N | ILE | A | 150 |
| SITE | 1 | AC1 | 2 | TYR | A | 256 | TYR | A | 257 | | | | | | | | |
| SITE | 1 | AC2 | 4 | ASN | A | 204 | ASN | A | 215 | HOH | A | 434 | HOH | A | 618 | | |
| SITE | 1 | AC3 | 6 | GLY | A | 106 | GLY | A | 108 | LYS | A | 143 | LYS | A | 243 | | |
| SITE | 2 | AC3 | 6 | HOH | A | 472 | HOH | A | 508 | | | | | | | | |
| SITE | 1 | AC4 | 4 | GLY | A | 164 | ALA | A | 165 | LYS | A | 175 | TYR | A | 177 | | |
| SITE | 1 | AC5 | 1 | GLU | A | 145 | | | | | | | | | | | |
| SITE | 1 | AC6 | 4 | PRO | A | 94 | LYS | A | 248 | HOH | A | 585 | HOH | A | 590 | | |
| SITE | 1 | AC7 | 6 | SER | A | 96 | GLU | A | 97 | SER | A | 98 | ASN | A | 218 | | |
| SITE | 2 | AC7 | 6 | HOH | A | 407 | HOH | A | 504 | | | | | | | | |
| SITE | 1 | AC8 | 3 | ALA | A | 74 | LYS | A | 85 | TRP | A | 214 | | | | | |
| SITE | 1 | AC9 | 6 | ASN | A | 101 | ASN | A | 112 | GLY | A | 114 | LYS | A | 115 | | |
| SITE | 2 | AC9 | 6 | HOH | A | 491 | HOH | A | 492 | | | | | | | | |
| CRYST1 | | 46.599 | | | 69.927 | | 73.268 | | 90.00 | | 90.00 | | 90.00 | | P 21 21 21 | | 4 |
| ORIGX1 | | 1.000000 | | | 0.000000 | | | 0.000000 | | | 0.00000 | | | | | | |
| ORIGX2 | | 0.000000 | | | 1.000000 | | | 0.000000 | | | 0.00000 | | | | | | |
| ORIGX3 | | 0.000000 | | | 0.000000 | | | 1.000000 | | | 0.00000 | | | | | | |
| SCALE1 | | 0.021460 | | | 0.000000 | | | 0.000000 | | | 0.00000 | | | | | | |
| SCALE2 | | 0.000000 | | | 0.014301 | | | 0.000000 | | | 0.00000 | | | | | | |
| SCALE3 | | 0.000000 | | | 0.000000 | | | 0.013649 | | | 0.00000 | | | | | | |
| Data | | | | | | | | | | | | | | | | | |
| ATOM | 1 | N | ALA | A | 32 | 2.887 | -1.791 | -39.094 | 1.00 | 52.61 | N |
| ATOM | 2 | CA | ALA | A | 32 | 4.235 | -1.614 | -39.730 | 1.00 | 49.15 | C |
| ATOM | 3 | C | ALA | A | 32 | 5.336 | -1.323 | -38.692 | 1.00 | 46.23 | C |
| ATOM | 4 | O | ALA | A | 32 | 6.239 | -2.145 | -38.508 | 1.00 | 44.29 | O |
| ATOM | 5 | CB | ALA | A | 32 | 4.194 | -0.529 | -40.802 | 1.00 | 52.21 | C |
| ATOM | 6 | N | ALA | A | 33 | 5.274 | -0.169 | -38.013 | 1.00 | 42.62 | N |
| ATOM | 7 | CA | ALA | A | 33 | 6.328 | 0.201 | -37.048 | 1.00 | 40.01 | C |
| ATOM | 8 | C | ALA | A | 33 | 6.082 | -0.407 | -35.654 | 1.00 | 38.69 | C |
| ATOM | 9 | O | ALA | A | 33 | 5.132 | -0.019 | -34.957 | 1.00 | 38.26 | O |
| ATOM | 10 | CB | ALA | A | 33 | 6.479 | 1.709 | -36.946 | 1.00 | 40.18 | C |
| ATOM | 11 | N | ALA | A | 34 | 6.952 | -1.345 | -35.263 | 1.00 | 35.68 | N |
| ATOM | 12 | CA | ALA | A | 34 | 6.908 | -1.989 | -33.939 | 1.00 | 36.70 | C |
| ATOM | 13 | C | ALA | A | 34 | 8.095 | -1.506 | -33.075 | 1.00 | 32.89 | C |
| ATOM | 14 | O | ALA | A | 34 | 8.540 | -2.179 | -32.106 | 1.00 | 36.83 | O |
| ATOM | 15 | CB | ALA | A | 34 | 6.938 | -3.503 | -34.097 | 1.00 | 34.69 | C |
| ATOM | 16 | N | ASN | A | 35 | 8.606 | -0.331 | -33.423 | 1.00 | 28.59 | N |
| ATOM | 17 | CA | ASN | A | 35 | 9.714 | 0.230 | -32.714 | 1.00 | 24.48 | C |
| ATOM | 18 | C | ASN | A | 35 | 9.220 | 1.141 | -31.587 | 1.00 | 21.91 | C |
| ATOM | 19 | O | ASN | A | 35 | 8.793 | 2.287 | -31.799 | 1.00 | 23.98 | O |
| ATOM | 20 | CB | ASN | A | 35 | 10.583 | 1.015 | -33.663 | 1.00 | 28.59 | C |
| ATOM | 21 | CG | ASN | A | 35 | 11.907 | 1.426 | -33.050 | 1.00 | 30.14 | C |
| ATOM | 22 | OD1 | ASN | A | 35 | 12.023 | 1.644 | -31.856 | 1.00 | 27.37 | O |
| ATOM | 23 | ND2 | ASN | A | 35 | 12.912 | 1.535 | -33.879 | 1.00 | 34.04 | N |
| ATOM | 24 | N | ASP | A | 36 | 9.360 | 0.621 | -30.372 | 1.00 | 15.66 | N |
| ATOM | 25 | CA | ASP | A | 36 | 8.920 | 1.327 | -29.171 | 1.00 | 14.24 | C |
| ATOM | 26 | C | ASP | A | 36 | 10.060 | 1.994 | -28.420 | 1.00 | 12.82 | C |
| ATOM | 27 | O | ASP | A | 36 | 9.899 | 2.435 | -27.272 | 1.00 | 12.99 | O |
| ATOM | 28 | CB | ASP | A | 36 | 8.235 | 0.366 | -28.217 | 1.00 | 16.30 | C |
| ATOM | 29 | CG | ASP | A | 36 | 9.043 | -0.891 | -27.967 | 1.00 | 19.31 | C |
| ATOM | 30 | OD1 | ASP | A | 36 | 10.238 | -0.877 | -28.264 | 1.00 | 15.46 | O |
| ATOM | 31 | OD2 | ASP | A | 36 | 8.495 | -1.963 | -27.585 | 1.00 | 24.87 | O |
| ATOM | 32 | N | VAL | A | 37 | 11.238 | 2.077 | -29.041 | 1.00 | 12.02 | N |
| ATOM | 33 | CA | VAL | A | 37 | 12.370 | 2.770 | -28.431 | 1.00 | 11.68 | C |
| ATOM | 34 | C | VAL | A | 37 | 12.322 | 4.211 | -28.940 | 1.00 | 13.11 | C |
| ATOM | 35 | O | VAL | A | 37 | 12.753 | 4.522 | -30.062 | 1.00 | 14.64 | O |
| ATOM | 36 | CB | VAL | A | 37 | 13.710 | 2.058 | -28.709 | 1.00 | 12.19 | C |
| ATOM | 37 | CG1 | VAL | A | 37 | 14.890 | 2.847 | -28.147 | 1.00 | 12.91 | C |
| ATOM | 38 | CG2 | VAL | A | 37 | 13.679 | 0.643 | -28.176 | 1.00 | 12.08 | C |
| ATOM | 39 | N | ASN | A | 38 | 11.798 | 5.089 | -28.115 | 1.00 | 10.08 | N |
| ATOM | 40 | CA | ASN | A | 38 | 11.456 | 6.451 | -28.507 | 1.00 | 9.90 | C |
| ATOM | 41 | C | ASN | A | 38 | 12.299 | 7.552 | -27.925 | 1.00 | 9.85 | C |
| ATOM | 42 | O | ASN | A | 38 | 12.394 | 8.656 | -28.516 | 1.00 | 11.43 | O |
| ATOM | 43 | CB | ASN | A | 38 | 10.021 | 6.703 | -28.061 | 1.00 | 9.86 | C |
| ATOM | 44 | CG | ASN | A | 38 | 9.017 | 6.051 | -28.943 | 1.00 | 12.62 | C |
| ATOM | 45 | OD1 | ASN | A | 38 | 9.297 | 5.717 | -30.127 | 1.00 | 13.95 | O |
| ATOM | 46 | ND2 | ASN | A | 38 | 7.824 | 5.792 | -28.398 | 1.00 | 12.04 | N |

TABLE 2-continued

X-RAY DIFFRACTION DATA OF *S. AUREUS* AUTOLYSIN E (AtlE 4PIA) RESIDUES 35-258

| ATOM | 47 | N | TYR | A | 39 | 12.932 | 7.339 | −26.774 | 1.00 | 8.55 | N |
|---|---|---|---|---|---|---|---|---|---|---|---|
| ATOM | 48 | CA | TYR | A | 39 | 13.623 | 8.403 | −25.993 | 1.00 | 8.56 | C |
| ATOM | 49 | C | TYR | A | 39 | 15.004 | 7.934 | −25.567 | 1.00 | 9.75 | C |
| ATOM | 50 | O | TYR | A | 39 | 15.227 | 6.746 | −25.341 | 1.00 | 9.87 | O |
| ATOM | 51 | CB | TYR | A | 39 | 12.822 | 8.778 | −24.736 | 1.00 | 8.95 | C |
| ATOM | 52 | CG | TYR | A | 39 | 11.535 | 9.444 | −25.069 | 1.00 | 8.84 | C |
| ATOM | 53 | CD1 | TYR | A | 39 | 11.519 | 10.816 | −25.344 | 1.00 | 9.00 | C |
| ATOM | 54 | CD2 | TYR | A | 39 | 10.346 | 8.764 | −25.187 | 1.00 | 8.99 | C |
| ATOM | 55 | CE1 | TYR | A | 39 | 10.351 | 11.453 | −25.652 | 1.00 | 9.97 | C |
| ATOM | 56 | CE2 | TYR | A | 39 | 9.171 | 9.416 | −25.535 | 1.00 | 8.56 | C |
| ATOM | 57 | CZ | TYR | A | 39 | 9.181 | 10.766 | −25.768 | 1.00 | 8.90 | C |
| ATOM | 58 | OH | TYR | A | 39 | 8.003 | 11.416 | −26.091 | 1.00 | 9.11 | O |
| ATOM | 59 | N | SER | A | 40 | 15.949 | 8.857 | −25.491 | 1.00 | 10.73 | N |
| ATOM | 60 | CA | SER | A | 40 | 17.183 | 8.598 | −24.787 | 1.00 | 11.27 | C |
| ATOM | 61 | C | SER | A | 40 | 16.920 | 8.453 | −23.294 | 1.00 | 10.90 | C |
| ATOM | 62 | O | SER | A | 40 | 15.887 | 8.939 | −22.747 | 1.00 | 10.82 | O |
| ATOM | 63 | CB | SER | A | 40 | 18.218 | 9.712 | −24.981 | 1.00 | 12.11 | C |
| ATOM | 64 | OG | SER | A | 40 | 17.803 | 10.858 | −24.297 | 1.00 | 13.09 | O |
| ATOM | 65 | N | PHE | A | 41 | 17.852 | 7.800 | −22.601 | 1.00 | 10.57 | N |
| ATOM | 66 | CA | PHE | A | 41 | 17.707 | 7.718 | −21.147 | 1.00 | 10.64 | C |
| ATOM | 67 | C | PHE | A | 41 | 17.603 | 9.056 | −20.497 | 1.00 | 11.38 | C |
| ATOM | 68 | O | PHE | A | 41 | 16.739 | 9.312 | −19.669 | 1.00 | 11.96 | O |
| ATOM | 69 | CB | PHE | A | 41 | 18.874 | 6.853 | −20.562 | 1.00 | 10.89 | C |
| ATOM | 40 | CG | PHE | A | 41 | 18.879 | 6.632 | −19.100 | 1.00 | 11.85 | C |
| ATOM | 71 | CD1 | PHE | A | 41 | 17.831 | 5.808 | −18.569 | 1.00 | 12.56 | C |
| ATOM | 72 | CD2 | PHE | A | 41 | 19.610 | 7.290 | −18.228 | 1.00 | 13.16 | C |
| ATOM | 73 | CE1 | PHE | A | 41 | 17.747 | 5.564 | −17.224 | 1.00 | 14.15 | C |
| ATOM | 74 | CE2 | PHE | A | 41 | 19.478 | 7.077 | −16.861 | 1.00 | 13.79 | C |
| ATOM | 75 | CZ | PHE | A | 41 | 18.566 | 6.185 | −16.368 | 1.00 | 14.56 | C |
| ATOM | 76 | N | ASP | A | 42 | 18.481 | 9.987 | −20.886 | 1.00 | 12.27 | N |
| ATOM | 77 | CA | ASP | A | 42 | 18.464 | 11.302 | −20.267 | 1.00 | 13.54 | C |
| ATOM | 78 | C | ASP | A | 42 | 17.168 | 12.071 | −20.525 | 1.00 | 11.93 | C |
| ATOM | 79 | O | ASP | A | 42 | 16.652 | 12.750 | −19.602 | 1.00 | 12.11 | O |
| ATOM | 80 | CB | ASP | A | 42 | 19.643 | 12.1418 | −20.774 | 1.00 | 16.27 | C |
| ATOM | 81 | CG | ASP | A | 42 | 20.980 | 11.720 | −20.189 | 1.00 | 20.56 | C |
| ATOM | 82 | OD1 | ASP | A | 42 | 21.026 | 10.927 | −19.245 | 1.00 | 22.33 | O |
| ATOM | 83 | OD2 | ASP | A | 42 | 21.984 | 12.249 | −20.768 | 1.00 | 24.00 | O |
| ATOM | 84 | N | GLU | A | 43 | 16.581 | 11.897 | −21.726 | 1.00 | 11.06 | N |
| ATOM | 85 | CA | GLU | A | 43 | 15.276 | 12.512 | −21.990 | 1.00 | 11.31 | C |
| ATOM | 86 | C | GLU | A | 43 | 14.187 | 11.929 | −21.072 | 1.00 | 9.74 | C |
| ATOM | 87 | O | GLU | A | 43 | 13.403 | 12.648 | −20.482 | 1.00 | 10.57 | O |
| ATOM | 88 | CB | GLU | A | 43 | 14.866 | 12.302 | −23.427 | 1.00 | 12.74 | C |
| ATOM | 89 | CG | GLU | A | 43 | 15.655 | 13.133 | −24.454 | 1.00 | 13.82 | C |
| ATOM | 90 | CD | GLU | A | 43 | 15.566 | 12.628 | −25.891 | 1.00 | 17.54 | C |
| ATOM | 91 | OE1 | GLU | A | 43 | 15.094 | 11.519 | −26.278 | 1.00 | 13.79 | O |
| ATOM | 92 | OE2 | GLU | A | 43 | 16.008 | 13.467 | −26.765 | 1.00 | 22.32 | O |
| ATOM | 93 | N | ALA | A | 44 | 14.186 | 10.602 | −20.953 | 1.00 | 9.66 | N |
| ATOM | 94 | CA | ALA | A | 44 | 13.213 | 9.949 | −20.071 | 1.00 | 9.03 | C |
| ATOM | 95 | C | ALA | A | 44 | 13.338 | 10.334 | −18.624 | 1.00 | 8.59 | C |
| ATOM | 96 | O | ALA | A | 44 | 12.363 | 10.586 | −17.909 | 1.00 | 8.73 | O |
| ATOM | 97 | CB | ALA | A | 44 | 13.318 | 8.459 | −20.227 | 1.00 | 9.61 | C |
| ATOM | 98 | N | VAL | A | 45 | 14.590 | 10.423 | −18.159 | 1.00 | 8.86 | N |
| ATOM | 99 | CA | VAL | A | 45 | 14.823 | 10.881 | −16.799 | 1.00 | 9.57 | C |
| ATOM | 100 | C | VAL | A | 45 | 14.234 | 12.271 | −16.555 | 1.00 | 9.28 | C |
| ATOM | 101 | O | VAL | A | 45 | 13.540 | 12.506 | −15.554 | 1.00 | 9.51 | O |
| ATOM | 102 | CB | VAL | A | 45 | 16.358 | 10.893 | −16.451 | 1.00 | 10.76 | C |
| ATOM | 103 | CG1 | VAL | A | 45 | 16.606 | 11.590 | −15.145 | 1.00 | 11.02 | C |
| ATOM | 104 | CG2 | VAL | A | 45 | 16.903 | 9.484 | −16.423 | 1.00 | 10.84 | C |
| ATOM | 105 | N | SER | A | 46 | 14.489 | 13.203 | −17.479 | 1.00 | 9.68 | N |
| ATOM | 106 | CA | ASER | A | 46 | 13.941 | 14.529 | −17.301 | 0.70 | 10.81 | C |
| ATOM | 107 | CA | BSER | A | 46 | 13.937 | 14.551 | −17.358 | 0.30 | 9.87 | C |
| ATOM | 108 | C | SER | A | 46 | 12.410 | 14.535 | −17.225 | 1.00 | 9.50 | C |
| ATOM | 109 | O | SER | A | 46 | 11.829 | 15.276 | −16.463 | 1.00 | 9.71 | O |
| ATOM | 110 | CB | ASER | A | 46 | 14.395 | 15.380 | −18.461 | 0.70 | 12.52 | C |
| ATOM | 111 | CB | BSER | A | 46 | 14.355 | 15.368 | −18.581 | 0.30 | 10.33 | C |
| ATOM | 112 | OG | ASER | A | 46 | 14.031 | 16.720 | −18.193 | 0.70 | 16.54 | O |
| ATOM | 113 | OG | BSER | A | 46 | 15.692 | 15.822 | −18.439 | 0.30 | 11.11 | O |
| ATOM | 114 | N | MET | A | 47 | 11.762 | 13.675 | −18.017 | 1.00 | 8.43 | N |
| ATOM | 115 | CA | MET | A | 47 | 10.316 | 13.526 | −17.974 | 1.00 | 8.20 | C |
| ATOM | 116 | C | MET | A | 47 | 9.857 | 12.983 | −16.616 | 1.00 | 8.00 | C |
| ATOM | 117 | O | MET | A | 47 | 8.908 | 13.474 | −16.068 | 1.00 | 8.28 | O |
| ATOM | 118 | CB | MET | A | 47 | 9.846 | 12.668 | −19.155 | 1.00 | 8.58 | C |
| ATOM | 119 | CG | MET | A | 47 | 10.122 | 13.339 | −20.477 | 1.00 | 8.66 | C |
| ATOM | 120 | SD | MET | A | 47 | 10.017 | 12.315 | −21.963 | 1.00 | 9.33 | S |
| ATOM | 121 | CE | MET | A | 47 | 8.234 | 12.156 | −22.121 | 1.00 | 10.28 | C |
| ATOM | 122 | N | GLN | A | 48 | 10.531 | 11.932 | −16.122 | 1.00 | 7.77 | N |
| ATOM | 123 | CA | GLN | A | 48 | 10.150 | 11.365 | −14.836 | 1.00 | 8.11 | C |
| ATOM | 124 | C | GLN | A | 48 | 10.335 | 12.350 | −13.674 | 1.00 | 8.44 | C |

TABLE 2-continued

X-RAY DIFFRACTION DATA OF *S. AUREUS* AUTOLYSIN E (AtlE 4PIA) RESIDUES 35-258

| ATOM | 125 | O | GLN | A | 48 | 9.635 | 12.252 | −12.674 | 1.00 | 9.07 | O |
|---|---|---|---|---|---|---|---|---|---|---|---|
| ATOM | 126 | CB | GLN | A | 48 | 10.995 | 10.131 | −14.559 | 1.00 | 8.23 | C |
| ATOM | 127 | CG | GLN | A | 48 | 10.863 | 8.984 | −15.534 | 1.00 | 7.89 | C |
| ATOM | 128 | CD | GLN | A | 48 | 9.542 | 8.256 | −15.495 | 1.00 | 7.63 | C |
| ATOM | 129 | OE1 | GLN | A | 48 | 8.694 | 8.485 | −14.636 | 1.00 | 8.36 | O |
| ATOM | 130 | NE2 | GLN | A | 48 | 9.394 | 7.327 | −16.390 | 1.00 | 7.67 | N |
| ATOM | 131 | N | GLN | A | 49 | 11.238 | 13.319 | −13.867 | 1.00 | 8.69 | N |
| ATOM | 132 | CA | GLN | A | 49 | 11.489 | 14.384 | −12.900 | 1.00 | 9.70 | C |
| ATOM | 133 | C | GLN | A | 49 | 10.625 | 15.611 | −13.071 | 1.00 | 10.38 | C |
| ATOM | 134 | O | GLN | A | 49 | 10.811 | 16.655 | −12.399 | 1.00 | 11.00 | O |
| ATOM | 135 | CB | GLN | A | 49 | 12.947 | 14.784 | −12.971 | 1.00 | 9.65 | C |
| ATOM | 136 | CG | GLN | A | 49 | 13.910 | 13.676 | −12.533 | 1.00 | 11.05 | C |
| ATOM | 137 | CD | GLN | A | 49 | 15.359 | 13.943 | −12.881 | 1.00 | 12.64 | C |
| ATOM | 138 | OE1 | GLN | A | 49 | 15.681 | 14.830 | −13.684 | 1.00 | 14.24 | O |
| ATOM | 139 | NE2 | GLN | A | 49 | 16.262 | 13.170 | −12.260 | 1.00 | 13.39 | N |
| ATOM | 140 | N | GLY | A | 50 | 9.659 | 15.531 | −13.987 | 1.00 | 8.85 | N |
| ATOM | 141 | CA | GLY | A | 50 | 8.893 | 16.691 | −14.366 | 1.00 | 9.43 | C |
| ATOM | 142 | C | GLY | A | 50 | 8.027 | 17.284 | −13.314 | 1.00 | 10.06 | C |
| ATOM | 143 | O | GLY | A | 50 | 7.745 | 16.671 | −12.239 | 1.00 | 11.24 | O |
| ATOM | 144 | N | LYS | A | 51 | 7.477 | 18.474 | −13.597 | 1.00 | 11.01 | N |
| ATOM | 145 | CA | LYS | A | 51 | 6.716 | 19.214 | −12.596 | 1.00 | 13.93 | C |
| ATOM | 146 | C | LYS | A | 51 | 5.512 | 18.484 | −12.070 | 1.00 | 13.99 | C |
| ATOM | 147 | O | LYS | A | 51 | 4.687 | 17.983 | −12.795 | 1.00 | 13.21 | O |
| ATOM | 148 | CB | LYS | A | 51 | 6.269 | 20.563 | −13.143 | 1.00 | 16.02 | C |
| ATOM | 149 | CG | LYS | A | 51 | 5.512 | 21.304 | −12.035 | 1.00 | 19.92 | C |
| ATOM | 150 | CD | LYS | A | 51 | 5.204 | 22.720 | −12.408 | 1.00 | 22.96 | C |
| ATOM | 151 | CE | LYS | A | 51 | 4.351 | 23.379 | −11.326 | 1.00 | 22.39 | C |
| ATOM | 152 | NZ | LYS | A | 51 | 5.139 | 23.650 | −10.079 | 1.00 | 27.37 | N |
| ATOM | 153 | N | GLY | A | 52 | 5.427 | 18.396 | −10.733 | 1.00 | 15.93 | N |
| ATOM | 154 | CA | GLY | A | 52 | 4.272 | 17.790 | −10.120 | 1.00 | 17.91 | C |
| ATOM | 155 | C | GLY | A | 52 | 4.183 | 16.282 | −10.105 | 1.00 | 18.74 | C |
| ATOM | 156 | O | GLY | A | 52 | 3.207 | 15.725 | −9.629 | 1.00 | 22.96 | O |
| ATOM | 157 | N | ILE | A | 53 | 5.164 | 15.585 | −10.677 | 1.00 | 15.59 | N |
| ATOM | 158 | CA | ILE | A | 53 | 5.096 | 14.158 | −10.793 | 1.00 | 16.44 | C |
| ATOM | 159 | C | ILE | A | 53 | 5.571 | 13.497 | −9.493 | 1.00 | 18.63 | C |
| ATOM | 160 | O | ILE | A | 53 | 6.711 | 13.701 | −9.055 | 1.00 | 19.29 | O |
| ATOM | 161 | CB | ILE | A | 53 | 5.955 | 13.684 | −11.942 | 1.00 | 15.44 | C |
| ATOM | 162 | CG1 | ILE | A | 53 | 5.339 | 14.170 | −13.272 | 1.00 | 15.04 | C |
| ATOM | 163 | CG2 | ILE | A | 53 | 6.042 | 12.159 | −11.990 | 1.00 | 17.43 | C |
| ATOM | 164 | CD1 | ILE | A | 53 | 6.198 | 13.874 | −14.452 | 1.00 | 14.22 | C |
| ATOM | 165 | N | VAL | A | 54 | 4.704 | 12.668 | −8.938 | 1.00 | 17.27 | N |
| ATOM | 166 | CA | VAL | A | 54 | 4.948 | 12.024 | −7.624 | 1.00 | 18.81 | C |
| ATOM | 167 | C | VAL | A | 54 | 5.719 | 10.735 | −7.783 | 1.00 | 16.27 | C |
| ATOM | 168 | O | VAL | A | 54 | 5.285 | 9.762 | −8.459 | 1.00 | 17.86 | O |
| ATOM | 169 | CB | VAL | A | 54 | 3.608 | 11.740 | −6.905 | 1.00 | 20.19 | C |
| ATOM | 170 | CG1 | VAL | A | 54 | 3.811 | 10.951 | −5.593 | 1.00 | 20.75 | C |
| ATOM | 171 | CG2 | VAL | A | 54 | 2.888 | 13.063 | −6.674 | 1.00 | 23.17 | C |
| ATOM | 172 | N | GLN | A | 55 | 6.917 | 10.761 | −7.248 | 1.00 | 13.30 | N |
| ATOM | 173 | CA | GLN | A | 55 | 7.753 | 9.583 | −7.207 | 1.00 | 12.60 | C |
| ATOM | 174 | C | GLN | A | 55 | 8.144 | 9.478 | −5.750 | 1.00 | 12.95 | C |
| ATOM | 175 | O | GLN | A | 55 | 8.674 | 10.434 | −5.177 | 1.00 | 14.01 | O |
| ATOM | 176 | CB | GLN | A | 55 | 8.963 | 9.698 | −8.107 | 1.00 | 12.83 | C |
| ATOM | 177 | CG | GLN | A | 55 | 8.700 | 10.232 | −9.545 | 1.00 | 13.00 | C |
| ATOM | 178 | CD | GLN | A | 55 | 8.564 | 9.211 | −10.665 | 1.00 | 12.55 | C |
| ATOM | 179 | OE1 | GLN | A | 55 | 8.677 | 9.567 | −11.871 | 1.00 | 11.92 | O |
| ATOM | 180 | NE2 | GLN | A | 55 | 8.333 | 8.025 | −10.367 | 1.00 | 11.21 | N |
| ATOM | 181 | N | THR | A | 56 | 7.961 | 8.285 | −5.175 | 1.00 | 12.32 | N |
| ATOM | 182 | CA | THR | A | 56 | 8.133 | 8.082 | −3.720 | 1.00 | 12.74 | C |
| ATOM | 183 | C | THR | A | 56 | 9.146 | 7.005 | −3.371 | 1.00 | 14.34 | C |
| ATOM | 184 | O | THR | A | 56 | 9.503 | 6.152 | −4.195 | 1.00 | 12.85 | O |
| ATOM | 185 | CB | THR | A | 56 | 6.844 | 7.817 | −3.043 | 1.00 | 13.72 | C |
| ATOM | 186 | OG1 | THR | A | 56 | 6.235 | 6.619 | −3.549 | 1.00 | 13.52 | O |
| ATOM | 187 | CG2 | THR | A | 56 | 5.898 | 9.023 | −3.203 | 1.00 | 15.37 | C |
| ATOM | 188 | N | LYS | A | 57 | 9.635 | 7.061 | −2.120 | 1.00 | 15.28 | N |
| ATOM | 189 | CA | LYS | A | 57 | 10.590 | 6.075 | −1.624 | 1.00 | 17.57 | C |
| ATOM | 190 | C | LYS | A | 57 | 10.291 | 5.833 | −0.142 | 1.00 | 19.35 | C |
| ATOM | 191 | O | LYS | A | 57 | 9.774 | 6.717 | 0.527 | 1.00 | 18.79 | O |
| ATOM | 192 | CB | LYS | A | 57 | 12.025 | 6.586 | −1.805 | 1.00 | 21.61 | C |
| ATOM | 193 | CG | LYS | A | 57 | 13.121 | 5.642 | −1.358 | 1.00 | 28.80 | C |
| ATOM | 194 | CD | LYS | A | 57 | 14.479 | 6.303 | −1.271 | 1.00 | 35.37 | C |
| ATOM | 195 | CE | LYS | A | 57 | 15.444 | 5.400 | −0.498 | 1.00 | 42.30 | C |
| ATOM | 196 | NZ | LYS | A | 57 | 16.836 | 5.495 | −1.024 | 1.00 | 47.58 | N |
| ATOM | 197 | N | GLU | A | 58 | 10.553 | 4.624 | 0.331 | 1.00 | 19.15 | N |
| ATOM | 198 | CA | GLU | A | 58 | 10.332 | 4.285 | 1.751 | 1.00 | 22.86 | C |
| ATOM | 199 | C | GLU | A | 58 | 11.578 | 4.701 | 2.534 | 1.00 | 26.59 | C |
| ATOM | 200 | O | GLU | A | 58 | 12.706 | 4.324 | 2.189 | 1.00 | 26.79 | O |
| ATOM | 201 | CB | GLU | A | 58 | 10.036 | 2.778 | 1.890 | 1.00 | 28.00 | C |
| ATOM | 202 | CG | GLU | A | 58 | 9.031 | 2.381 | 2.968 | 1.00 | 35.93 | C |

TABLE 2-continued

X-RAY DIFFRACTION DATA OF S. AUREUS AUTOLYSIN E (AtlE 4PIA) RESIDUES 35-258

| ATOM | 203 | CD | GLU | A | 58 | 8.290 | 1.076 | 2.629 | 1.00 | 41.37 | C |
|---|---|---|---|---|---|---|---|---|---|---|---|
| ATOM | 204 | OE1 | GLU | A | 58 | 8.826 | 0.259 | 1.829 | 1.00 | 42.32 | O |
| ATOM | 205 | OE2 | GLU | A | 58 | 7.165 | 0.857 | 3.162 | 1.00 | 46.12 | O |
| ATOM | 206 | N | GLU | A | 59 | 11.343 | 5.505 | 3.563 | 1.00 | 25.97 | N |
| ATOM | 207 | CA | GLU | A | 59 | 12.378 | 5.933 | 4.488 | 1.00 | 32.09 | C |
| ATOM | 208 | C | GLU | A | 59 | 11.758 | 6.160 | 5.868 | 1.00 | 27.53 | C |
| ATOM | 209 | O | GLU | A | 59 | 10.648 | 6.660 | 5.970 | 1.00 | 29.08 | O |
| ATOM | 210 | CB | GLU | A | 59 | 13.017 | 7.227 | 3.995 | 1.00 | 34.91 | C |
| ATOM | 211 | CG | GLU | A | 59 | 14.286 | 6.997 | 3.206 | 1.00 | 44.55 | C |
| ATOM | 212 | CD | GLU | A | 59 | 14.719 | 8.235 | 2.460 | 1.00 | 49.72 | C |
| ATOM | 213 | OE1 | GLU | A | 59 | 14.494 | 9.355 | 2.986 | 1.00 | 50.09 | O |
| ATOM | 214 | OE2 | GLU | A | 59 | 15.284 | 8.082 | 1.352 | 1.00 | 59.01 | O |
| ATOM | 215 | N | ASP | A | 60 | 12.504 | 5.808 | 6.919 | 1.00 | 30.78 | N |
| ATOM | 216 | CA | ASP | A | 60 | 12.069 | 6.016 | 8.322 | 1.00 | 30.17 | C |
| ATOM | 217 | C | ASP | A | 60 | 10.661 | 5.499 | 8.569 | 1.00 | 27.39 | C |
| ATOM | 218 | O | ASP | A | 60 | 9.856 | 6.149 | 9.235 | 1.00 | 29.92 | O |
| ATOM | 219 | CB | ASP | A | 60 | 12.142 | 7.509 | 8.738 | 1.00 | 36.59 | C |
| ATOM | 220 | CG | ASP | A | 60 | 13.522 | 8.132 | 8.520 | 1.00 | 40.73 | C |
| ATOM | 221 | OD1 | ASP | A | 60 | 14.569 | 7.471 | 8.742 | 1.00 | 43.76 | O |
| ATOM | 222 | OD2 | ASP | A | 60 | 13.551 | 9.314 | 8.120 | 1.00 | 46.48 | O |
| ATOM | 223 | N | GLY | A | 61 | 10.339 | 4.346 | 7.987 | 1.00 | 24.29 | N |
| ATOM | 224 | CA | GLY | A | 61 | 9.047 | 3.725 | 8.169 | 1.00 | 24.48 | C |
| ATOM | 225 | C | GLY | A | 61 | 7.852 | 4.187 | 7.337 | 1.00 | 26.72 | C |
| ATOM | 226 | O | GLY | A | 61 | 6.725 | 3.741 | 7.554 | 1.00 | 27.47 | O |
| ATOM | 227 | N | LYS | A | 62 | 8.079 | 5.085 | 6.383 | 1.00 | 24.80 | N |
| ATOM | 228 | CA | LYS | A | 62 | 6.947 | 5.599 | 5.622 | 1.00 | 23.66 | C |
| ATOM | 229 | C | LYS | A | 62 | 7.414 | 6.026 | 4.254 | 1.00 | 21.31 | C |
| ATOM | 230 | O | LYS | A | 62 | 8.592 | 6.037 | 3.974 | 1.00 | 21.94 | O |
| ATOM | 231 | CB | LYS | A | 62 | 6.310 | 6.766 | 6.359 | 1.00 | 29.91 | C |
| ATOM | 232 | CG | LYS | A | 62 | 7.255 | 7.927 | 6.595 | 1.00 | 31.81 | C |
| ATOM | 233 | CD | LYS | A | 62 | 6.563 | 8.952 | 7.496 | 1.00 | 38.79 | C |
| ATOM | 234 | CE | LYS | A | 62 | 6.789 | 10.370 | 7.007 | 1.00 | 42.03 | C |
| ATOM | 235 | NZ | LYS | A | 62 | 8.214 | 10.778 | 7.173 | 1.00 | 44.24 | N |
| ATOM | 236 | N | PHE | A | 63 | 6.464 | 6.441 | 3.441 | 1.00 | 21.59 | N |
| ATOM | 237 | CA | PHE | A | 63 | 6.808 | 6.954 | 2.106 | 1.00 | 20.61 | C |
| ATOM | 238 | C | PHE | A | 63 | 6.998 | 8.448 | 2.109 | 1.00 | 20.37 | C |
| ATOM | 239 | O | PHE | A | 63 | 6.191 | 9.175 | 2.714 | 1.00 | 24.87 | O |
| ATOM | 240 | CB | PHE | A | 63 | 5.734 | 6.544 | 1.120 | 1.00 | 21.40 | C |
| ATOM | 241 | CG | PHE | A | 63 | 5.871 | 5.133 | 0.694 | 1.00 | 21.27 | C |
| ATOM | 242 | CD1 | PHE | A | 63 | 6.742 | 4.807 | −0.324 | 1.00 | 20.89 | C |
| ATOM | 243 | CD2 | PHE | A | 63 | 5.198 | 4.125 | 1.377 | 1.00 | 26.11 | C |
| ATOM | 244 | CE1 | PHE | A | 63 | 6.866 | 3.501 | −0.738 | 1.00 | 24.44 | C |
| ATOM | 245 | CE2 | PHE | A | 63 | 5.343 | 2.799 | 0.985 | 1.00 | 26.70 | C |
| ATOM | 246 | CZ | PHE | A | 63 | 6.184 | 2.496 | −0.080 | 1.00 | 25.68 | C |
| ATOM | 247 | N | VAL | A | 64 | 8.082 | 8.885 | 1.482 | 1.00 | 20.15 | N |
| ATOM | 248 | CA | VAL | A | 64 | 8.386 | 10.292 | 1.241 | 1.00 | 20.78 | C |
| ATOM | 249 | C | VAL | A | 64 | 8.691 | 10.523 | −0.242 | 1.00 | 20.01 | C |
| ATOM | 250 | O | VAL | A | 64 | 8.898 | 9.578 | −1.015 | 1.00 | 17.55 | O |
| ATOM | 251 | CB | VAL | A | 64 | 9.593 | 10.736 | 2.080 | 1.00 | 23.23 | C |
| ATOM | 252 | CG1 | VAL | A | 64 | 9.357 | 10.443 | 3.573 | 1.00 | 26.08 | C |
| ATOM | 253 | CG2 | VAL | A | 64 | 10.879 | 10.073 | 1.649 | 1.00 | 21.71 | C |
| ATOM | 254 | N | GLU | A | 65 | 8.727 | 11.772 | −0.679 | 1.00 | 19.26 | N |
| ATOM | 255 | CA | GLU | A | 65 | 9.067 | 12.058 | −2.078 | 1.00 | 18.64 | C |
| ATOM | 256 | C | GLU | A | 65 | 10.504 | 11.705 | −2.351 | 1.00 | 18.55 | C |
| ATOM | 257 | O | GLU | A | 65 | 11.431 | 12.028 | −1.593 | 1.00 | 20.32 | O |
| ATOM | 258 | CB | GLU | A | 65 | 8.773 | 13.543 | −2.430 | 1.00 | 20.30 | C |
| ATOM | 259 | CG | GLU | A | 65 | 8.883 | 13.827 | −3.929 | 1.00 | 20.56 | C |
| ATOM | 260 | CD | GLU | A | 65 | 7.715 | 13.267 | −4.757 | 1.00 | 21.82 | C |
| ATOM | 261 | OE1 | GLU | A | 65 | 6.717 | 12.783 | −4.227 | 1.00 | 24.78 | O |
| ATOM | 262 | OE2 | GLU | A | 65 | 7.790 | 13.334 | −6.018 | 1.00 | 21.81 | O |
| ATOM | 263 | N | ALA | A | 66 | 10.777 | 11.007 | −3.463 | 1.00 | 16.00 | N |
| ATOM | 264 | CA | ALA | A | 66 | 12.100 | 10.688 | −3.880 | 1.00 | 16.32 | C |
| ATOM | 265 | C | ALA | A | 66 | 12.733 | 11.932 | −4.503 | 1.00 | 16.97 | C |
| ATOM | 266 | O | ALA | A | 66 | 12.013 | 12.671 | −5.190 | 1.00 | 18.47 | O |
| ATOM | 267 | CB | ALA | A | 66 | 12.076 | 9.547 | −4.907 | 1.00 | 17.76 | C |
| ATOM | 268 | N | ASN | A | 67 | 14.038 | 12.109 | −4.369 | 1.00 | 17.37 | N |
| ATOM | 269 | CA | ASN | A | 67 | 14.665 | 13.227 | −5.057 | 1.00 | 17.30 | C |
| ATOM | 270 | C | ASN | A | 67 | 15.037 | 12.853 | −6.494 | 1.00 | 18.18 | C |
| ATOM | 271 | O | ASN | A | 67 | 14.936 | 11.688 | −6.910 | 1.00 | 16.63 | O |
| ATOM | 272 | CB | ASN | A | 67 | 15.861 | 13.789 | −4.252 | 1.00 | 18.42 | C |
| ATOM | 273 | CG | ASN | A | 67 | 16.964 | 12.827 | −4.098 | 1.00 | 20.58 | C |
| ATOM | 274 | OD1 | ASN | A | 67 | 17.359 | 12.138 | −5.015 | 1.00 | 18.66 | O |
| ATOM | 275 | ND2 | ASN | A | 67 | 17.583 | 12.833 | −2.889 | 1.00 | 25.30 | N |
| ATOM | 276 | N | ASN | A | 67 | 15.507 | 13.813 | −7.286 | 1.00 | 16.23 | N |
| ATOM | 277 | CA | ASN | A | 67 | 15.843 | 13.561 | −8.646 | 1.00 | 16.52 | C |
| ATOM | 278 | C | ASN | A | 67 | 16.923 | 12.523 | −8.828 | 1.00 | 16.04 | C |
| ATOM | 279 | O | ASN | A | 67 | 16.854 | 11.699 | −9.752 | 1.00 | 14.61 | O |
| ATOM | 280 | CB | ASN | A | 67 | 16.246 | 14.879 | −9.328 | 1.00 | 16.20 | C |

TABLE 2-continued

X-RAY DIFFRACTION DATA OF S. AUREUS AUTOLYSIN E (AtlE 4PIA) RESIDUES 35-258

| ATOM | 281 | CG | ASN | A | 68 | 15.083 | 15.746 | −9.721 | 1.00 | 17.35 | C |
|------|-----|-----|-----|---|-----|--------|--------|--------|------|-------|---|
| ATOM | 282 | OD1 | ASN | A | 68 | 15.301 | 16.922 | −10.119 | 1.00 | 26.40 | O |
| ATOM | 283 | ND2 | ASN | A | 68 | 13.885 | 15.262 | −9.603 | 1.00 | 15.74 | N |
| ATOM | 284 | N | ASN | A | 69 | 17.956 | 12.525 | −7.974 | 1.00 | 17.17 | N |
| ATOM | 285 | CA | ASN | A | 69 | 18.990 | 11.506 | −8.109 | 1.00 | 18.83 | C |
| ATOM | 286 | C | ASN | A | 69 | 18.434 | 10.102 | −7.833 | 1.00 | 15.62 | C |
| ATOM | 287 | O | ASN | A | 69 | 18.830 | 9.171 | −8.527 | 1.00 | 16.15 | O |
| ATOM | 288 | CB | ASN | A | 69 | 20.190 | 11.783 | −7.165 | 1.00 | 22.39 | C |
| ATOM | 289 | CG | ASN | A | 69 | 21.005 | 12.976 | −7.624 | 1.00 | 30.98 | C |
| ATOM | 290 | OD1 | ASN | A | 69 | 21.050 | 13.286 | −8.812 | 1.00 | 35.68 | O |
| ATOM | 291 | ND2 | ASN | A | 69 | 21.645 | 13.662 | −6.689 | 1.00 | 35.75 | N |
| ATOM | 292 | N | GLU | A | 70 | 17.564 | 9.980 | −6.852 | 1.00 | 14.97 | N |
| ATOM | 293 | CA | GLU | A | 70 | 17.000 | 8.685 | −6.510 | 1.00 | 15.51 | C |
| ATOM | 294 | C | GLU | A | 70 | 16.134 | 8.153 | −7.656 | 1.00 | 14.44 | C |
| ATOM | 295 | O | GLU | A | 70 | 16.153 | 6.990 | −7.965 | 1.00 | 14.94 | O |
| ATOM | 296 | CB | GLU | A | 70 | 16.188 | 8.773 | −5.256 | 1.00 | 16.11 | C |
| ATOM | 297 | CG | GLU | A | 70 | 17.111 | 8.948 | −4.041 | 1.00 | 18.28 | C |
| ATOM | 298 | CD | GLU | A | 70 | 16.378 | 9.405 | −2.812 | 1.00 | 20.91 | C |
| ATOM | 299 | OE1 | GLU | A | 70 | 15.312 | 10.033 | −2.850 | 1.00 | 20.82 | O |
| ATOM | 300 | OE2 | GLU | A | 70 | 16.932 | 9.149 | −1.688 | 1.00 | 25.04 | O |
| ATOM | 301 | N | ILE | A | 71 | 15.408 | 9.051 | −8.288 | 1.00 | 14.15 | N |
| ATOM | 302 | CA | ILE | A | 71 | 14.530 | 8.649 | −9.436 | 1.00 | 12.01 | C |
| ATOM | 303 | C | ILE | A | 71 | 15.405 | 8.163 | −10.550 | 1.00 | 12.33 | C |
| ATOM | 304 | O | ILE | A | 71 | 15.189 | 7.073 | −11.083 | 1.00 | 11.90 | O |
| ATOM | 305 | CB | ILE | A | 71 | 13.730 | 9.853 | −9.925 | 1.00 | 12.43 | C |
| ATOM | 306 | CG1 | ILE | A | 71 | 12.660 | 10.202 | −8.953 | 1.00 | 12.90 | C |
| ATOM | 307 | CG2 | ILE | A | 71 | 13.045 | 9.530 | −11.280 | 1.00 | 11.69 | C |
| ATOM | 308 | CD1 | ILE | A | 71 | 12.092 | 11.618 | −9.135 | 1.00 | 14.32 | C |
| ATOM | 309 | N | ALA | A | 72 | 16.453 | 8.903 | −10.919 | 1.00 | 12.16 | N |
| ATOM | 310 | CA | ALA | A | 72 | 17.354 | 8.512 | −11.956 | 1.00 | 13.18 | C |
| ATOM | 311 | C | ALA | A | 72 | 18.041 | 7.171 | −11.684 | 1.00 | 13.53 | C |
| ATOM | 312 | O | ALA | A | 72 | 18.161 | 6.331 | −12.582 | 1.00 | 14.62 | O |
| ATOM | 313 | CB | ALA | A | 72 | 18.423 | 9.609 | −12.198 | 1.00 | 13.37 | C |
| ATOM | 314 | N | LYS | A | 73 | 18.461 | 6.959 | −10.419 | 1.00 | 14.30 | N |
| ATOM | 315 | CA | LYS | A | 73 | 19.115 | 5.697 | −10.107 | 1.00 | 17.04 | C |
| ATOM | 316 | C | LYS | A | 73 | 18.136 | 4.546 | −10.200 | 1.00 | 14.67 | C |
| ATOM | 317 | O | LYS | A | 73 | 18.482 | 3.478 | −10.709 | 1.00 | 14.89 | O |
| ATOM | 318 | CB | LYS | A | 73 | 19.746 | 5.818 | −8.709 | 1.00 | 19.83 | C |
| ATOM | 319 | CG | LYS | A | 73 | 20.979 | 6.731 | −8.704 | 1.00 | 26.39 | C |
| ATOM | 320 | CD | LYS | A | 73 | 21.675 | 6.861 | −7.345 | 1.00 | 33.08 | C |
| ATOM | 321 | CE | LYS | A | 73 | 22.614 | 8.078 | −7.383 | 1.00 | 37.13 | C |
| ATOM | 322 | NZ | LYS | A | 73 | 23.427 | 8.322 | −6.157 | 1.00 | 43.31 | N |
| ATOM | 323 | N | ALA | A | 74 | 16.913 | 4.772 | −9.759 | 1.00 | 13.64 | N |
| ATOM | 324 | CA | ALA | A | 74 | 15.900 | 3.689 | −9.744 | 1.00 | 12.63 | C |
| ATOM | 325 | C | ALA | A | 74 | 15.535 | 3.197 | −11.126 | 1.00 | 13.29 | C |
| ATOM | 326 | O | ALA | A | 74 | 15.265 | 2.011 | −11.346 | 1.00 | 14.88 | O |
| ATOM | 327 | CB | ALA | A | 74 | 14.673 | 4.102 | −8.964 | 1.00 | 13.11 | C |
| ATOM | 328 | N | MET | A | 75 | 15.568 | 4.101 | −12.102 | 1.00 | 12.75 | N |
| ATOM | 329 | CA | MET | A | 75 | 15.191 | 3.734 | −13.459 | 1.00 | 13.17 | C |
| ATOM | 330 | C | MET | A | 75 | 16.352 | 3.231 | −14.306 | 1.00 | 13.36 | C |
| ATOM | 331 | O | MET | A | 75 | 16.173 | 2.764 | −15.433 | 1.00 | 13.13 | O |
| ATOM | 332 | CB | MET | A | 75 | 14.386 | 4.910 | −14.093 | 1.00 | 16.87 | C |
| ATOM | 333 | CG | MET | A | 75 | 15.116 | 6.148 | −14.238 | 1.00 | 16.12 | C |
| ATOM | 334 | SD | MET | A | 75 | 14.057 | 7.538 | −14.804 | 1.00 | 11.79 | S |
| ATOM | 335 | CE | MET | A | 75 | 13.921 | 7.112 | −16.529 | 1.00 | 11.78 | C |
| ATOM | 336 | N | THR | A | 76 | 17.591 | 3.255 | −13.776 | 1.00 | 14.14 | N |
| ATOM | 337 | CA | THR | A | 76 | 18.710 | 2.700 | −14.476 | 1.00 | 15.83 | C |
| ATOM | 338 | C | THR | A | 76 | 18.573 | 1.191 | −14.653 | 1.00 | 16.94 | C |
| ATOM | 339 | O | THR | A | 76 | 18.051 | 0.512 | −13.787 | 1.00 | 18.64 | O |
| ATOM | 340 | CB | THR | A | 76 | 20.001 | 3.057 | −13.688 | 1.00 | 18.74 | C |
| ATOM | 341 | OG1 | THR | A | 76 | 20.122 | 4.478 | −13.650 | 1.00 | 21.20 | O |
| ATOM | 342 | CG2 | THR | A | 76 | 21.216 | 2.536 | −14.325 | 1.00 | 20.55 | C |
| ATOM | 343 | N | ILE | A | 77 | 19.016 | 0.675 | −15.786 | 1.00 | 18.90 | N |
| ATOM | 344 | CA | ILE | A | 77 | 18.871 | −0.737 | −16.060 | 1.00 | 21.35 | C |
| ATOM | 345 | C | ILE | A | 77 | 20.085 | −1.534 | −15.615 | 1.00 | 26.22 | C |
| ATOM | 346 | O | ILE | A | 77 | 21.190 | −1.257 | −16.059 | 1.00 | 25.60 | O |
| ATOM | 347 | CB | ILE | A | 77 | 18.548 | −0.978 | −17.512 | 1.00 | 23.15 | C |
| ATOM | 348 | CG1 | ILE | A | 77 | 17.098 | −0.484 | −17.758 | 1.00 | 25.49 | C |
| ATOM | 349 | CG2 | ILE | A | 77 | 18.629 | −2.464 | −17.853 | 1.00 | 22.44 | C |
| ATOM | 350 | CD1 | ILE | A | 77 | 16.949 | 0.109 | −19.095 | 1.00 | 27.57 | C |
| ATOM | 351 | N | SER | A | 78 | 19.839 | −2.514 | −14.755 | 1.00 | 28.05 | N |
| ATOM | 352 | CA | SER | A | 78 | 20.919 | −3.271 | −14.086 | 1.00 | 35.77 | C |
| ATOM | 353 | C | SER | A | 78 | 20.566 | −4.743 | −13.934 | 1.00 | 38.52 | C |
| ATOM | 354 | O | SER | A | 78 | 20.020 | −5.337 | −14.867 | 1.00 | 46.11 | O |
| ATOM | 355 | CB | SER | A | 78 | 21.193 | −2.690 | −12.707 | 1.00 | 39.22 | C |
| ATOM | 356 | OG | SER | A | 78 | 21.436 | −1.299 | −12.791 | 1.00 | 49.48 | O |
| ATOM | 357 | N | ASP | A | 81 | 17.749 | −9.240 | −9.122 | 1.00 | 29.91 | N |
| ATOM | 358 | CA | ASP | A | 81 | 16.763 | −10.324 | −8.942 | 1.00 | 30.18 | C |

TABLE 2-continued

X-RAY DIFFRACTION DATA OF *S. AUREUS* AUTOLYSIN E (AtlE 4PIA) RESIDUES 35-258

| ATOM | 359 | C | ASP | A | 81 | 16.650 | −11.158 | −10.213 | 1.00 | 29.37 | C |
|---|---|---|---|---|---|---|---|---|---|---|---|
| ATOM | 360 | O | ASP | A | 81 | 15.518 | −11.413 | −10.630 | 1.00 | 27.18 | O |
| ATOM | 361 | CB | ASP | A | 81 | 15.327 | −9.792 | −8.535 | 1.00 | 29.40 | C |
| ATOM | 362 | CG | ASP | A | 81 | 15.304 | −9.039 | −7.174 | 1.00 | 33.79 | C |
| ATOM | 363 | OD1 | ASP | A | 81 | 15.894 | −9.591 | −6.206 | 1.00 | 35.75 | O |
| ATOM | 364 | OD2 | ASP | A | 81 | 14.684 | −7.923 | −7.027 | 1.00 | 33.56 | O |
| ATOM | 365 | N | ASN | A | 82 | 17.791 | −11.614 | −10.783 | 1.00 | 28.93 | N |
| ATOM | 366 | CA | ASN | A | 82 | 17.828 | −12.503 | −11.978 | 1.00 | 24.97 | C |
| ATOM | 367 | C | ASN | A | 82 | 16.993 | −11.910 | −13.138 | 1.00 | 23.71 | C |
| ATOM | 368 | O | ASN | A | 82 | 16.385 | −12.638 | −13.990 | 1.00 | 23.74 | O |
| ATOM | 369 | CB | ASN | A | 82 | 17.347 | −13.919 | −11.637 | 1.00 | 27.93 | C |
| ATOM | 370 | CG | ASN | A | 82 | 18.345 | −14.664 | −10.778 | 1.00 | 29.75 | C |
| ATOM | 371 | OD1 | ASN | A | 82 | 19.241 | −15.375 | −11.282 | 1.00 | 35.66 | O |
| ATOM | 372 | ND2 | ASN | A | 82 | 18.234 | −14.472 | −9.487 | 1.00 | 26.95 | N |
| ATOM | 373 | N | ASP | A | 83 | 16.976 | −10.565 | −13.154 | 1.00 | 20.97 | N |
| ATOM | 374 | CA | ASP | A | 83 | 16.309 | −9.854 | −14.235 | 1.00 | 22.23 | C |
| ATOM | 375 | C | ASP | A | 83 | 14.819 | −10.120 | −14.246 | 1.00 | 18.07 | C |
| ATOM | 376 | O | ASP | A | 83 | 14.183 | −9.958 | −15.312 | 1.00 | 14.19 | O |
| ATOM | 377 | CB | ASP | A | 83 | 16.876 | −10.186 | −15.620 | 1.00 | 27.65 | C |
| ATOM | 378 | CG | ASP | A | 83 | 18.338 | −9.769 | −15.837 | 1.00 | 31.98 | C |
| ATOM | 379 | OD1 | ASP | A | 83 | 18.754 | −8.620 | −15.601 | 1.00 | 36.88 | O |
| ATOM | 380 | OD2 | ASP | A | 83 | 19.055 | −10.636 | −16.372 | 1.00 | 38.49 | O |
| ATOM | 381 | N | MET | A | 84 | 14.204 | −10.488 | −13.128 | 1.00 | 13.74 | N |
| ATOM | 382 | CA | MET | A | 84 | 12.766 | −10.700 | −13.081 | 1.00 | 14.26 | C |
| ATOM | 383 | C | MET | A | 84 | 12.023 | −9.406 | −13.433 | 1.00 | 11.96 | C |
| ATOM | 384 | O | MET | A | 84 | 10.922 | −9.496 | −13.981 | 1.00 | 11.99 | O |
| ATOM | 385 | CB | MET | A | 84 | 12.188 | −11.139 | −11.698 | 1.00 | 15.85 | C |
| ATOM | 386 | CG | MET | A | 84 | 12.336 | −12.519 | −11.129 | 1.00 | 20.01 | C |
| ATOM | 387 | SD | MET | A | 84 | 11.258 | −13.670 | −12.051 | 1.00 | 26.25 | S |
| ATOM | 388 | CE | MET | A | 84 | 12.651 | −14.093 | −12.949 | 1.00 | 16.45 | C |
| ATOM | 389 | N | LYS | A | 85 | 12.563 | −8.217 | −13.149 | 1.00 | 10.40 | N |
| ATOM | 390 | CA | ALYS | A | 85 | 11.938 | −6.925 | −13.531 | 0.70 | 10.95 | C |
| ATOM | 391 | CA | BLYS | A | 85 | 11.788 | −7.030 | −13.520 | 0.30 | 10.01 | C |
| ATOM | 392 | C | LYS | A | 85 | 11.826 | −6.793 | −15.024 | 1.00 | 10.17 | C |
| ATOM | 393 | O | LYS | A | 85 | 11.038 | −5.946 | −15.512 | 1.00 | 9.05 | O |
| ATOM | 394 | CB | ALYS | A | 85 | 12.793 | −5.753 | −13.020 | 0.70 | 12.73 | C |
| ATOM | 395 | CB | BLYS | A | 85 | 12.211 | −5.813 | −12.724 | 0.30 | 10.03 | C |
| ATOM | 396 | CG | ALYS | A | 85 | 12.853 | −5.618 | −11.507 | 0.70 | 16.14 | C |
| ATOM | 397 | CG | BLYS | A | 85 | 13.595 | −5.311 | −13.067 | 0.30 | 10.33 | C |
| ATOM | 398 | CF | ALYS | A | 85 | 13.360 | −4.238 | −11.077 | 0.70 | 16.2 | C |
| ATOM | 399 | CF | BLYS | A | 85 | 13.880 | −4.016 | −12.331 | 0.30 | 10.73 | C |
| ATOM | 400 | CE | ALYS | A | 85 | 14.792 | −3.899 | −11.515 | 0.70 | 18.08 | C |
| ATOM | 401 | CE | BLYS | A | 85 | 14.470 | −4.207 | −10.940 | 0.30 | 11.00 | C |
| ATOM | 402 | NZ | ALYS | A | 85 | 15.169 | −2.629 | −10.807 | 0.70 | 17.19 | N |
| ATOM | 403 | NZ | BLYS | A | 85 | 14.951 | −2.880 | −10.414 | 0.30 | 10.70 | N |
| ATOM | 404 | N | TYR | A | 86 | 12.680 | −7.492 | −15.768 | 1.00 | 8.67 | N |
| ATOM | 405 | CA | TYR | A | 86 | 12.759 | −7.359 | −17.210 | 1.00 | 9.18 | C |
| ATOM | 406 | C | TYR | A | 86 | 12.191 | −8.526 | −17.961 | 1.00 | 9.12 | C |
| ATOM | 407 | O | TYR | A | 86 | 12.320 | −8.626 | −19.186 | 1.00 | 9.75 | O |
| ATOM | 408 | CB | TYR | A | 86 | 14.253 | −7.126 | −17.586 | 1.00 | 9.54 | C |
| ATOM | 409 | CG | TYR | A | 86 | 14.895 | −6.003 | −16.844 | 1.00 | 10.25 | C |
| ATOM | 410 | CD1 | TYR | A | 86 | 14.522 | −4.704 | −17.062 | 1.00 | 11.51 | C |
| ATOM | 411 | CD2 | TYR | A | 86 | 15.842 | −6.228 | −15.867 | 1.00 | 11.51 | C |
| ATOM | 412 | CE1 | TYR | A | 86 | 15.040 | −3.677 | −16.352 | 1.00 | 12.06 | C |
| ATOM | 413 | CE2 | TYR | A | 86 | 16.413 | −5.195 | −15.166 | 1.00 | 13.01 | C |
| ATOM | 414 | CZ | TYR | A | 86 | 16.020 | −3.917 | −15.415 | 1.00 | 13.13 | C |
| ATOM | 415 | OH | TYR | A | 86 | 16.606 | −2.902 | −14.659 | 1.00 | 15.89 | O |
| ATOM | 416 | N | MET | A | 87 | 11.514 | −9.439 | −17.252 | 1.00 | 8.35 | N |
| ATOM | 417 | CA | MET | A | 87 | 10.998 | −10.647 | −17.824 | 1.00 | 8.34 | C |
| ATOM | 418 | C | MET | A | 87 | 9.544 | −10.509 | −18.245 | 1.00 | 8.28 | C |
| ATOM | 419 | O | MET | A | 87 | 8.681 | −10.033 | −17.476 | 1.00 | 8.19 | O |
| ATOM | 420 | CB | MET | A | 87 | 11.086 | −11.802 | −16.791 | 1.00 | 8.79 | C |
| ATOM | 421 | CG | MET | A | 87 | 10.741 | −13.145 | −17.384 | 1.00 | 8.66 | C |
| ATOM | 422 | SD | MET | A | 87 | 10.516 | −14.431 | −16.127 | 1.00 | 9.82 | S |
| ATOM | 423 | CE | MET | A | 87 | 8.974 | −13.860 | −15.454 | 1.00 | 10.45 | C |
| ATOM | 424 | N | ASP | A | 88 | 9.208 | −10.968 | −19.434 | 1.00 | 8.46 | N |
| ATOM | 425 | CA | ASP | A | 88 | 7.842 | −10.959 | −19.919 | 1.00 | 8.62 | C |
| ATOM | 426 | C | ASP | A | 88 | 6.945 | −11.720 | −18.951 | 1.00 | 8.30 | C |
| ATOM | 427 | O | ASP | A | 88 | 7.227 | −12.920 | −18.677 | 1.00 | 8.85 | O |
| ATOM | 428 | CB | ASP | A | 88 | 7.866 | −11.654 | −21.301 | 1.00 | 9.83 | C |
| ATOM | 429 | CG | ASP | A | 88 | 6.577 | −11.697 | −21.985 | 1.00 | 11.82 | C |
| ATOM | 430 | OD1 | ASP | A | 88 | 5.503 | −11.347 | −21.486 | 1.00 | 10.23 | O |
| ATOM | 431 | OD2 | ASP | A | 88 | 6.617 | −12.171 | −23.165 | 1.00 | 17.68 | O |
| ATOM | 432 | N | ILE | A | 89 | 5.895 | −11.068 | −18.450 | 1.00 | 7.20 | N |
| ATOM | 433 | CA | ILE | A | 89 | 4.945 | −11.682 | −17.505 | 1.00 | 7.68 | C |
| ATOM | 434 | C | ILE | A | 89 | 3.600 | −11.894 | −18.154 | 1.00 | 7.54 | C |
| ATOM | 435 | O | ILE | A | 89 | 2.577 | −12.121 | −17.458 | 1.00 | 7.42 | O |
| ATOM | 436 | CB | ILE | A | 89 | 4.850 | −10.846 | −16.200 | 1.00 | 7.37 | C |

TABLE 2-continued

X-RAY DIFFRACTION DATA OF *S. AUREUS* AUTOLYSIN E (AtlE 4PIA) RESIDUES 35-258

| ATOM | 437 | CG1 | ILE | A | 89 | 4.711 | −9.325 | −16.485 | 1.00 | 7.30 | C |
|---|---|---|---|---|---|---|---|---|---|---|---|
| ATOM | 438 | CG2 | ILE | A | 89 | 6.036 | −11.160 | −15.298 | 1.00 | 7.41 | C |
| ATOM | 439 | CD1 | ILE | A | 89 | 4.392 | −8.462 | −15.267 | 1.00 | 7.30 | C |
| ATOM | 440 | N | THR | A | 90 | 3.572 | −11.856 | −19.499 | 1.00 | 7.80 | N |
| ATOM | 441 | CA | THR | A | 90 | 2.348 | −12.014 | −20.262 | 1.00 | 8.47 | C |
| ATOM | 442 | C | THR | A | 90 | 2.205 | −13.424 | −20.766 | 1.00 | 9.89 | C |
| ATOM | 443 | O | THR | A | 90 | 1.355 | −13.627 | −21.644 | 1.00 | 10.30 | O |
| ATOM | 444 | CB | THR | A | 90 | 2.288 | −10.953 | −21.439 | 1.00 | 9.39 | C |
| ATOM | 445 | OG1 | THR | A | 90 | 3.112 | −11.412 | −22.513 | 1.00 | 11.38 | O |
| ATOM | 446 | CG2 | THR | A | 90 | 2.655 | −9.625 | −20.981 | 1.00 | 10.26 | C |
| ATOM | 447 | N | GLU | A | 91 | 2.951 | −14.355 | −20.227 | 1.00 | 10.10 | N |
| ATOM | 448 | CA | AGLU | A | 91 | 2.834 | −15.788 | −20.545 | 0.50 | 12.01 | C |
| ATOM | 449 | CA | BGLU | A | 91 | 2.747 | −15.764 | −20.545 | 0.50 | 12.03 | C |
| ATOM | 450 | C | GLU | A | 91 | 2.449 | −16.503 | −19.263 | 1.00 | 12.99 | C |
| ATOM | 451 | O | GLU | A | 91 | 2.477 | −15.938 | −18.196 | 1.00 | 13.57 | O |
| ATOM | 452 | CB | AGLU | A | 91 | 4.170 | −16.351 | −21.070 | 0.50 | 13.47 | C |
| ATOM | 453 | CB | BGLU | A | 91 | 3.972 | −16.299 | −21.266 | 0.50 | 13.97 | C |
| ATOM | 454 | CG | AGLU | A | 91 | 4.774 | −15.645 | −22.288 | 0.50 | 15.79 | C |
| ATOM | 455 | CG | BGLU | A | 91 | 4.159 | −15.626 | −22.625 | 0.50 | 16.36 | C |
| ATOM | 456 | CD | AGLU | A | 91 | 4.091 | −15.985 | −23.607 | 0.50 | 18.48 | C |
| ATOM | 457 | CD | BGLU | A | 91 | 5.047 | −16.424 | −23.536 | 0.50 | 19.06 | C |
| ATOM | 458 | OE1 | AGLU | A | 91 | 2.978 | −16.511 | −23.624 | 0.50 | 22.02 | O |
| ATOM | 459 | OE1 | BGLU | A | 91 | 6.217 | −16.598 | −23.174 | 0.50 | 21.30 | O |
| ATOM | 460 | OE2 | AGLU | A | 91 | 4.707 | −15.731 | −24.665 | 0.50 | 23.00 | O |
| ATOM | 461 | OE2 | BGLU | A | 91 | 4.546 | −16.875 | −24.609 | 0.50 | 24.10 | O |
| ATOM | 462 | N | LYS | A | 92 | 2.069 | −17.730 | −19.385 | 1.00 | 11.71 | N |
| ATOM | 463 | CA | LYS | A | 92 | 1.605 | −18.552 | −18.266 | 1.00 | 11.28 | C |
| ATOM | 464 | C | LYS | A | 92 | 2.707 | −19.402 | −17.766 | 1.00 | 11.53 | C |
| ATOM | 465 | O | LYS | A | 92 | 3.672 | −19.673 | −18.513 | 1.00 | 12.63 | O |
| ATOM | 466 | CB | LYS | A | 92 | 0.447 | −19.371 | −18.726 | 1.00 | 12.06 | C |
| ATOM | 467 | CG | LYS | A | 92 | −0.682 | −18.486 | −19.159 | 1.00 | 12.14 | C |
| ATOM | 468 | CD | LYS | A | 92 | −1.908 | −19.241 | −19.509 | 1.00 | 13.26 | C |
| ATOM | 469 | CE | LYS | A | 92 | −1.694 | −19.998 | −20.799 | 1.00 | 16.69 | C |
| ATOM | 470 | NZ | LYS | A | 92 | −2.969 | −20.498 | −21.223 | 1.00 | 18.41 | N |
| ATOM | 471 | N | VAL | A | 93 | 2.650 | −19.819 | −16.503 | 1.00 | 9.15 | N |
| ATOM | 472 | CA | VAL | A | 93 | 3.630 | −20.728 | −15.931 | 1.00 | 9.90 | C |
| ATOM | 473 | C | VAL | A | 93 | 2.942 | −21.973 | −15.440 | 1.00 | 9.37 | C |
| ATOM | 474 | O | VAL | A | 93 | 1.785 | −21.937 | −15.043 | 1.00 | 9.19 | O |
| ATOM | 475 | CB | VAL | A | 93 | 4.441 | −20.073 | −14.791 | 1.00 | 9.88 | C |
| ATOM | 476 | CG1 | VAL | A | 93 | 5.396 | −19.034 | −15.369 | 1.00 | 11.74 | C |
| ATOM | 477 | CG2 | VAL | A | 93 | 3.513 | −19.549 | −13.721 | 1.00 | 10.87 | C |
| ATOM | 478 | N | PRO | A | 94 | 3.692 | −23.079 | −15.426 | 1.00 | 10.41 | N |
| ATOM | 479 | CA | PRO | A | 94 | 3.118 | −24.349 | −15.030 | 1.00 | 10.62 | C |
| ATOM | 480 | C | PRO | A | 94 | 3.130 | −24.462 | −13.524 | 1.00 | 11.29 | C |
| ATOM | 481 | O | PRO | A | 94 | 4.089 | −24.907 | −12.890 | 1.00 | 15.61 | O |
| ATOM | 482 | CB | PRO | A | 94 | 4.101 | −25.382 | −15.662 | 1.00 | 11.06 | C |
| ATOM | 483 | CG | PRO | A | 94 | 5.417 | −24.673 | −15.722 | 1.00 | 12.08 | C |
| ATOM | 484 | CD | PRO | A | 94 | 5.049 | −23.220 | −15.982 | 1.00 | 11.41 | C |
| ATOM | 485 | N | MET | A | 95 | 2.074 | −23.965 | −12.913 | 1.00 | 8.87 | N |
| ATOM | 486 | CA | MET | A | 95 | 1.862 | −24.033 | −11.484 | 1.00 | 8.96 | C |
| ATOM | 487 | C | MET | A | 95 | 0.498 | −24.628 | −11.215 | 1.00 | 8.49 | C |
| ATOM | 488 | O | MET | A | 95 | −0.514 | −24.054 | −11.632 | 1.00 | 9.06 | O |
| ATOM | 489 | CB | MET | A | 95 | 1.920 | −22.636 | −10.854 | 1.00 | 8.80 | C |
| ATOM | 490 | CG | MET | A | 95 | 3.340 | −22.095 | −10.756 | 1.00 | 9.53 | C |
| ATOM | 491 | SD | MET | A | 95 | 4.378 | −22.750 | −9.457 | 1.00 | 10.80 | S |
| ATOM | 492 | CE | MET | A | 95 | 3.689 | −21.895 | −8.070 | 1.00 | 11.28 | C |
| ATOM | 493 | N | SER | A | 96 | 0.455 | −25.722 | −10.487 | 1.00 | 7.98 | N |
| ATOM | 494 | CA | SER | A | 96 | −0.844 | −26.323 | −10.123 | 1.00 | 9.02 | C |
| ATOM | 495 | C | SER | A | 96 | −1.545 | −25.554 | −9.031 | 1.00 | 8.82 | C |
| ATOM | 496 | O | SER | A | 96 | −0.906 | −24.722 | −8.351 | 1.00 | 7.77 | O |
| ATOM | 497 | CB | SER | A | 96 | −0.630 | −27.731 | −9.671 | 1.00 | 9.38 | C |
| ATOM | 498 | OG | SER | A | 96 | 0.071 | −27.713 | −8.447 | 1.00 | 9.85 | O |
| ATOM | 499 | N | GLU | A | 97 | −2.818 | −25.823 | −8.800 | 1.00 | 8.52 | N |
| ATOM | 500 | CA | GLU | A | 97 | −3.518 | −25.122 | −7.726 | 1.00 | 10.00 | C |
| ATOM | 501 | C | GLU | A | 97 | −2.878 | −25.472 | −6.388 | 1.00 | 10.09 | C |
| ATOM | 502 | O | GLU | A | 97 | −2.805 | −24.605 | −5.519 | 1.00 | 9.76 | O |
| ATOM | 503 | CB | GLU | A | 97 | −5.001 | −25.401 | −7.781 | 1.00 | 12.99 | C |
| ATOM | 504 | CG | GLU | A | 97 | −5.413 | −26.777 | −7.474 | 1.00 | 17.01 | C |
| ATOM | 505 | CD | GLU | A | 97 | −5.674 | −27.055 | −5.992 | 1.00 | 21.45 | C |
| ATOM | 506 | OE1 | GLU | A | 97 | −5.766 | −28.258 | −5.609 | 1.00 | 23.75 | O |
| ATOM | 507 | OE2 | GLU | A | 97 | −5.781 | −26.081 | −5.208 | 1.00 | 25.48 | O |
| ATOM | 508 | N | SER | A | 98 | −2.337 | −26.664 | −6.222 | 1.00 | 9.61 | N |
| ATOM | 509 | CA | ASER | A | 98 | −1.650 | −27.049 | −4.992 | 0.50 | 9.84 | C |
| ATOM | 510 | CA | BSER | A | 98 | −1.726 | −26.967 | −4.946 | 0.50 | 10.33 | C |
| ATOM | 511 | C | SER | A | 98 | −0.425 | −26.171 | −4.795 | 1.00 | 9.61 | C |
| ATOM | 512 | O | SER | A | 98 | −0.189 | −25.651 | −3.726 | 1.00 | 9.80 | O |
| ATOM | 513 | CB | ASER | A | 98 | −1.185 | −28.475 | −5.103 | 0.50 | 10.59 | C |
| ATOM | 514 | CB | BSER | A | 98 | −1.536 | −28.450 | −4.771 | 0.50 | 11.67 | C |

TABLE 2-continued

X-RAY DIFFRACTION DATA OF *S. AUREUS* AUTOLYSIN E (AtlE 4PIA) RESIDUES 35-258

| ATOM | 515 | OG | ASER | A | 98 | −2.263 | −29.390 | −4.986 | 0.50 | 11.69 | O |
|---|---|---|---|---|---|---|---|---|---|---|---|
| ATOM | 516 | OG | BSER | A | 98 | −0.595 | −28.973 | −5.693 | 0.50 | 14.49 | O |
| ATOM | 517 | N | GLU | A | 99 | 0.356 | −25.983 | −5.864 | 1.00 | 8.51 | N |
| ATOM | 518 | CA | GLU | A | 99 | 1.548 | −25.139 | −5.768 | 1.00 | 8.92 | C |
| ATOM | 519 | C | GLU | A | 99 | 1.217 | −23.695 | −5.487 | 1.00 | 8.55 | C |
| ATOM | 520 | O | GLU | A | 99 | 1.881 | −23.036 | −4.641 | 1.00 | 8.89 | O |
| ATOM | 521 | CB | GLU | A | 99 | 2.360 | −25.242 | −7.036 | 1.00 | 9.61 | C |
| ATOM | 522 | CG | GLU | A | 99 | 3.020 | −26.622 | −7.207 | 1.00 | 11.26 | C |
| ATOM | 523 | CD | GLU | A | 99 | 3.628 | −26.708 | −8.567 | 1.00 | 12.96 | C |
| ATOM | 524 | OE1 | GLU | A | 99 | 3.018 | −26.617 | −9.631 | 1.00 | 11.71 | O |
| ATOM | 525 | OE2 | GLU | A | 99 | 4.906 | −26.928 | −8.624 | 1.00 | 22.38 | O |
| ATOM | 526 | N | VAL | A | 100 | 0.203 | −23.158 | −6.143 | 1.00 | 7.88 | N |
| ATOM | 527 | CA | VAL | A | 100 | −0.192 | −21.769 | −5.866 | 1.00 | 7.97 | C |
| ATOM | 528 | C | VAL | A | 100 | −0.675 | −21.630 | −4.423 | 1.00 | 8.83 | C |
| ATOM | 529 | O | VAL | A | 100 | −0.300 | −20.659 | −3.743 | 1.00 | 9.14 | O |
| ATOM | 530 | CB | VAL | A | 100 | −1.219 | −21.280 | −6.902 | 1.00 | 8.30 | C |
| ATOM | 531 | CG1 | VAL | A | 100 | −1.619 | −19.836 | −6.582 | 1.00 | 8.66 | C |
| ATOM | 532 | CG2 | VAL | A | 100 | −0.610 | −21.363 | −8.310 | 1.00 | 7.94 | C |
| ATOM | 533 | N | ASN | A | 101 | −1.453 | −22.573 | −3.948 | 1.00 | 8.38 | N |
| ATOM | 534 | CA | ASN | A | 101 | −1.932 | −22.514 | −2.538 | 1.00 | 8.64 | C |
| ATOM | 535 | C | ASN | A | 101 | −0.793 | −22.636 | −1.567 | 1.00 | 9.24 | C |
| ATOM | 536 | O | ASN | A | 101 | −0.804 | −22.022 | −0.499 | 1.00 | 10.73 | O |
| ATOM | 537 | CB | ASN | A | 101 | −3.014 | −23.532 | −2.279 | 1.00 | 8.69 | C |
| ATOM | 538 | CG | ASN | A | 101 | −4.346 | −23.016 | −2.725 | 1.00 | 9.04 | C |
| ATOM | 539 | OD1 | ASN | A | 101 | −4.624 | −21.843 | −2.574 | 1.00 | 9.61 | O |
| ATOM | 540 | ND2 | ASN | A | 101 | −5.194 | −23.881 | −3.229 | 1.00 | 11.02 | N |
| ATOM | 541 | N | GLN | A | 102 | 0.260 | −23.337 | −1.954 | 1.00 | 9.84 | N |
| ATOM | 542 | CA | GLN | A | 102 | 1.468 | −23.378 | −1.092 | 1.00 | 10.88 | C |
| ATOM | 543 | C | GLN | A | 102 | 2.028 | −21.984 | −0.934 | 1.00 | 11.90 | C |
| ATOM | 544 | O | GLN | A | 102 | 2.411 | −21.554 | 0.195 | 1.00 | 13.07 | O |
| ATOM | 545 | CB | GLN | A | 102 | 2.548 | −24.373 | −1.636 | 1.00 | 11.93 | C |
| ATOM | 546 | CG | GLN | A | 102 | 2.176 | −25.833 | −1.484 | 1.00 | 13.56 | C |
| ATOM | 547 | CD | GLN | A | 102 | 2.712 | −26.820 | −2.553 | 1.00 | 16.52 | C |
| ATOM | 548 | OE1 | GLN | A | 102 | 3.758 | −26.605 | −3.103 | 1.00 | 13.95 | O |
| ATOM | 549 | NE2 | GLN | A | 102 | 2.000 | −27.933 | −2.802 | 1.00 | 19.51 | N |
| ATOM | 550 | N | LEU | A | 103 | 2.104 | −21.191 | −2.012 | 1.00 | 10.81 | N |
| ATOM | 551 | CA | LEU | A | 103 | 2.559 | −19.796 | −1.930 | 1.00 | 11.86 | C |
| ATOM | 552 | C | LEU | A | 103 | 1.664 | −18.937 | −1.094 | 1.00 | 12.35 | C |
| ATOM | 553 | O | LEU | A | 103 | 2.117 | −17.964 | −0.561 | 1.00 | 13.65 | O |
| ATOM | 554 | CB | LEU | A | 103 | 2.722 | −19.142 | −3.287 | 1.00 | 13.39 | C |
| ATOM | 555 | CG | LEU | A | 103 | 3.845 | −19.683 | −4.158 | 1.00 | 14.81 | C |
| ATOM | 556 | CD1 | LEU | A | 103 | 3.777 | −18.956 | −5.449 | 1.00 | 15.22 | C |
| ATOM | 557 | CD2 | LEU | A | 103 | 5.178 | −19.490 | −3.504 | 1.00 | 15.04 | C |
| ATOM | 558 | N | LEU | A | 104 | 0.364 | −19.241 | −1.055 | 1.00 | 10.26 | N |
| ATOM | 559 | CA | LEU | A | 104 | −0.614 | −18.414 | −0.350 | 1.00 | 9.22 | C |
| ATOM | 560 | C | LEU | A | 104 | −0.876 | −18.859 | 1.062 | 1.00 | 9.62 | C |
| ATOM | 561 | O | LEU | A | 104 | −1.625 | −18.212 | 1.744 | 1.00 | 9.83 | O |
| ATOM | 562 | CB | LEU | A | 104 | −1.910 | −18.419 | −1.148 | 1.00 | 8.86 | C |
| ATOM | 563 | CG | LEU | A | 104 | −1.835 | −17.781 | −2.559 | 1.00 | 8.53 | C |
| ATOM | 564 | CD1 | LEU | A | 104 | −3.151 | −18.028 | −3.285 | 1.00 | 8.70 | C |
| ATOM | 565 | CD2 | LEU | A | 104 | −1.486 | −16.350 | −2.488 | 1.00 | 9.69 | C |
| ATOM | 566 | N | LYS | A | 105 | −0.258 | −19.939 | 1.484 | 1.00 | 10.21 | N |
| ATOM | 567 | CA | LYS | A | 105 | −0.444 | −20.431 | 2.852 | 1.00 | 11.03 | C |
| ATOM | 568 | C | LYS | A | 105 | 0.072 | −19.355 | 3.829 | 1.00 | 11.31 | C |
| ATOM | 569 | O | LYS | A | 105 | 1.162 | −18.784 | 3.665 | 1.00 | 12.43 | O |
| ATOM | 570 | CB | LYS | A | 105 | 0.294 | −21.754 | 3.085 | 1.00 | 13.39 | C |
| ATOM | 571 | CG | LYS | A | 105 | −0.046 | −22.456 | 4.395 | 1.00 | 17.18 | C |
| ATOM | 572 | CD | LYS | A | 105 | −1.489 | −22.984 | 4.272 | 1.00 | 22.14 | C |
| ATOM | 573 | CE | LYS | A | 105 | −2.015 | −23.682 | 5.509 | 1.00 | 29.14 | C |
| ATOM | 574 | NZ | LYS | A | 105 | −3.423 | −24.077 | 5.190 | 1.00 | 33.24 | N |
| ATOM | 575 | N | GLY | A | 106 | −0.756 | −19.043 | 4.829 | 1.00 | 11.10 | N |
| ATOM | 576 | CA | GLY | A | 106 | −0.400 | −17.991 | 5.752 | 1.00 | 11.09 | C |
| ATOM | 577 | C | GLY | A | 106 | −0.491 | −16.576 | 5.228 | 1.00 | 10.78 | C |
| ATOM | 578 | O | GLY | A | 106 | 0.011 | −15.614 | 5.871 | 1.00 | 13.32 | O |
| ATOM | 579 | N | LYS | A | 107 | −1.220 | −16.347 | 4.120 | 1.00 | 10.32 | N |
| ATOM | 580 | CA | LYS | A | 107 | −1.312 | −15.044 | 3.511 | 1.00 | 10.14 | C |
| ATOM | 581 | C | LYS | A | 107 | −2.719 | −14.440 | 3.626 | 1.00 | 9.55 | C |
| ATOM | 582 | O | LYS | A | 107 | −3.294 | −13.884 | 2.706 | 1.00 | 8.67 | O |
| ATOM | 583 | CB | LYS | A | 107 | −0.874 | −15.107 | 2.020 | 1.00 | 10.51 | C |
| ATOM | 584 | CG | LYS | A | 107 | 0.510 | −15.683 | 1.780 | 1.00 | 11.01 | C |
| ATOM | 585 | CD | LYS | A | 107 | 1.607 | −15.001 | 2.584 | 1.00 | 13.60 | C |
| ATOM | 586 | CE | LYS | A | 107 | 2.976 | −15.476 | 2.139 | 1.00 | 16.14 | C |
| ATOM | 587 | NZ | LYS | A | 107 | 4.027 | −14.752 | 2.917 | 1.00 | 20.86 | N |
| ATOM | 588 | N | GLY | A | 108 | −3.247 | −14.513 | 4.845 | 1.00 | 8.91 | N |
| ATOM | 589 | CA | GLY | A | 108 | −4.416 | −13.766 | 5.172 | 1.00 | 8.32 | C |
| ATOM | 590 | C | GLY | A | 108 | −5.644 | −14.033 | 4.289 | 1.00 | 7.86 | C |
| ATOM | 591 | O | GLY | A | 108 | −5.999 | −15.180 | 4.073 | 1.00 | 7.44 | O |
| ATOM | 592 | N | ILE | A | 109 | −6.227 | −12.974 | 3.777 | 1.00 | 7.60 | N |

TABLE 2-continued

X-RAY DIFFRACTION DATA OF *S. AUREUS* AUTOLYSIN E (AtlE 4PIA) RESIDUES 35-258

| ATOM | 593 | CA | ILE | A | 109 | −7.388 | −13.052 | 2.884 | 1.00 | 8.09 | C |
|---|---|---|---|---|---|---|---|---|---|---|---|
| ATOM | 594 | C | ILE | A | 109 | −7.077 | −13.772 | 1.571 | 1.00 | 7.60 | C |
| ATOM | 595 | O | ILE | A | 109 | −8.021 | −14.195 | 0.904 | 1.00 | 8.06 | O |
| ATOM | 596 | CB | ILE | A | 109 | −7.999 | −11.676 | 2.664 | 1.00 | 7.96 | C |
| ATOM | 597 | CG1 | ILE | A | 109 | −9.406 | −11.750 | 2.125 | 1.00 | 7.94 | C |
| ATOM | 598 | CG2 | ILE | A | 109 | −7.110 | −10.819 | 1.791 | 1.00 | 8.35 | C |
| ATOM | 599 | CD1 | ILE | A | 109 | −10.148 | −10.449 | 2.322 | 1.00 | 7.40 | C |
| ATOM | 600 | N | LEU | A | 110 | −5.808 | −13.913 | 1.227 | 1.00 | 7.86 | N |
| ATOM | 601 | CA | LEU | A | 110 | −5.457 | −14.606 | −0.001 | 1.00 | 7.42 | C |
| ATOM | 602 | C | LEU | A | 110 | −5.239 | −16.085 | 0.169 | 1.00 | 7.66 | C |
| ATOM | 603 | O | LEU | A | 110 | −5.171 | −16.818 | −0.833 | 1.00 | 7.83 | O |
| ATOM | 604 | CB | LEU | A | 110 | −4.224 | −13.945 | −0.622 | 1.00 | 8.05 | C |
| ATOM | 605 | CG | LEU | A | 110 | −4.355 | −12.480 | −0.926 | 1.00 | 8.95 | C |
| ATOM | 606 | CD1 | LEU | A | 110 | −3.011 | −11.941 | −1.416 | 1.00 | 11.01 | C |
| ATOM | 607 | CD2 | LEU | A | 110 | −5.483 | −12.166 | −1.904 | 1.00 | 9.35 | C |
| ATOM | 608 | N | GLU | A | 111 | −5.105 | −16.588 | 1.409 | 1.00 | 7.45 | N |
| ATOM | 609 | CA | GLU | A | 111 | −4.900 | −17.972 | 1.661 | 1.00 | 7.85 | C |
| ATOM | 610 | C | GLU | A | 111 | −6.024 | −18.800 | 1.035 | 1.00 | 7.85 | C |
| ATOM | 611 | O | GLU | A | 111 | −7.215 | −18.468 | 1.180 | 1.00 | 7.89 | O |
| ATOM | 612 | CB | GLU | A | 111 | −4.775 | −18.244 | 3.192 | 1.00 | 8.78 | C |
| ATOM | 613 | CG | GLU | A | 111 | −4.546 | −19.689 | 3.528 | 1.00 | 9.27 | C |
| ATOM | 614 | CD | GLU | A | 111 | −4.372 | −19.839 | 5.026 | 1.00 | 11.58 | C |
| ATOM | 615 | OE1 | GLU | A | 111 | −5.413 | −19.773 | 5.727 | 1.00 | 12.28 | O |
| ATOM | 616 | OE2 | GLU | A | 111 | −3.218 | −19.954 | 5.498 | 1.00 | 12.02 | O |
| ATOM | 617 | N | ASN | A | 112 | −5.657 | −19.921 | 0.428 | 1.00 | 8.12 | N |
| ATOM | 618 | CA | ASN | A | 112 | −6.577 | −20.845 | −0.139 | 1.00 | 9.56 | C |
| ATOM | 619 | C | ASN | A | 112 | −7.434 | −20.262 | −1.232 | 1.00 | 8.71 | C |
| ATOM | 620 | O | ASN | A | 112 | −8.547 | −20.704 | −1.487 | 1.00 | 10.62 | O |
| ATOM | 621 | CB | ASN | A | 112 | −7.394 | −21.574 | 0.951 | 1.00 | 10.76 | C |
| ATOM | 622 | CG | ASN | A | 112 | −6.628 | −22.712 | 1.597 | 1.00 | 14.64 | C |
| ATOM | 623 | OD1 | ASN | A | 112 | −6.866 | −23.045 | 2.762 | 1.00 | 19.98 | O |
| ATOM | 624 | ND2 | ASN | A | 112 | −5.661 | −23.263 | 0.890 | 1.00 | 16.46 | N |
| ATOM | 625 | N | ARG | A | 113 | −6.887 | −19.289 | −1.975 | 1.00 | 7.64 | N |
| ATOM | 626 | CA | ARG | A | 113 | −7.526 | −18.722 | −3.145 | 1.00 | 7.57 | C |
| ATOM | 627 | C | ARG | A | 113 | −6.740 | −19.057 | −4.432 | 1.00 | 6.96 | C |
| ATOM | 628 | O | ARG | A | 113 | −6.941 | −18.423 | −5.483 | 1.00 | 7.19 | O |
| ATOM | 629 | CB | ARG | A | 113 | −7.823 | −17.209 | −3.034 | 1.00 | 7.60 | C |
| ATOM | 630 | CG | ARG | A | 113 | −8.720 | −16.949 | −1.825 | 1.00 | 7.92 | C |
| ATOM | 631 | CD | ARG | A | 113 | −9.273 | −15.557 | −1.849 | 1.00 | 8.34 | C |
| ATOM | 632 | NE | ARG | A | 113 | −10.046 | −15.316 | −0.616 | 1.00 | 9.26 | N |
| ATOM | 633 | CZ | ARG | A | 113 | −11.321 | −15.618 | −0.416 | 1.00 | 9.69 | C |
| ATOM | 634 | NH1 | ARG | A | 113 | −12.078 | −16.071 | −1.386 | 1.00 | 9.99 | N |
| ATOM | 635 | NH2 | ARG | A | 113 | −11.849 | −15.412 | 0.761 | 1.00 | 10.68 | N |
| ATOM | 636 | N | GLY | A | 114 | −5.878 | −20.066 | −4.349 | 1.00 | 6.95 | N |
| ATOM | 637 | CA | GLY | A | 114 | −5.065 | −20.443 | −5.504 | 1.00 | 7.17 | C |
| ATOM | 638 | C | GLY | A | 114 | −5.882 | −20.812 | −6.727 | 1.00 | 7.63 | C |
| ATOM | 639 | O | GLY | A | 114 | −5.448 | −20.584 | −7.881 | 1.00 | 8.50 | O |
| ATOM | 640 | N | LYS | A | 115 | −6.995 | −21.504 | −6.527 | 1.00 | 7.70 | N |
| ATOM | 641 | CA | ALYS | A | 115 | −7.773 | −21.904 | −7.700 | 0.60 | 8.59 | C |
| ATOM | 642 | CA | BLYS | A | 115 | −7.907 | −21.883 | −7.616 | 0.40 | 8.13 | C |
| ATOM | 643 | C | LYS | A | 115 | −8.221 | −20.691 | −8.496 | 1.00 | 8.25 | C |
| ATOM | 644 | O | LYS | A | 115 | −8.293 | −20.749 | −9.750 | 1.00 | 8.11 | O |
| ATOM | 645 | CB | ALYS | A | 115 | −8.971 | −22.809 | −7.397 | 0.60 | 10.46 | C |
| ATOM | 646 | CB | BLYS | A | 115 | −9.221 | −22.417 | −7.021 | 0.40 | 9.12 | C |
| ATOM | 647 | CG | ALYS | A | 115 | −8.617 | −24.183 | −6.882 | 0.60 | 12.46 | C |
| ATOM | 648 | CG | BLYS | A | 115 | −10.405 | −22.435 | −7.945 | 0.40 | 9.60 | C |
| ATOM | 649 | CD | ALYS | A | 115 | −9.957 | −24.761 | −6.473 | 0.60 | 15.40 | C |
| ATOM | 650 | CD | BLYS | A | 115 | −11.623 | −22.968 | −7.284 | 0.40 | 10.43 | C |
| ATOM | 651 | CE | ALYS | A | 115 | −9.937 | −26.006 | −5.714 | 0.60 | 17.77 | C |
| ATOM | 652 | CE | BLYS | A | 115 | −12.752 | −23.120 | −8.270 | 0.40 | 10.49 | C |
| ATOM | 653 | NZ | ALYS | A | 115 | −11.342 | −26.174 | −5.391 | 0.60 | 20.66 | N |
| ATOM | 654 | NZ | BLYS | A | 115 | −13.886 | −23.819 | −7.676 | 0.40 | 10.66 | N |
| ATOM | 655 | N | VAL | A | 116 | −8.515 | −19.579 | −7.820 | 1.00 | 7.79 | N |
| ATOM | 656 | CA | VAL | A | 116 | −8.984 | −18.369 | −8.484 | 1.00 | 8.11 | C |
| ATOM | 657 | C | VAL | A | 116 | −7.835 | −17.608 | −9.161 | 1.00 | 7.43 | C |
| ATOM | 658 | O | VAL | A | 116 | −7.959 | −17.079 | −10.264 | 1.00 | 7.87 | O |
| ATOM | 659 | CB | VAL | A | 116 | −9.786 | −17.505 | −7.502 | 1.00 | 9.94 | C |
| ATOM | 660 | CG1 | VAL | A | 116 | −10.250 | −16.261 | −8.190 | 1.00 | 10.14 | C |
| ATOM | 661 | CG2 | VAL | A | 116 | −11.015 | −18.284 | −7.015 | 1.00 | 11.71 | C |
| ATOM | 662 | N | PHE | A | 117 | −6.674 | −17.558 | −8.504 | 1.00 | 6.80 | N |
| ATOM | 663 | CA | PHE | A | 117 | −5.502 | −17.020 | −9.203 | 1.00 | 6.68 | C |
| ATOM | 664 | C | PHE | A | 117 | −5.241 | −17.783 | −10.526 | 1.00 | 6.57 | C |
| ATOM | 665 | O | PHE | A | 117 | −4.836 | −17.179 | −11.506 | 1.00 | 6.36 | O |
| ATOM | 666 | CB | PHE | A | 117 | −4.292 | −17.066 | −8.282 | 1.00 | 7.12 | C |
| ATOM | 667 | CG | PHE | A | 117 | −4.183 | −15.901 | −7.309 | 1.00 | 7.07 | C |
| ATOM | 668 | CD1 | PHE | A | 117 | −3.566 | −14.722 | −7.705 | 1.00 | 7.49 | C |
| ATOM | 669 | CD2 | PHE | A | 117 | −4.745 | −15.934 | −6.039 | 1.00 | 7.19 | C |
| ATOM | 670 | CE1 | PHE | A | 117 | −3.443 | −13.614 | −6.831 | 1.00 | 7.29 | C |

TABLE 2-continued

X-RAY DIFFRACTION DATA OF *S. AUREUS* AUTOLYSIN E (AtlE 4PIA) RESIDUES 35-258

| ATOM | 671 | CE2 | PHE | A | 117 | −4.586 | −14.847 | −5.164 | 1.00 | 7.84 | C |
|---|---|---|---|---|---|---|---|---|---|---|---|
| ATOM | 672 | CZ | PHE | A | 117 | −3.981 | −13.687 | −5.578 | 1.00 | 8.01 | C |
| ATOM | 673 | N | LEU | A | 118 | −5.407 | −19.113 | −10.515 | 1.00 | 7.10 | N |
| ATOM | 674 | CA | LEU | A | 118 | −5.189 | −19.853 | −11.751 | 1.00 | 7.12 | C |
| ATOM | 675 | C | LEU | A | 118 | −6.339 | −19.644 | −12.760 | 1.00 | 6.69 | C |
| ATOM | 676 | O | LEU | A | 118 | −6.032 | −19.615 | −13.968 | 1.00 | 6.72 | O |
| ATOM | 677 | CB | LEU | A | 118 | −5.001 | −21.339 | −11.445 | 1.00 | 7.31 | C |
| ATOM | 678 | CG | LEU | A | 118 | −3.604 | −21.641 | −10.910 | 1.00 | 8.29 | C |
| ATOM | 679 | CD1 | LEU | A | 118 | −3.576 | −23.054 | −10.361 | 1.00 | 9.66 | C |
| ATOM | 680 | CD2 | LEU | A | 118 | −2.506 | −21.382 | −11.925 | 1.00 | 8.59 | C |
| ATOM | 681 | N | GLU | A | 119 | −7.581 | −19.493 | −12.332 | 1.00 | 6.87 | N |
| ATOM | 682 | CA | GLU | A | 119 | −8.623 | −19.042 | −13.245 | 1.00 | 7.96 | C |
| ATOM | 683 | C | GLU | A | 119 | −8.196 | −17.768 | −13.957 | 1.00 | 7.79 | C |
| ATOM | 684 | O | GLU | A | 119 | −8.333 | −17.695 | −15.190 | 1.00 | 7.93 | O |
| ATOM | 685 | CB | GLU | A | 119 | −9.940 | −18.821 | −12.548 | 1.00 | 10.12 | C |
| ATOM | 686 | CG | GLU | A | 119 | −10.593 | −20.058 | −11.990 | 1.00 | 13.93 | C |
| ATOM | 687 | CD | GLU | A | 119 | −11.785 | −19.729 | −11.074 | 1.00 | 19.54 | C |
| ATOM | 688 | OE1 | GLU | A | 119 | −12.155 | −18.544 | −10.922 | 1.00 | 23.43 | O |
| ATOM | 689 | OE2 | GLU | A | 119 | −12.357 | −20.674 | −10.486 | 1.00 | 26.48 | O |
| ATOM | 690 | N | ALA | A | 120 | −7.677 | −16.803 | −13.192 | 1.00 | 7.92 | N |
| ATOM | 691 | CA | ALA | A | 120 | −7.199 | −15.568 | −13.779 | 1.00 | 7.95 | C |
| ATOM | 692 | C | ALA | A | 120 | −6.064 | −15.785 | −14.764 | 1.00 | 7.26 | C |
| ATOM | 693 | O | ALA | A | 120 | −6.038 | −15.216 | −15.870 | 1.00 | 7.30 | O |
| ATOM | 694 | CB | ALA | A | 120 | −6.775 | −14.648 | −12.652 | 1.00 | 8.18 | C |
| ATOM | 695 | N | GLN | A | 121 | −5.083 | −16.611 | −14.385 | 1.00 | 6.76 | N |
| ATOM | 696 | CA | GLN | A | 121 | −3.974 | −16.883 | −15.304 | 1.00 | 6.72 | C |
| ATOM | 697 | C | GLN | A | 121 | −4.487 | −17.392 | −16.652 | 1.00 | 7.64 | C |
| ATOM | 698 | O | GLN | A | 121 | −4.025 | −16.938 | −17.711 | 1.00 | 7.78 | O |
| ATOM | 699 | CB | GLN | A | 121 | −2.962 | −17.894 | −14.691 | 1.00 | 6.78 | C |
| ATOM | 700 | CG | GLN | A | 121 | −1.973 | −18.359 | −15.745 | 1.00 | 6.98 | C |
| ATOM | 701 | CD | GLN | A | 121 | −0.775 | −19.123 | −15.256 | 1.00 | 6.64 | C |
| ATOM | 702 | OE1 | GLN | A | 121 | 0.323 | −18.619 | −15.043 | 1.00 | 6.57 | O |
| ATOM | 703 | NE2 | GLN | A | 121 | −0.971 | −20.436 | −15.122 | 1.00 | 8.15 | N |
| ATOM | 704 | N | GLU | A | 122 | −5.382 | −18.387 | −16.607 | 1.00 | 7.84 | N |
| ATOM | 705 | CA | GLU | A | 122 | −5.792 | −19.021 | −17.845 | 1.00 | 8.16 | C |
| ATOM | 706 | C | GLU | A | 122 | −6.754 | −18.128 | −18.622 | 1.00 | 8.14 | C |
| ATOM | 707 | O | GLU | A | 122 | −6.650 | −18.062 | −19.853 | 1.00 | 8.85 | O |
| ATOM | 708 | CB | GLU | A | 122 | −6.430 | −20.385 | −17.608 | 1.00 | 9.37 | C |
| ATOM | 709 | CG | GLU | A | 122 | −5.520 | −21.374 | −16.837 | 1.00 | 10.77 | C |
| ATOM | 710 | CD | GLU | A | 122 | −4.212 | −21.601 | −17.526 | 1.00 | 14.44 | C |
| ATOM | 711 | OE1 | GLU | A | 122 | −4.231 | −21.727 | −18.751 | 1.00 | 18.07 | O |
| ATOM | 712 | OE2 | GLU | A | 122 | −3.155 | −21.670 | −16.878 | 1.00 | 16.64 | O |
| ATOM | 713 | N | LYS | A | 123 | −7.672 | −17.455 | −17.965 | 1.00 | 8.18 | N |
| ATOM | 714 | CA | LYS | A | 123 | −8.626 | −16.617 | −18.680 | 1.00 | 8.51 | C |
| ATOM | 715 | C | LYS | A | 123 | −7.942 | −15.473 | −19.401 | 1.00 | 8.27 | C |
| ATOM | 716 | O | LYS | A | 123 | −8.261 | −15.143 | −20.549 | 1.00 | 9.12 | O |
| ATOM | 717 | CB | LYS | A | 123 | −9.684 | −16.071 | −17.727 | 1.00 | 10.40 | C |
| ATOM | 718 | CG | LYS | A | 123 | −10.695 | −17.105 | −17.284 | 1.00 | 13.19 | C |
| ATOM | 719 | CD | LYS | A | 123 | −11.481 | −16.695 | −16.065 | 1.00 | 16.46 | C |
| ATOM | 720 | CE | LYS | A | 123 | −12.251 | −15.439 | −16.250 | 1.00 | 20.64 | C |
| ATOM | 721 | NZ | LYS | A | 123 | −13.357 | −15.591 | −17.241 | 1.00 | 24.59 | N |
| ATOM | 722 | N | TYR | A | 124 | −6.964 | −14.855 | −18.736 | 1.00 | 8.17 | N |
| ATOM | 723 | CA | TYR | A | 124 | −6.396 | −13.587 | −19.242 | 1.00 | 8.61 | C |
| ATOM | 724 | C | TYR | A | 124 | −4.955 | −13.663 | −19.668 | 1.00 | 8.38 | C |
| ATOM | 725 | O | TYR | A | 124 | −4.385 | −12.637 | −20.081 | 1.00 | 9.11 | O |
| ATOM | 726 | CB | TYR | A | 124 | −6.622 | −12.500 | −18.194 | 1.00 | 9.12 | C |
| ATOM | 727 | CG | TYR | A | 124 | −8.077 | −12.250 | −17.935 | 1.00 | 10.17 | C |
| ATOM | 728 | CD1 | TYR | A | 124 | −8.865 | −11.789 | −18.974 | 1.00 | 12.12 | C |
| ATOM | 729 | CD2 | TYR | A | 124 | −8.703 | −12.501 | −16.716 | 1.00 | 11.43 | C |
| ATOM | 730 | CE1 | TYR | A | 124 | −10.221 | −11.576 | −18.805 | 1.00 | 15.63 | C |
| ATOM | 731 | CE2 | TYR | A | 124 | −10.049 | −12.289 | −16.580 | 1.00 | 13.12 | C |
| ATOM | 732 | CZ | TYR | A | 124 | −10.781 | −11.838 | −17.610 | 1.00 | 15.53 | C |
| ATOM | 733 | OH | TYR | A | 124 | −12.167 | −11.632 | −17.479 | 1.00 | 20.84 | O |
| ATOM | 734 | N | GLU | A | 125 | −4.333 | −14.835 | −19.561 | 1.00 | 8.10 | N |
| ATOM | 735 | CA | GLU | A | 125 | −2.931 | −15.026 | −19.994 | 1.00 | 8.35 | C |
| ATOM | 736 | C | GLU | A | 125 | −2.008 | −14.094 | −19.200 | 1.00 | 8.73 | C |
| ATOM | 737 | O | GLU | A | 125 | −1.310 | −13.245 | −19.738 | 1.00 | 8.60 | O |
| ATOM | 738 | CB | GLU | A | 125 | −2.755 | −14.865 | −21.499 | 1.00 | 9.55 | C |
| ATOM | 739 | CG | GLU | A | 125 | −1.452 | −15.438 | −22.013 | 1.00 | 11.63 | C |
| ATOM | 740 | CD | GLU | A | 125 | −1.270 | −15.357 | −23.504 | 1.00 | 14.78 | C |
| ATOM | 741 | OE1 | GLU | A | 125 | −1.921 | −14.539 | −24.097 | 1.00 | 17.12 | O |
| ATOM | 742 | OE2 | GLU | A | 125 | −0.414 | −16.075 | −24.031 | 1.00 | 22.37 | O |
| ATOM | 743 | N | VAL | A | 126 | −2.065 | −14.298 | −17.881 | 1.00 | 7.76 | N |
| ATOM | 744 | CA | VAL | A | 126 | −1.284 | −13.483 | −16.931 | 1.00 | 7.56 | C |
| ATOM | 745 | C | VAL | A | 126 | −0.497 | −14.442 | −16.054 | 1.00 | 6.91 | C |
| ATOM | 746 | O | VAL | A | 126 | −1.079 | −15.286 | −15.385 | 1.00 | 8.12 | O |
| ATOM | 747 | CB | VAL | A | 126 | −2.177 | −12.604 | −16.059 | 1.00 | 7.91 | C |
| ATOM | 748 | CG1 | VAL | A | 126 | −1.340 | −11.835 | −15.043 | 1.00 | 8.63 | C |

TABLE 2-continued

X-RAY DIFFRACTION DATA OF S. AUREUS AUTOLYSIN E (AtlE 4PIA) RESIDUES 35-258

| ATOM | 749 | CG2 | VAL | A | 126 | −3.012 | −11.644 | −16.910 | 1.00 | 8.53 | C |
|---|---|---|---|---|---|---|---|---|---|---|---|
| ATOM | 750 | N | ASN | A | 127 | 0.799 | −14.260 | −16.027 | 1.00 | 6.40 | N |
| ATOM | 751 | CA | ASN | A | 127 | 1.708 | −15.123 | −15.221 | 1.00 | 6.47 | C |
| ATOM | 752 | C | ASN | A | 127 | 1.286 | −15.184 | −13.759 | 1.00 | 6.18 | C |
| ATOM | 753 | O | ASN | A | 127 | 1.194 | −14.141 | −13.095 | 1.00 | 6.41 | O |
| ATOM | 754 | CB | ASN | A | 127 | 3.117 | −14.553 | −15.388 | 1.00 | 6.38 | C |
| ATOM | 755 | CG | ASN | A | 127 | 4.191 | −15.261 | −14.594 | 1.00 | 7.02 | C |
| ATOM | 756 | OD1 | ASN | A | 127 | 4.014 | −15.565 | −13.407 | 1.00 | 6.96 | O |
| ATOM | 757 | ND2 | ASN | A | 127 | 5.347 | −15.467 | −15.216 | 1.00 | 7.65 | N |
| ATOM | 758 | N | VAL | A | 128 | 0.961 | −16.374 | −13.293 | 1.00 | 6.13 | N |
| ATOM | 759 | CA | VAL | A | 128 | 0.312 | −16.475 | −11.974 | 1.00 | 6.44 | C |
| ATOM | 760 | C | VAL | A | 128 | 1.305 | −16.203 | −10.863 | 1.00 | 6.25 | C |
| ATOM | 761 | O | VAL | A | 128 | 0.863 | −15.740 | −9.761 | 1.00 | 6.88 | O |
| ATOM | 762 | CB | VAL | A | 128 | −0.389 | −17.840 | −11.745 | 1.00 | 6.28 | C |
| ATOM | 763 | CG1 | VAL | A | 128 | 0.614 | −18.970 | −11.449 | 1.00 | 7.35 | C |
| ATOM | 764 | CG2 | VAL | A | 128 | −1.430 | −17.740 | −10.630 | 1.00 | 6.53 | C |
| ATOM | 765 | N | ILE | A | 129 | 2.595 | −16.479 | −11.059 | 1.00 | 5.87 | N |
| ATOM | 766 | CA | ILE | A | 129 | 3.566 | −16.120 | −10.027 | 1.00 | 6.09 | C |
| ATOM | 767 | C | ILE | A | 129 | 3.663 | −14.622 | −9.902 | 1.00 | 6.67 | C |
| ATOM | 768 | O | ILE | A | 129 | 3.722 | −14.067 | −8.792 | 1.00 | 6.57 | O |
| ATOM | 769 | CB | ILE | A | 129 | 4.880 | −16.803 | −10.245 | 1.00 | 6.67 | C |
| ATOM | 770 | CG1 | ILE | A | 129 | 4.778 | −18.290 | −9.931 | 1.00 | 7.34 | C |
| ATOM | 771 | CG2 | ILE | A | 129 | 5.959 | −16.172 | −9.400 | 1.00 | 7.22 | C |
| ATOM | 772 | CD1 | ILE | A | 129 | 5.960 | −19.142 | −10.348 | 1.00 | 8.61 | C |
| ATOM | 773 | N | TYR | A | 130 | 3.674 | −13.883 | −11.010 | 1.00 | 5.83 | N |
| ATOM | 774 | CA | TYR | A | 130 | 3.593 | −12.448 | −10.969 | 1.00 | 5.97 | C |
| ATOM | 775 | C | TYR | A | 130 | 2.343 | −11.988 | −10.259 | 1.00 | 6.12 | C |
| ATOM | 776 | O | TYR | A | 130 | 2.387 | −11.101 | −9.397 | 1.00 | 6.25 | O |
| ATOM | 777 | CB | TYR | A | 130 | 3.655 | −11.901 | −12.422 | 1.00 | 6.08 | C |
| ATOM | 778 | CG | TYR | A | 130 | 2.947 | −10.576 | −12.532 | 1.00 | 6.11 | C |
| ATOM | 779 | CD1 | TYR | A | 130 | 3.439 | −9.419 | −11.883 | 1.00 | 6.13 | C |
| ATOM | 780 | CD2 | TYR | A | 130 | 1.715 | −10.458 | −13.141 | 1.00 | 6.36 | C |
| ATOM | 781 | CE1 | TYR | A | 130 | 2.709 | −8.259 | −11.821 | 1.00 | 6.47 | C |
| ATOM | 782 | CE2 | TYR | A | 130 | 1.023 | −9.271 | −13.163 | 1.00 | 7.06 | C |
| ATOM | 783 | CZ | TYR | A | 130 | 1.498 | −8.196 | −12.468 | 1.00 | 6.52 | C |
| ATOM | 784 | OH | TYR | A | 130 | 0.747 | −7.026 | −12.378 | 1.00 | 8.23 | O |
| ATOM | 785 | N | LEU | A | 131 | 1.198 | −12.550 | −10.620 | 1.00 | 6.32 | N |
| ATOM | 786 | CA | LEU | A | 131 | −0.067 | −12.088 | −10.074 | 1.00 | 6.92 | C |
| ATOM | 787 | C | LEU | A | 131 | −0.103 | −12.260 | −8.549 | 1.00 | 6.79 | C |
| ATOM | 788 | O | LEU | A | 131 | −0.480 | −11.342 | −7.796 | 1.00 | 6.46 | O |
| ATOM | 789 | CB | LEU | A | 131 | −1.252 | −12.804 | −10.746 | 1.00 | 8.60 | C |
| ATOM | 790 | CG | LEU | A | 131 | −2.637 | −12.189 | −10.591 | 1.00 | 10.25 | C |
| ATOM | 791 | CD1 | LEU | A | 131 | −2.680 | −10.828 | −11.251 | 1.00 | 9.89 | C |
| ATOM | 792 | CD2 | LEU | A | 131 | −3.700 | −13.123 | −11.173 | 1.00 | 10.87 | C |
| ATOM | 793 | N | VAL | A | 132 | 0.307 | −13.418 | −8.065 | 1.00 | 6.82 | N |
| ATOM | 794 | CA | VAL | A | 132 | 0.388 | −13.708 | −6.621 | 1.00 | 7.32 | C |
| ATOM | 795 | C | VAL | A | 132 | 1.371 | −12.734 | −6.000 | 1.00 | 7.43 | C |
| ATOM | 796 | O | VAL | A | 132 | 1.058 | −12.152 | −4.929 | 1.00 | 7.73 | O |
| ATOM | 797 | CB | VAL | A | 132 | 0.798 | −15.166 | −6.376 | 1.00 | 8.13 | C |
| ATOM | 798 | CG1 | VAL | A | 132 | 1.247 | −15.308 | −4.920 | 1.00 | 8.94 | C |
| ATOM | 799 | CG2 | VAL | A | 132 | −0.386 | −16.097 | −6.698 | 1.00 | 8.79 | C |
| ATOM | 800 | N | SER | A | 133 | 2.555 | −12.532 | −6.591 | 1.00 | 6.32 | N |
| ATOM | 801 | CA | SER | A | 133 | 3.595 | −11.673 | −5.984 | 1.00 | 7.29 | C |
| ATOM | 802 | C | SER | A | 133 | 3.086 | −10.254 | −5.904 | 1.00 | 6.98 | C |
| ATOM | 803 | O | SER | A | 133 | 3.323 | −9.580 | −4.876 | 1.00 | 7.83 | O |
| ATOM | 804 | CB | SER | A | 133 | 4.902 | −11.799 | −6.739 | 1.00 | 7.20 | C |
| ATOM | 805 | OG | SER | A | 133 | 5.373 | −13.128 | −6.776 | 1.00 | 7.83 | O |
| ATOM | 806 | N | HIS | A | 134 | 2.451 | −9.738 | −6.932 | 1.00 | 6.96 | N |
| ATOM | 807 | CA | HIS | A | 134 | 1.921 | −8.363 | −6.924 | 1.00 | 7.07 | C |
| ATOM | 808 | C | HIS | A | 134 | 0.875 | −8.258 | −5.807 | 1.00 | 7.51 | C |
| ATOM | 809 | O | HIS | A | 134 | 0.929 | −7.309 | −4.988 | 1.00 | 7.90 | O |
| ATOM | 810 | CB | HIS | A | 134 | 1.360 | −8.085 | −8.308 | 1.00 | 7.33 | C |
| ATOM | 811 | CG | HIS | A | 134 | 0.880 | −6.696 | −8.503 | 1.00 | 7.71 | C |
| ATOM | 812 | ND1 | HIS | A | 134 | 0.535 | −6.202 | −9.731 | 1.00 | 8.28 | N |
| ATOM | 813 | CD2 | HIS | A | 134 | 0.738 | −5.678 | −7.620 | 1.00 | 8.37 | C |
| ATOM | 814 | CE1 | HIS | A | 134 | 0.184 | −4.936 | −9.600 | 1.00 | 8.93 | C |
| ATOM | 815 | NE2 | HIS | A | 134 | 0.291 | −4.598 | −8.334 | 1.00 | 8.59 | N |
| ATOM | 816 | N | ALA | A | 135 | −0.038 | −9.216 | −5.716 | 1.00 | 7.61 | N |
| ATOM | 817 | CA | ALA | A | 135 | −1.076 | −9.142 | −4.661 | 1.00 | 7.88 | C |
| ATOM | 818 | C | ALA | A | 135 | −0.439 | −9.200 | −3.306 | 1.00 | 8.64 | C |
| ATOM | 819 | O | ALA | A | 135 | −0.913 | −8.475 | −2.377 | 1.00 | 9.55 | O |
| ATOM | 820 | CB | ALA | A | 135 | −2.047 | −10.275 | −4.847 | 1.00 | 9.07 | C |
| ATOM | 821 | N | LEU | A | 136 | 0.576 | −9.999 | −3.100 | 1.00 | 8.20 | N |
| ATOM | 822 | CA | LEU | A | 136 | 1.184 | −10.104 | −1.742 | 1.00 | 9.40 | C |
| ATOM | 823 | C | LEU | A | 136 | 1.874 | −8.832 | −1.372 | 1.00 | 10.49 | C |
| ATOM | 824 | O | LEU | A | 136 | 1.816 | −8.421 | −0.174 | 1.00 | 12.23 | O |
| ATOM | 825 | CB | LEU | A | 136 | 2.134 | −11.241 | −1.702 | 1.00 | 9.44 | C |
| ATOM | 826 | CG | LEU | A | 136 | 1.528 | −12.632 | −1.753 | 1.00 | 10.07 | C |

TABLE 2-continued

X-RAY DIFFRACTION DATA OF S. AUREUS AUTOLYSIN E (AtlE 4PIA) RESIDUES 35-258

| ATOM | 827 | CD1 | LEU | A | 136 | 2.573 | −13.735 | −1.920 | 1.00 | 10.72 | C |
|---|---|---|---|---|---|---|---|---|---|---|---|
| ATOM | 828 | CD2 | LEU | A | 136 | 0.672 | −12.992 | −0.534 | 1.00 | 11.10 | C |
| ATOM | 829 | N | VAL | A | 137 | 2.560 | −8.180 | −2.296 | 1.00 | 9.88 | N |
| ATOM | 830 | CA | VAL | A | 137 | 3.180 | −6.906 | −1.948 | 1.00 | 11.54 | C |
| ATOM | 831 | C | VAL | A | 137 | 2.099 | −5.913 | −1.615 | 1.00 | 12.20 | C |
| ATOM | 832 | O | VAL | A | 137 | 2.163 | −5.253 | −0.525 | 1.00 | 13.74 | O |
| ATOM | 833 | CB | VAL | A | 137 | 4.101 | −6.406 | −3.070 | 1.00 | 11.33 | C |
| ATOM | 834 | CG1 | VAL | A | 137 | 4.643 | −5.022 | −2.653 | 1.00 | 13.21 | C |
| ATOM | 835 | CG2 | VAL | A | 137 | 5.256 | −7.341 | −3.269 | 1.00 | 10.79 | C |
| ATOM | 836 | N | GLU | A | 138 | 1.084 | −5.760 | −2.449 | 1.00 | 10.81 | N |
| ATOM | 837 | CA | GLU | A | 138 | 0.082 | −4.712 | −2.298 | 1.00 | 11.29 | C |
| ATOM | 838 | C | GLU | A | 138 | −0.738 | −4.864 | −1.052 | 1.00 | 12.33 | C |
| ATOM | 839 | O | GLU | A | 138 | −1.061 | −3.857 | −0.382 | 1.00 | 16.05 | O |
| ATOM | 840 | CB | GLU | A | 138 | −0.837 | −4.702 | −3.522 | 1.00 | 14.11 | C |
| ATOM | 841 | CG | GLU | A | 138 | −1.932 | −3.694 | −3.501 | 1.00 | 18.76 | C |
| ATOM | 842 | CD | GLU | A | 138 | −1.474 | −2.244 | −3.437 | 1.00 | 26.12 | C |
| ATOM | 843 | OE1 | GLU | A | 138 | −2.249 | −1.483 | −2.790 | 1.00 | 33.62 | O |
| ATOM | 844 | OE2 | GLU | A | 138 | −0.434 | −1.875 | −4.036 | 1.00 | 30.66 | O |
| ATOM | 845 | N | THR | A | 139 | −1.022 | −6.083 | −0.659 | 1.00 | 10.45 | N |
| ATOM | 846 | CA | THR | A | 139 | −1.944 | −6.359 | 0.466 | 1.00 | 10.54 | C |
| ATOM | 847 | C | THR | A | 139 | −1.218 | −6.630 | 1.777 | 1.00 | 11.10 | C |
| ATOM | 848 | O | THR | A | 139 | −1.828 | −7.006 | 2.782 | 1.00 | 11.59 | O |
| ATOM | 849 | CB | THR | A | 139 | −2.827 | −7.602 | 0.171 | 1.00 | 11.09 | C |
| ATOM | 850 | OG1 | THR | A | 139 | −2.039 | −8.763 | 0.027 | 1.00 | 10.07 | O |
| ATOM | 851 | CG2 | THR | A | 139 | −3.704 | −7.380 | −1.039 | 1.00 | 12.72 | C |
| ATOM | 852 | N | GLY | A | 140 | 0.112 | −6.514 | 1.764 | 1.00 | 10.29 | N |
| ATOM | 853 | CA | GLY | A | 140 | 0.874 | −6.870 | 2.958 | 1.00 | 11.09 | C |
| ATOM | 854 | C | GLY | A | 140 | 0.711 | −8.318 | 3.319 | 1.00 | 11.29 | C |
| ATOM | 855 | O | GLY | A | 140 | 0.288 | −8.673 | 4.422 | 1.00 | 11.16 | O |
| ATOM | 856 | N | ASN | A | 141 | 1.050 | −9.224 | 2.403 | 1.00 | 12.13 | N |
| ATOM | 857 | CA | ASN | A | 141 | 0.939 | −10.635 | 2.670 | 1.00 | 12.49 | C |
| ATOM | 858 | C | ASN | A | 141 | −0.503 | −11.053 | 2.971 | 1.00 | 11.09 | C |
| ATOM | 859 | O | ASN | A | 141 | −0.740 | −11.974 | 3.748 | 1.00 | 12.32 | O |
| ATOM | 860 | CB | ASN | A | 141 | 1.894 | −11.127 | 3.762 | 1.00 | 14.48 | C |
| ATOM | 861 | CG | ASN | A | 141 | 3.276 | −11.436 | 3.236 | 1.00 | 17.63 | C |
| ATOM | 862 | OD1 | ASN | A | 141 | 4.279 | −11.278 | 4.008 | 1.00 | 27.51 | O |
| ATOM | 863 | ND2 | ASN | A | 141 | 3.393 | −11.789 | 1.982 | 1.00 | 16.25 | N |
| ATOM | 864 | N | GLY | A | 142 | −1.443 | −10.370 | 2.352 | 1.00 | 10.81 | N |
| ATOM | 865 | CA | GLY | A | 142 | −2.851 | −10.665 | 2.556 | 1.00 | 10.66 | C |
| ATOM | 866 | C | GLY | A | 142 | −3.431 | −10.256 | 3.874 | 1.00 | 11.36 | C |
| ATOM | 867 | O | GLY | A | 142 | −4.605 | −10.502 | 4.151 | 1.00 | 11.65 | O |
| ATOM | 868 | N | LYS | A | 143 | −2.676 | −9.496 | 4.665 | 1.00 | 12.13 | N |
| ATOM | 869 | CA | LYS | A | 143 | −3.028 | −9.270 | 6.080 | 1.00 | 13.27 | C |
| ATOM | 870 | C | LYS | A | 143 | −3.305 | −7.835 | 6.389 | 1.00 | 13.02 | C |
| ATOM | 871 | O | LYS | A | 143 | −3.658 | −7.527 | 7.570 | 1.00 | 16.06 | O |
| ATOM | 872 | CB | LYS | A | 143 | −1.950 | −9.812 | 6.978 | 1.00 | 14.56 | C |
| ATOM | 873 | CG | LYS | A | 143 | −1.908 | −11.334 | 6.998 | 1.00 | 17.20 | C |
| ATOM | 874 | CD | LYS | A | 143 | −0.741 | −11.784 | 7.805 | 1.00 | 22.00 | C |
| ATOM | 875 | CE | LYS | A | 143 | −0.457 | −13.228 | 7.581 | 1.00 | 27.18 | C |
| ATOM | 876 | NZ | LYS | A | 143 | 0.975 | −13.471 | 7.935 | 1.00 | 33.47 | N |
| ATOM | 877 | N | SER | A | 144 | −3.221 | −6.918 | 5.458 | 1.00 | 12.33 | N |
| ATOM | 878 | CA | SER | A | 144 | −3.490 | −5.496 | 5.773 | 1.00 | 13.51 | C |
| ATOM | 879 | C | SER | A | 144 | −4.967 | −5.263 | 6.032 | 1.00 | 15.16 | C |
| ATOM | 880 | O | SER | A | 144 | −5.853 | −6.004 | 5.572 | 1.00 | 14.24 | O |
| ATOM | 881 | CB | SER | A | 144 | −3.076 | −4.594 | 4.616 | 1.00 | 13.23 | C |
| ATOM | 882 | OG | SER | A | 144 | −3.937 | −4.675 | 3.505 | 1.00 | 13.70 | O |
| ATOM | 883 | N | GLU | A | 145 | −5.277 | −4.208 | 6.797 | 1.00 | 16.08 | N |
| ATOM | 884 | CA | GLU | A | 145 | −6.659 | −3.855 | 6.991 | 1.00 | 17.75 | C |
| ATOM | 885 | C | GLU | A | 145 | −7.376 | −3.514 | 5.680 | 1.00 | 16.15 | C |
| ATOM | 886 | O | GLU | A | 145 | −8.512 | −3.913 | 5.444 | 1.00 | 15.69 | O |
| ATOM | 887 | CB | GLU | A | 145 | −6.757 | −2.675 | 7.974 | 1.00 | 23.35 | C |
| ATOM | 888 | CG | GLU | A | 145 | −8.212 | −2.345 | 8.338 | 1.00 | 28.95 | C |
| ATOM | 889 | CD | GLU | A | 145 | −8.858 | −3.377 | 9.258 | 1.00 | 36.54 | C |
| ATOM | 890 | OE1 | GLU | A | 145 | −8.267 | −4.464 | 9.527 | 1.00 | 45.69 | O |
| ATOM | 891 | OE2 | GLU | A | 145 | −9.993 | −3.102 | 9.743 | 1.00 | 50.72 | O |
| ATOM | 892 | N | LEU | A | 146 | −6.722 | −2.772 | 4.788 | 1.00 | 15.60 | N |
| ATOM | 893 | CA | LEU | A | 146 | −7.322 | −2.422 | 3.538 | 1.00 | 16.16 | C |
| ATOM | 894 | C | LEU | A | 146 | −7.670 | −3.637 | 2.665 | 1.00 | 12.77 | C |
| ATOM | 895 | O | LEU | A | 146 | −8.596 | −3.577 | 1.888 | 1.00 | 13.41 | O |
| ATOM | 896 | CB | LEU | A | 146 | −6.405 | −1.463 | 2.772 | 1.00 | 19.73 | C |
| ATOM | 897 | CG | LEU | A | 146 | −6.919 | −0.841 | 1.526 | 1.00 | 23.19 | C |
| ATOM | 898 | CD1 | LEU | A | 146 | −8.126 | 0.043 | 1.846 | 1.00 | 25.94 | C |
| ATOM | 899 | CD2 | LEU | A | 146 | −5.776 | −0.021 | 0.892 | 1.00 | 26.74 | C |
| ATOM | 900 | N | ALA | A | 147 | −6.885 | −4.688 | 2.795 | 1.00 | 12.41 | N |
| ATOM | 901 | CA | ALA | A | 147 | −7.181 | −5.882 | 1.993 | 1.00 | 11.19 | C |
| ATOM | 902 | C | ALA | A | 147 | −8.534 | −6.478 | 2.365 | 1.00 | 11.15 | C |
| ATOM | 903 | O | ALA | A | 147 | −9.123 | −7.123 | 1.554 | 1.00 | 10.39 | O |
| ATOM | 904 | CB | ALA | A | 147 | −6.104 | −6.892 | 2.179 | 1.00 | 10.71 | C |

TABLE 2-continued

X-RAY DIFFRACTION DATA OF *S. AUREUS* AUTOLYSIN E (AtlE 4PIA) RESIDUES 35-258

| ATOM | 905 | N | LYS | A | 148 | −9.062 | −6.152 | 3.556 | 1.00 | 10.90 | N |
|---|---|---|---|---|---|---|---|---|---|---|---|
| ATOM | 906 | CA | LYS | A | 148 | −10.379 | −6.593 | 3.937 | 1.00 | 11.03 | C |
| ATOM | 907 | C | LYS | A | 148 | −11.499 | −5.752 | 3.377 | 1.00 | 11.21 | C |
| ATOM | 908 | O | LYS | A | 148 | −12.669 | −6.008 | 3.670 | 1.00 | 12.03 | O |
| ATOM | 909 | CB | LYS | A | 148 | −10.455 | −6.786 | 5.474 | 1.00 | 12.65 | C |
| ATOM | 910 | CG | LYS | A | 148 | −9.477 | −7.832 | 6.010 | 1.00 | 14.18 | C |
| ATOM | 911 | CD | LYS | A | 148 | −9.693 | −8.280 | 7.474 | 1.00 | 15.45 | C |
| ATOM | 912 | CE | LYS | A | 148 | −8.492 | −9.006 | 8.039 | 1.00 | 18.31 | C |
| ATOM | 913 | NZ | LYS | A | 148 | −7.899 | −10.133 | 7.271 | 1.00 | 19.78 | N |
| ATOM | 914 | N | GLY | A | 149 | −11.203 | −4.740 | 2.544 | 1.00 | 11.24 | N |
| ATOM | 915 | CA | GLY | A | 149 | −12.211 | −4.146 | 1.752 | 1.00 | 11.90 | C |
| ATOM | 916 | C | GLY | A | 149 | −12.854 | −2.896 | 2.355 | 1.00 | 12.37 | C |
| ATOM | 917 | O | GLY | A | 149 | −12.540 | −2.552 | 3.480 | 1.00 | 15.68 | O |
| ATOM | 918 | N | ILE | A | 150 | −13.691 | −2.300 | 1.562 | 1.00 | 13.35 | N |
| ATOM | 919 | CA | ILE | A | 150 | −14.362 | −1.014 | 1.922 | 1.00 | 14.97 | C |
| ATOM | 920 | C | ILE | A | 150 | −15.851 | −1.198 | 1.753 | 1.00 | 14.74 | C |
| ATOM | 921 | O | ILE | A | 150 | −16.361 | −1.619 | 0.748 | 1.00 | 14.07 | O |
| ATOM | 922 | CB | ILE | A | 150 | −13.872 | 0.119 | 1.029 | 1.00 | 17.38 | C |
| ATOM | 923 | CG1 | ILE | A | 150 | −12.403 | 0.327 | 1.233 | 1.00 | 18.09 | C |
| ATOM | 924 | CG2 | ILE | A | 150 | −14.601 | 1.447 | 1.352 | 1.00 | 18.80 | C |
| ATOM | 925 | CD1 | ILE | A | 150 | −11.797 | 1.178 | 0.122 | 1.00 | 21.67 | C |
| ATOM | 926 | N | LYS | A | 151 | −16.564 | −0.856 | 2.828 | 1.00 | 17.86 | N |
| ATOM | 927 | CA | LYS | A | 151 | −18.003 | −1.022 | 2.888 | 1.00 | 20.82 | C |
| ATOM | 928 | C | LYS | A | 151 | −18.715 | 0.091 | 2.145 | 1.00 | 21.11 | C |
| ATOM | 929 | O | LYS | A | 151 | −18.257 | 1.230 | 2.174 | 1.00 | 22.12 | O |
| ATOM | 930 | CB | LYS | A | 151 | −18.426 | −1.051 | 4.359 | 1.00 | 25.53 | C |
| ATOM | 931 | CG | LYS | A | 151 | −19.879 | −1.383 | 4.585 | 1.00 | 33.29 | C |
| ATOM | 932 | CD | LYS | A | 151 | −20.210 | −1.329 | 6.073 | 1.00 | 38.11 | C |
| ATOM | 933 | CE | LYS | A | 151 | −21.700 | −1.540 | 6.328 | 1.00 | 42.75 | C |
| ATOM | 934 | NZ | LYS | A | 151 | −22.547 | −0.510 | 5.646 | 1.00 | 46.33 | N |
| ATOM | 935 | N | ASP | A | 152 | −19.768 | −0.263 | 1.423 | 1.00 | 20.28 | N |
| ATOM | 936 | CA | ASP | A | 152 | −20.715 | 0.718 | 0.876 | 1.00 | 24.19 | C |
| ATOM | 937 | C | ASP | A | 152 | −22.078 | 0.076 | 0.741 | 1.00 | 24.13 | C |
| ATOM | 938 | O | ASP | A | 152 | −22.295 | −0.884 | −0.022 | 1.00 | 23.13 | O |
| ATOM | 939 | CB | ASP | A | 152 | −20.246 | 1.261 | −0.467 | 1.00 | 29.52 | C |
| ATOM | 940 | CG | ASP | A | 152 | −21.141 | 2.388 | −0.965 | 1.00 | 34.23 | C |
| ATOM | 941 | OD1 | ASP | A | 152 | −21.153 | 3.467 | −0.337 | 1.00 | 39.62 | O |
| ATOM | 942 | OD2 | ASP | A | 152 | −21.829 | 2.176 | −1.970 | 1.00 | 39.95 | O |
| ATOM | 943 | N | GLY | A | 153 | −23.025 | 0.606 | 1.519 | 1.00 | 26.24 | N |
| ATOM | 944 | CA | GLY | A | 153 | −24.350 | 0.000 | 1.627 | 1.00 | 23.41 | C |
| ATOM | 945 | C | GLY | A | 153 | −24.229 | −1.411 | 2.162 | 1.00 | 21.65 | C |
| ATOM | 946 | O | GLY | A | 153 | −23.569 | −1.650 | 3.146 | 1.00 | 25.00 | O |
| ATOM | 947 | N | LYS | A | 154 | −24.859 | −2.350 | 1.493 | 1.00 | 19.76 | N |
| ATOM | 948 | CA | LYS | A | 154 | −24.802 | −3.728 | 1.956 | 1.00 | 20.22 | C |
| ATOM | 949 | C | LYS | A | 154 | −23.669 | −4.548 | 1.363 | 1.00 | 17.98 | C |
| ATOM | 950 | O | LYS | A | 154 | −23.557 | −5.748 | 1.630 | 1.00 | 16.13 | O |
| ATOM | 951 | CB | LYS | A | 154 | −26.153 | −4.379 | 1.728 | 1.00 | 21.58 | C |
| ATOM | 952 | CG | LYS | A | 154 | −27.230 | −3.562 | 2.457 | 1.00 | 26.02 | C |
| ATOM | 953 | CD | LYS | A | 154 | −28.248 | −4.410 | 3.188 | 1.00 | 27.45 | C |
| ATOM | 954 | CE | LYS | A | 154 | −29.439 | −3.547 | 3.651 | 1.00 | 26.37 | C |
| ATOM | 955 | NZ | LYS | A | 154 | −30.388 | −4.302 | 4.526 | 1.00 | 28.16 | N |
| ATOM | 956 | N | LYS | A | 155 | −22.811 | −3.887 | 0.588 | 1.00 | 17.05 | N |
| ATOM | 957 | CA | LYS | A | 155 | −21.715 | −4.552 | −0.101 | 1.00 | 16.46 | C |
| ATOM | 958 | C | LYS | A | 155 | −20.375 | −4.141 | 0.461 | 1.00 | 16.14 | C |
| ATOM | 959 | O | LYS | A | 155 | −20.229 | −3.158 | 1.176 | 1.00 | 17.69 | O |
| ATOM | 960 | CB | LYS | A | 155 | −21.787 | −4.197 | −1.588 | 1.00 | 20.02 | C |
| ATOM | 961 | CG | LYS | A | 155 | −23.029 | −4.708 | −2.317 | 1.00 | 23.11 | C |
| ATOM | 962 | CD | LYS | A | 155 | −23.071 | −4.070 | −3.686 | 1.00 | 28.72 | C |
| ATOM | 963 | CE | LYS | A | 155 | −24.201 | −4.616 | −4.528 | 1.00 | 35.93 | C |
| ATOM | 964 | NZ | LYS | A | 155 | −24.423 | −3.693 | −5.679 | 1.00 | 40.80 | N |
| ATOM | 965 | N | ARG | A | 156 | −19.346 | −4.925 | 0.152 | 1.00 | 15.35 | N |
| ATOM | 966 | CA | ARG | A | 156 | −17.956 | −4.569 | 0.463 | 1.00 | 14.92 | C |
| ATOM | 967 | C | ARG | A | 156 | −17.225 | −4.716 | −0.831 | 1.00 | 12.58 | C |
| ATOM | 968 | O | ARG | A | 156 | −17.438 | −5.711 | −1.557 | 1.00 | 12.90 | O |
| ATOM | 969 | CB | ARG | A | 156 | −17.313 | −5.480 | 1.496 | 1.00 | 18.24 | C |
| ATOM | 970 | CG | ARG | A | 156 | −17.796 | −5.241 | 2.876 | 1.00 | 22.55 | C |
| ATOM | 971 | CD | ARG | A | 156 | −16.963 | −5.956 | 3.892 | 1.00 | 25.24 | C |
| ATOM | 972 | NE | ARG | A | 156 | −17.554 | −5.738 | 5.197 | 1.00 | 31.63 | N |
| ATOM | 973 | CZ | ARG | A | 156 | −16.966 | −6.024 | 6.360 | 1.00 | 37.60 | C |
| ATOM | 974 | NH1 | ARG | A | 156 | −15.748 | −6.568 | 6.409 | 1.00 | 36.26 | N |
| ATOM | 975 | NH2 | ARG | A | 156 | −17.615 | −5.757 | 7.494 | 1.00 | 40.08 | N |
| ATOM | 976 | N | TYR | A | 157 | −16.316 | −3.769 | −1.076 | 1.00 | 11.89 | N |
| ATOM | 977 | CA | TYR | A | 157 | −15.473 | −3.788 | −2.283 | 1.00 | 11.56 | C |
| ATOM | 978 | C | TYR | A | 157 | −14.040 | −4.108 | −1.891 | 1.00 | 9.70 | C |
| ATOM | 979 | O | TYR | A | 157 | −13.526 | −3.692 | −0.885 | 1.00 | 10.77 | O |
| ATOM | 980 | CB | TYR | A | 157 | −15.578 | −2.464 | −3.026 | 1.00 | 13.28 | C |
| ATOM | 981 | CG | TYR | A | 157 | −17.000 | −2.255 | −3.503 | 1.00 | 15.44 | C |
| ATOM | 982 | CD1 | TYR | A | 157 | −17.480 | −2.822 | −4.659 | 1.00 | 15.95 | C |

TABLE 2-continued

X-RAY DIFFRACTION DATA OF *S. AUREUS* AUTOLYSIN E (AtlE 4PIA) RESIDUES 35-258

| ATOM | 983 | CD2 | TYR | A | 157 | −17.903 | −1.584 | −2.701 | 1.00 | 19.95 | C |
|---|---|---|---|---|---|---|---|---|---|---|---|
| ATOM | 984 | CE1 | TYR | A | 157 | −18.820 | −2.691 | −5.060 | 1.00 | 18.07 | C |
| ATOM | 985 | CE2 | TYR | A | 157 | −19.240 | −1.454 | −3.097 | 1.00 | 21.45 | C |
| ATOM | 986 | CZ | TYR | A | 157 | −19.665 | −1.972 | −4.266 | 1.00 | 20.91 | C |
| ATOM | 987 | OH | TYR | A | 157 | −20.986 | −1.804 | −4.709 | 1.00 | 26.55 | O |
| ATOM | 988 | N | TYR | A | 158 | −13.417 | −4.901 | −2.784 | 1.00 | 9.40 | N |
| ATOM | 989 | CA | TYR | A | 158 | −12.057 | −5.442 | −2.564 | 1.00 | 9.30 | C |
| ATOM | 990 | C | TYR | A | 158 | −11.163 | −5.012 | −3.713 | 1.00 | 8.23 | C |
| ATOM | 991 | O | TYR | A | 158 | −11.618 | −4.833 | −4.832 | 1.00 | 9.33 | O |
| ATOM | 992 | CB | TYR | A | 158 | −12.094 | −6.982 | −2.466 | 1.00 | 9.29 | C |
| ATOM | 993 | CG | TYR | A | 158 | −12.879 | −7.452 | −1.274 | 1.00 | 8.71 | C |
| ATOM | 994 | CD1 | TYR | A | 158 | −14.264 | −7.601 | −1.396 | 1.00 | 8.89 | C |
| ATOM | 995 | CD2 | TYR | A | 158 | −12.287 | −7.761 | −0.083 | 1.00 | 8.75 | C |
| ATOM | 996 | CE1 | TYR | A | 158 | −15.026 | −7.999 | −0.286 | 1.00 | 9.56 | C |
| ATOM | 997 | CE2 | TYR | A | 158 | −13.045 | −8.144 | 1.027 | 1.00 | 9.82 | C |
| ATOM | 998 | CZ | TYR | A | 158 | −14.410 | −8.282 | 0.880 | 1.00 | 9.26 | C |
| ATOM | 999 | OH | TYR | A | 158 | −15.168 | −8.694 | 1.984 | 1.00 | 10.35 | O |
| ATOM | 1000 | N | ASN | A | 159 | −9.873 | −4.898 | −3.403 | 1.00 | 8.55 | N |
| ATOM | 1001 | CA | ASN | A | 159 | −8.885 | −4.478 | −4.445 | 1.00 | 8.39 | C |
| ATOM | 1002 | C | ASN | A | 159 | −7.540 | −4.913 | −3.957 | 1.00 | 8.49 | C |
| ATOM | 1003 | O | ASN | A | 159 | −7.052 | −4.491 | −2.946 | 1.00 | 9.94 | O |
| ATOM | 1004 | CB | ASN | A | 159 | −8.952 | −2.938 | −4.557 | 1.00 | 9.24 | C |
| ATOM | 1005 | CG | ASN | A | 159 | −8.151 | −2.366 | −5.735 | 1.00 | 10.96 | C |
| ATOM | 1006 | OD1 | ASN | A | 159 | −7.182 | −2.958 | −6.236 | 1.00 | 11.33 | O |
| ATOM | 1007 | ND2 | ASN | A | 159 | −8.595 | −1.204 | −6.207 | 1.00 | 11.67 | N |
| ATOM | 1008 | N | PHE | A | 160 | −6.963 | −5.873 | −4.692 | 1.00 | 8.09 | N |
| ATOM | 1009 | CA | PHE | A | 160 | −5.699 | −6.465 | −4.289 | 1.00 | 7.56 | C |
| ATOM | 1010 | C | PHE | A | 160 | −4.462 | −6.028 | −5.090 | 1.00 | 7.63 | C |
| ATOM | 1011 | O | PHE | A | 160 | −3.375 | −6.557 | −4.895 | 1.00 | 8.90 | O |
| ATOM | 1012 | CB | PHE | A | 160 | −5.782 | −8.001 | −4.293 | 1.00 | 8.01 | C |
| ATOM | 1013 | CG | PHE | A | 160 | −6.872 | −8.574 | −3.389 | 1.00 | 8.64 | C |
| ATOM | 1014 | CD1 | PHE | A | 160 | −7.174 | −8.014 | −2.174 | 1.00 | 8.60 | C |
| ATOM | 1015 | CD2 | PHE | A | 160 | −7.562 | −9.718 | −3.770 | 1.00 | 8.92 | C |
| ATOM | 1016 | CE1 | PHE | A | 160 | −8.185 | −8.561 | −1.371 | 1.00 | 9.32 | C |
| ATOM | 1017 | CE2 | PHE | A | 160 | −8.514 | −10.284 | −2.957 | 1.00 | 9.63 | C |
| ATOM | 1018 | CZ | PHE | A | 160 | −8.832 | −9.707 | −1.776 | 1.00 | 8.98 | C |
| ATOM | 1019 | N | PHE | A | 161 | −4.668 | −5.093 | −5.999 | 1.00 | 7.82 | N |
| ATOM | 1020 | CA | PHE | A | 161 | −3.596 | −4.673 | −6.919 | 1.00 | 8.40 | C |
| ATOM | 1021 | C | PHE | A | 161 | −3.384 | −3.186 | −6.983 | 1.00 | 9.78 | C |
| ATOM | 1022 | O | PHE | A | 161 | −2.748 | −2.732 | −7.947 | 1.00 | 11.10 | O |
| ATOM | 1023 | CB | PHE | A | 161 | −3.825 | −5.316 | −8.294 | 1.00 | 8.17 | C |
| ATOM | 1024 | CG | PHE | A | 161 | −3.926 | −6.820 | −8.265 | 1.00 | 7.60 | C |
| ATOM | 1025 | CD1 | PHE | A | 161 | −2.804 | −7.634 | −8.279 | 1.00 | 7.97 | C |
| ATOM | 1026 | CD2 | PHE | A | 161 | −5.162 | −7.410 | −8.220 | 1.00 | 7.70 | C |
| ATOM | 1027 | CE1 | PHE | A | 161 | −2.913 | −9.002 | −8.209 | 1.00 | 7.97 | C |
| ATOM | 1028 | CE2 | PHE | A | 161 | −5.287 | −8.776 | −8.160 | 1.00 | 8.28 | C |
| ATOM | 1029 | CZ | PHE | A | 161 | −4.172 | −9.604 | −8.163 | 1.00 | 8.10 | C |
| ATOM | 1030 | N | GLY | A | 162 | −3.950 | −2.422 | −6.066 | 1.00 | 9.69 | N |
| ATOM | 1031 | CA | GLY | A | 162 | −3.723 | −0.984 | −6.148 | 1.00 | 10.72 | C |
| ATOM | 1032 | C | GLY | A | 162 | −4.265 | −0.345 | −7.368 | 1.00 | 11.64 | C |
| ATOM | 1033 | O | GLY | A | 162 | −3.643 | 0.609 | −7.897 | 1.00 | 13.66 | O |
| ATOM | 1034 | N | ILE | A | 163 | −5.400 | −0.790 | −7.873 | 1.00 | 10.29 | N |
| ATOM | 1035 | CA | ILE | A | 163 | −6.001 | −0.272 | −9.081 | 1.00 | 10.88 | C |
| ATOM | 1036 | C | ILE | A | 163 | −6.971 | 0.830 | −8.796 | 1.00 | 12.62 | C |
| ATOM | 1037 | O | ILE | A | 163 | −8.022 | 0.664 | −8.163 | 1.00 | 12.13 | O |
| ATOM | 1038 | CB | ILE | A | 163 | −6.675 | −1.398 | −9.862 | 1.00 | 10.52 | C |
| ATOM | 1039 | CG1 | ILE | A | 163 | −5.649 | −2.480 | −10.253 | 1.00 | 10.49 | C |
| ATOM | 1040 | CG2 | ILE | A | 163 | −7.360 | −0.811 | −11.068 | 1.00 | 11.06 | C |
| ATOM | 1041 | CD1 | ILE | A | 163 | −6.256 | −3.790 | −10.654 | 1.00 | 10.53 | C |
| ATOM | 1042 | N | GLY | A | 164 | −6.601 | 2.016 | −9.305 | 1.00 | 14.03 | N |
| ATOM | 1043 | CA | GLY | A | 164 | −7.460 | 3.204 | −9.136 | 1.00 | 15.22 | C |
| ATOM | 1044 | C | GLY | A | 164 | −7.522 | 3.702 | −7.735 | 1.00 | 16.47 | C |
| ATOM | 1045 | O | GLY | A | 164 | −6.713 | 3.349 | −6.890 | 1.00 | 18.13 | O |
| ATOM | 1046 | N | ALA | A | 165 | −8.502 | 4.589 | −7.475 | 1.00 | 17.40 | N |
| ATOM | 1047 | CA | ALA | A | 165 | −8.654 | 5.094 | −6.135 | 1.00 | 17.47 | C |
| ATOM | 1048 | C | ALA | A | 165 | −9.448 | 4.101 | −5.282 | 1.00 | 15.06 | C |
| ATOM | 1049 | O | ALA | A | 165 | −10.456 | 3.586 | −5.703 | 1.00 | 17.71 | O |
| ATOM | 1050 | CB | ALA | A | 165 | −9.337 | 6.460 | −6.119 | 1.00 | 17.86 | C |
| ATOM | 1051 | N | PHE | A | 166 | −8.880 | 3.858 | −4.130 | 1.00 | 17.68 | N |
| ATOM | 1052 | CA | PHE | A | 166 | −9.415 | 2.860 | −3.191 | 1.00 | 16.94 | C |
| ATOM | 1053 | C | PHE | A | 166 | −9.288 | 3.271 | −1.742 | 1.00 | 18.64 | C |
| ATOM | 1054 | O | PHE | A | 166 | −8.362 | 2.900 | −1.037 | 1.00 | 21.06 | O |
| ATOM | 1055 | CB | PHE | A | 166 | −8.788 | 1.493 | −3.488 | 1.00 | 15.21 | C |
| ATOM | 1056 | CG | PHE | A | 166 | −9.544 | 0.336 | −2.806 | 1.00 | 13.54 | C |
| ATOM | 1057 | CD1 | PHE | A | 166 | −10.775 | −0.014 | −3.271 | 1.00 | 13.14 | C |
| ATOM | 1058 | CD2 | PHE | A | 166 | −9.011 | −0.324 | −1.759 | 1.00 | 13.60 | C |
| ATOM | 1059 | CE1 | PHE | A | 166 | −11.525 | −1.067 | −2.656 | 1.00 | 14.01 | C |
| ATOM | 1060 | CE2 | PHE | A | 166 | −9.727 | −1.406 | −1.143 | 1.00 | 14.07 | C |

TABLE 2-continued

X-RAY DIFFRACTION DATA OF *S. AUREUS* AUTOLYSIN E (AtlE 4PIA) RESIDUES 35-258

| ATOM | 1061 | CZ | PHE | A | 166 | −10.948 | −1.725 | −1.598 | 1.00 | 12.66 | C |
|---|---|---|---|---|---|---|---|---|---|---|---|
| ATOM | 1062 | N | ASP | A | 167 | −10.282 | 4.076 | −1.355 | 1.00 | 24.94 | N |
| ATOM | 1063 | CA | ASP | A | 167 | −10.501 | 4.512 | 0.031 | 1.00 | 26.64 | C |
| ATOM | 1064 | C | ASP | A | 167 | −11.994 | 4.805 | 0.207 | 1.00 | 24.99 | C |
| ATOM | 1065 | O | ASP | A | 167 | −12.767 | 4.782 | −0.754 | 1.00 | 26.37 | O |
| ATOM | 1066 | CB | ASP | A | 167 | −9.626 | 5.728 | 0.360 | 1.00 | 30.81 | C |
| ATOM | 1067 | CG | ASP | A | 167 | −9.850 | 6.900 | −0.569 | 1.00 | 32.54 | C |
| ATOM | 1068 | OD1 | ASP | A | 167 | −10.994 | 7.194 | −0.968 | 1.00 | 35.13 | O |
| ATOM | 1069 | OD2 | ASP | A | 167 | −8.846 | 7.553 | −0.909 | 1.00 | 40.97 | O |
| ATOM | 1070 | N | SER | A | 168 | −12.401 | 5.113 | 1.452 | 1.00 | 31.69 | N |
| ATOM | 1071 | CA | SER | A | 168 | −13.814 | 5.344 | 1.755 | 1.00 | 33.30 | C |
| ATOM | 1072 | C | SER | A | 168 | −14.430 | 6.488 | 0.989 | 1.00 | 32.40 | C |
| ATOM | 1073 | O | SER | A | 168 | −15.510 | 6.317 | 0.454 | 1.00 | 32.86 | O |
| ATOM | 1074 | CB | SER | A | 168 | −14.041 | 5.541 | 3.254 | 1.00 | 39.75 | C |
| ATOM | 1075 | OG | SER | A | 168 | −13.655 | 4.368 | 3.945 | 1.00 | 45.60 | O |
| ATOM | 1076 | N | SER | A | 169 | −13.724 | 7.617 | 0.875 | 1.00 | 35.48 | N |
| ATOM | 1077 | CA | SER | A | 169 | −14.211 | 8.741 | 0.063 | 1.00 | 37.10 | C |
| ATOM | 1078 | C | SER | A | 169 | −14.528 | 8.277 | −1.348 | 1.00 | 35.55 | C |
| ATOM | 1079 | O | SER | A | 169 | −15.660 | 8.437 | −1.825 | 1.00 | 34.19 | O |
| ATOM | 1080 | CB | SER | A | 169 | −13.183 | 9.886 | −0.015 | 1.00 | 41.12 | C |
| ATOM | 1081 | OG | SER | A | 169 | −12.698 | 10.244 | 1.261 | 1.00 | 45.25 | O |
| ATOM | 1082 | N | ALA | A | 170 | −13.536 | 7.653 | −2.006 | 1.00 | 31.96 | N |
| ATOM | 1083 | CA | ALA | A | 170 | −13.673 | 7.293 | −3.414 | 1.00 | 30.78 | C |
| ATOM | 1084 | C | ALA | A | 170 | −14.780 | 6.283 | −3.612 | 1.00 | 27.53 | C |
| ATOM | 1085 | O | ALA | A | 170 | −15.539 | 6.338 | −4.569 | 1.00 | 31.58 | O |
| ATOM | 1086 | CB | ALA | A | 170 | −12.347 | 6.748 | −3.955 | 1.00 | 26.95 | C |
| ATOM | 1087 | N | VAL | A | 171 | −14.865 | 5.324 | −2.694 | 1.00 | 32.42 | N |
| ATOM | 1088 | CA | VAL | A | 171 | −15.908 | 4.299 | −2.757 | 1.00 | 35.74 | C |
| ATOM | 1089 | C | VAL | A | 171 | −17.299 | 4.919 | −2.497 | 1.00 | 36.55 | C |
| ATOM | 1090 | O | VAL | A | 171 | −18.227 | 4.671 | −3.260 | 1.00 | 35.20 | O |
| ATOM | 1091 | CB | VAL | A | 171 | −15.626 | 3.113 | −1.786 | 1.00 | 34.33 | C |
| ATOM | 1092 | CG1 | VAL | A | 171 | −16.817 | 2.154 | −1.764 | 1.00 | 32.75 | C |
| ATOM | 1093 | CG2 | VAL | A | 171 | −14.375 | 2.364 | −2.217 | 1.00 | 33.40 | C |
| ATOM | 1094 | N | ARG | A | 172 | −17.424 | 5.765 | −1.472 | 1.00 | 45.16 | N |
| ATOM | 1095 | CA | ARG | A | 172 | −18.707 | 6.466 | −1.209 | 1.00 | 50.95 | C |
| ATOM | 1096 | C | ARG | A | 172 | −19.191 | 7.307 | −2.412 | 1.00 | 53.17 | C |
| ATOM | 1097 | O | ARG | A | 172 | −20.372 | 7.251 | −2.776 | 1.00 | 54.99 | O |
| ATOM | 1098 | CB | ARG | A | 172 | −18.610 | 7.332 | 0.052 | 1.00 | 56.55 | C |
| ATOM | 1099 | CG | ARG | A | 172 | −18.498 | 6.531 | 1.350 | 1.00 | 61.00 | C |
| ATOM | 1100 | CD | ARG | A | 172 | −18.742 | 7.399 | 2.581 | 1.00 | 65.06 | C |
| ATOM | 1101 | NE | ARG | A | 172 | −17.931 | 8.626 | 2.583 | 1.00 | 67.07 | N |
| ATOM | 1102 | CZ | ARG | A | 172 | −16.814 | 8.832 | 3.291 | 1.00 | 69.01 | C |
| ATOM | 1103 | NH1 | ARG | A | 172 | −16.182 | 10.002 | 3.193 | 1.00 | 70.62 | N |
| ATOM | 1104 | NH2 | ARG | A | 172 | −16.316 | 7.896 | 4.097 | 1.00 | 67.75 | N |
| ATOM | 1105 | N | SER | A | 173 | −18.276 | 8.045 | −3.047 | 1.00 | 49.50 | N |
| ATOM | 1106 | CA | SER | A | 173 | −18.622 | 8.909 | −4.184 | 1.00 | 50.52 | C |
| ATOM | 1107 | C | SER | A | 173 | −18.805 | 8.185 | −5.526 | 1.00 | 50.89 | C |
| ATOM | 1108 | O | SER | A | 173 | −19.270 | 8.792 | −6.489 | 1.00 | 54.62 | O |
| ATOM | 1109 | CB | SER | A | 173 | −17.529 | 9.953 | −4.365 | 1.00 | 52.02 | C |
| ATOM | 1110 | OG | SER | A | 173 | −16.328 | 9.332 | −4.795 | 1.00 | 50.30 | O |
| ATOM | 1111 | N | GLY | A | 174 | −18.403 | 6.915 | −5.601 | 1.00 | 47.33 | N |
| ATOM | 1112 | CA | GLY | A | 174 | −18.498 | 6.139 | −6.836 | 1.00 | 44.83 | C |
| ATOM | 1113 | C | GLY | A | 174 | −17.382 | 6.489 | −7.811 | 1.00 | 43.77 | C |
| ATOM | 1114 | O | GLY | A | 174 | −17.451 | 6.124 | −8.975 | 1.00 | 43.92 | O |
| ATOM | 1115 | N | LYS | A | 175 | −16.350 | 7.187 | −7.340 | 1.00 | 38.42 | N |
| ATOM | 1116 | CA | LYS | A | 175 | −15.156 | 7.460 | −8.149 | 1.00 | 39.75 | C |
| ATOM | 1117 | C | LYS | A | 175 | −14.095 | 6.422 | −7.778 | 1.00 | 34.68 | C |
| ATOM | 1118 | O | LYS | A | 175 | −12.921 | 6.761 | −7.542 | 1.00 | 37.72 | O |
| ATOM | 1119 | CB | LYS | A | 175 | −14.655 | 8.894 | −7.920 | 1.00 | 47.12 | C |
| ATOM | 1120 | CG | LYS | A | 175 | −15.343 | 9.934 | −8.809 | 1.00 | 52.60 | C |
| ATOM | 1121 | CD | LYS | A | 175 | −15.294 | 11.336 | −8.214 | 1.00 | 56.75 | C |
| ATOM | 1122 | CE | LYS | A | 175 | −16.590 | 11.659 | −7.484 | 1.00 | 61.98 | C |
| ATOM | 1123 | NZ | LYS | A | 175 | −16.512 | 12.866 | −6.609 | 1.00 | 65.10 | N |
| ATOM | 1124 | N | SER | A | 176 | −14.529 | 5.165 | −7.688 | 1.00 | 27.00 | N |
| ATOM | 1125 | CA | SER | A | 176 | −13.615 | 4.034 | −7.381 | 1.00 | 23.61 | C |
| ATOM | 1126 | C | SER | A | 176 | −13.791 | 2.912 | −8.382 | 1.00 | 19.11 | C |
| ATOM | 1127 | O | SER | A | 176 | −14.878 | 2.396 | −8.620 | 1.00 | 17.36 | O |
| ATOM | 1128 | CB | SER | A | 176 | −13.821 | 3.532 | −5.959 | 1.00 | 23.47 | C |
| ATOM | 1129 | OG | SER | A | 176 | −13.074 | 2.349 | −5.717 | 1.00 | 24.64 | O |
| ATOM | 1130 | N | TYR | A | 177 | −12.672 | 2.529 | −9.002 | 1.00 | 17.68 | N |
| ATOM | 1131 | CA | TYR | A | 177 | −12.682 | 1.525 | −10.026 | 1.00 | 15.76 | C |
| ATOM | 1132 | C | TYR | A | 177 | −13.215 | 0.165 | −9.499 | 1.00 | 14.04 | C |
| ATOM | 1133 | O | TYR | A | 177 | −13.989 | −0.499 | −10.164 | 1.00 | 14.24 | O |
| ATOM | 1134 | CB | TYR | A | 177 | −11.278 | 1.333 | −10.627 | 1.00 | 17.64 | C |
| ATOM | 1135 | CG | TYR | A | 177 | −11.296 | 0.595 | −11.926 | 1.00 | 18.62 | C |
| ATOM | 1136 | CD1 | TYR | A | 177 | −11.660 | 1.239 | −13.095 | 1.00 | 21.83 | C |
| ATOM | 1137 | CD2 | TYR | A | 177 | −10.916 | −0.740 | −12.010 | 1.00 | 18.42 | C |
| ATOM | 1138 | CE1 | TYR | A | 177 | −11.659 | 0.586 | −14.306 | 1.00 | 22.58 | C |

TABLE 2-continued

X-RAY DIFFRACTION DATA OF *S. AUREUS* AUTOLYSIN E (AtlE 4PIA) RESIDUES 35-258

| ATOM | 1139 | CE2 | TYR | A | 177 | −10.912 | −1.409 | −13.207 | 1.00 | 20.88 | C |
|---|---|---|---|---|---|---|---|---|---|---|---|
| ATOM | 1140 | CZ | TYR | A | 177 | −11.269 | −0.734 | −14.373 | 1.00 | 21.36 | C |
| ATOM | 1141 | OH | TYR | A | 177 | −11.263 | −1.405 | −15.543 | 1.00 | 26.71 | O |
| ATOM | 1142 | N | ALA | A | 178 | −12.817 | −0.128 | −8.268 | 1.00 | 14.26 | N |
| ATOM | 1143 | CA | ALA | A | 178 | −13.277 | −1.382 | −7.637 | 1.00 | 14.75 | C |
| ATOM | 1144 | C | ALA | A | 178 | −14.795 | −1.447 | −7.567 | 1.00 | 15.07 | C |
| ATOM | 1145 | O | ALA | A | 178 | −15.403 | −2.496 | −7.749 | 1.00 | 14.79 | O |
| ATOM | 1146 | CB | ALA | A | 178 | −12.666 | −1.605 | −6.291 | 1.00 | 14.19 | C |
| ATOM | 1147 | N | GLU | A | 179 | −15.403 | −0.317 | −7.256 | 1.00 | 15.92 | N |
| ATOM | 1148 | CA | GLU | A | 179 | −16.872 | −0.221 | −7.221 | 1.00 | 18.91 | C |
| ATOM | 1149 | C | GLU | A | 179 | −17.497 | −0.228 | −8.618 | 1.00 | 18.17 | C |
| ATOM | 1150 | O | GLU | A | 179 | −18.456 | −0.940 | −8.861 | 1.00 | 18.43 | O |
| ATOM | 1151 | CB | GLU | A | 179 | −17.238 | 1.044 | −6.453 | 1.00 | 21.29 | C |
| ATOM | 1152 | CG | GLU | A | 179 | −18.723 | 1.238 | −6.255 | 1.00 | 27.74 | C |
| ATOM | 1153 | CD | GLU | A | 179 | −19.029 | 2.270 | −5.181 | 1.00 | 34.74 | C |
| ATOM | 1154 | OE1 | GLU | A | 179 | −18.168 | 3.144 | −4.891 | 1.00 | 41.21 | O |
| ATOM | 1155 | OE2 | GLU | A | 179 | −20.156 | 2.194 | −4.650 | 1.00 | 45.93 | O |
| ATOM | 1156 | N | LYS | A | 180 | −16.888 | 0.506 | −9.561 | 1.00 | 18.03 | N |
| ATOM | 1157 | CA | LYS | A | 180 | −17.356 | 0.525 | −10.923 | 1.00 | 19.60 | C |
| ATOM | 1158 | C | LYS | A | 180 | −17.394 | −0.873 | −11.535 | 1.00 | 19.34 | C |
| ATOM | 1159 | O | LYS | A | 180 | −18.332 | −1.252 | −12.213 | 1.00 | 20.03 | O |
| ATOM | 1160 | CB | LYS | A | 180 | −16.483 | 1.485 | −11.733 | 1.00 | 24.42 | C |
| ATOM | 1161 | CG | LYS | A | 180 | −16.894 | 1.665 | −13.168 | 1.00 | 31.57 | C |
| ATOM | 1162 | CD | LYS | A | 180 | −16.343 | 2.988 | −13.705 | 1.00 | 36.49 | C |
| ATOM | 1163 | CE | LYS | A | 180 | −16.112 | 2.940 | −15.206 | 1.00 | 41.85 | C |
| ATOM | 1164 | NZ | LYS | A | 180 | −14.840 | 2.218 | −15.509 | 1.00 | 42.37 | N |
| ATOM | 1165 | N | GLU | A | 181 | −16.373 | −1.687 | −11.254 | 1.00 | 15.93 | N |
| ATOM | 1166 | CA | GLU | A | 181 | −16.318 | −3.032 | −11.772 | 1.00 | 17.03 | C |
| ATOM | 1167 | C | GLU | A | 181 | −16.953 | −4.097 | −10.853 | 1.00 | 15.53 | C |
| ATOM | 1168 | O | GLU | A | 181 | −16.936 | −5.283 | −11.146 | 1.00 | 17.03 | O |
| ATOM | 1169 | CB | GLU | A | 181 | −14.833 | −3.397 | −12.025 | 1.00 | 18.52 | C |
| ATOM | 1170 | CG | GLU | A | 181 | −14.189 | −2.555 | −13.122 | 1.00 | 21.26 | C |
| ATOM | 1171 | CD | GLU | A | 181 | −14.937 | −2.628 | −14.425 | 1.00 | 26.39 | C |
| ATOM | 1172 | OE1 | GLU | A | 181 | −15.319 | −3.744 | −14.846 | 1.00 | 33.15 | O |
| ATOM | 1173 | OE2 | GLU | A | 181 | −15.125 | −1.565 | −15.023 | 1.00 | 33.72 | O |
| ATOM | 1174 | N | GLN | A | 182 | −17.534 | −3.636 | −9.766 | 1.00 | 15.01 | N |
| ATOM | 1175 | CA | GLN | A | 182 | −18.278 | −4.510 | −8.846 | 1.00 | 16.69 | C |
| ATOM | 1176 | C | GLN | A | 182 | −17.439 | −5.660 | −8.315 | 1.00 | 14.18 | C |
| ATOM | 1177 | O | GLN | A | 182 | −17.834 | −6.826 | −8.352 | 1.00 | 14.46 | O |
| ATOM | 1178 | CB | GLN | A | 182 | −19.628 | −4.965 | −9.451 | 1.00 | 19.53 | C |
| ATOM | 1179 | CG | GLN | A | 182 | −20.611 | −3.785 | −9.557 | 1.00 | 21.50 | C |
| ATOM | 1180 | CD | GLN | A | 182 | −21.036 | −3.184 | −8.190 | 1.00 | 23.84 | C |
| ATOM | 1181 | OE1 | GLN | A | 182 | −20.793 | −2.013 | −7.876 | 1.00 | 29.75 | O |
| ATOM | 1182 | NE2 | GLN | A | 182 | −21.637 | −4.005 | −7.368 | 1.00 | 24.83 | N |
| ATOM | 1183 | N | TRP | A | 183 | −16.259 | −5.282 | −7.781 | 1.00 | 12.49 | N |
| ATOM | 1184 | CA | TRP | A | 183 | −15.383 | −6.248 | −7.146 | 1.00 | 11.05 | C |
| ATOM | 1185 | C | TRP | A | 183 | −15.876 | −6.434 | −5.717 | 1.00 | 9.90 | C |
| ATOM | 1186 | O | TRP | A | 183 | −15.290 | −5.980 | −4.732 | 1.00 | 10.60 | O |
| ATOM | 1187 | CB | TRP | A | 183 | −13.921 | −5.816 | −7.127 | 1.00 | 10.73 | C |
| ATOM | 1188 | CG | TRP | A | 183 | −13.342 | −5.732 | −8.547 | 1.00 | 11.01 | C |
| ATOM | 1189 | CD1 | TRP | A | 183 | −13.852 | −6.271 | −9.703 | 1.00 | 10.93 | C |
| ATOM | 1190 | CD2 | TRP | A | 183 | −12.108 | −5.113 | −8.900 | 1.00 | 9.86 | C |
| ATOM | 1191 | NE1 | TRP | A | 183 | −13.037 | −5.957 | −10.771 | 1.00 | 11.53 | N |
| ATOM | 1192 | CE2 | TRP | A | 183 | −11.971 | −5.238 | −10.283 | 1.00 | 10.19 | C |
| ATOM | 1193 | CE3 | TRP | A | 183 | −11.163 | −4.385 | −8.179 | 1.00 | 10.00 | C |
| ATOM | 1194 | CZ2 | TRP | A | 183 | −10.890 | −4.681 | −10.957 | 1.00 | 9.45 | C |
| ATOM | 1195 | CZ3 | TRP | A | 183 | −10.114 | −3.849 | −8.853 | 1.00 | 9.69 | C |
| ATOM | 1196 | CH2 | TRP | A | 183 | −9.992 | −4.015 | −10.234 | 1.00 | 9.69 | C |
| ATOM | 1197 | N | THR | A | 184 | −16.969 | −7.190 | −5.611 | 1.00 | 10.93 | N |
| ATOM | 1198 | CA | THR | A | 184 | −17.701 | −7.328 | −4.356 | 1.00 | 10.93 | C |
| ATOM | 1199 | C | THR | A | 184 | −17.319 | −8.551 | −3.529 | 1.00 | 11.44 | C |
| ATOM | 1200 | O | THR | A | 184 | −17.898 | −8.865 | −2.496 | 1.00 | 11.45 | O |
| ATOM | 1201 | CB | THR | A | 184 | −19.231 | −7.427 | −4.679 | 1.00 | 12.83 | C |
| ATOM | 1202 | OG1 | THR | A | 184 | −19.459 | −8.458 | −5.624 | 1.00 | 13.84 | O |
| ATOM | 1203 | CG2 | THR | A | 184 | −19.736 | −6.093 | −5.212 | 1.00 | 14.48 | C |
| ATOM | 1204 | N | SER | A | 185 | −16.247 | −9.233 | −3.938 | 1.00 | 10.11 | N |
| ATOM | 1205 | CA | SER | A | 185 | −15.678 | −10.357 | −3.203 | 1.00 | 9.58 | C |
| ATOM | 1206 | C | SER | A | 185 | −14.180 | −10.467 | −3.484 | 1.00 | 8.62 | C |
| ATOM | 1207 | O | SER | A | 185 | −13.718 | −9.924 | −4.503 | 1.00 | 9.66 | O |
| ATOM | 1208 | CB | SER | A | 185 | −16.333 | −11.679 | −3.606 | 1.00 | 10.12 | C |
| ATOM | 1209 | OG | SER | A | 185 | −15.968 | −12.049 | −4.938 | 1.00 | 10.44 | O |
| ATOM | 1210 | N | PRO | A | 186 | −13.446 | −11.170 | −2.614 | 1.00 | 8.46 | N |
| ATOM | 1211 | CA | PRO | A | 186 | −12.015 | −11.416 | −2.885 | 1.00 | 8.89 | C |
| ATOM | 1212 | C | PRO | A | 186 | −11.836 | −12.099 | −4.214 | 1.00 | 8.80 | C |
| ATOM | 1213 | O | PRO | A | 186 | −10.929 | −11.699 | −5.006 | 1.00 | 9.12 | O |
| ATOM | 1214 | CB | PRO | A | 186 | −11.600 | −12.270 | −1.728 | 1.00 | 8.25 | C |
| ATOM | 1215 | CG | PRO | A | 186 | −12.497 | −11.802 | −0.583 | 1.00 | 8.40 | C |
| ATOM | 1216 | CD | PRO | A | 186 | −13.788 | −11.629 | −1.240 | 1.00 | 8.23 | C |

TABLE 2-continued

X-RAY DIFFRACTION DATA OF *S. AUREUS* AUTOLYSIN E (AtlE 4PIA) RESIDUES 35-258

| ATOM | 1217 | N | ASP | A | 187 | −12.652 | −13.085 | −4.574 | 1.00 | 8.01 | N |
|---|---|---|---|---|---|---|---|---|---|---|---|
| ATOM | 1218 | CA | ASP | A | 187 | −12.428 | −13.783 | −5.832 | 1.00 | 8.22 | C |
| ATOM | 1219 | C | ASP | A | 187 | −12.650 | −12.869 | −7.012 | 1.00 | 8.43 | C |
| ATOM | 1220 | O | ASP | A | 187 | −11.894 | −12.896 | −8.002 | 1.00 | 8.56 | O |
| ATOM | 1221 | CB | ASP | A | 187 | −13.318 | −15.014 | −5.939 | 1.00 | 9.31 | C |
| ATOM | 1222 | CG | ASP | A | 187 | −12.942 | −16.109 | −4.943 | 1.00 | 10.89 | C |
| ATOM | 1223 | OD1 | ASP | A | 187 | −11.874 | −16.075 | −4.303 | 1.00 | 11.15 | O |
| ATOM | 1224 | OD2 | ASP | A | 187 | −13.752 | −17.100 | −4.803 | 1.00 | 13.42 | O |
| ATOM | 1225 | N | LYS | A | 188 | −13.693 | −12.031 | −6.959 | 1.00 | 8.19 | N |
| ATOM | 1226 | CA | LYS | A | 188 | −13.918 | −11.049 | −8.003 | 1.00 | 9.47 | C |
| ATOM | 1227 | C | LYS | A | 188 | −12.782 | −10.047 | −8.147 | 1.00 | 8.94 | C |
| ATOM | 1228 | O | LYS | A | 188 | −12.449 | −9.665 | −9.292 | 1.00 | 9.02 | O |
| ATOM | 1229 | CB | LYS | A | 188 | −15.247 | −10.306 | −7.830 | 1.00 | 11.21 | C |
| ATOM | 1230 | CG | LYS | A | 188 | −16.424 | −11.196 | −8.098 | 1.00 | 12.70 | C |
| ATOM | 1231 | CD | LYS | A | 188 | −17.747 | −10.547 | −7.607 | 1.00 | 13.92 | C |
| ATOM | 1232 | CE | LYS | A | 188 | −18.941 | −11.450 | −7.950 | 1.00 | 17.18 | C |
| ATOM | 1233 | NZ | LYS | A | 188 | −19.253 | −11.330 | −9.398 | 1.00 | 21.83 | N |
| ATOM | 1234 | N | ALA | A | 189 | −12.164 | −9.671 | −7.040 | 1.00 | 8.88 | N |
| ATOM | 1235 | CA | ALA | A | 189 | −10.997 | −8.759 | −7.084 | 1.00 | 8.58 | C |
| ATOM | 1236 | C | ALA | A | 189 | −9.778 | −9.425 | −7.710 | 1.00 | 7.82 | C |
| ATOM | 1237 | O | ALA | A | 189 | −8.972 | −8.760 | −8.377 | 1.00 | 8.05 | O |
| ATOM | 1238 | CB | ALA | A | 189 | −10.682 | −8.228 | −5.719 | 1.00 | 8.69 | C |
| ATOM | 1239 | N | ILE | A | 190 | −9.638 | −10.719 | −7.526 | 1.00 | 7.26 | N |
| ATOM | 1240 | CA | ILE | A | 190 | −8.480 | −11.424 | −8.137 | 1.00 | 7.28 | C |
| ATOM | 1241 | C | ILE | A | 190 | −8.666 | −11.546 | −9.632 | 1.00 | 8.15 | C |
| ATOM | 1242 | O | ILE | A | 190 | −7.788 | −11.129 | −10.404 | 1.00 | 8.51 | O |
| ATOM | 1243 | CB | ILE | A | 190 | −8.318 | −12.835 | −7.506 | 1.00 | 7.38 | C |
| ATOM | 1244 | CG1 | ILE | A | 190 | −7.898 | −12.732 | −6.027 | 1.00 | 7.57 | C |
| ATOM | 1245 | CG2 | ILE | A | 190 | −7.285 | −13.640 | −8.261 | 1.00 | 7.56 | C |
| ATOM | 1246 | CD1 | ILE | A | 190 | −8.181 | −14.002 | −5.234 | 1.00 | 7.32 | C |
| ATOM | 1247 | N | ILE | A | 191 | −9.835 | −12.016 | −10.077 | 1.00 | 7.82 | N |
| ATOM | 1248 | CA | ILE | A | 191 | −10.135 | −12.116 | −11.522 | 1.00 | 9.42 | C |
| ATOM | 1249 | C | ILE | A | 191 | −10.102 | −10.741 | −12.129 | 1.00 | 8.62 | C |
| ATOM | 1250 | O | ILE | A | 191 | −9.516 | −10.543 | −13.215 | 1.00 | 8.61 | O |
| ATOM | 1251 | CB | ILE | A | 191 | −11.523 | −12.753 | −11.765 | 1.00 | 11.52 | C |
| ATOM | 1252 | CG1 | ILE | A | 191 | −11.544 | −14.158 | −11.219 | 1.00 | 14.38 | C |
| ATOM | 1253 | CG2 | ILE | A | 191 | −11.914 | −12.697 | −13.239 | 1.00 | 12.42 | C |
| ATOM | 1254 | CD1 | ILE | A | 191 | −10.574 | −15.094 | −11.826 | 1.00 | 14.62 | C |
| ATOM | 1255 | N | ILE | A | 192 | −10.714 | −9.762 | −11.472 | 1.00 | 8.05 | N |
| ATOM | 1256 | CA | GLY | A | 192 | −10.817 | −8.450 | −12.060 | 1.00 | 8.45 | C |
| ATOM | 1257 | C | GLY | A | 192 | −9.491 | −7.730 | −12.165 | 1.00 | 8.36 | C |
| ATOM | 1258 | O | GLY | A | 192 | −9.212 | −7.003 | −13.135 | 1.00 | 8.84 | O |
| ATOM | 1259 | N | GLY | A | 193 | −8.637 | −7.941 | −11.168 | 1.00 | 7.86 | N |
| ATOM | 1260 | CA | GLY | A | 193 | −7.290 | −7.366 | −11.209 | 1.00 | 8.01 | C |
| ATOM | 1261 | C | GLY | A | 193 | −6.515 | −7.890 | −12.408 | 1.00 | 7.68 | C |
| ATOM | 1262 | O | GLY | A | 193 | −5.895 | −7.126 | −13.150 | 1.00 | 7.95 | O |
| ATOM | 1263 | N | ALA | A | 194 | −6.556 | −9.201 | −12.624 | 1.00 | 7.52 | N |
| ATOM | 1264 | CA | ALA | A | 194 | −5.900 | −9.806 | −13.769 | 1.00 | 7.51 | C |
| ATOM | 1265 | C | ALA | A | 194 | −6.458 | −9.274 | −15.068 | 1.00 | 7.54 | C |
| ATOM | 1266 | O | ALA | A | 194 | −5.692 | −8.991 | −16.017 | 1.00 | 7.40 | O |
| ATOM | 1267 | CB | ALA | A | 194 | −6.006 | −11.329 | −13.715 | 1.00 | 7.98 | C |
| ATOM | 1268 | N | LYS | A | 195 | −7.776 | −9.137 | −15.188 | 1.00 | 7.38 | N |
| ATOM | 1269 | CA | LYS | A | 195 | −8.361 | −8.603 | −16.373 | 1.00 | 7.84 | C |
| ATOM | 1270 | C | LYS | A | 195 | −7.880 | −7.209 | −16.661 | 1.00 | 7.80 | C |
| ATOM | 1271 | O | LYS | A | 195 | −7.548 | −6.881 | −17.809 | 1.00 | 8.19 | O |
| ATOM | 1272 | CB | LYS | A | 195 | −9.878 | −8.616 | −16.193 | 1.00 | 8.93 | C |
| ATOM | 1273 | CG | LYS | A | 195 | −10.626 | −8.113 | −17.430 | 1.00 | 11.15 | C |
| ATOM | 1274 | CD | LYS | A | 195 | −12.143 | −8.217 | −17.274 | 1.00 | 15.05 | C |
| ATOM | 1275 | CE | LYS | A | 195 | −12.799 | −7.627 | −18.529 | 1.00 | 19.02 | C |
| ATOM | 1276 | NZ | LYS | A | 195 | −14.283 | −7.538 | −18.382 | 1.00 | 24.21 | N |
| ATOM | 1277 | N | PHE | A | 196 | −7.819 | −6.380 | −15.636 | 1.00 | 7.56 | N |
| ATOM | 1278 | CA | PHE | A | 196 | −7.304 | −5.023 | −15.758 | 1.00 | 8.40 | C |
| ATOM | 1279 | C | PHE | A | 196 | −5.838 | −4.986 | −16.216 | 1.00 | 7.99 | C |
| ATOM | 1280 | O | PHE | A | 196 | −5.456 | −4.242 | −17.150 | 1.00 | 8.27 | O |
| ATOM | 1281 | CB | PHE | A | 196 | −7.462 | −4.291 | −14.452 | 1.00 | 8.70 | C |
| ATOM | 1282 | CG | PHE | A | 196 | −6.824 | −2.900 | −14.453 | 1.00 | 9.42 | C |
| ATOM | 1283 | CD1 | PHE | A | 196 | −7.537 | −1.806 | −14.934 | 1.00 | 10.37 | C |
| ATOM | 1284 | CD2 | PHE | A | 196 | −5.541 | −2.707 | −13.985 | 1.00 | 9.93 | C |
| ATOM | 1285 | CE1 | PHE | A | 196 | −6.969 | −0.526 | −14.921 | 1.00 | 11.34 | C |
| ATOM | 1286 | CE2 | PHE | A | 196 | −4.980 | −1.443 | −14.031 | 1.00 | 11.14 | C |
| ATOM | 1287 | CZ | PHE | A | 196 | −5.706 | −0.388 | −14.498 | 1.00 | 11.40 | C |
| ATOM | 1288 | N | ILE | A | 197 | −5.001 | −5.784 | −15.597 | 1.00 | 7.59 | N |
| ATOM | 1289 | CA | ILE | A | 197 | −3.593 | −5.775 | −15.939 | 1.00 | 7.56 | C |
| ATOM | 1290 | C | ILE | A | 197 | −3.396 | −6.199 | −17.379 | 1.00 | 7.62 | C |
| ATOM | 1291 | O | ILE | A | 197 | −2.671 | −5.550 | −18.140 | 1.00 | 7.13 | O |
| ATOM | 1292 | CB | ILE | A | 197 | −2.773 | −6.643 | −14.964 | 1.00 | 8.40 | C |
| ATOM | 1293 | CG1 | ILE | A | 197 | −2.806 | −6.020 | −13.565 | 1.00 | 9.41 | C |
| ATOM | 1294 | CG2 | ILE | A | 197 | −1.330 | −6.815 | −15.474 | 1.00 | 9.06 | C |

TABLE 2-continued

X-RAY DIFFRACTION DATA OF *S. AUREUS* AUTOLYSIN E (AtlE 4PIA) RESIDUES 35-258

| ATOM | 1295 | CD1 | ILE | A | 197 | -2.636 | -6.983 | -12.433 | 1.00 | 10.67 | C |
|---|---|---|---|---|---|---|---|---|---|---|---|
| ATOM | 1296 | N | ARG | A | 198 | -4.089 | -7.256 | -17.814 | 1.00 | 7.14 | N |
| ATOM | 1297 | CA | ARG | A | 198 | -4.016 | -7.707 | -19.190 | 1.00 | 7.82 | C |
| ATOM | 1298 | C | ARG | A | 198 | -4.506 | -6.609 | -20.142 | 1.00 | 7.51 | C |
| ATOM | 1299 | O | ARG | A | 198 | -3.832 | -6.264 | -21.114 | 1.00 | 8.14 | O |
| ATOM | 1300 | CB | ARG | A | 198 | -4.820 | -8.994 | -19.384 | 1.00 | 8.17 | C |
| ATOM | 1301 | CG | ARG | A | 198 | -5.227 | -9.330 | -20.828 | 1.00 | 8.63 | C |
| ATOM | 1302 | CD | ARG | A | 198 | -4.123 | -9.454 | -21.860 | 1.00 | 8.33 | C |
| ATOM | 1303 | NE | ARG | A | 198 | -3.184 | -10.522 | -21.577 | 1.00 | 8.47 | N |
| ATOM | 1304 | CZ | ARG | A | 198 | -2.123 | -10.747 | -22.302 | 1.00 | 8.30 | C |
| ATOM | 1305 | NH1 | ARG | A | 198 | -1.277 | -11.723 | -22.043 | 1.00 | 8.98 | N |
| ATOM | 1306 | NH2 | ARG | A | 198 | -1.869 | -9.912 | -23.329 | 1.00 | 10.05 | N |
| ATOM | 1307 | N | ASN | A | 199 | -5.707 | -6.087 | -19.900 | 1.00 | 8.40 | N |
| ATOM | 1308 | CA | ASN | A | 199 | -6.319 | -5.175 | -20.905 | 1.00 | 9.74 | C |
| ATOM | 1309 | C | ASN | A | 199 | -5.708 | -3.814 | -20.884 | 1.00 | 10.20 | C |
| ATOM | 1310 | O | ASN | A | 199 | -5.651 | -3.181 | -21.944 | 1.00 | 11.44 | O |
| ATOM | 1311 | CB | ASN | A | 199 | -7.813 | -5.110 | -20.652 | 1.00 | 11.98 | C |
| ATOM | 1312 | CG | ASN | A | 199 | -8.509 | -6.384 | -21.092 | 1.00 | 15.08 | C |
| ATOM | 1313 | OD1 | ASN | A | 199 | -8.024 | -7.112 | -21.942 | 1.00 | 20.93 | O |
| ATOM | 1314 | ND2 | ASN | A | 199 | -9.678 | -6.591 | -20.573 | 1.00 | 21.89 | N |
| ATOM | 1315 | N | GLU | A | 200 | -5.209 | -3.342 | -19.735 | 1.00 | 9.06 | N |
| ATOM | 1316 | CA | GLU | A | 200 | -4.754 | -1.948 | -19.668 | 1.00 | 9.88 | C |
| ATOM | 1317 | C | GLU | A | 200 | -3.255 | -1.811 | -19.776 | 1.00 | 9.21 | C |
| ATOM | 1318 | O | GLU | A | 200 | -2.761 | -0.779 | -20.252 | 1.00 | 9.76 | O |
| ATOM | 1319 | CB | GLU | A | 200 | -5.295 | -1.302 | -18.413 | 1.00 | 12.69 | C |
| ATOM | 1320 | CG | GLU | A | 200 | -6.784 | -1.204 | -18.369 | 1.00 | 16.37 | C |
| ATOM | 1321 | CD | GLU | A | 200 | -7.399 | -0.633 | -19.628 | 1.00 | 22.92 | C |
| ATOM | 1322 | OE1 | GLU | A | 200 | -6.931 | 0.459 | -20.045 | 1.00 | 23.97 | O |
| ATOM | 1323 | OE2 | GLU | A | 200 | -8.380 | -1.259 | -20.134 | 1.00 | 30.07 | O |
| ATOM | 1324 | N | TYR | A | 201 | -2.503 | -2.821 | -19.356 | 1.00 | 8.16 | N |
| ATOM | 1325 | CA | TYR | A | 201 | -1.031 | -2.804 | -19.415 | 1.00 | 7.54 | C |
| ATOM | 1326 | C | TYR | A | 201 | -0.511 | -3.764 | -20.463 | 1.00 | 7.33 | C |
| ATOM | 1327 | O | TYR | A | 201 | 0.253 | -3.326 | -21.360 | 1.00 | 7.33 | O |
| ATOM | 1328 | CB | TYR | A | 201 | -0.384 | -3.066 | -18.054 | 1.00 | 7.65 | C |
| ATOM | 1329 | CG | TYR | A | 201 | -0.433 | -1.863 | -17.174 | 1.00 | 7.88 | C |
| ATOM | 1330 | CD1 | TYR | A | 201 | -1.585 | -1.522 | -16.496 | 1.00 | 8.91 | C |
| ATOM | 1331 | CD2 | TYR | A | 201 | 0.634 | -0.944 | -17.107 | 1.00 | 8.35 | C |
| ATOM | 1332 | CE1 | TYR | A | 201 | -1.671 | -0.392 | -15.719 | 1.00 | 9.75 | C |
| ATOM | 1333 | CE2 | TYR | A | 201 | 0.538 | 0.217 | -16.376 | 1.00 | 9.03 | C |
| ATOM | 1334 | CZ | TYR | A | 201 | -0.587 | 0.479 | -15.682 | 1.00 | 9.87 | C |
| ATOM | 1335 | OH | TYR | A | 201 | -0.665 | 1.670 | -14.962 | 1.00 | 13.30 | O |
| ATOM | 1336 | N | PHE | A | 202 | -0.842 | -5.063 | -20.409 | 1.00 | 7.27 | N |
| ATOM | 1337 | CA | PHE | A | 202 | -0.230 | -5.994 | -21.371 | 1.00 | 8.04 | C |
| ATOM | 1338 | C | PHE | A | 202 | -0.643 | -5.692 | -22.820 | 1.00 | 9.72 | C |
| ATOM | 1339 | O | PHE | A | 202 | 0.196 | -5.839 | -23.742 | 1.00 | 13.06 | O |
| ATOM | 1340 | CB | PHE | A | 202 | -0.520 | -7.456 | -21.026 | 1.00 | 7.55 | C |
| ATOM | 1341 | CG | PHE | A | 202 | -0.003 | -7.902 | -19.681 | 1.00 | 7.31 | C |
| ATOM | 1342 | CD1 | PHE | A | 202 | 0.879 | -7.165 | -18.897 | 1.00 | 7.21 | C |
| ATOM | 1343 | CD2 | PHE | A | 202 | -0.367 | -9.138 | -19.242 | 1.00 | 7.49 | C |
| ATOM | 1344 | CE1 | PHE | A | 202 | 1.385 | -7.663 | -17.729 | 1.00 | 7.77 | C |
| ATOM | 1345 | CE2 | PHE | A | 202 | 0.160 | -9.664 | -18.086 | 1.00 | 8.05 | C |
| ATOM | 1346 | CZ | PHE | A | 202 | 1.028 | -8.921 | -17.314 | 1.00 | 8.15 | C |
| ATOM | 1347 | N | GLU | A | 203 | -1.853 | -5.229 | -23.014 | 1.00 | 9.34 | N |
| ATOM | 1348 | CA | GLU | A | 203 | -2.343 | -4.853 | -24.345 | 1.00 | 10.34 | C |
| ATOM | 1349 | C | GLU | A | 203 | -1.862 | -3.490 | -24.744 | 1.00 | 11.30 | C |
| ATOM | 1350 | O | GLU | A | 203 | -2.124 | -3.060 | -25.894 | 1.00 | 13.90 | O |
| ATOM | 1351 | CB | GLU | A | 203 | -3.863 | -4.952 | -24.402 | 1.00 | 11.29 | C |
| ATOM | 1352 | CG | GLU | A | 203 | -4.381 | -6.375 | -24.313 | 1.00 | 12.97 | C |
| ATOM | 1353 | CD | GLU | A | 203 | -3.911 | -7.242 | -25.404 | 1.00 | 15.87 | C |
| ATOM | 1354 | OE1 | GLU | A | 203 | -4.053 | -6.884 | -26.619 | 1.00 | 19.60 | O |
| ATOM | 1355 | OE2 | GLU | A | 203 | -3.372 | -8.316 | -25.139 | 1.00 | 15.76 | O |
| ATOM | 1356 | N | ASN | A | 204 | -1.151 | -2.777 | -23.864 | 1.00 | 9.41 | N |
| ATOM | 1357 | CA | ASN | A | 204 | -0.512 | -1.452 | -24.125 | 1.00 | 9.73 | C |
| ATOM | 1358 | C | ASN | A | 204 | 1.013 | -1.604 | -24.290 | 1.00 | 9.49 | C |
| ATOM | 1359 | O | ASN | A | 204 | 1.734 | -0.607 | -24.096 | 1.00 | 10.48 | O |
| ATOM | 1360 | CB | ASN | A | 204 | -0.843 | -0.454 | -23.031 | 1.00 | 10.24 | C |
| ATOM | 1361 | CG | ASN | A | 204 | -0.482 | 0.981 | -23.392 | 1.00 | 11.41 | C |
| ATOM | 1362 | OD1 | ASN | A | 204 | -0.868 | 1.439 | -24.502 | 1.00 | 14.31 | O |
| ATOM | 1363 | ND2 | ASN | A | 204 | 0.207 | 1.665 | -22.522 | 1.00 | 11.45 | N |
| ATOM | 1364 | N | ASN | A | 205 | 1.497 | -2.824 | -24.544 | 1.00 | 9.76 | N |
| ATOM | 1365 | CA | ASN | A | 205 | 2.925 | -3.046 | -24.746 | 1.00 | 10.66 | C |
| ATOM | 1366 | C | ASN | A | 205 | 3.763 | -2.755 | -23.497 | 1.00 | 10.24 | C |
| ATOM | 1367 | O | ASN | A | 205 | 4.948 | -2.480 | -23.580 | 1.00 | 11.65 | O |
| ATOM | 1368 | CB | ASN | A | 205 | 3.461 | -2.259 | -25.978 | 1.00 | 12.47 | C |
| ATOM | 1369 | CG | ASN | A | 205 | 4.835 | -2.740 | -26.423 | 1.00 | 16.50 | C |
| ATOM | 1370 | OD1 | ASN | A | 205 | 5.072 | -3.968 | -26.457 | 1.00 | 19.03 | O |
| ATOM | 1371 | ND2 | ASN | A | 205 | 5.755 | -1.802 | -26.795 | 1.00 | 19.61 | N |
| ATOM | 1372 | N | GLN | A | 206 | 3.153 | -2.906 | -22.321 | 1.00 | 7.91 | N |

TABLE 2-continued

X-RAY DIFFRACTION DATA OF S. AUREUS AUTOLYSIN E (AtlE 4PIA) RESIDUES 35-258

| ATOM | 1373 | CA | GLN | A | 206 | 3.870 | −2.845 | −21.052 | 1.00 | 7.51 | C |
|---|---|---|---|---|---|---|---|---|---|---|---|
| ATOM | 1374 | C | GLN | A | 206 | 3.845 | −4.270 | −20.505 | 1.00 | 7.69 | C |
| ATOM | 1375 | O | GLN | A | 206 | 2.871 | −4.666 | −19.862 | 1.00 | 8.24 | O |
| ATOM | 1376 | CB | GLN | A | 206 | 3.223 | −1.821 | −20.121 | 1.00 | 7.54 | C |
| ATOM | 1377 | CG | GLN | A | 206 | 3.407 | −0.379 | −20.586 | 1.00 | 7.50 | C |
| ATOM | 1378 | CD | GLN | A | 206 | 2.625 | 0.605 | −19.762 | 1.00 | 8.05 | C |
| ATOM | 1379 | OE1 | GLN | A | 206 | 1.443 | 0.851 | −20.054 | 1.00 | 9.06 | O |
| ATOM | 1380 | NE2 | GLN | A | 206 | 3.234 | 1.157 | −18.740 | 1.00 | 7.49 | N |
| ATOM | 1381 | N | LEU | A | 207 | 4.874 | −5.021 | −20.865 | 1.00 | 7.12 | N |
| ATOM | 1382 | CA | LEU | A | 207 | 4.895 | −6.485 | −20.783 | 1.00 | 8.15 | C |
| ATOM | 1383 | C | LEU | A | 207 | 5.728 | −7.007 | −19.638 | 1.00 | 7.25 | C |
| ATOM | 1384 | O | LEU | A | 207 | 5.741 | −8.237 | −19.425 | 1.00 | 8.07 | O |
| ATOM | 1385 | CB | LEU | A | 207 | 5.421 | −7.114 | −22.101 | 1.00 | 9.90 | C |
| ATOM | 1386 | CG | LEU | A | 207 | 4.910 | −6.545 | −23.400 | 1.00 | 11.10 | C |
| ATOM | 1387 | CD1 | LEU | A | 207 | 5.569 | −7.308 | −24.583 | 1.00 | 11.81 | C |
| ATOM | 1388 | CD2 | LEU | A | 207 | 3.392 | −6.687 | −23.462 | 1.00 | 10.71 | C |
| ATOM | 1389 | N | ASN | A | 208 | 6.440 | −6.144 | −18.941 | 1.00 | 7.13 | N |
| ATOM | 1390 | CA | ASN | A | 208 | 7.243 | −6.544 | −17.785 | 1.00 | 6.60 | C |
| ATOM | 1391 | C | ASN | A | 208 | 7.129 | −5.470 | −16.756 | 1.00 | 6.65 | C |
| ATOM | 1392 | O | ASN | A | 208 | 6.586 | −4.381 | −16.972 | 1.00 | 6.08 | O |
| ATOM | 1393 | CB | ASN | A | 208 | 8.668 | −6.907 | −18.232 | 1.00 | 6.89 | C |
| ATOM | 1394 | CG | ASN | A | 208 | 9.432 | −5.740 | −18.792 | 1.00 | 6.61 | C |
| ATOM | 1395 | OD1 | ASN | A | 208 | 9.307 | −4.583 | −18.351 | 1.00 | 7.50 | O |
| ATOM | 1396 | ND2 | ASN | A | 208 | 10.329 | −6.041 | −19.755 | 1.00 | 7.61 | N |
| ATOM | 1397 | N | LEU | A | 209 | 7.665 | −5.763 | −15.570 | 1.00 | 6.24 | N |
| ATOM | 1398 | CA | LEU | A | 209 | 7.502 | −4.853 | −14.441 | 1.00 | 6.28 | C |
| ATOM | 1399 | C | LEU | A | 209 | 8.168 | −3.492 | −14.728 | 1.00 | 5.86 | C |
| ATOM | 1400 | O | LEU | A | 209 | 7.677 | −2.429 | −14.382 | 1.00 | 6.04 | O |
| ATOM | 1401 | CB | LEU | A | 209 | 8.099 | −5.433 | −13.169 | 1.00 | 6.65 | C |
| ATOM | 1402 | CG | LEU | A | 209 | 7.354 | −6.672 | −12.635 | 1.00 | 7.16 | C |
| ATOM | 1403 | CD1 | LEU | A | 209 | 8.175 | −7.306 | −11.528 | 1.00 | 8.03 | C |
| ATOM | 1404 | CD2 | LEU | A | 209 | 6.007 | −6.318 | −12.145 | 1.00 | 7.74 | C |
| ATOM | 1405 | N | TYR | A | 210 | 9.344 | −3.531 | −15.342 | 1.00 | 6.21 | N |
| ATOM | 1406 | CA | TYR | A | 210 | 10.048 | −2.286 | −15.690 | 1.00 | 6.57 | C |
| ATOM | 1407 | C | TYR | A | 210 | 9.153 | −1.389 | −16.565 | 1.00 | 6.35 | C |
| ATOM | 1408 | O | TYR | A | 210 | 9.074 | −0.189 | −16.317 | 1.00 | 6.65 | O |
| ATOM | 1409 | CB | TYR | A | 210 | 11.400 | −2.580 | −16.385 | 1.00 | 7.03 | C |
| ATOM | 1410 | CG | TYR | A | 210 | 12.190 | −1.307 | −16.597 | 1.00 | 7.47 | C |
| ATOM | 1411 | CD1 | TYR | A | 210 | 12.972 | −0.751 | −15.581 | 1.00 | 7.34 | C |
| ATOM | 1412 | CD2 | TYR | A | 210 | 12.124 | −0.616 | −17.796 | 1.00 | 8.27 | C |
| ATOM | 1413 | CE1 | TYR | A | 210 | 13.664 | 0.441 | −15.749 | 1.00 | 7.88 | C |
| ATOM | 1414 | CE2 | TYR | A | 210 | 12.803 | 0.569 | −17.952 | 1.00 | 7.75 | C |
| ATOM | 1415 | CZ | TYR | A | 210 | 13.572 | 1.100 | −16.950 | 1.00 | 8.52 | C |
| ATOM | 1416 | OH | TYR | A | 210 | 14.248 | 2.307 | −17.094 | 1.00 | 9.62 | O |
| ATOM | 1417 | N | GLN | A | 211 | 8.540 | −1.953 | −17.596 | 1.00 | 6.46 | N |
| ATOM | 1418 | CA | GLN | A | 211 | 7.713 | −1.162 | −18.485 | 1.00 | 6.33 | C |
| ATOM | 1419 | C | GLN | A | 211 | 6.470 | −0.683 | −17.786 | 1.00 | 6.37 | C |
| ATOM | 1420 | O | GLN | A | 211 | 5.965 | 0.398 | −18.056 | 1.00 | 6.53 | O |
| ATOM | 1421 | CB | GLN | A | 211 | 7.365 | −1.957 | −19.738 | 1.00 | 7.08 | C |
| ATOM | 1422 | CG | GLN | A | 211 | 8.524 | −2.240 | −20.679 | 1.00 | 7.78 | C |
| ATOM | 1423 | CD | GLN | A | 211 | 8.123 | −3.147 | −21.791 | 1.00 | 10.07 | C |
| ATOM | 1424 | OE1 | GLN | A | 211 | 7.515 | −4.194 | −21.575 | 1.00 | 10.30 | O |
| ATOM | 1425 | NE2 | GLN | A | 211 | 8.525 | −2.777 | −23.014 | 1.00 | 12.59 | N |
| ATOM | 1426 | N | MET | A | 212 | 5.879 | −1.529 | −16.934 | 1.00 | 6.50 | N |
| ATOM | 1427 | CA | MET | A | 212 | 4.710 | −1.113 | −16.151 | 1.00 | 6.34 | C |
| ATOM | 1428 | C | MET | A | 212 | 5.012 | 0.099 | −15.272 | 1.00 | 6.21 | C |
| ATOM | 1429 | O | MET | A | 212 | 4.163 | 0.983 | −15.067 | 1.00 | 6.78 | O |
| ATOM | 1430 | CB | MET | A | 212 | 4.190 | −2.274 | −15.297 | 1.00 | 6.69 | C |
| ATOM | 1431 | CG | MET | A | 212 | 3.580 | −3.385 | −16.138 | 1.00 | 6.84 | C |
| ATOM | 1432 | SD | MET | A | 212 | 3.061 | −4.836 | −15.151 | 1.00 | 7.41 | S |
| ATOM | 1433 | CE | MET | A | 212 | 1.616 | −4.207 | −14.303 | 1.00 | 8.80 | C |
| ATOM | 1434 | N | ARG | A | 213 | 6.213 | 0.098 | −14.685 | 1.00 | 5.84 | N |
| ATOM | 1435 | CA | ARG | A | 213 | 6.594 | 1.145 | −13.760 | 1.00 | 6.51 | C |
| ATOM | 1436 | C | ARG | A | 213 | 7.132 | 2.416 | −14.422 | 1.00 | 6.39 | C |
| ATOM | 1437 | O | ARG | A | 213 | 6.873 | 3.506 | −13.930 | 1.00 | 6.80 | O |
| ATOM | 1438 | CB | ARG | A | 213 | 7.643 | 0.606 | −12.754 | 1.00 | 6.88 | C |
| ATOM | 1439 | CG | ARG | A | 213 | 8.148 | 1.657 | −11.792 | 1.00 | 7.26 | C |
| ATOM | 1440 | CD | ARG | A | 213 | 7.059 | 2.240 | −10.916 | 1.00 | 7.79 | C |
| ATOM | 1441 | NE | ARG | A | 213 | 7.549 | 3.256 | −10.000 | 1.00 | 8.27 | N |
| ATOM | 1442 | CZ | ARG | A | 213 | 7.809 | 4.524 | −10.323 | 1.00 | 8.92 | C |
| ATOM | 1443 | NH1 | ARG | A | 213 | 7.656 | 4.981 | −11.575 | 1.00 | 9.05 | N |
| ATOM | 1444 | NH2 | ARG | A | 213 | 8.222 | 5.373 | −9.384 | 1.00 | 10.03 | N |
| ATOM | 1445 | N | TRP | A | 214 | 7.899 | 2.260 | −15.503 | 1.00 | 6.03 | N |
| ATOM | 1446 | CA | TRP | A | 214 | 8.654 | 3.382 | −16.085 | 1.00 | 6.29 | C |
| ATOM | 1447 | C | TRP | A | 214 | 8.244 | 3.716 | −17.503 | 1.00 | 6.56 | C |
| ATOM | 1448 | O | TRP | A | 214 | 8.839 | 4.651 | −18.091 | 1.00 | 6.89 | O |
| ATOM | 1449 | CB | TRP | A | 214 | 10.170 | 3.130 | −15.986 | 1.00 | 6.80 | C |
| ATOM | 1450 | CG | TRP | A | 214 | 10.654 | 2.956 | −14.578 | 1.00 | 7.02 | C |

TABLE 2-continued

X-RAY DIFFRACTION DATA OF S. AUREUS AUTOLYSIN E (AtlE 4PIA) RESIDUES 35-258

| ATOM | 1451 | CD1 | TRP | A | 214 | 11.071 | 1.806 | −14.025 | 1.00 | 8.23 | C |
|---|---|---|---|---|---|---|---|---|---|---|---|
| ATOM | 1452 | CD2 | TRP | A | 214 | 10.810 | 3.981 | −13.582 | 1.00 | 7.33 | C |
| ATOM | 1453 | NE1 | TRP | A | 214 | 11.473 | 2.053 | −12.757 | 1.00 | 8.29 | N |
| ATOM | 1454 | CE2 | TRP | A | 214 | 11.294 | 3.362 | −12.429 | 1.00 | 7.98 | C |
| ATOM | 1455 | CE3 | TRP | A | 214 | 10.558 | 5.357 | −13.549 | 1.00 | 7.76 | C |
| ATOM | 1456 | CZ2 | TRP | A | 214 | 11.557 | 4.080 | −11.244 | 1.00 | 8.94 | C |
| ATOM | 1457 | CZ3 | TRP | A | 214 | 10.841 | 6.067 | −12.390 | 1.00 | 8.61 | C |
| ATOM | 1458 | CH2 | TRP | A | 214 | 11.310 | 5.400 | −11.239 | 1.00 | 9.27 | C |
| ATOM | 1459 | N | ASN | A | 215 | 7.340 | 2.954 | −18.092 | 1.00 | 6.77 | N |
| ATOM | 1460 | CA | ASN | A | 215 | 6.826 | 3.144 | −19.466 | 1.00 | 7.03 | C |
| ATOM | 1461 | C | ASN | A | 215 | 7.813 | 3.842 | −20.383 | 1.00 | 7.20 | C |
| ATOM | 1462 | O | ASN | A | 215 | 7.554 | 4.966 | −20.844 | 1.00 | 7.12 | O |
| ATOM | 1463 | CB | ASN | A | 215 | 5.505 | 3.899 | −19.418 | 1.00 | 7.25 | C |
| ATOM | 1464 | CG | ASN | A | 215 | 4.682 | 3.759 | −20.672 | 1.00 | 7.99 | C |
| ATOM | 1465 | OD1 | ASN | A | 215 | 4.991 | 2.955 | −21.540 | 1.00 | 9.17 | O |
| ATOM | 1466 | ND2 | ASN | A | 215 | 3.600 | 4.470 | −20.739 | 1.00 | 8.48 | N |
| ATOM | 1467 | N | PRO | A | 216 | 8.930 | 3.231 | −20.698 | 1.00 | 7.26 | N |
| ATOM | 1468 | CA | PRO | A | 216 | 9.944 | 3.947 | −21.468 | 1.00 | 7.94 | C |
| ATOM | 1469 | C | PRO | A | 216 | 9.499 | 4.349 | −22.852 | 1.00 | 7.81 | C |
| ATOM | 1470 | O | PRO | A | 216 | 10.085 | 5.305 | −23.448 | 1.00 | 8.19 | O |
| ATOM | 1471 | CB | PRO | A | 216 | 11.108 | 2.944 | −21.563 | 1.00 | 8.36 | C |
| ATOM | 1472 | CG | PRO | A | 216 | 10.539 | 1.658 | −21.075 | 1.00 | 10.18 | C |
| ATOM | 1473 | CD | PRO | A | 216 | 9.404 | 1.940 | −20.188 | 1.00 | 8.06 | C |
| ATOM | 1474 | N | GLU | A | 217 | 8.492 | 3.700 | −23.409 | 1.00 | 7.41 | N |
| ATOM | 1475 | CA | GLU | A | 217 | 7.928 | 4.105 | −24.726 | 1.00 | 8.39 | C |
| ATOM | 1476 | C | GLU | A | 217 | 7.270 | 5.466 | −24.630 | 1.00 | 8.27 | C |
| ATOM | 1477 | O | GLU | A | 217 | 7.323 | 6.266 | −25.595 | 1.00 | 9.09 | O |
| ATOM | 1478 | CB | GLU | A | 217 | 6.925 | 3.087 | −25.215 | 1.00 | 9.46 | C |
| ATOM | 1479 | CG | GLU | A | 217 | 6.417 | 3.250 | −26.635 | 1.00 | 11.15 | C |
| ATOM | 1480 | CD | GLU | A | 217 | 5.548 | 2.097 | −27.087 | 1.00 | 14.15 | C |
| ATOM | 1481 | OE1 | GLU | A | 217 | 5.197 | 1.160 | −26.328 | 1.00 | 16.32 | O |
| ATOM | 1482 | OE2 | GLU | A | 217 | 5.267 | 2.061 | −28.295 | 1.00 | 15.75 | O |
| ATOM | 1483 | N | ASN | A | 218 | 6.673 | 5.808 | −23.481 | 1.00 | 7.35 | N |
| ATOM | 1484 | CA | ASN | A | 218 | 6.025 | 7.086 | −23.205 | 1.00 | 7.25 | C |
| ATOM | 1485 | C | ASN | A | 218 | 6.260 | 7.487 | −21.736 | 1.00 | 6.73 | C |
| ATOM | 1486 | O | ASN | A | 218 | 5.373 | 7.358 | −20.874 | 1.00 | 6.63 | O |
| ATOM | 1487 | CB | ASN | A | 218 | 4.515 | 7.104 | −23.525 | 1.00 | 7.13 | C |
| ATOM | 1488 | CG | ASN | A | 218 | 4.237 | 7.015 | −24.997 | 1.00 | 7.78 | C |
| ATOM | 1489 | OD1 | ASN | A | 218 | 3.919 | 5.911 | −25.518 | 1.00 | 11.30 | O |
| ATOM | 1490 | ND2 | ASN | A | 218 | 4.370 | 8.069 | −25.662 | 1.00 | 6.47 | N |
| ATOM | 1491 | N | PRO | A | 219 | 7.481 | 7.965 | −21.449 | 1.00 | 6.75 | N |
| ATOM | 1492 | CA | PRO | A | 219 | 7.878 | 8.140 | −20.048 | 1.00 | 7.10 | C |
| ATOM | 1493 | C | PRO | A | 219 | 6.941 | 9.049 | −19.262 | 1.00 | 7.33 | C |
| ATOM | 1494 | O | PRO | A | 219 | 6.491 | 10.114 | −19.748 | 1.00 | 7.68 | O |
| ATOM | 1495 | CB | PRO | A | 219 | 9.272 | 8.756 | −20.168 | 1.00 | 6.88 | C |
| ATOM | 1496 | CG | PRO | A | 219 | 9.799 | 8.227 | −21.446 | 1.00 | 7.12 | C |
| ATOM | 1497 | CD | PRO | A | 219 | 8.601 | 8.210 | −22.367 | 1.00 | 6.98 | C |
| ATOM | 1498 | N | ALA | A | 220 | 6.672 | 8.667 | −18.019 | 1.00 | 7.60 | N |
| ATOM | 1499 | CA | ALA | A | 220 | 5.918 | 9.400 | −17.033 | 1.00 | 9.04 | C |
| ATOM | 1500 | C | ALA | A | 220 | 4.424 | 9.292 | −17.210 | 1.00 | 10.08 | C |
| ATOM | 1501 | O | ALA | A | 220 | 3.679 | 9.852 | −16.374 | 1.00 | 15.33 | O |
| ATOM | 1502 | CB | ALA | A | 220 | 6.434 | 10.824 | −16.848 | 1.00 | 9.71 | C |
| ATOM | 1503 | N | GLN | A | 221 | 3.950 | 8.641 | −18.253 | 1.00 | 8.06 | N |
| ATOM | 1504 | CA | GLN | A | 221 | 2.545 | 8.401 | −18.480 | 1.00 | 8.88 | C |
| ATOM | 1505 | C | GLN | A | 221 | 2.226 | 6.954 | −18.213 | 1.00 | 8.23 | C |
| ATOM | 1506 | O | GLN | A | 221 | 3.053 | 6.077 | −18.467 | 1.00 | 8.67 | O |
| ATOM | 1507 | CB | GLN | A | 221 | 2.143 | 8.659 | −19.970 | 1.00 | 10.96 | C |
| ATOM | 1508 | CG | GLN | A | 221 | 2.264 | 10.115 | −20.323 | 1.00 | 13.36 | C |
| ATOM | 1509 | CD | GLN | A | 221 | 1.601 | 10.391 | −21.628 | 1.00 | 15.17 | C |
| ATOM | 1510 | OE1 | GLN | A | 221 | 2.227 | 10.475 | −22.696 | 1.00 | 14.40 | O |
| ATOM | 1511 | NE2 | GLN | A | 221 | 0.319 | 10.467 | −21.561 | 1.00 | 17.70 | N |
| ATOM | 1512 | N | HIS | A | 222 | 1.005 | 6.682 | −17.749 | 1.00 | 8.27 | N |
| ATOM | 1513 | CA | HIS | A | 222 | 0.489 | 5.336 | −17.661 | 1.00 | 8.86 | C |
| ATOM | 1514 | C | HIS | A | 222 | 1.453 | 4.399 | −16.921 | 1.00 | 7.81 | C |
| ATOM | 1515 | O | HIS | A | 222 | 1.762 | 3.289 | −17.383 | 1.00 | 8.43 | O |
| ATOM | 1516 | CB | HIS | A | 222 | 0.047 | 4.818 | −19.005 | 1.00 | 10.19 | C |
| ATOM | 1517 | CG | HIS | A | 222 | −0.858 | 3.663 | −18.899 | 1.00 | 12.71 | C |
| ATOM | 1518 | ND1 | HIS | A | 222 | −2.204 | 3.748 | −18.577 | 1.00 | 16.88 | N |
| ATOM | 1519 | CD2 | HIS | A | 222 | −0.574 | 2.353 | −18.973 | 1.00 | 10.87 | C |
| ATOM | 1520 | CE1 | HIS | A | 222 | −2.701 | 2.514 | −18.510 | 1.00 | 17.21 | C |
| ATOM | 1521 | NE2 | HIS | A | 222 | −1.730 | 1.662 | −18.815 | 1.00 | 16.74 | N |
| ATOM | 1522 | N | GLN | A | 223 | 1.873 | 4.833 | −15.750 | 1.00 | 7.61 | N |
| ATOM | 1523 | CA | GLN | A | 223 | 2.780 | 4.083 | −14.857 | 1.00 | 7.70 | C |
| ATOM | 1524 | C | GLN | A | 223 | 2.024 | 3.565 | −13.676 | 1.00 | 7.72 | C |
| ATOM | 1525 | O | GLN | A | 223 | 1.129 | 4.187 | −13.147 | 1.00 | 8.85 | O |
| ATOM | 1526 | CB | GLN | A | 223 | 4.009 | 4.913 | −14.476 | 1.00 | 7.61 | C |
| ATOM | 1527 | CG | GLN | A | 223 | 4.867 | 5.209 | −15.700 | 1.00 | 7.38 | C |
| ATOM | 1528 | CD | GLN | A | 223 | 6.054 | 6.111 | −15.542 | 1.00 | 7.38 | C |

TABLE 2-continued

X-RAY DIFFRACTION DATA OF *S. AUREUS* AUTOLYSIN E (AtlE 4PIA) RESIDUES 35-258

| ATOM | 1529 | OE1 | GLN | A | 223 | 6.804 | 6.208 | −16.522 | 1.00 | 7.62 | O |
|------|------|-----|-----|---|-----|-------|-------|---------|------|------|---|
| ATOM | 1530 | NE2 | GLN | A | 223 | 6.254 | 6.762 | −14.395 | 1.00 | 8.38 | N |
| ATOM | 1531 | N | TYR | A | 224 | 2.422 | 2.359 | −13.235 | 1.00 | 7.71 | N |
| ATOM | 1532 | CA | TYR | A | 224 | 1.546 | 1.627 | −12.280 | 1.00 | 8.87 | C |
| ATOM | 1533 | C | TYR | A | 224 | 1.579 | 2.240 | −10.910 | 1.00 | 9.34 | C |
| ATOM | 1534 | O | TYR | A | 224 | 0.558 | 2.143 | −10.189 | 1.00 | 11.57 | O |
| ATOM | 1535 | CB | TYR | A | 224 | 1.987 | 0.120 | −12.222 | 1.00 | 8.94 | C |
| ATOM | 1536 | CG | TYR | A | 224 | 0.826 | −0.753 | −11.797 | 1.00 | 8.89 | C |
| ATOM | 1537 | CD1 | TYR | A | 224 | 0.533 | −0.891 | −10.445 | 1.00 | 9.85 | C |
| ATOM | 1538 | CD2 | TYR | A | 224 | 0.031 | −1.347 | −12.719 | 1.00 | 8.86 | C |
| ATOM | 1539 | CE1 | TYR | A | 224 | −0.601 | −1.619 | −10.054 | 1.00 | 9.71 | C |
| ATOM | 1540 | CE2 | TYR | A | 224 | −1.108 | −2.077 | −12.320 | 1.00 | 10.55 | C |
| ATOM | 1541 | CZ | TYR | A | 224 | −1.355 | −2.189 | −10.987 | 1.00 | 9.87 | C |
| ATOM | 1542 | OH | TYR | A | 224 | −2.506 | −2.958 | −10.641 | 1.00 | 11.85 | O |
| ATOM | 1543 | N | ALA | A | 225 | 2.711 | 2.785 | −10.478 | 1.00 | 9.37 | N |
| ATOM | 1544 | CA | ALA | A | 225 | 2.915 | 3.186 | −9.095 | 1.00 | 11.00 | C |
| ATOM | 1545 | C | ALA | A | 225 | 3.896 | 4.311 | −8.986 | 1.00 | 11.56 | C |
| ATOM | 1546 | O | ALA | A | 225 | 4.747 | 4.497 | −9.864 | 1.00 | 11.95 | O |
| ATOM | 1547 | CB | ALA | A | 225 | 3.421 | 1.998 | −8.288 | 1.00 | 12.74 | C |
| ATOM | 1548 | N | SER | A | 226 | 3.854 | 5.005 | −7.839 | 1.00 | 11.98 | N |
| ATOM | 1549 | CA | ASER | A | 226 | 4.812 | 6.043 | −7.495 | 0.60 | 12.16 | C |
| ATOM | 1550 | CA | BSER | A | 226 | 4.812 | 6.048 | −7.510 | 0.40 | 11.85 | C |
| ATOM | 1551 | C | SER | A | 226 | 6.053 | 5.551 | −6.778 | 1.00 | 11.20 | C |
| ATOM | 1552 | O | SER | A | 226 | 7.101 | 6.177 | −6.860 | 1.00 | 10.45 | O |
| ATOM | 1553 | CB | ASER | A | 226 | 4.150 | 7.134 | −6.652 | 0.60 | 13.31 | C |
| ATOM | 1554 | CB | BSER | A | 226 | 4.140 | 7.165 | −6.707 | 0.40 | 12.48 | C |
| ATOM | 1555 | OG | ASER | A | 226 | 3.179 | 7.842 | −7.392 | 0.60 | 15.79 | O |
| ATOM | 1556 | OG | BSER | A | 226 | 3.893 | 6.778 | −5.364 | 0.40 | 13.70 | O |
| ATOM | 1557 | N | ASP | A | 227 | 5.940 | 4.400 | −6.060 | 1.00 | 10.94 | N |
| ATOM | 1558 | CA | ASP | A | 227 | 7.065 | 3.852 | −5.330 | 1.00 | 10.68 | C |
| ATOM | 1559 | C | ASP | A | 227 | 8.171 | 3.514 | −6.328 | 1.00 | 9.88 | C |
| ATOM | 1560 | O | ASP | A | 227 | 7.972 | 2.665 | −7.207 | 1.00 | 9.07 | O |
| ATOM | 1561 | CB | ASP | A | 227 | 6.642 | 2.586 | −4.569 | 1.00 | 12.10 | C |
| ATOM | 1562 | CG | ASP | A | 227 | 7.748 | 1.938 | −3.817 | 1.00 | 11.76 | C |
| ATOM | 1563 | OD1 | ASP | A | 227 | 8.886 | 2.347 | −3.775 | 1.00 | 12.89 | O |
| ATOM | 1564 | OD2 | ASP | A | 227 | 7.343 | 0.876 | −3.213 | 1.00 | 15.20 | O |
| ATOM | 1565 | N | ILE | A | 228 | 9.327 | 4.144 | −6.220 | 1.00 | 9.30 | N |
| ATOM | 1566 | CA | ILE | A | 228 | 10.459 | 3.886 | −7.080 | 1.00 | 10.18 | C |
| ATOM | 1567 | C | ILE | A | 228 | 11.009 | 2.441 | −7.015 | 1.00 | 9.78 | C |
| ATOM | 1568 | O | ILE | A | 228 | 11.754 | 2.031 | −7.897 | 1.00 | 10.41 | O |
| ATOM | 1569 | CB | ILE | A | 228 | 11.573 | 4.921 | −6.923 | 1.00 | 11.26 | C |
| ATOM | 1570 | CG1 | ILE | A | 228 | 12.306 | 4.808 | −5.589 | 1.00 | 12.58 | C |
| ATOM | 1571 | CG2 | ILE | A | 228 | 11.082 | 6.319 | −7.198 | 1.00 | 12.04 | C |
| ATOM | 1572 | CD1 | ILE | A | 228 | 13.431 | 5.813 | −5.439 | 1.00 | 14.00 | C |
| ATOM | 1573 | N | ARG | A | 229 | 10.676 | 1.733 | −5.915 | 1.00 | 10.12 | N |
| ATOM | 1574 | CA | AARG | A | 229 | 11.065 | 0.306 | −5.829 | 0.60 | 11.12 | C |
| ATOM | 1575 | CA | BARG | A | 229 | 11.003 | 0.322 | −5.696 | 0.40 | 10.78 | C |
| ATOM | 1576 | C | ARG | A | 229 | 9.875 | −0.650 | −5.949 | 1.00 | 9.73 | C |
| ATOM | 1577 | O | ARG | A | 229 | 10.000 | −1.845 | −5.642 | 1.00 | 9.48 | O |
| ATOM | 1578 | CB | AARG | A | 229 | 11.940 | 0.010 | −4.581 | 0.60 | 12.50 | C |
| ATOM | 1579 | CB | BARG | A | 229 | 11.430 | 0.132 | −4.249 | 0.40 | 11.71 | C |
| ATOM | 1580 | CG | AARG | A | 229 | 13.316 | 0.696 | −4.638 | 0.60 | 14.75 | C |
| ATOM | 1581 | CG | BARG | A | 229 | 12.610 | 1.007 | −3.892 | 0.40 | 13.52 | C |
| ATOM | 1582 | CD | AARG | A | 229 | 14.209 | 0.332 | −3.470 | 0.60 | 18.05 | C |
| ATOM | 1583 | CD | BARG | A | 229 | 13.324 | 0.424 | −2.698 | 0.40 | 16.03 | C |
| ATOM | 1584 | NE | AARG | A | 229 | 14.564 | −1.080 | −3.498 | 0.60 | 21.14 | N |
| ATOM | 1585 | NE | BARG | A | 229 | 14.046 | −0.809 | −3.008 | 0.40 | 18.32 | N |
| ATOM | 1586 | CZ | AARG | A | 229 | 15.523 | −1.633 | −4.224 | 0.60 | 23.81 | C |
| ATOM | 1587 | CZ | BARG | A | 229 | 13.712 | −2.031 | −2.586 | 0.40 | 18.64 | C |
| ATOM | 1588 | NH1 | AARG | A | 229 | 16.303 | −0.919 | −5.031 | 0.60 | 26.97 | N |
| ATOM | 1589 | NH1 | BARG | A | 229 | 12.641 | −2.238 | −1.839 | 0.40 | 18.97 | N |
| ATOM | 1590 | NH2 | AARG | A | 229 | 15.697 | −2.927 | −4.135 | 0.60 | 24.59 | N |
| ATOM | 1591 | NH2 | BARG | A | 229 | 14.464 | −3.064 | −2.945 | 0.40 | 21.03 | N |
| ATOM | 1592 | N | TRP | A | 230 | 8.766 | −0.187 | −6.538 | 1.00 | 8.52 | N |
| ATOM | 1593 | CA | TRP | A | 230 | 7.610 | −1.056 | −6.796 | 1.00 | 8.16 | C |
| ATOM | 1594 | C | TRP | A | 230 | 7.992 | −2.324 | −7.548 | 1.00 | 8.72 | C |
| ATOM | 1595 | O | TRP | A | 230 | 7.565 | −3.435 | −7.195 | 1.00 | 9.72 | O |
| ATOM | 1596 | CB | TRP | A | 230 | 6.556 | −0.294 | −7.615 | 1.00 | 8.38 | C |
| ATOM | 1597 | CG | TRP | A | 230 | 5.372 | −1.046 | −8.043 | 1.00 | 8.01 | C |
| ATOM | 1598 | CD1 | TRP | A | 230 | 4.190 | −1.245 | −7.322 | 1.00 | 8.11 | C |
| ATOM | 1599 | CD2 | TRP | A | 230 | 5.138 | −1.691 | −9.319 | 1.00 | 7.44 | C |
| ATOM | 1600 | NE1 | TRP | A | 230 | 3.281 | −1.926 | −8.092 | 1.00 | 8.31 | N |
| ATOM | 1601 | CE2 | TRP | A | 230 | 3.834 | −2.200 | −9.313 | 1.00 | 7.84 | C |
| ATOM | 1602 | CE3 | TRP | A | 230 | 5.906 | −1.862 | −10.459 | 1.00 | 7.69 | C |
| ATOM | 1603 | CZ2 | TRP | A | 230 | 3.329 | −2.944 | −10.378 | 1.00 | 7.46 | C |
| ATOM | 1604 | CZ3 | TRP | A | 230 | 5.401 | −2.525 | −11.500 | 1.00 | 7.49 | C |
| ATOM | 1605 | CH2 | TRP | A | 230 | 4.136 | −3.069 | −11.478 | 1.00 | 7.36 | C |
| ATOM | 1606 | N | ALA | A | 231 | 8.764 | −2.192 | −8.620 | 1.00 | 7.66 | N |

TABLE 2-continued

X-RAY DIFFRACTION DATA OF *S. AUREUS* AUTOLYSIN E (AtlE 4PIA) RESIDUES 35-258

| ATOM | 1607 | CA | ALA | A | 231 | 9.141 | −3.354 | −9.434 | 1.00 | 8.11 | C |
|------|------|-----|-----|---|-----|--------|---------|---------|------|-------|---|
| ATOM | 1608 | C | ALA | A | 231 | 10.044 | −4.262 | −8.677 | 1.00 | 8.88 | C |
| ATOM | 1609 | O | ALA | A | 231 | 9.938 | −5.490 | −8.779 | 1.00 | 9.79 | O |
| ATOM | 1610 | CB | ALA | A | 231 | 9.771 | −2.897 | −10.740 | 1.00 | 8.21 | C |
| ATOM | 1611 | N | ASP | A | 232 | 10.990 | −3.681 | −7.939 | 1.00 | 8.54 | N |
| ATOM | 1612 | CA | ASP | A | 232 | 11.935 | −4.510 | −7.176 | 1.00 | 9.45 | C |
| ATOM | 1613 | C | ASP | A | 232 | 11.229 | −5.376 | −6.157 | 1.00 | 8.67 | C |
| ATOM | 1614 | O | ASP | A | 232 | 11.623 | −6.536 | −5.959 | 1.00 | 9.74 | O |
| ATOM | 1615 | CB | ASP | A | 232 | 12.973 | −3.600 | −6.448 | 1.00 | 11.74 | C |
| ATOM | 1616 | CG | ASP | A | 232 | 13.720 | −2.756 | −7.407 | 1.00 | 15.12 | C |
| ATOM | 1617 | OD1 | ASP | A | 232 | 14.613 | −3.300 | −8.085 | 1.00 | 19.62 | O |
| ATOM | 1618 | OD2 | ASP | A | 232 | 13.313 | −1.615 | −7.665 | 1.00 | 19.29 | O |
| ATOM | 1619 | N | LYS | A | 233 | 10.225 | −4.857 | −5.468 | 1.00 | 8.57 | N |
| ATOM | 1620 | CA | LYS | A | 233 | 9.534 | −5.616 | −4.409 | 1.00 | 8.87 | C |
| ATOM | 1621 | C | LYS | A | 233 | 8.838 | −6.821 | −5.014 | 1.00 | 8.92 | C |
| ATOM | 1622 | O | LYS | A | 233 | 8.910 | −7.939 | −4.475 | 1.00 | 9.50 | O |
| ATOM | 1623 | CB | LYS | A | 233 | 8.571 | −4.711 | −3.669 | 1.00 | 10.21 | C |
| ATOM | 1624 | CG | LYS | A | 233 | 9.275 | −3.678 | −2.816 | 1.00 | 12.00 | C |
| ATOM | 1625 | CD | LYS | A | 233 | 8.336 | −2.593 | −2.337 | 1.00 | 15.08 | C |
| ATOM | 1626 | CE | LYS | A | 233 | 9.112 | −1.588 | −1.506 | 1.00 | 19.08 | C |
| ATOM | 1627 | NZ | LYS | A | 233 | 8.190 | −0.536 | −1.019 | 1.00 | 22.77 | N |
| ATOM | 1628 | N | ILE | A | 234 | 8.156 | −6.613 | −6.130 | 1.00 | 8.10 | N |
| ATOM | 1629 | CA | ILE | A | 234 | 7.401 | −7.707 | −6.738 | 1.00 | 7.35 | C |
| ATOM | 1630 | C | ILE | A | 234 | 8.386 | −8.723 | −7.308 | 1.00 | 6.93 | C |
| ATOM | 1631 | O | ILE | A | 234 | 8.216 | −9.942 | −7.183 | 1.00 | 6.78 | O |
| ATOM | 1632 | CB | ILE | A | 234 | 6.424 | −7.140 | −7.804 | 1.00 | 6.89 | C |
| ATOM | 1633 | CG1 | ILE | A | 234 | 5.382 | −6.240 | −7.147 | 1.00 | 7.52 | C |
| ATOM | 1634 | CG2 | ILE | A | 234 | 5.781 | −8.307 | −8.554 | 1.00 | 6.94 | C |
| ATOM | 1635 | CD1 | ILE | A | 234 | 4.578 | −5.443 | −8.156 | 1.00 | 8.31 | C |
| ATOM | 1636 | N | ALA | A | 235 | 9.426 | −8.257 | −7.997 | 1.00 | 7.53 | N |
| ATOM | 1637 | CA | ALA | A | 235 | 10.448 | −9.124 | −8.634 | 1.00 | 7.91 | C |
| ATOM | 1638 | C | ALA | A | 235 | 11.141 | −10.002 | −7.595 | 1.00 | 8.47 | C |
| ATOM | 1639 | O | ALA | A | 235 | 11.474 | −11.167 | −7.888 | 1.00 | 8.24 | O |
| ATOM | 1640 | CB | ALA | A | 235 | 11.476 | −8.270 | −9.374 | 1.00 | 8.69 | C |
| ATOM | 1641 | N | LYS | A | 236 | 11.386 | −9.482 | −6.386 | 1.00 | 8.78 | N |
| ATOM | 1642 | CA | LYS | A | 236 | 12.112 | −10.275 | −5.365 | 1.00 | 9.92 | C |
| ATOM | 1643 | C | LYS | A | 236 | 11.247 | −11.451 | −4.979 | 1.00 | 9.35 | C |
| ATOM | 1644 | O | LYS | A | 236 | 11.726 | −12.584 | −4.862 | 1.00 | 9.53 | O |
| ATOM | 1645 | CB | LYS | A | 236 | 12.373 | −9.409 | −4.148 | 1.00 | 12.90 | C |
| ATOM | 1646 | CG | LYS | A | 236 | 13.179 | −10.173 | −3.100 | 1.00 | 17.22 | C |
| ATOM | 1647 | CD | LYS | A | 236 | 13.573 | −9.300 | −1.920 | 1.00 | 22.63 | C |
| ATOM | 1648 | CE | LYS | A | 236 | 12.447 | −9.057 | −0.948 | 1.00 | 28.29 | C |
| ATOM | 1649 | NZ | LYS | A | 236 | 11.702 | −10.247 | −0.503 | 1.00 | 33.02 | N |
| ATOM | 1650 | N | LEU | A | 237 | 9.949 | −11.266 | −4.824 | 1.00 | 8.51 | N |
| ATOM | 1651 | CA | LEU | A | 237 | 9.077 | −12.382 | −4.474 | 1.00 | 9.46 | C |
| ATOM | 1652 | C | LEU | A | 237 | 8.975 | −13.326 | −5.616 | 1.00 | 8.68 | C |
| ATOM | 1653 | O | LEU | A | 237 | 8.962 | −14.558 | −5.475 | 1.00 | 8.63 | O |
| ATOM | 1654 | CB | LEU | A | 237 | 7.655 | −11.966 | −4.082 | 1.00 | 11.04 | C |
| ATOM | 1655 | CG | LEU | A | 237 | 7.482 | −11.104 | −2.844 | 1.00 | 13.90 | C |
| ATOM | 1656 | CD1 | LEU | A | 237 | 5.992 | −10.987 | −2.492 | 1.00 | 14.91 | C |
| ATOM | 1657 | CD2 | LEU | A | 237 | 8.279 | −11.620 | −1.666 | 1.00 | 16.69 | C |
| ATOM | 1658 | N | MET | A | 238 | 8.869 | −12.821 | −6.844 | 1.00 | 7.60 | N |
| ATOM | 1659 | CA | MET | A | 238 | 8.805 | −13.687 | −8.005 | 1.00 | 8.38 | C |
| ATOM | 1660 | C | MET | A | 238 | 10.024 | −14.546 | −8.113 | 1.00 | 7.72 | C |
| ATOM | 1661 | O | MET | A | 238 | 9.909 | −15.761 | −8.401 | 1.00 | 7.58 | O |
| ATOM | 1662 | CB | MET | A | 238 | 8.704 | −12.881 | −9.288 | 1.00 | 8.37 | C |
| ATOM | 1663 | CG | MET | A | 238 | 7.339 | −12.239 | −9.473 | 1.00 | 8.34 | C |
| ATOM | 1664 | SD | MET | A | 238 | 7.287 | −11.237 | −10.996 | 1.00 | 10.44 | S |
| ATOM | 1665 | CE | MET | A | 238 | 7.393 | −12.539 | −12.130 | 1.00 | 14.22 | C |
| ATOM | 1666 | N | ASP | A | 239 | 11.198 | −13.983 | −7.869 | 1.00 | 7.85 | N |
| ATOM | 1667 | CA | ASP | A | 239 | 12.439 | −14.783 | −8.001 | 1.00 | 8.35 | C |
| ATOM | 1668 | C | ASP | A | 239 | 12.469 | −15.885 | −6.951 | 1.00 | 7.52 | C |
| ATOM | 1669 | O | ASP | A | 239 | 12.838 | −17.024 | −7.289 | 1.00 | 7.90 | O |
| ATOM | 1670 | CB | ASP | A | 239 | 13.669 | −13.884 | −7.854 | 1.00 | 9.82 | C |
| ATOM | 1671 | CG | ASP | A | 239 | 14.876 | −14.404 | −8.622 | 1.00 | 13.02 | C |
| ATOM | 1672 | OD1 | ASP | A | 239 | 14.712 | −15.192 | −9.557 | 1.00 | 16.65 | O |
| ATOM | 1673 | OD2 | ASP | A | 239 | 15.969 | −13.902 | −8.302 | 1.00 | 17.18 | O |
| ATOM | 1674 | N | LYS | A | 240 | 12.033 | −15.597 | −5.744 | 1.00 | 7.34 | N |
| ATOM | 1675 | CA | LYS | A | 240 | 11.981 | −16.661 | −4.727 | 1.00 | 8.07 | C |
| ATOM | 1676 | C | LYS | A | 240 | 11.058 | −17.756 | −5.187 | 1.00 | 8.58 | C |
| ATOM | 1677 | O | LYS | A | 240 | 11.353 | −18.961 | −5.061 | 1.00 | 8.95 | O |
| ATOM | 1678 | CB | LYS | A | 240 | 11.537 | −16.130 | −3.426 | 1.00 | 9.33 | C |
| ATOM | 1679 | CG | LYS | A | 240 | 12.580 | −15.267 | −2.749 | 1.00 | 10.99 | C |
| ATOM | 1680 | CD | LYS | A | 240 | 12.082 | −14.633 | −1.458 | 1.00 | 12.12 | C |
| ATOM | 1681 | CE | LYS | A | 240 | 12.169 | −15.592 | −0.326 | 1.00 | 12.89 | C |
| ATOM | 1682 | NZ | LYS | A | 240 | 11.846 | −14.852 | 0.960 | 1.00 | 14.11 | N |
| ATOM | 1683 | N | SER | A | 241 | 9.868 | −17.407 | −5.747 | 1.00 | 7.98 | N |
| ATOM | 1684 | CA | SER | A | 241 | 8.932 | −18.453 | −6.144 | 1.00 | 8.66 | C |

TABLE 2-continued

X-RAY DIFFRACTION DATA OF *S. AUREUS* AUTOLYSIN E (AtlE 4PIA) RESIDUES 35-258

| ATOM | 1685 | C | SER | A | 241 | 9.430 | −19.260 | −7.333 | 1.00 | 8.98 | C |
|---|---|---|---|---|---|---|---|---|---|---|---|
| ATOM | 1686 | O | SER | A | 241 | 9.252 | −20.484 | −7.380 | 1.00 | 8.80 | O |
| ATOM | 1687 | CB | SER | A | 241 | 7.580 | −17.793 | −6.473 | 1.00 | 9.98 | C |
| ATOM | 1688 | OG | SER | A | 241 | 7.041 | −17.193 | −5.335 | 1.00 | 11.45 | O |
| ATOM | 1689 | N | TYR | A | 242 | 10.086 | −18.590 | −8.281 | 1.00 | 8.22 | N |
| ATOM | 1690 | CA | TYR | A | 242 | 10.721 | −19.278 | −9.375 | 1.00 | 8.41 | C |
| ATOM | 1691 | C | TYR | A | 242 | 11.710 | −20.316 | −8.876 | 1.00 | 9.28 | C |
| ATOM | 1692 | O | TYR | A | 242 | 11.760 | −21.434 | −9.403 | 1.00 | 10.26 | O |
| ATOM | 1693 | CB | TYR | A | 242 | 11.385 | −18.287 | −10.385 | 1.00 | 8.81 | C |
| ATOM | 1694 | CG | TYR | A | 242 | 10.451 | −17.876 | −11.491 | 1.00 | 8.19 | C |
| ATOM | 1695 | CD1 | TYR | A | 242 | 9.283 | −17.160 | −11.223 | 1.00 | 8.80 | C |
| ATOM | 1696 | CD2 | TYR | A | 242 | 10.732 | −18.178 | −12.802 | 1.00 | 9.42 | C |
| ATOM | 1697 | CE1 | TYR | A | 242 | 8.414 | −16.815 | −12.241 | 1.00 | 9.71 | C |
| ATOM | 1698 | CE2 | TYR | A | 242 | 9.836 | −17.800 | −13.837 | 1.00 | 9.77 | C |
| ATOM | 1699 | CZ | TYR | A | 242 | 8.681 | −17.125 | −13.508 | 1.00 | 9.10 | C |
| ATOM | 1700 | OH | TYR | A | 242 | 7.793 | −16.794 | −14.506 | 1.00 | 8.88 | O |
| ATOM | 1701 | N | LYS | A | 243 | 12.563 | −19.922 | −7.949 | 1.00 | 8.60 | N |
| ATOM | 1702 | CA | LYS | A | 243 | 13.602 | −20.842 | −7.458 | 1.00 | 9.19 | C |
| ATOM | 1703 | C | LYS | A | 243 | 13.045 | −21.906 | −6.538 | 1.00 | 10.00 | C |
| ATOM | 1704 | O | LYS | A | 243 | 13.614 | −23.027 | −6.448 | 1.00 | 13.52 | O |
| ATOM | 1705 | CB | LYS | A | 243 | 14.721 | −20.023 | −6.812 | 1.00 | 8.88 | C |
| ATOM | 1706 | CG | LYS | A | 243 | 15.485 | −19.201 | −7.816 | 1.00 | 9.25 | C |
| ATOM | 1707 | CD | LYS | A | 243 | 16.616 | −18.349 | −7.257 | 1.00 | 10.46 | C |
| ATOM | 1708 | CE | LYS | A | 243 | 17.248 | −17.582 | −8.402 | 1.00 | 11.85 | C |
| ATOM | 1709 | NZ | LYS | A | 243 | 18.409 | −16.784 | −7.926 | 1.00 | 12.92 | N |
| ATOM | 1710 | N | GLN | A | 244 | 11.922 | −21.660 | −5.918 | 1.00 | 8.82 | N |
| ATOM | 1711 | CA | GLN | A | 244 | 11.231 | −22.631 | −5.056 | 1.00 | 9.11 | C |
| ATOM | 1712 | C | GLN | A | 244 | 10.677 | −23.760 | −5.924 | 1.00 | 9.92 | C |
| ATOM | 1713 | O | GLN | A | 244 | 10.775 | −24.966 | −5.554 | 1.00 | 11.13 | O |
| ATOM | 1714 | CB | GLN | A | 244 | 10.146 | −21.979 | −4.194 | 1.00 | 9.73 | C |
| ATOM | 1715 | CG | GLN | A | 244 | 9.338 | −22.967 | −3.373 | 1.00 | 9.77 | C |
| ATOM | 1716 | CD | GLN | A | 244 | 8.454 | −22.300 | −2.385 | 1.00 | 11.38 | C |
| ATOM | 1717 | OE1 | GLN | A | 244 | 8.638 | −21.131 | −2.090 | 1.00 | 14.86 | O |
| ATOM | 1718 | NE2 | GLN | A | 244 | 7.586 | −23.042 | −1.801 | 1.00 | 13.79 | N |
| ATOM | 1719 | N | PHE | A | 245 | 10.091 | −23.455 | −7.091 | 1.00 | 9.57 | N |
| ATOM | 1720 | CA | PHE | A | 245 | 9.416 | −24.468 | −7.919 | 1.00 | 11.08 | C |
| ATOM | 1721 | C | PHE | A | 245 | 10.197 | −24.842 | −9.151 | 1.00 | 12.49 | C |
| ATOM | 1722 | O | PHE | A | 245 | 9.755 | −25.723 | −9.877 | 1.00 | 14.14 | O |
| ATOM | 1723 | CB | PHE | A | 245 | 8.017 | −23.934 | −8.232 | 1.00 | 10.85 | C |
| ATOM | 1724 | CG | PHE | A | 245 | 7.140 | −23.825 | −7.033 | 1.00 | 10.74 | C |
| ATOM | 1725 | CD1 | PHE | A | 245 | 6.576 | −24.977 | −6.467 | 1.00 | 11.73 | C |
| ATOM | 1726 | CD2 | PHE | A | 245 | 6.924 | −22.615 | −6.391 | 1.00 | 12.01 | C |
| ATOM | 1727 | CE1 | PHE | A | 245 | 5.791 | −24.893 | −5.349 | 1.00 | 11.61 | C |
| ATOM | 1728 | CE2 | PHE | A | 245 | 6.138 | −22.552 | −5.250 | 1.00 | 12.24 | C |
| ATOM | 1729 | CZ | PHE | A | 245 | 5.585 | −23.708 | −4.747 | 1.00 | 11.82 | C |
| ATOM | 1730 | N | GLY | A | 246 | 11.321 | −24.197 | −9.432 | 1.00 | 10.78 | N |
| ATOM | 1731 | CA | GLY | A | 246 | 12.136 | −24.577 | −10.566 | 1.00 | 12.04 | C |
| ATOM | 1732 | C | GLY | A | 246 | 11.529 | −24.131 | −11.882 | 1.00 | 12.28 | C |
| ATOM | 1733 | O | GLY | A | 246 | 11.546 | −24.883 | −12.884 | 1.00 | 14.60 | O |
| ATOM | 1734 | N | ILE | A | 247 | 10.985 | −22.920 | −11.924 | 1.00 | 11.02 | N |
| ATOM | 1735 | CA | ILE | A | 247 | 10.268 | −22.440 | −13.119 | 1.00 | 11.61 | C |
| ATOM | 1736 | C | ILE | A | 247 | 11.253 | −21.769 | −14.076 | 1.00 | 11.15 | C |
| ATOM | 1737 | O | ILE | A | 247 | 12.141 | −21.036 | −13.629 | 1.00 | 12.49 | O |
| ATOM | 1738 | CB | ILE | A | 247 | 9.161 | −21.448 | −12.671 | 1.00 | 11.24 | C |
| ATOM | 1739 | CG1 | ILE | A | 247 | 8.194 | −22.036 | −11.600 | 1.00 | 12.62 | C |
| ATOM | 1740 | CG2 | ILE | A | 247 | 8.339 | −20.946 | −13.850 | 1.00 | 12.14 | C |
| ATOM | 1741 | CD1 | ILE | A | 247 | 7.406 | −23.237 | −12.039 | 1.00 | 13.37 | C |
| ATOM | 1742 | N | LYS | A | 248 | 11.064 | −22.020 | −15.373 | 1.00 | 12.90 | N |
| ATOM | 1743 | CA | LYS | A | 248 | 11.883 | −21.455 | −16.417 | 1.00 | 14.30 | C |
| ATOM | 1744 | C | LYS | A | 248 | 11.404 | −20.014 | −16.705 | 1.00 | 12.81 | C |
| ATOM | 1745 | O | LYS | A | 248 | 10.205 | −19.791 | −16.912 | 1.00 | 13.27 | O |
| ATOM | 1746 | CB | LYS | A | 248 | 11.778 | −22.317 | −17.667 | 1.00 | 19.07 | C |
| ATOM | 1747 | CG | LYS | A | 248 | 12.627 | −21.784 | −18.805 | 1.00 | 26.78 | C |
| ATOM | 1748 | CD | LYS | A | 248 | 12.854 | −22.793 | −19.913 | 1.00 | 32.82 | C |
| ATOM | 1749 | CE | LYS | A | 248 | 13.947 | −22.316 | −20.863 | 1.00 | 39.04 | C |
| ATOM | 1750 | NZ | LYS | A | 248 | 13.618 | −22.731 | −22.257 | 1.00 | 41.83 | N |
| ATOM | 1751 | N | LYS | A | 249 | 12.372 | −19.107 | −16.783 | 1.00 | 13.30 | N |
| ATOM | 1752 | CA | LYS | A | 249 | 12.130 | −17.695 | −17.112 | 1.00 | 12.64 | C |
| ATOM | 1753 | C | LYS | A | 249 | 11.705 | −17.557 | −18.573 | 1.00 | 12.82 | C |
| ATOM | 1754 | O | LYS | A | 249 | 12.215 | −18.266 | −19.478 | 1.00 | 15.20 | O |
| ATOM | 1755 | CB | LYS | A | 249 | 13.372 | −16.843 | −16.857 | 1.00 | 15.15 | C |
| ATOM | 1756 | CG | LYS | A | 249 | 13.739 | −16.730 | −15.383 | 1.00 | 18.53 | C |
| ATOM | 1757 | CD | LYS | A | 249 | 14.765 | −15.650 | −15.144 | 1.00 | 23.21 | C |
| ATOM | 1758 | CE | LYS | A | 249 | 16.021 | −15.843 | −15.985 | 1.00 | 28.72 | C |
| ATOM | 1759 | NZ | LYS | A | 249 | 17.151 | −14.972 | −15.527 | 1.00 | 32.25 | N |
| ATOM | 1760 | N | ASP | A | 250 | 10.799 | −16.606 | −18.822 | 1.00 | 11.89 | N |
| ATOM | 1761 | CA | ASP | A | 250 | 10.394 | −16.187 | −20.159 | 1.00 | 13.17 | C |
| ATOM | 1762 | C | ASP | A | 250 | 11.375 | −15.094 | −20.625 | 1.00 | 11.67 | C |

TABLE 2-continued

X-RAY DIFFRACTION DATA OF *S. AUREUS* AUTOLYSIN E (AtlE 4PIA) RESIDUES 35-258

| ATOM | 1763 | O | ASP | A | 250 | 12.429 | −14.870 | −20.026 | 1.00 | 12.03 | O |
|---|---|---|---|---|---|---|---|---|---|---|---|
| ATOM | 1764 | CB | ASP | A | 250 | 8.885 | −15.769 | −20.138 | 1.00 | 13.96 | C |
| ATOM | 1765 | CG | ASP | A | 250 | 7.931 | −16.987 | −20.143 | 1.00 | 19.37 | C |
| ATOM | 1766 | OD1 | ASP | A | 250 | 8.025 | −17.792 | −21.118 | 1.00 | 26.27 | O |
| ATOM | 1767 | OD2 | ASP | A | 250 | 7.095 | −17.185 | −19.181 | 1.00 | 19.97 | O |
| ATOM | 1768 | N | ASP | A | 251 | 11.067 | −14.481 | −21.760 | 1.00 | 13.72 | N |
| ATOM | 1769 | CA | ASP | A | 251 | 12.024 | −13.587 | −22.419 | 1.00 | 15.01 | C |
| ATOM | 1770 | C | ASP | A | 251 | 12.422 | −12.403 | −21.556 | 1.00 | 12.88 | C |
| ATOM | 1771 | O | ASP | A | 251 | 11.568 | −11.796 | −20.899 | 1.00 | 11.90 | O |
| ATOM | 1772 | CB | ASP | A | 251 | 11.426 | −12.984 | −23.699 | 1.00 | 18.70 | C |
| ATOM | 1773 | CG | ASP | A | 251 | 11.122 | −13.991 | −24.756 | 1.00 | 25.89 | C |
| ATOM | 1774 | OD1 | ASP | A | 251 | 11.732 | −15.075 | −24.771 | 1.00 | 28.98 | O |
| ATOM | 1775 | OD2 | ASP | A | 251 | 10.247 | −13.664 | −25.614 | 1.00 | 37.49 | O |
| ATOM | 1776 | N | ILE | A | 252 | 13.693 | −12.036 | −21.523 | 1.00 | 11.96 | N |
| ATOM | 1777 | CA | ILE | A | 252 | 14.242 | −10.917 | −20.791 | 1.00 | 13.34 | C |
| ATOM | 1778 | C | ILE | A | 252 | 14.618 | −9.845 | −21.810 | 1.00 | 13.93 | C |
| ATOM | 1779 | O | ILE | A | 252 | 15.303 | −10.110 | −22.806 | 1.00 | 14.12 | O |
| ATOM | 1780 | CB | ILE | A | 252 | 15.537 | −11.307 | −20.086 | 1.00 | 14.50 | C |
| ATOM | 1781 | CG1 | ILE | A | 252 | 15.313 | −12.533 | −19.202 | 1.00 | 16.30 | C |
| ATOM | 1782 | CG2 | ILE | A | 252 | 16.183 | −10.118 | −19.383 | 1.00 | 15.15 | C |
| ATOM | 1783 | CD1 | ILE | A | 252 | 14.348 | −12.281 | −18.135 | 1.00 | 16.79 | C |
| ATOM | 1784 | N | ARG | A | 253 | 14.156 | −8.648 | −21.570 | 1.00 | 11.73 | N |
| ATOM | 1785 | CA | ARG | A | 253 | 14.450 | −7.496 | −22.474 | 1.00 | 11.81 | C |
| ATOM | 1786 | C | ARG | A | 253 | 15.264 | −6.480 | −21.705 | 1.00 | 12.05 | C |
| ATOM | 1787 | O | ARG | A | 253 | 14.859 | −6.021 | −20.638 | 1.00 | 13.99 | O |
| ATOM | 1788 | CB | ARG | A | 253 | 13.145 | −6.872 | −22.941 | 1.00 | 12.00 | C |
| ATOM | 1789 | CG | ARG | A | 253 | 13.372 | −5.572 | −23.719 | 1.00 | 11.89 | C |
| ATOM | 1790 | CD | ARG | A | 253 | 12.112 | −5.026 | −24.314 | 1.00 | 11.33 | C |
| ATOM | 1791 | NE | ARG | A | 253 | 12.406 | −3.751 | −24.962 | 1.00 | 10.87 | N |
| ATOM | 1792 | CZ | ARG | A | 253 | 11.584 | −3.075 | −25.715 | 1.00 | 11.37 | C |
| ATOM | 1793 | NH1 | ARG | A | 253 | 10.342 | −3.474 | −25.906 | 1.00 | 12.79 | N |
| ATOM | 1794 | NH2 | ARG | A | 253 | 12.004 | −1.909 | −26.222 | 1.00 | 11.06 | N |
| ATOM | 1795 | N | GLN | A | 254 | 16.411 | −6.036 | −22.253 | 1.00 | 17.74 | N |
| ATOM | 1796 | CA | GLN | A | 254 | 17.139 | −5.016 | −21.516 | 1.00 | 19.27 | C |
| ATOM | 1797 | C | GLN | A | 254 | 17.368 | −3.729 | −22.329 | 1.00 | 14.52 | C |
| ATOM | 1798 | O | GLN | A | 254 | 17.862 | −2.808 | −21.751 | 1.00 | 18.07 | O |
| ATOM | 1799 | CB | GLN | A | 254 | 18.437 | −5.522 | −20.835 | 1.00 | 24.51 | C |
| ATOM | 1800 | CG | GLN | A | 254 | 18.099 | −6.410 | −19.630 | 1.00 | 28.36 | C |
| ATOM | 1801 | CD | GLN | A | 254 | 19.265 | −6.712 | −18.724 | 1.00 | 34.64 | C |
| ATOM | 1802 | OE1 | GLN | A | 254 | 20.034 | −5.819 | −18.377 | 1.00 | 40.94 | O |
| ATOM | 1803 | NE2 | GLN | A | 254 | 19.387 | −7.987 | −18.307 | 1.00 | 38.87 | N |
| ATOM | 1804 | N | THR | A | 255 | 16.832 | −3.612 | −23.545 | 1.00 | 13.49 | N |
| ATOM | 1805 | CA | THR | A | 255 | 17.015 | −2.360 | −24.326 | 1.00 | 13.10 | C |
| ATOM | 1806 | C | THR | A | 255 | 15.679 | −1.611 | −24.419 | 1.00 | 11.00 | C |
| ATOM | 1807 | O | THR | A | 255 | 14.683 | −2.086 | −24.972 | 1.00 | 11.38 | O |
| ATOM | 1808 | CB | THR | A | 255 | 17.566 | −2.620 | −25.720 | 1.00 | 15.77 | C |
| ATOM | 1809 | OG1 | THR | A | 255 | 18.878 | −3.177 | −25.556 | 1.00 | 18.94 | O |
| ATOM | 1810 | CG2 | THR | A | 255 | 17.729 | −1.331 | −26.508 | 1.00 | 15.90 | C |
| ATOM | 1811 | N | TYR | A | 256 | 15.689 | −0.416 | −23.830 | 1.00 | 9.59 | N |
| ATOM | 1812 | CA | TYR | A | 256 | 14.481 | 0.475 | −23.789 | 1.00 | 9.52 | C |
| ATOM | 1813 | C | TYR | A | 256 | 14.683 | 1.862 | −24.308 | 1.00 | 9.95 | C |
| ATOM | 1814 | O | TYR | A | 256 | 13.658 | 2.527 | −24.560 | 1.00 | 9.89 | O |
| ATOM | 1815 | CB | TYR | A | 256 | 13.968 | 0.538 | −22.336 | 1.00 | 9.58 | C |
| ATOM | 1816 | CG | TYR | A | 256 | 13.609 | −0.811 | −21.782 | 1.00 | 10.10 | C |
| ATOM | 1817 | CD1 | TYR | A | 256 | 12.382 | −1.405 | −22.010 | 1.00 | 10.12 | C |
| ATOM | 1818 | CD2 | TYR | A | 256 | 14.540 | −1.523 | −21.048 | 1.00 | 10.02 | C |
| ATOM | 1819 | CE1 | TYR | A | 256 | 12.103 | −2.666 | −21.495 | 1.00 | 10.17 | C |
| ATOM | 1820 | CE2 | TYR | A | 256 | 14.250 | −2.801 | −20.570 | 1.00 | 10.46 | C |
| ATOM | 1821 | CZ | TYR | A | 256 | 13.022 | −3.316 | −20.810 | 1.00 | 10.46 | C |
| ATOM | 1822 | OH | TYR | A | 256 | 12.732 | −4.594 | −20.327 | 1.00 | 12.81 | O |
| ATOM | 1823 | N | TYR | A | 257 | 15.932 | 2.328 | −24.438 | 1.00 | 9.59 | N |
| ATOM | 1824 | CA | TYR | A | 257 | 16.242 | 3.729 | −24.701 | 1.00 | 10.02 | C |
| ATOM | 1825 | C | TYR | A | 257 | 17.174 | 3.822 | −25.897 | 1.00 | 11.75 | C |
| ATOM | 1826 | O | TYR | A | 257 | 17.873 | 2.878 | −26.211 | 1.00 | 13.21 | O |
| ATOM | 1827 | CB | TYR | A | 257 | 16.875 | 4.377 | −23.481 | 1.00 | 10.49 | C |
| ATOM | 1828 | CG | TYR | A | 257 | 15.980 | 4.324 | −22.248 | 1.00 | 9.36 | C |
| ATOM | 1829 | CD1 | TYR | A | 257 | 14.873 | 5.137 | −22.124 | 1.00 | 9.77 | C |
| ATOM | 1830 | CD2 | TYR | A | 257 | 16.244 | 3.441 | −21.226 | 1.00 | 8.97 | C |
| ATOM | 1831 | CE1 | TYR | A | 257 | 14.024 | 5.066 | −21.016 | 1.00 | 9.19 | C |
| ATOM | 1832 | CE2 | TYR | A | 257 | 15.446 | 3.404 | −20.090 | 1.00 | 9.18 | C |
| ATOM | 1833 | CZ | TYR | A | 257 | 14.341 | 4.214 | −19.983 | 1.00 | 9.28 | C |
| ATOM | 1834 | OH | TYR | A | 257 | 13.467 | 4.202 | −18.895 | 1.00 | 9.02 | O |
| ATOM | 1835 | N | LYS | A | 258 | 17.116 | 4.981 | −26.543 | 1.00 | 12.59 | N |
| ATOM | 1836 | CA | LYS | A | 258 | 17.971 | 5.246 | −27.696 | 1.00 | 15.57 | C |
| ATOM | 1837 | C | LYS | A | 258 | 19.435 | 5.318 | −27.308 | 1.00 | 20.82 | C |
| ATOM | 1838 | O | LYS | A | 258 | 19.757 | 5.768 | −26.249 | 1.00 | 26.94 | O |
| ATOM | 1839 | CB | LYS | A | 258 | 17.567 | 6.592 | −28.284 | 1.00 | 16.01 | C |
| ATOM | 1840 | CG | LYS | A | 258 | 16.197 | 6.561 | −28.892 | 1.00 | 18.32 | C |

TABLE 2-continued

X-RAY DIFFRACTION DATA OF S. AUREUS AUTOLYSIN E (AtlE 4PIA) RESIDUES 35-258

| ATOM | 1841 | CD | LYS | A | 258 | 15.836 | 7.805 | −30.648 | 1.00 | 29.23 | C |
|---|---|---|---|---|---|---|---|---|---|---|---|
| ATOM | 1842 | CE | LYS | A | 258 | 14.681 | 7.482 | −30.648 | 1.00 | 29.23 | C |
| ATOM | 1843 | NZ | LYS | A | 258 | 15.151 | 6.758 | −31.872 | 1.00 | 35.93 | N |
| ATOM | 1844 | OXT | LYS | A | 258 | 20.275 | 4.919 | −28.115 | 1.00 | 25.57 | O |
| TER | 1845 | | LYS | A | 258 | | | | | | |
| HETATM | 1846 | CL | CL | A | 301 | 18.426 | 0.821 | −22.858 | 1.00 | 15.14 | CL |
| HETATM | 1847 | CL | CL | A | 302 | 1.177 | 4.791 | −22.820 | 1.00 | 25.04 | CL |
| HETATM | 1848 | CL | CL | A | 303 | 20.450 | −18.960 | −7.618 | 1.00 | 18.49 | CL |
| HETATM | 1849 | CL | CL | A | 304 | −10.599 | 5.000 | −9.695 | 1.00 | 30.38 | CL |
| HETATM | 1850 | CL | CL | A | 305 | 26.057 | 2.491 | −28.651 | 1.00 | 39.32 | CL |
| HETATM | 1851 | CL | CL | A | 306 | 8.900 | −24.064 | −16.338 | 1.00 | 25.76 | CL |
| HETATM | 1852 | CL | CL | A | 307 | −3.163 | −29.477 | −7.877 | 1.00 | 13.36 | CL |
| HETATM | 1853 | CL | CL | A | 308 | 12.791 | −0.604 | −11.548 | 1.00 | 13.72 | CL |
| HETATM | 1854 | CL | CL | A | 309 | −8.084 | −22.697 | −3.752 | 1.00 | 17.50 | CL |
| HETATM | 1855 | O | HOH | A | 401 | 16.090 | −11.781 | −6.254 | 1.00 | 34.86 | O |
| HETATM | 1856 | O | HOH | A | 402 | −14.132 | −19.872 | −8.850 | 1.00 | 37.20 | O |
| HETATM | 1857 | O | HOH | A | 403 | 16.131 | 17.765 | −16.811 | 1.00 | 29.85 | O |
| HETATM | 1858 | O | HOH | A | 404 | 7.357 | −4.302 | −25.248 | 1.00 | 30.64 | O |
| HETATM | 1859 | O | HOH | A | 405 | −2.143 | −9.749 | −26.947 | 1.00 | 40.89 | O |
| HETATM | 1860 | O | HOH | A | 406 | 17.534 | 5.286 | −3.547 | 1.00 | 39.90 | O |
| HETATM | 1861 | O | HOH | A | 407 | 5.756 | 4.173 | −29.801 | 1.00 | 17.63 | O |
| HETATM | 1862 | O | HOH | A | 408 | 3.900 | −5.133 | 1.473 | 1.00 | 28.17 | O |
| HETATM | 1863 | O | HOH | A | 409 | −14.059 | −8.159 | 4.356 | 1.00 | 14.03 | O |
| HETATM | 1864 | O | HOH | A | 410 | −15.047 | −7.068 | 8.919 | 1.00 | 33.68 | O |
| HETATM | 1865 | O | HOH | A | 411 | −17.649 | −9.591 | 1.698 | 1.00 | 18.95 | O |
| HETATM | 1866 | O | HOH | A | 412 | −2.471 | −20.765 | 7.918 | 1.00 | 27.95 | O |
| HETATM | 1867 | O | HOH | A | 413 | 20.042 | 5.050 | −30.776 | 1.00 | 36.76 | O |
| HETATM | 1868 | O | HOH | A | 414 | −4.247 | −8.999 | −28.246 | 1.00 | 44.19 | O |
| HETATM | 1869 | O | HOH | A | 415 | −10.451 | −5.948 | 9.962 | 1.00 | 46.96 | O |
| HETATM | 1870 | O | HOH | A | 416 | 4.349 | 16.958 | −15.247 | 1.00 | 11.74 | O |
| HETATM | 1871 | O | HOH | A | 417 | −7.925 | −19.390 | 4.850 | 1.00 | 11.14 | O |
| HETATM | 1872 | O | HOH | A | 418 | −17.932 | −10.827 | −0.654 | 1.00 | 16.23 | O |
| HETATM | 1873 | O | HOH | A | 419 | −1.657 | −14.374 | −26.782 | 1.00 | 31.11 | O |
| HETATM | 1874 | O | HOH | A | 420 | −12.601 | −14.980 | −19.776 | 1.00 | 31.01 | O |
| HETATM | 1875 | O | HOH | A | 421 | 17.299 | −9.165 | −3.916 | 1.00 | 35.26 | O |
| HETATM | 1876 | O | HOH | A | 422 | 12.658 | −12.259 | 1.194 | 1.00 | 23.63 | O |
| HETATM | 1877 | O | HOH | A | 423 | −6.393 | −8.764 | 5.259 | 1.00 | 15.78 | O |
| HETATM | 1878 | O | HOH | A | 424 | 19.514 | 12.920 | −24.819 | 1.00 | 27.99 | O |
| HETATM | 1879 | O | HOH | A | 425 | 13.057 | −19.812 | −3.099 | 1.00 | 8.50 | O |
| HETATM | 1880 | O | HOH | A | 426 | −8.067 | −16.933 | 3.290 | 1.00 | 8.15 | O |
| HETATM | 1881 | O | HOH | A | 427 | 12.459 | 17.742 | −15.412 | 1.00 | 19.96 | O |
| HETATM | 1882 | O | HOH | A | 428 | −10.338 | −13.828 | −21.798 | 1.00 | 29.02 | O |
| HETATM | 1883 | O | HOH | A | 429 | 16.149 | 9.614 | 9.485 | 1.00 | 40.74 | O |
| HETATM | 1884 | O | HOH | A | 430 | −24.880 | −8.180 | 1.476 | 1.00 | 17.79 | O |
| HETATM | 1885 | O | HOH | A | 431 | 3.044 | −27.966 | −12.055 | 1.00 | 27.97 | O |
| HETATM | 1886 | O | HOH | A | 432 | 5.782 | −26.346 | −11.225 | 1.00 | 26.25 | O |
| HETATM | 1887 | O | HOH | A | 433 | −14.955 | −18.012 | −7.142 | 1.00 | 34.75 | O |
| HETATM | 1888 | O | HOH | A | 434 | 0.268 | 3.782 | −25.515 | 1.00 | 36.61 | O |
| HETATM | 1889 | O | HOH | A | 435 | 10.787 | 4.686 | −32.254 | 1.00 | 31.84 | O |
| HETATM | 1890 | O | HOH | A | 436 | −17.128 | −14.488 | −5.668 | 1.00 | 21.53 | O |
| HETATM | 1891 | O | HOH | A | 437 | 5.955 | 10.113 | −24.583 | 1.00 | 9.65 | O |
| HETATM | 1892 | O | HOH | A | 438 | 18.446 | 1.470 | −28.573 | 1.00 | 32.18 | O |
| HETATM | 1893 | O | HOH | A | 439 | 12.098 | −16.288 | 3.363 | 1.00 | 18.77 | O |
| HETATM | 1894 | O | HOH | A | 440 | 11.556 | −2.418 | −30.217 | 1.00 | 29.87 | O |
| HETATM | 1895 | O | HOH | A | 441 | −8.728 | −21.890 | 4.530 | 1.00 | 16.31 | O |
| HETATM | 1896 | O | HOH | A | 442 | −14.103 | −17.085 | −9.494 | 1.00 | 38.37 | O |
| HETATM | 1897 | O | HOH | A | 443 | 2.260 | 16.550 | −12.547 | 1.00 | 24.83 | O |
| HETATM | 1898 | O | HOH | A | 444 | 14.856 | 3.774 | −31.804 | 1.00 | 25.75 | O |
| HETATM | 1899 | O | HOH | A | 445 | −1.585 | −22.776 | −19.019 | 1.00 | 24.29 | O |
| HETATM | 1900 | O | HOH | A | 446 | −0.018 | −6.768 | 6.537 | 1.00 | 25.08 | O |
| HETATM | 1901 | O | HOH | A | 447 | 5.057 | 10.814 | −22.125 | 1.00 | 10.01 | O |
| HETATM | 1902 | O | HOH | A | 448 | 17.212 | 5.096 | −6.082 | 1.00 | 22.49 | O |
| HETATM | 1903 | O | HOH | A | 449 | −20.371 | −5.149 | 5.235 | 1.00 | 29.36 | O |
| HETATM | 1904 | O | HOH | A | 450 | −19.889 | −11.126 | −4.608 | 1.00 | 19.55 | O |
| HETATM | 1905 | O | HOH | A | 451 | 14.921 | 4.206 | 6.848 | 1.00 | 43.30 | O |
| HETATM | 1906 | O | HOH | A | 452 | 13.010 | 15.114 | −21.961 | 1.00 | 24.86 | O |
| HETATM | 1907 | O | HOH | A | 453 | 9.030 | −6.394 | −22.727 | 1.00 | 22.35 | O |
| HETATM | 1908 | O | HOH | A | 454 | −20.069 | −7.400 | −1.215 | 1.00 | 13.15 | O |
| HETATM | 1909 | O | HOH | A | 455 | 3.004 | −23.747 | 2.028 | 1.00 | 18.76 | O |
| HETATM | 1910 | O | HOH | A | 456 | 1.742 | −30.056 | −7.908 | 1.00 | 18.51 | O |
| HETATM | 1911 | O | HOH | A | 457 | 14.305 | 6.104 | 11.325 | 1.00 | 30.32 | O |
| HETATM | 1912 | O | HOH | A | 458 | 8.329 | −10.612 | −24.974 | 1.00 | 27.98 | O |
| HETATM | 1913 | O | HOH | A | 459 | 3.405 | −14.421 | 5.801 | 1.00 | 37.95 | O |
| HETATM | 1914 | O | HOH | A | 460 | 5.913 | −16.955 | 2.266 | 1.00 | 38.68 | O |
| HETATM | 1915 | O | HOH | A | 461 | −20.976 | −0.544 | −11.049 | 1.00 | 39.86 | O |
| HETATM | 1916 | O | HOH | A | 462 | −1.076 | 8.801 | −17.435 | 1.00 | 20.87 | O |
| HETATM | 1917 | O | HOH | A | 463 | 11.838 | 0.207 | −0.314 | 1.00 | 18.96 | O |
| HETATM | 1918 | O | HOH | A | 464 | −0.768 | 11.241 | −18.882 | 1.00 | 23.55 | O |

TABLE 2-continued

X-RAY DIFFRACTION DATA OF *S. AUREUS* AUTOLYSIN E (AtlE 4PIA) RESIDUES 35-258

| | | | | | | | | | | | |
|---|---|---|---|---|---|---|---|---|---|---|---|
| HETATM | 1919 | O | HOH | A | 465 | 13.821 | 2.538 | 0.046 | 1.00 | 32.29 | O |
| HETATM | 1920 | O | HOH | A | 466 | 0.320 | −11.514 | −24.708 | 1.00 | 29.80 | O |
| HETATM | 1921 | O | HOH | A | 467 | 8.234 | −15.650 | −2.714 | 1.00 | 28.49 | O |
| HETATM | 1922 | O | HOH | A | 468 | 2.052 | 12.013 | −10.318 | 1.00 | 22.42 | O |
| HETATM | 1923 | O | HOH | A | 469 | −11.956 | −4.817 | 8.101 | 1.00 | 41.49 | O |
| HETATM | 1924 | O | HOH | A | 470 | −5.815 | −12.211 | 8.210 | 1.00 | 17.11 | O |
| HETATM | 1925 | O | HOH | A | 471 | 7.757 | −3.393 | −40.942 | 1.00 | 44.06 | O |
| HETATM | 1926 | O | HOH | A | 472 | −0.121 | −16.246 | 8.934 | 1.00 | 38.49 | O |
| HETATM | 1927 | O | HOH | A | 473 | −7.014 | −9.111 | −24.152 | 1.00 | 30.53 | O |
| HETATM | 1928 | O | HOH | A | 474 | −14.742 | −14.639 | −2.806 | 1.00 | 10.35 | O |
| HETATM | 1929 | O | HOH | A | 475 | 2.855 | −22.706 | −18.778 | 1.00 | 26.49 | O |
| HETATM | 1930 | O | HOH | A | 476 | 16.425 | 1.807 | −6.615 | 1.00 | 26.84 | O |
| HETATM | 1931 | O | HOH | A | 477 | 4.200 | 21.186 | −8.310 | 1.00 | 40.53 | O |
| HETATM | 1932 | O | HOH | A | 478 | 17.460 | 15.754 | −21.085 | 1.00 | 41.43 | O |
| HETATM | 1933 | O | HOH | A | 479 | 14.815 | 17.167 | −21.246 | 1.00 | 31.95 | O |
| HETATM | 1934 | O | HOH | A | 480 | −4.434 | −26.895 | −2.388 | 1.00 | 23.84 | O |
| HETATM | 1935 | O | HOH | A | 481 | −1.593 | −21.221 | −24.060 | 1.00 | 27.38 | O |
| HETATM | 1936 | O | HOH | A | 482 | −0.907 | 7.640 | −22.595 | 1.00 | 31.78 | O |
| HETATM | 1937 | O | HOH | A | 483 | 5.915 | −21.386 | 0.447 | 1.00 | 23.60 | O |
| HETATM | 1938 | O | HOH | A | 484 | 2.850 | 2.090 | −38.189 | 1.00 | 24.31 | O |
| HETATM | 1939 | O | HOH | A | 485 | −22.761 | −8.475 | −4.929 | 1.00 | 28.48 | O |
| HETATM | 1940 | O | HOH | A | 486 | −13.100 | −24.447 | −3.041 | 1.00 | 32.17 | O |
| HETATM | 1941 | O | HOH | A | 487 | 21.426 | 8.424 | −27.700 | 1.00 | 38.97 | O |
| HETATM | 1942 | O | HOH | A | 488 | 3.758 | −9.908 | 7.180 | 1.00 | 23.82 | O |
| HETATM | 1943 | O | HOH | A | 489 | −3.014 | 7.153 | −18.193 | 1.00 | 34.01 | O |
| HETATM | 1944 | O | HOH | A | 490 | 3.654 | −7.695 | 4.881 | 1.00 | 26.55 | O |
| HETATM | 1945 | O | HOH | A | 491 | −10.023 | −20.608 | −4.767 | 1.00 | 26.61 | O |
| HETATM | 1946 | O | HOH | A | 492 | −8.164 | −24.677 | −1.392 | 1.00 | 32.12 | O |
| HETATM | 1947 | O | HOH | A | 493 | 3.677 | −21.166 | 4.715 | 1.00 | 33.68 | O |
| HETATM | 1948 | O | HOH | A | 494 | 16.720 | −8.351 | −25.636 | 1.00 | 32.32 | O |
| HETATM | 1949 | O | HOH | A | 495 | −1.220 | −25.370 | 0.931 | 1.00 | 20.53 | O |
| HETATM | 1950 | O | HOH | A | 496 | 12.555 | −10.054 | −25.244 | 1.00 | 39.99 | O |
| HETATM | 1951 | O | HOH | A | 497 | −8.041 | −12.212 | 10.361 | 1.00 | 22.52 | O |
| HETATM | 1952 | O | HOH | A | 498 | −23.777 | 1.060 | 8.821 | 1.00 | 41.39 | O |
| HETATM | 1953 | O | HOH | A | 499 | −32.328 | −6.495 | 2.164 | 1.00 | 28.68 | O |
| HETATM | 1954 | O | HOH | A | 500 | 2.089 | −20.451 | 6.924 | 1.00 | 36.54 | O |
| HETATM | 1955 | O | HOH | A | 501 | 22.164 | −17.228 | −9.757 | 1.00 | 39.28 | O |
| HETATM | 1956 | O | HOH | A | 502 | 15.513 | −24.690 | −12.348 | 1.00 | 36.57 | O |
| HETATM | 1957 | O | HOH | A | 503 | 6.223 | −3.630 | 0.616 | 1.00 | 40.31 | O |
| HETATM | 1958 | O | HOH | A | 504 | 1.387 | 3.338 | −27.619 | 1.00 | 32.60 | O |
| HETATM | 1959 | O | HOH | A | 505 | −22.062 | −9.319 | −2.258 | 1.00 | 16.76 | O |
| HETATM | 1960 | O | HOH | A | 506 | −8.549 | −11.290 | −22.586 | 1.00 | 26.34 | O |
| HETATM | 1961 | O | HOH | A | 507 | 13.291 | 8.908 | 12.587 | 1.00 | 33.89 | O |
| HETATM | 1962 | O | HOH | A | 508 | 18.726 | −21.018 | −9.136 | 1.00 | 21.89 | O |
| HETATM | 1963 | O | HOH | A | 509 | 7.374 | −8.358 | 0.294 | 1.00 | 44.49 | O |
| HETATM | 1964 | O | HOH | A | 510 | 15.779 | 5.574 | −36.635 | 1.00 | 46.32 | O |
| HETATM | 1965 | O | HOH | A | 511 | −3.604 | −24.163 | 1.819 | 1.00 | 30.02 | O |
| HETATM | 1966 | O | HOH | A | 512 | 13.202 | −5.289 | −2.871 | 1.00 | 36.41 | O |
| HETATM | 1967 | O | HOH | A | 513 | 3.431 | −19.605 | 2.054 | 1.00 | 27.16 | O |
| HETATM | 1968 | O | HOH | A | 514 | −3.102 | 5.855 | −15.731 | 1.00 | 39.11 | O |
| HETATM | 1969 | O | HOH | A | 515 | 11.646 | −6.283 | −0.945 | 1.00 | 27.17 | O |
| HETATM | 1970 | O | HOH | A | 516 | 4.785 | −12.879 | −24.924 | 1.00 | 24.03 | O |
| HETATM | 1971 | O | HOH | A | 517 | 2.641 | −10.163 | −24.906 | 1.00 | 23.34 | O |
| HETATM | 1972 | O | HOH | A | 518 | 11.103 | 1.492 | −24.919 | 1.00 | 11.20 | O |
| HETATM | 1973 | O | HOH | A | 519 | 12.162 | 4.904 | −25.194 | 1.00 | 9.44 | O |
| HETATM | 1974 | O | HOH | A | 520 | 0.478 | −8.400 | −24.943 | 1.00 | 35.83 | O |
| HETATM | 1975 | O | HOH | A | 521 | 6.538 | −0.371 | −24.357 | 1.00 | 18.46 | O |
| HETATM | 1976 | O | HOH | A | 522 | 9.381 | −0.359 | −23.992 | 1.00 | 18.38 | O |
| HETATM | 1977 | O | HOH | A | 523 | 15.732 | −14.001 | −22.817 | 1.00 | 20.23 | O |
| HETATM | 1978 | O | HOH | A | 524 | 20.928 | 9.366 | −22.600 | 1.00 | 16.64 | O |
| HETATM | 1979 | O | HOH | A | 525 | 1.085 | −18.411 | −22.415 | 1.00 | 16.82 | O |
| HETATM | 1980 | O | HOH | A | 526 | 7.054 | 1.260 | −22.273 | 1.00 | 11.29 | O |
| HETATM | 1981 | O | HOH | A | 527 | −11.381 | −9.178 | −21.659 | 1.00 | 26.83 | O |
| HETATM | 1982 | O | HOH | A | 528 | 10.316 | −8.624 | −21.374 | 1.00 | 12.36 | O |
| HETATM | 1983 | O | HOH | A | 529 | 14.905 | −15.986 | −20.343 | 1.00 | 23.12 | O |
| HETATM | 1984 | O | HOH | A | 530 | −13.293 | −10.568 | −20.110 | 1.00 | 38.80 | O |
| HETATM | 1985 | O | HOH | A | 531 | 7.834 | −21.301 | −17.558 | 1.00 | 27.58 | O |
| HETATM | 1986 | O | HOH | A | 532 | 20.309 | 2.474 | −17.683 | 1.00 | 25.74 | O |
| HETATM | 1987 | O | HOH | A | 533 | 11.154 | 6.029 | −18.590 | 1.00 | 8.19 | O |
| HETATM | 1988 | O | HOH | A | 534 | 5.574 | −14.977 | −18.103 | 1.00 | 10.79 | O |
| HETATM | 1989 | O | HOH | A | 535 | 8.384 | −17.678 | −16.952 | 1.00 | 11.85 | O |
| HETATM | 1990 | O | HOH | A | 536 | 18.325 | 13.947 | −17.675 | 1.00 | 20.76 | O |
| HETATM | 1991 | O | HOH | A | 537 | 15.407 | −19.958 | −16.473 | 1.00 | 20.50 | O |
| HETATM | 1992 | O | HOH | A | 538 | −13.967 | −11.167 | −15.840 | 1.00 | 29.40 | O |
| HETATM | 1993 | O | HOH | A | 539 | 8.668 | −8.478 | −15.192 | 1.00 | 8.66 | O |
| HETATM | 1994 | O | HOH | A | 540 | −11.095 | −5.466 | −14.424 | 1.00 | 18.33 | O |
| HETATM | 1995 | O | HOH | A | 541 | 17.506 | 15.432 | −15.536 | 1.00 | 26.48 | O |
| HETATM | 1996 | O | HOH | A | 542 | −13.565 | −6.442 | −13.802 | 1.00 | 15.00 | O |

TABLE 2-continued

X-RAY DIFFRACTION DATA OF *S. AUREUS* AUTOLYSIN E (AtlE 4PIA) RESIDUES 35-258

| | | | | | | | | | | | |
|---|---|---|---|---|---|---|---|---|---|---|---|
| HETATM | 1997 | O | HOH | A | 543 | 15.491 | −0.724 | −13.165 | 1.00 | 18.09 | O |
| HETATM | 1998 | O | HOH | A | 544 | 14.965 | 17.479 | −14.028 | 1.00 | 23.71 | O |
| HETATM | 1999 | O | HOH | A | 545 | 19.235 | 13.396 | −12.609 | 1.00 | 27.75 | O |
| HETATM | 2000 | O | HOH | A | 546 | 15.188 | −16.785 | −11.740 | 1.00 | 44.36 | O |
| HETATM | 2001 | O | HOH | A | 547 | −15.303 | −12.650 | −11.594 | 1.00 | 19.45 | O |
| HETATM | 2002 | O | HOH | A | 548 | −14.371 | −9.848 | −11.305 | 1.00 | 16.30 | O |
| HETATM | 2003 | O | HOH | A | 549 | −16.692 | −8.385 | −11.063 | 1.00 | 29.16 | O |
| HETATM | 2004 | O | HOH | A | 550 | 9.191 | 13.782 | −10.295 | 1.00 | 16.83 | O |
| HETATM | 2005 | O | HOH | A | 551 | 14.678 | −6.195 | −8.911 | 1.00 | 29.32 | O |
| HETATM | 2006 | O | HOH | A | 552 | 10.503 | −0.009 | −9.447 | 1.00 | 12.11 | O |
| HETATM | 2007 | O | HOH | A | 553 | 7.407 | 16.193 | −8.454 | 1.00 | 33.83 | O |
| HETATM | 2008 | O | HOH | A | 554 | 14.245 | 0.558 | −8.754 | 1.00 | 23.28 | O |
| HETATM | 2009 | O | HOH | A | 555 | −8.254 | −6.239 | −7.389 | 1.00 | 8.90 | O |
| HETATM | 2010 | O | HOH | A | 556 | 15.583 | 16.745 | −6.243 | 1.00 | 22.88 | O |
| HETATM | 2011 | O | HOH | A | 557 | 5.223 | −15.225 | −4.797 | 1.00 | 13.57 | O |
| HETATM | 2012 | O | HOH | A | 558 | 20.608 | 11.197 | −3.159 | 1.00 | 37.10 | O |
| HETATM | 2013 | O | HOH | A | 559 | 9.497 | −8.022 | −1.781 | 1.00 | 17.57 | O |
| HETATM | 2014 | O | HOH | A | 560 | 4.663 | −16.974 | −0.718 | 1.00 | 21.71 | O |
| HETATM | 2015 | O | HOH | A | 561 | −9.519 | −5.033 | −0.463 | 1.00 | 11.26 | O |
| HETATM | 2016 | O | HOH | A | 562 | −3.134 | −21.342 | 0.778 | 1.00 | 10.07 | O |
| HETATM | 2017 | O | HOH | A | 563 | −11.427 | 8.200 | 2.397 | 1.00 | 42.57 | O |
| HETATM | 2018 | O | HOH | A | 564 | −4.208 | −1.220 | 5.498 | 1.00 | 21.15 | O |
| HETATM | 2019 | O | HOH | A | 565 | −10.930 | −2.843 | 5.660 | 1.00 | 25.10 | O |
| HETATM | 2020 | O | HOH | A | 566 | −15.206 | 0.555 | 5.175 | 1.00 | 26.68 | O |
| HETATM | 2021 | O | HOH | A | 567 | 3.160 | −5.569 | −27.349 | 1.00 | 28.09 | O |
| HETATM | 2022 | O | HOH | A | 568 | 22.674 | 4.700 | −26.006 | 1.00 | 45.88 | O |
| HETATM | 2023 | O | HOH | A | 569 | 0.755 | −5.048 | −26.272 | 1.00 | 27.10 | O |
| HETATM | 2024 | O | HOH | A | 570 | 21.006 | −2.108 | −24.067 | 1.00 | 45.19 | O |
| HETATM | 2025 | O | HOH | A | 571 | 20.435 | 2.367 | −24.918 | 1.00 | 33.27 | O |
| HETATM | 2026 | O | HOH | A | 572 | 2.033 | −13.563 | −24.356 | 1.00 | 23.32 | O |
| HETATM | 2027 | O | HOH | A | 573 | −4.681 | −1.091 | −23.574 | 1.00 | 28.15 | O |
| HETATM | 2028 | O | HOH | A | 574 | 19.994 | 6.513 | −23.921 | 1.00 | 21.49 | O |
| HETATM | 2029 | O | HOH | A | 575 | 17.869 | −10.864 | −23.308 | 1.00 | 36.78 | O |
| HETATM | 2030 | O | HOH | A | 576 | 21.427 | 4.675 | −22.385 | 1.00 | 31.58 | O |
| HETATM | 2031 | O | HOH | A | 577 | 1.794 | −22.001 | −21.357 | 1.00 | 35.24 | O |
| HETATM | 2032 | O | HOH | A | 578 | 20.237 | −1.529 | −21.318 | 1.00 | 32.05 | O |
| HETATM | 2033 | O | HOH | A | 579 | −3.981 | 1.214 | −21.799 | 1.00 | 26.87 | O |
| HETATM | 2034 | O | HOH | A | 580 | 9.463 | −20.337 | −20.300 | 1.00 | 41.44 | O |
| HETATM | 2035 | O | HOH | A | 581 | 18.873 | −13.363 | −20.506 | 1.00 | 42.05 | O |
| HETATM | 2036 | O | HOH | A | 582 | 19.899 | 2.707 | −20.767 | 1.00 | 28.68 | O |
| HETATM | 2037 | O | HOH | A | 583 | 4.978 | −24.363 | −19.541 | 1.00 | 36.69 | O |
| HETATM | 2038 | O | HOH | A | 584 | 5.999 | −19.625 | −19.368 | 1.00 | 24.07 | O |
| HETATM | 2039 | O | HOH | A | 585 | 7.781 | −24.160 | −18.739 | 1.00 | 40.71 | O |
| HETATM | 2040 | O | HOH | A | 586 | −10.625 | −4.395 | −18.233 | 1.00 | 31.52 | O |
| HETATM | 2041 | O | HOH | A | 587 | −9.993 | 0.929 | −17.580 | 1.00 | 50.09 | O |
| HETATM | 2042 | O | HOH | A | 588 | −15.658 | −9.725 | −17.467 | 1.00 | 43.12 | O |
| HETATM | 2043 | O | HOH | A | 589 | 20.083 | 11.714 | −16.656 | 1.00 | 35.35 | O |
| HETATM | 2044 | O | HOH | A | 590 | 8.554 | −26.278 | −14.624 | 1.00 | 31.77 | O |
| HETATM | 2045 | O | HOH | A | 591 | −15.050 | −14.627 | −13.858 | 1.00 | 42.58 | O |
| HETATM | 2046 | O | HOH | A | 592 | −13.641 | −9.289 | −13.881 | 1.00 | 22.69 | O |
| HETATM | 2047 | O | HOH | A | 593 | 17.944 | −3.324 | −11.992 | 1.00 | 33.34 | O |
| HETATM | 2048 | O | HOH | A | 594 | −12.911 | 4.662 | −11.937 | 1.00 | 40.22 | O |
| HETATM | 2049 | O | HOH | A | 595 | 14.108 | −20.749 | −11.497 | 1.00 | 25.29 | O |
| HETATM | 2050 | O | HOH | A | 596 | −17.919 | −12.557 | −11.453 | 1.00 | 41.57 | O |
| HETATM | 2051 | O | HOH | A | 597 | 12.773 | 18.165 | −11.360 | 1.00 | 33.13 | O |
| HETATM | 2052 | O | HOH | A | 598 | −19.219 | −8.583 | −10.346 | 1.00 | 36.79 | O |
| HETATM | 2053 | O | HOH | A | 599 | 9.317 | 16.534 | −10.166 | 1.00 | 19.85 | O |
| HETATM | 2054 | O | HOH | A | 600 | 18.134 | 17.935 | −10.143 | 1.00 | 38.52 | O |
| HETATM | 2055 | O | HOH | A | 601 | −14.939 | −14.502 | −9.308 | 1.00 | 22.73 | O |
| HETATM | 2056 | O | HOH | A | 602 | 11.222 | 15.581 | −9.089 | 1.00 | 32.45 | O |
| HETATM | 2057 | O | HOH | A | 603 | −17.126 | −15.004 | −8.212 | 1.00 | 34.47 | O |
| HETATM | 2058 | O | HOH | A | 604 | 10.117 | 14.018 | −7.057 | 1.00 | 35.85 | O |
| HETATM | 2059 | O | HOH | A | 605 | 18.565 | 15.074 | −6.285 | 1.00 | 23.02 | O |
| HETATM | 2060 | O | HOH | A | 606 | 4.764 | 12.709 | −2.474 | 1.00 | 43.09 | O |
| HETATM | 2061 | O | HOH | A | 607 | 10.680 | 2.579 | −1.794 | 1.00 | 27.19 | O |
| HETATM | 2062 | O | HOH | A | 608 | 5.446 | −13.431 | 0.552 | 1.00 | 30.13 | O |
| HETATM | 2063 | O | HOH | A | 609 | −10.498 | 4.721 | 3.190 | 1.00 | 46.04 | O |
| HETATM | 2064 | O | HOH | A | 610 | −21.591 | 2.307 | 4.061 | 1.00 | 38.24 | O |
| HETATM | 2065 | O | HOH | A | 611 | 3.493 | 6.317 | 4.216 | 1.00 | 33.51 | O |
| HETATM | 2066 | O | HOH | A | 612 | −5.135 | −2.490 | −3.550 | 1.00 | 19.36 | O |
| HETATM | 2067 | O | HOH | A | 613 | −2.436 | −0.927 | 3.082 | 1.00 | 33.03 | O |
| HETATM | 2068 | O | HOH | A | 614 | 0.537 | −2.084 | −6.675 | 1.00 | 12.37 | O |
| HETATM | 2069 | O | HOH | A | 615 | 2.682 | −3.440 | −4.739 | 1.00 | 23.13 | O |
| HETATM | 2070 | O | HOH | A | 616 | 5.446 | −3.198 | −5.100 | 1.00 | 20.59 | O |
| HETATM | 2071 | O | HOH | A | 617 | 4.953 | 6.718 | −11.716 | 1.00 | 15.12 | O |
| HETATM | 2072 | O | HOH | A | 618 | 3.617 | 3.399 | −23.913 | 1.00 | 16.70 | O |
| HETATM | 2073 | O | HOH | A | 619 | −10.394 | 1.192 | −7.002 | 1.00 | 16.39 | O |
| HETATM | 2074 | O | HOH | A | 620 | 1.520 | 7.541 | −14.539 | 1.00 | 19.80 | O |

TABLE 2-continued

X-RAY DIFFRACTION DATA OF S. AUREUS AUTOLYSIN E (AtlE 4PIA) RESIDUES 35-258

| HETATM | 2075 | O | HOH | A | 621 | 5.193 | −0.563 | −3.872 | 1.00 | 20.83 | O |
|---|---|---|---|---|---|---|---|---|---|---|---|
| HETATM | 2076 | O | HOH | A | 622 | 5.753 | −15.162 | −2.041 | 1.00 | 23.03 | O |
| HETATM | 2077 | O | HOH | A | 623 | −5.455 | −4.233 | −0.501 | 1.00 | 29.89 | O |
| HETATM | 2078 | O | HOH | A | 624 | −5.256 | 1.960 | −5.029 | 1.00 | 28.68 | O |
| HETATM | 2079 | O | HOH | A | 625 | 7.689 | 13.866 | 1.359 | 1.00 | 27.79 | O |
| HETATM | 2080 | O | HOH | A | 626 | −2.970 | −3.115 | 1.568 | 1.00 | 29.49 | O |
| HETATM | 2081 | O | HOH | A | 627 | 4.970 | −1.481 | −0.890 | 1.00 | 34.34 | O |
| HETATM | 2082 | O | HOH | A | 628 | −3.836 | 3.749 | −8.092 | 1.00 | 34.92 | O |
| HETATM | 2083 | O | HOH | A | 629 | −4.710 | −9.385 | 9.378 | 1.00 | 28.21 | O |
| HETATM | 2084 | O | HOH | A | 630 | 14.516 | −7.872 | −11.050 | 1.00 | 25.16 | O |
| HETATM | 2085 | O | HOH | A | 631 | −1.108 | 5.740 | −14.154 | 1.00 | 35.08 | O |
| HETATM | 2086 | O | HOH | A | 632 | 15.802 | 14.097 | −0.237 | 1.00 | 47.68 | O |
| HETATM | 2087 | O | HOH | A | 633 | 3.927 | 5.732 | −2.638 | 1.00 | 31.35 | O |
| HETATM | 2088 | O | HOH | A | 634 | 0.082 | −3.041 | 3.104 | 1.00 | 35.58 | O |
| HETATM | 2089 | O | HOH | A | 635 | 8.524 | −14.329 | −23.396 | 1.00 | 26.24 | O |
| HETATM | 2090 | O | HOH | A | 636 | −7.302 | −3.807 | −24.128 | 1.00 | 30.17 | O |
| HETATM | 2091 | O | HOH | A | 637 | −5.390 | 2.171 | −17.173 | 1.00 | 28.70 | O |
| HETATM | 2092 | O | HOH | A | 638 | −8.032 | 3.002 | −12.999 | 1.00 | 46.92 | O |
| HETATM | 2093 | O | HOH | A | 639 | −6.613 | 5.460 | −3.014 | 1.00 | 33.40 | O |
| HETATM | 2094 | O | HOH | A | 640 | 2.433 | −1.897 | −2.309 | 1.00 | 31.32 | O |
| HETATM | 2095 | O | HOH | A | 641 | 0.308 | −1.486 | −0.028 | 1.00 | 34.95 | O |
| HETATM | 2096 | O | HOH | A | 642 | 11.404 | 13.663 | 0.654 | 1.00 | 32.09 | O |
| HETATM | 2097 | O | HOH | A | 643 | −20.585 | −8.163 | −8.163 | 1.00 | 42.15 | O |
| HETATM | 2098 | O | HOH | A | 644 | −5.665 | 0.364 | −3.219 | 1.00 | 36.91 | O |
| HETATM | 2099 | O | HOH | A | 645 | 2.637 | 1.436 | −25.511 | 1.00 | 30.90 | O |
| HETATM | 2100 | O | HOH | A | 646 | 1.410 | 5.788 | −10.687 | 1.00 | 37.16 | O |
| HETATM | 2101 | O | HOH | A | 647 | 17.547 | 0.214 | −11.281 | 1.00 | 39.34 | O |
| HETATM | 2102 | O | HOH | A | 648 | −2.919 | −4.742 | −28.133 | 1.00 | 40.96 | O |
| HETATM | 2103 | O | HOH | A | 649 | 3.290 | 3.520 | −4.923 | 1.00 | 20.97 | O |
| HETATM | 2104 | O | HOH | A | 650 | 7.434 | 19.750 | −8.876 | 1.00 | 25.30 | O |
| HETATM | 2105 | O | HOH | A | 651 | −4.452 | 2.471 | −10.917 | 1.00 | 23.59 | O |
| HETATM | 2106 | O | HOH | A | 652 | 1.227 | 4.726 | −6.191 | 1.00 | 24.61 | O |
| HETATM | 2107 | O | HOH | A | 653 | 2.902 | 0.896 | −4.431 | 1.00 | 25.62 | O |
| HETATM | 2108 | O | HOH | A | 654 | −0.670 | 0.995 | −7.854 | 1.00 | 26.21 | O |
| HETATM | 2109 | O | HOH | A | 655 | −2.948 | 2.308 | −13.755 | 1.00 | 29.76 | O |
| HETATM | 2110 | O | HOH | A | 656 | −10.710 | −3.677 | −16.328 | 1.00 | 32.90 | O |
| HETATM | 2111 | O | HOH | A | 657 | −2.819 | 1.447 | 11.702 | 1.00 | 39.16 | O |
| HETATM | 2112 | O | HOH | A | 658 | −5.415 | 2.009 | 19.376 | 1.00 | 31.72 | O |
| MASTER | 318 | 0 | 9 | 14 | 4 | 0 | 12 | 6 | 2076 | 1 | 0 | 18 |

The invention claimed is:

1. A crystal comprising N-acetylglucosimindase autolysin E (AtlE) of *Staphylococcus aureus* (*S. aureus*), or fragment thereof, wherein said crystal is characterized by (a) the space group symmetry $P2_12_12_1$ and (b) the unit cell dimensions of a=46.6 Å±1-2 Å, b=69.9 Å±1-2 Å, and c=73.3 Å±1-2 Å, with α=90°, β=90°, and γ=90°, and wherein said fragment is an N-terminal truncation of AtlE lacking the N-terminal transmembrane region.

2. The crystal according to claim 1, wherein AtlE or the fragment thereof contains glutamic acid, or an equivalent thereof, as the catalytic residue.

3. The crystal according to claim 1, wherein the crystal is a co-crystal and comprises a substrate and/or a candidate compound.

4. The crystal according to claim 1, wherein said crystal is characterized by (a) the space group symmetry $P2_12_12_1$ and (b) the unit cell dimensions of a=46.6 Å±1 Å, b=69.9 Å±1 Å, and c=73.3 Å±1 Å, with α=90°, β=90°, and γ=90°.

5. A method for producing a crystal comprising N-acetylglucosiminidase autolysin E (AtlE) of *S. aureus* or a fragment thereof, said method comprising the steps of
(a) preparing a solution of said AtlE in a crystallization buffer containing 2 M NaCl and 2 M $(NH_4)_2SO4$, and
(b) crystallizing said AtlE by vapor diffusion, wherein said crystal is characterized by (a) the space group symmetry $P2_12_12_1$ and (b) the unit cell dimensions of a=46.6 Å±1-2 Å, b=69.9 Å±1-2 Å, and c=73.3 Å±1-2 Å, with α=90°, β=90°, and γ=90°, and wherein said fragment is an N-terminal truncation of AtlE lacking the N-terminal transmembrane region, and wherein said fragment is an N-terminal truncation of AtlE lacking the N-terminal transmembrane region.

6. A method for obtaining the atomic coordinates of N-acetylglucosiminidase autolysin E (AtlE) of *Staphylococcus aureus* (*S. aureus*), or a fragment thereof by subjecting the crystal as defined in claim 1 to X-ray diffraction and solving the three-dimensional thereby obtaining said atomic coordinates.

7. A method for screening, identifying, designing, or optimizing a binding compound by contacting the binding compound with the crystal according to claim 6, prior to X-ray diffraction.

8. A method for screening, identifying, designing, or optimizing a naturally occurring or synthetic ligand or inhibitor of AtlE by contacting a naturally occurring or synthetic ligand or inhibitor of AtlE with the crystal according to claim 6, prior to X-ray diffraction.

9. A method for screening a binding compound or inhibitor of the N-acetylglucosaminidase activity of autolysin E (AtlE) of *S. aureus*, said method comprising the steps of:
(a) providing a solution of said AtlE or fragment thereof,
(b) contacting at least one candidate compound with the AtlE in said solution,
(C) preparing crystals of said AtlE according to claim 5, and
(d) identifying a binding compound of said AtlE by solving the X-ray diffraction structure, wherein said crystal is characterized by (a) the space group symmetry $P2_12_12_1$ and (b) the unit cell dimensions of a=46.6 Å±1-2 Å, b=69.9 Å±1-2 Å, and c=73.3 Å±1-2 Å, with α=90°, β=90°, and γ=90°, and wherein said fragment is an N-terminal truncation of AtlE lacking the N-terminal transmembrane region.

10. The method of claim 9, wherein, said AtlE or a crystallizable fragment thereof contains glutamic acid, or an equivalent thereof, as the catalytic residue.

11. The method of claim 9, wherein, the fragment of AtlE is a N-terminal truncation lacking the N-terminal transmembrane region of AtlE said fragment comprising the amino acid sequence of SEQ ID NO: 2.

12. The method of claim 9, wherein, said AtlE comprises the amino acid sequence of the N-glucosaminidase domain of SEQ ID NO: 2, SEQ ID NO: 3, SEQ ID NO: 4, SEQ ID NO: 5, or SEQ ID NO: 6.

13. The method according to claim 9, wherein, in step (d), the binding of the candidate compound to the active site is determined.

14. The method according to claim 13, wherein the active site is characterized by the regions of SEQ ID NO: 1 from methionine 47 (M) to glutamic acid 65(E), from leucine 136 (L) to glycine 140 (G), from asparagine 159 (N) to glutamic acid 181(E), from phenylalanine 196 (F) to asparagine 204 (N) and/or from proline 219 (P) to lysine 233 (K), or wherein the active site is characterized by the regions of SEQ ID NO: 1 from methionine 47 (M) to glutamic acid 65 (E), from leucine 136 (L) to glycine 140 (G), from asparagine 159 (N) to glutamic acid 181 (E), from phenylalanine 196 (F) to asparagine 204 (N) and/or from proline 219 (P) to lysine 233 (K), and the catalytic glutamic acid (E) at position 138.

15. The method according to claim 13, wherein the active site is characterized by the regions of SEQ ID NO: 1 from methionine 47 (M) to glutamic acid 65(E), from leucine 136 (L) to glycine 140 (G), from asparagine 159 (N) to glutamic acid 181(E), from phenylalanine 196 (F) to asparagine 204 (N) and/or from proline 219 (P) to lysine 233 (K), and the catalytic glutamic acid (E) at position 138, and further by an aspartic acid (D) at position 167, an phenylalanine (F) at position 224, an aspartic acid (D) at position 227 and/or a tyrosine (Y) at position 201.

16. A method for in silico screening the ability of a candidate compound to bind to N-acetylglucosiminidase AtlE and/or another *S. aureus* autolysin comprising the amino acid sequence selected from the group consisting of SEQ ID NO: 2, 3, 4, and 5, the method comprising,
(a) employing on a computer the structural coordinates of AtlE according to Table 2 to generate a three-dimensional model of said AtlE binding pocket or enzyme on a computer, wherein said computer comprises the means for generating said three-dimensional model;
(b) identifying the active site amino acids selected from the group consisting of E138, E145, D167, D227 or combinations thereof; and (c) employing the residues identified in (b) to design, select and/or optimize said candidate compound by performing a fitting operation between said candidate compound and said three-dimensional structural information of all or part of said binding pocket or protein.

* * * * *